US012685437B2

(12) United States Patent
Boyd et al.

(10) Patent No.: US 12,685,437 B2
(45) Date of Patent: Jul. 21, 2026

(54) DETECTION, PREDICTION, AND CLASSIFICATION FOR OCULAR DISEASE

(71) Applicant: Tracery Ophthalmics Inc., Toronto (CA)

(72) Inventors: Shelley Boyd, Toronto (CA); Natalie Pankova, Ottawa (CA); Nehad Hirmiz, Toronto (CA); Huiyuan Liang, Toronto (CA)

(73) Assignee: Tracery Ophthalmics Inc., Toronto (CA)

( * ) Notice: Subject to any disclaimer, the term of this patent is extended or adjusted under 35 U.S.C. 154(b) by 853 days.

(21) Appl. No.: 17/604,251

(22) PCT Filed: Apr. 18, 2019

(86) PCT No.: PCT/CA2019/050495
§ 371 (c)(1),
(2) Date: Oct. 15, 2021

(87) PCT Pub. No.: WO2020/210891
PCT Pub. Date: Oct. 22, 2020

(65) Prior Publication Data
US 2022/0207729 A1     Jun. 30, 2022

(51) Int. Cl.
*G06K 9/00*        (2022.01)
*A61B 3/00*        (2006.01)
(Continued)

(52) U.S. Cl.
CPC .............. *A61B 3/0025* (2013.01); *A61B 3/12* (2013.01); *G06T 7/0012* (2013.01);
(Continued)

(58) Field of Classification Search
CPC ...... A61B 3/0025; A61B 3/12; G06V 40/197; G06V 10/771; G06V 10/7715;
(Continued)

(56) References Cited

U.S. PATENT DOCUMENTS 4,451,477 A     5/1984   Silvestrini et al.
4,999,367 A     3/1991   Baiocchi et al.
(Continued)

FOREIGN PATENT DOCUMENTS

CA        3040419 A1     4/2018
EP        0131317 B1     1/1985
(Continued)

OTHER PUBLICATIONS

Pankova, Natalie, et al. "Delayed near-infrared analysis permits visualization of rodent retinal pigment epithelium layer in vivo." Journal of Biomedical Optics 19.7 (2014): 076007-076007. (Year: 2014).*

(Continued)

*Primary Examiner* — Avinash Yentrapati
(74) *Attorney, Agent, or Firm* — Morgan, Lewis & Bockius LLP

(57) ABSTRACT

Computer systems and computer-implemented methods for performing classification, detection, and/or prediction based on processing of ocular images obtained from various imaging modalities are disclosed. Use of delayed near-infrared analysis (DNIRA) as one of the imaging modality is also disclosed.

20 Claims, 86 Drawing Sheets

(51) Int. Cl.

| | |
|---|---|
| *A61B 3/12* | (2006.01) |
| *G06T 7/00* | (2017.01) |
| *G06V 10/77* | (2022.01) |
| *G06V 10/771* | (2022.01) |
| *G06V 10/774* | (2022.01) |
| *G06V 10/82* | (2022.01) |
| *G06V 40/18* | (2022.01) |
| *G06V 40/19* | (2022.01) |

(52) U.S. Cl.
CPC ........ *G06V 10/771* (2022.01); *G06V 10/7715* (2022.01); *G06V 10/774* (2022.01); *G06V 10/82* (2022.01); *G06V 40/19* (2022.01); *G06V 40/193* (2022.01); *G06V 40/197* (2022.01); *G06T 2207/10048* (2013.01); *G06T 2207/10101* (2013.01); *G06T 2207/20081* (2013.01); *G06T 2207/20084* (2013.01); *G06T 2207/30041* (2013.01); *G06V 2201/032* (2022.01)

(58) Field of Classification Search
CPC ...... G06V 10/82; G06V 40/19; G06V 40/193; G06V 10/774; G06V 2201/032; G06T 7/0012; G06T 2207/10048; G06T 2207/10101; G06T 2207/20081; G06T 2207/20084; G06T 2207/30041
See application file for complete search history.

(56) References Cited

U.S. PATENT DOCUMENTS

| | | | |
|---|---|---|---|
| 5,112,986 A | 5/1992 | Baiocchi et al. | |
| 5,278,183 A | 1/1994 | Silvestrini | |
| 6,020,356 A | 2/2000 | Guglielmotti et al. | |
| 6,093,743 A | 7/2000 | Lai et al. | |
| 6,274,627 B1 | 8/2001 | Lai et al. | |
| 6,316,502 B1 | 11/2001 | Lai et al. | |
| 6,319,517 B1 | 11/2001 | Cavallo et al. | |
| 6,337,087 B1 | 1/2002 | Cavallo et al. | |
| 6,534,534 B1 | 3/2003 | Guglielmotti et al. | |
| 6,589,991 B1 | 7/2003 | Lai et al. | |
| 6,596,770 B2 | 7/2003 | Lai et al. | |
| 6,649,591 B2 | 11/2003 | Lai | |
| 6,673,908 B1 | 1/2004 | Stanton, Jr. | |
| 7,553,496 B2 | 6/2009 | Ambati | |
| 7,732,162 B2 | 6/2010 | Hoffman et al. | |
| 7,816,497 B2 | 10/2010 | Ambati | |
| 7,928,284 B2 | 4/2011 | Ambati | |
| 8,008,092 B2 | 8/2011 | Ambati | |
| 8,067,031 B2 | 11/2011 | Daniloff et al. | |
| 8,158,152 B2 | 4/2012 | Papelu | |
| 8,198,310 B2 | 6/2012 | Guglielmotti et al. | |
| 8,232,265 B2 | 7/2012 | Rogers et al. | |
| 9,016,862 B2 | 4/2015 | Carnevale | |
| 9,999,688 B2 | 6/2018 | Boyd | |
| 10,251,550 B2 * | 4/2019 | Jia ...................... | A61B 3/0025 |
| 2003/0207309 A1 | 11/2003 | Hageman et al. | |
| 2004/0177387 A1 | 9/2004 | Jayakrishna | |
| 2006/0067935 A1 | 3/2006 | Ambati | |
| 2006/0135423 A1 | 6/2006 | Ambati | |
| 2006/0263409 A1 | 11/2006 | Peyman | |
| 2007/0190055 A1 | 8/2007 | Ambati | |
| 2007/0191273 A1 | 8/2007 | Ambati et al. | |
| 2008/0299130 A1 | 12/2008 | Ambati | |
| 2009/0123375 A1 | 5/2009 | Ambati | |
| 2009/0186376 A1 | 7/2009 | Ambati et al. | |
| 2009/0260091 A1 | 10/2009 | Ambati | |
| 2009/0304591 A1 | 12/2009 | Russman et al. | |
| 2010/0260396 A1 * | 10/2010 | Brandt ................ | G06V 10/764 |
| | | | 382/131 |
| 2011/0097390 A1 | 4/2011 | Ambati | |
| 2011/0137157 A1 | 6/2011 | Imamura et al. | |
| 2011/0182517 A1 | 7/2011 | Farsiu et al. | |

| | | | |
|---|---|---|---|
| 2011/0182908 A1 | 7/2011 | Hageman et al. | |
| 2011/0234977 A1 | 9/2011 | Verdooner | |
| 2011/0268723 A1 | 11/2011 | Ambati | |
| 2012/0064010 A1 | 3/2012 | Ambati et al. | |
| 2013/0295014 A1 | 11/2013 | Boyd | |
| 2013/0308094 A1 | 11/2013 | Mohan et al. | |
| 2014/0029820 A1 * | 1/2014 | Srivastava ........... | G06T 7/0014 |
| | | | 382/131 |
| 2015/0065868 A1 * | 3/2015 | Liang ............... | A61B 1/000094 |
| | | | 600/425 |
| 2015/0088870 A1 * | 3/2015 | Jayasundera ......... | G16H 50/20 |
| | | | 707/723 |
| 2015/0201829 A1 | 7/2015 | Yang et al. | |
| 2018/0263490 A1 * | 9/2018 | Jia ........................... | G06F 18/23 |
| 2019/0046030 A9 | 2/2019 | Jia et al. | |
| 2020/0051259 A1 * | 2/2020 | Sylvestre ............. | A61B 5/6821 |
| 2020/0242763 A1 * | 7/2020 | Bhuiyan .................. | G06T 7/38 |
| 2021/0279874 A1 * | 9/2021 | Boyd ...................... | A61B 3/14 |

FOREIGN PATENT DOCUMENTS

| | | | |
|---|---|---|---|
| JP | 2008-029732 A | 2/2008 | |
| JP | 2011-120656 A | 6/2011 | |
| JP | 2013-527775 A | 7/2013 | |
| JP | 2013-542840 A | 11/2013 | |
| JP | 2014-217441 A | 11/2014 | |
| JP | 2015-523546 A | 8/2015 | |
| JP | 2016-509914 A | 4/2016 | |
| JP | 2016-107148 A | 6/2016 | |
| WO | WO 97/16185 A2 | 5/1997 | |
| WO | WO 98/36735 A1 | 8/1998 | |
| WO | WO 98/36736 A1 | 8/1998 | |
| WO | WO 03/053230 A1 | 7/2003 | |
| WO | WO 2004/041160 A2 | 5/2004 | |
| WO | WO 2005/108431 A1 | 11/2005 | |
| WO | WO 2007/079207 A2 | 7/2007 | |
| WO | WO 2007/098113 A2 | 8/2007 | |
| WO | WO 2007/133800 A2 | 11/2007 | |
| WO | WO 2008/061671 A2 | 5/2008 | |
| WO | WO 2009/104528 A1 | 8/2009 | |
| WO | WO 2009/105260 A2 | 8/2009 | |
| WO | WO 2010/044791 A1 | 4/2010 | |
| WO | WO 2010/138591 A1 | 12/2010 | |
| WO | WO 2011/036047 A1 | 3/2011 | |
| WO | WO 2011/119602 A2 | 9/2011 | |
| WO | WO 2011/153234 A2 | 12/2011 | |
| WO | WO 2012/061835 A3 | 5/2012 | |
| WO | WO 2012/068408 A1 | 5/2012 | |
| WO | WO 2013/163758 A1 | 11/2013 | |
| WO | WO 2014/140258 A2 | 9/2014 | |
| WO | WO 2015/173786 A1 | 11/2015 | |
| WO | WO 2016/073556 A1 | 5/2016 | |
| WO | WO 2016/203313 A1 | 12/2016 | |
| WO | WO-2018069768 A2 * | 4/2018 | ............. A61B 3/024 |

OTHER PUBLICATIONS

Tou, Jing Yi, Yong Haur Tay, and Phooi Yee Lau. "One-dimensional grey-level co-occurrence matrices for texture classification." 2008 International Symposium on Information Technology. vol. 3. IEEE, 2008. (Year: 2008).*

Rahebi, Javad, and Frat Hardalaç. "Retinal blood vessel segmentation with neural network by using gray-level co-occurrence matrix-based features." Journal of medical systems 38.8 (2014): 85. (Year: 2014).*

Ambati, et al., "An animal model of age-related macular degeneration in senescent Ccl-2 or Ccr-2-deficient mice," Nature Medicine, 2003, vol. 9, No. 11, pp. 1390-1397.

Arnold, J., et al., "Indocyanine Green Angiography of Drusen," American Journal of Ophthalmology, 1997, vol. 124, No. 3, pp. 344-356.

Arnold, J.J., et al., "Reticular Pseudodrusen. A Risk Factor in Age-Related Maculopathy," Retina, vol. 15, pp. 183-191 (1995).

Beckmann, N., et al., "In vivo visualization of macrophage infiltration and activity in inflammation using magnetic resonance imaging," WIREs Nanomed. Nanobiotechnol., vol. 1, pp. 272-298 (2009).

(56)　　　　　　References Cited

OTHER PUBLICATIONS

Bindewald, A., et al., "Classification of abnormal fundus autofluorescence patterns in the junctional zone of geographic atrophy in patients with age related macular degeneration," Br. J. Ophthalmol., vol. 89, pp. 874-878 (2005).

Bindewald, A., et al., "Classification of Fundus Autofluorescence Patterns in Early Age-Related Macular Disease," Invest. Ophthalmol. Vis. Sci., vol. 46, pp. 3309-3314 (2005).

Boretsky, A., et al., "Quantitative Evaluation of Retinal Response to Laser Photocoagulation Using Dual-Wavelength Fundus Autofluorescence Imaging in a Small Animal Model," Invest. Ophthalmol. Vis. Sci., vol. 52, pp. 6300-6307 (2011).

Boyd, S. R., et al., "Reticular Fundus Autofluorescence (FAF) in the Evolution of Geographic Atrophy (GA) in a Rat Model of RPE Toxicity," 2012 ARVO Annual Meeting, Abstract of Program#/ Poster# 6504/A430, 2 pages (May 10, 2012).

Brayton, "Spontaneous Diseases in Commonly Used Mouse Strains / Stocks," 2014, 85 pages.

Buono, C., et al., "Fluorescent pegylated nanoparticles demonstrate fluid-phase pinocytosis by macrophages in mouse atherosclerotic lesions," J. Clin. Invest., vol. 119, No. 5, pp. 1373-1381 (2009).

Cone, R. E., et al., "Regulation of Experimental Autoimmune Uveitis (EAU) Induction in Mice by the Phosphodiesterase Inhibitor Dipyrimidol and of Active EAU by Bindarit, an Inhibitor of Monocyte Chemotactic Proteins," 2011 ARVO Annual Meeting, Abstract of Program#/Poster# 2260/A426, 5 pages (May 2, 2011).

Duker, J.S., "The complete trial for dry AMD: Results," Review of Ophthalmology, Sep. 6, 2012, 3 pages.

Enzmann, V., et al., "Behavioral and anatomical abnormalities in a sodium iodate-induced model of retinal pigment epithelium degeneration," Exp. Eye Res., vol. 82, pp. 441-448 (2006).

Eter, N., et al., "In Vivo Visualization of Dendritic Cells, Macrophages, and Microglial Cells Responding to Laser-Induced Damage in the Fundus of the Eye," Invest. Ophthalmol. Vis. Sci., vol. 49, No. 8, pp. 3649-3658 (2008).

Fleckenstein, M., et al., "Fundus Autofluorescence and Spectral-Domain Optical Coherence Tomography Characteristics in a Rapidly Progressing Form of Geographic Atrophy," Invest. Ophthalmol. Vis. Sci., vol. 52, No. 6, pp. 3761-3766 (2011).

Fleckenstein, M., et al., "High-Resolution Spectral Domain-OCT Imaging in Geographic Atrophy Associated with Age-Related Macular Degeneration," Invest Ophthalmol Vis Sci. 2008, vol. 49, pp. 4137-4144.

Franco, L. M., et al., "Decreased Visual Function after Patchy Loss of Retinal Pigment Epithelium Induced by Low-Dose Sodium Iodate," Invest. Ophthalmol. Vis. Sci., vol. 50, No. 8, pp. 4004-4010 (2009).

Hua, et al., "In vivo imaging of choroidal angiogenesis using fluorescence-labeled cationic liposomes," Molecular Vision 2012, vol. 18, pp. 1045-1054.

International Search Report & Written Opinion, PCT Application No. PCT/CA2013/050335, dated Aug. 23, 2013, 12 pages.

International Search Report dated Sep. 19, 2018, for International Application No. PCT/IB2017/001399.

International Preliminary Report on Patentability, issued Apr. 16, 2019, for International Application No. PCT/IB2017/001399.

Kiuchi, K., et al., "Morphologic characteristics of retinal degeneration induced by sodium iodate in mice," Curr. Eye Res., vol. 25, No. 6, pp. 373-379 (2002).

Ladewig, M. S., et al., "Prostaglandin E1 infusion therapy in dry age-related macular degeneration," Prostaglandins, Leukotrienes and Essential Fatty Acids, vol. 72, pp. 251-256 (2005).

Lois, N., et al., "Fundus Autofluorescence in Patients With Age-related Macular Degeneration and High Risk of Visual Loss," Am. J. Ophthalmol., vol. 133, pp. 341-349 (2002).

Luhmann, U. F. O., et al., "The Drusenlike Phenotype in Aging Ccl2-Knockout Mice is Caused by an Accelerated Accumulation of Swollen Autofluorescent Subrelinal Macrophages," Invest. Ophthalmol. Vis. Sci., vol. 50, pp. 5934-5943 (2009).

Mattapallil, et al., "The Rd8 Mutation of the Crb1 Gene is Present in Vendor Line of C57BL/6N Mice and Embryonic Stem Cells, and Confounds Ocular Induced Mutant Phenotypes," IOVS, May 2012, vol. 53, No. 6, pp. 2921-2927.

Mendes-Jorge, L., et al., "Scavenger Function of Resident Autofluorescent Perivascular Macrophages and Their Contribution to the Maintenance of the Blood-Retinal Barrier," Invest. Ophthalmol. Vis. Sci., vol. 50, No. 12, pp. 5997-6005 (2009).

Mizota, A., et al., "Functional Recovery of Retina After Sodium Iodate Injection in Mice," Vision Res., vol. 37, No. 14, pp. 1859-1865 (1997).

Mori, et al., "The Ultra-Late Phase of Indocycanine Green Angiography for healthy subjects and patients with age-related macular degeneration," Retina, vol. 22, pp. 309-316, 2002.

Obata, R., et al., "Retinal degeneration is delayed by tissue factor pathway inhibitor-2 in RCS rats and a sodium-iodate-induced model in rabbits," Eye, vol. 19, pp. 464-468 (2005).

Ohtaka, K., et al., "Protective Effect of Hepatocyte Growth Factor Against Degeneration of the Retinal Pigment Epithelium and Photoreceptor in Sodium Iodate-Injected Rats," Curr. Eye Res., vol. 31, pp. 347-355 (2006).

Pankova, N., et al., "Delayed near-infrared analysis permits visualization of rodent retinal pigment epithelium layer In vivo," Journal of Biomedical Optics, 2014, vol. 19, No. 7, 9 pages.

Pankova, N., et al., "Delayed Near-Infrared Analysis (DNIRA) is a Novel Technique That Permits Visualization of Rat Retinal Pigment Epithelium (RPE) Layer In Vivo," ARVO Annual Meeting Abstract, 2014, 2 pages.

Pankova, N., et al., "Immuno-DNIRA (ImmunoD) is a novel imaging technique that identifies ex vivo labelled macrophages in the eye with confocal Scanning Laser Ophthalmoscopy (cSLO)," ARVO Annual Meeting Abstract, 2015, 2 pages.

Pankova, N., "Innate Immune Response Polarization and Treatment Potential in a Preclinical Model of Dry Age-Related Macular Degeneration," Doctor of Philosophy, Laboratory Medicine and Pathobiology, 2016.

Rodrigues, E.B., et al., "The Use of Vital Dyes in Ocular Surgery", Survey of Ophthalmology, 2009, vol. 54, No. 5, pp. 576-617.

Ross, R. J., et al., "Immunological protein expression profile in Ccl2/Cx3cr1 deficient mice with lesions similar to age-related macular degeneration," Exp. Eye Res., vol. 86, No. 4, pp. 675-683 (2008).

Sarks, J., et al., "Evolution of reticular pseudodrusen," Br. J. Ophthalmol., vol. 95, pp. 979-985 (2011).

Spencer, D. B., et al., "In vivo imaging of the immune response in the eye," Semin. Immunopathol., vol. 30, pp. 179-190 (2008).

Supplementary European Search Report, dated May 13, 2020, for Application No. EP 17860434, (10 pages).

Tanaka, M., et al., "Third-Order Neuronal Responses Contribute to Shaping the Negative Electroretinogram in Sodium Iodate-Treated Rats," Curr. Eye Res., vol. 30, pp. 443-453 (2005).

Weinberger, A., et al., "Fundus Near Infrared Fluorescence Correlates with Fundus Near Infrared Reflectance," Invest. Opthlamol. Vis. Sci., 2006, vol. 47, No. 1, pp. 3098-3108.

Written Opinion of the International Searching Authority, dated Sep. 19, 2018, for International Application No. PCT/IB2017/001399.

Wroblewski, et al., "Indocyanine Green Angiography in Stargardt's Flavimaculatus," Am. J Ophthalmolgy, 1995, vol. 120, pp. 208-218.

Wu, Dezheng "Ocular Indocyanine Green Angiography," Liaoning Science and Technology Press, 2002, 17 pages.

Yam, H., et al., "Effect of Indocyanine Green and Illumination on Gene Expression in Human Retinal Pigment Epithelial Cells," IOVS, 2003, vol. 44, No. 1, pp. 370-377.

Zeng, X-X, et al., "Labelling of retinal microglial cells following an intravenous injection of a fluorescent dye into rats of different ages," J. Anat., vol. 196, pp. 173-179 (2000).

Zhao, X., et al., "Patches of RPE Loss Can Be Detected In Vivo in the Rat Eye Using Confocal Scanning Laser Ophthalmoscopy," 2011 ARVO Annual Meeting, Abstract of Program#/Poster# 969/ A161, 2 pages (May 1, 2011).

(56)                 References Cited

OTHER PUBLICATIONS

Zweifel, S. A., et al., "Prevalence and Significance of Subretinal Drusenoid Deposits (Reticular Pseudodrusen) in Age-Related Macular Degeneration," Ophthalmology, vol. 117, No. 9, pp. 1775-1781 (2010).

Zweifel, S. A., et al., "Reticular Pseudodrusen are Subretinal Drusenoid Deposits," Ophthalmology, vol. 117, No. 2, pp. 303-312 (2010).

International Search Report & Written Opinion PCT Application No. PCT/CA2019/050495, dated Dec. 16, 2019, 10 pages.

* cited by examiner

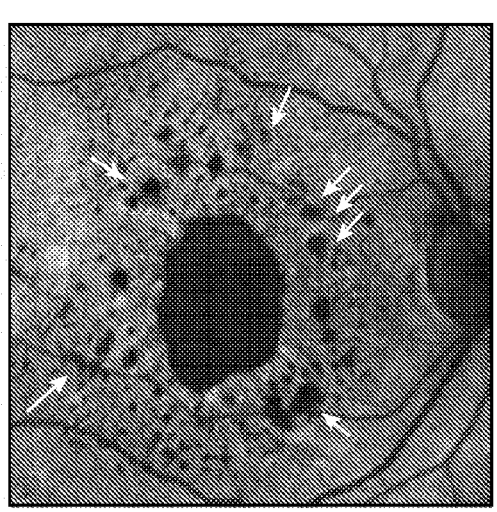
FIG. 14

T = 1                          T = 2

Session 1          Session 2          Session 3

Session 1 vs 2 vs 3

Optical Coherence Tomography (OCT) Tumor Region Scan

Optical Coherence Tomography (OCT) Fluid Region Scan

TAM Imaging (TAMi)

Manual Cell Count

Regions of Interest

Colour Fundus Photography (CFP)

Fundus Autofluorescence (FAF)

| One-Way ANOVA and Bonferroni multiple comparisons analysis of Dot Density (DD) differences between risk groups in each Region of Interest | | | | |
|---|---|---|---|---|
| | F | P-Value | Multiple Comparisons | Adj. P-Value |
| Lesion (Tumour & Fluid) Dot Density | 11.02 | 0.003 | Nevus vs. Indeterminate | > 0.999 |
| | | | Nevus vs. Melanoma | 0.008 |
| | | | Indeterminate vs. Melanoma | 0.008 |
| Tumour-only DD | 6.29 | 0.012 | Nevus vs. Indeterminate | > 0.999 |
| | | | Nevus vs. Melanoma | 0.027 |
| | | | Indeterminate vs. Melanoma | 0.025 |
| Fluid-only DD | 7.38 | 0.007 | Nevus vs. Indeterminate | > 0.999 |
| | | | Nevus vs. Melanoma | 0.011 |
| | | | Indeterminate vs. Melanoma | 0.025 |
| Peripheral (non-lesion) DD | 1.48 | 0.263 | Nevus vs. Indeterminate | > 0.999 |
| | | | Nevus vs. Melanoma | 0.689 |
| | | | Indeterminate vs. Melanoma | 0.364 |

FIG. 19I

Bonferroni's multiple comparisons of Dot Densities (DD) between Regions of Interest (RoI) in each risk group

| | Multiple Comparisons | Adj. P-Value |
|---|---|---|
| Nevus | Lesion RoI DD vs. Fluid RoI DD | 0.782 |
| | Lesion RoI DD vs. Peripheral RoI DD | > 0.999 |
| | Fluid RoI DD vs. Peripheral RoI DD | > 0.999 |
| Indeterminate | Lesion DD vs. Fluid DD | > 0.999 |
| | Lesion DD vs. Peripheral DD | 0.846 |
| | Fluid DD vs. Peripheral DD | > 0.999 |
| Melanoma | Lesion DD vs. Fluid DD | 0.958 |
| | Lesion DD vs. Peripheral DD | 0.008 |
| | Fluid DD vs. Peripheral DD | < 0.001 |

FIG. 19J

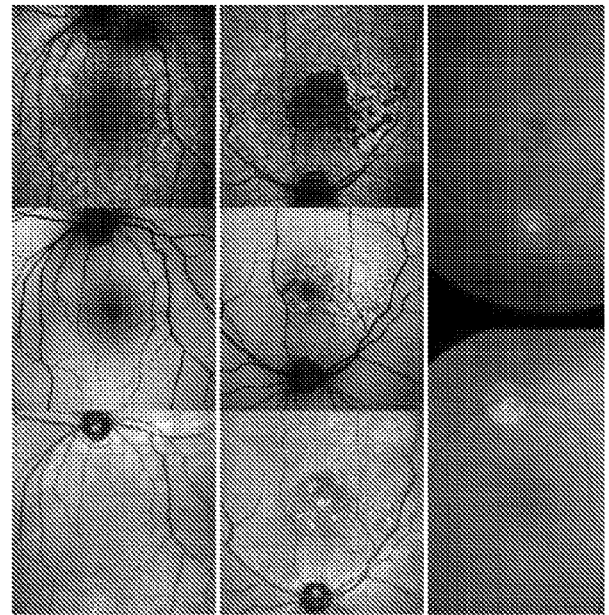
FIG. 27B
FIG. 27A

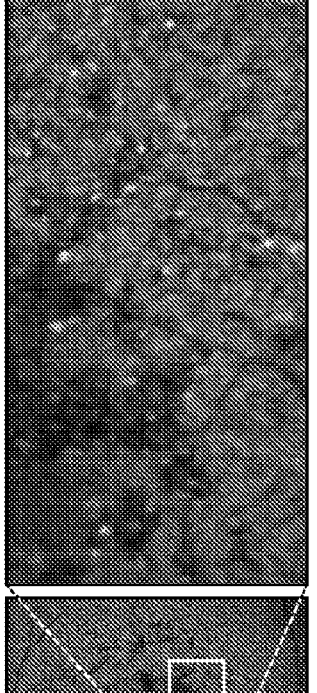
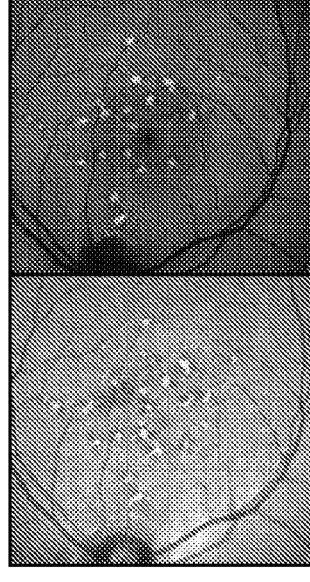
FIG. 28A

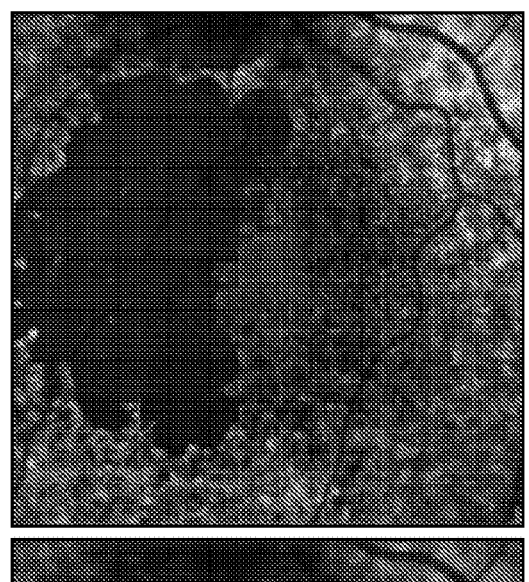
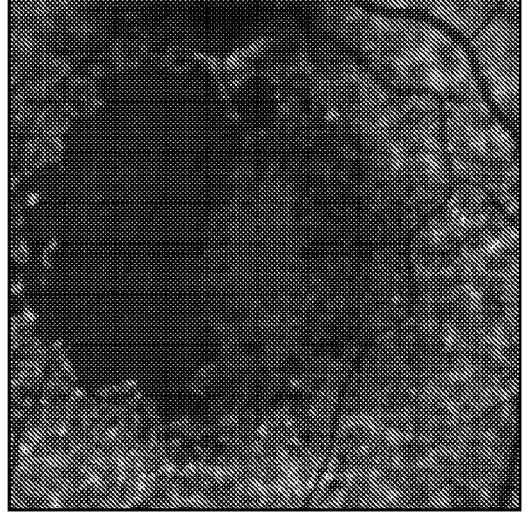
FIG. 28B

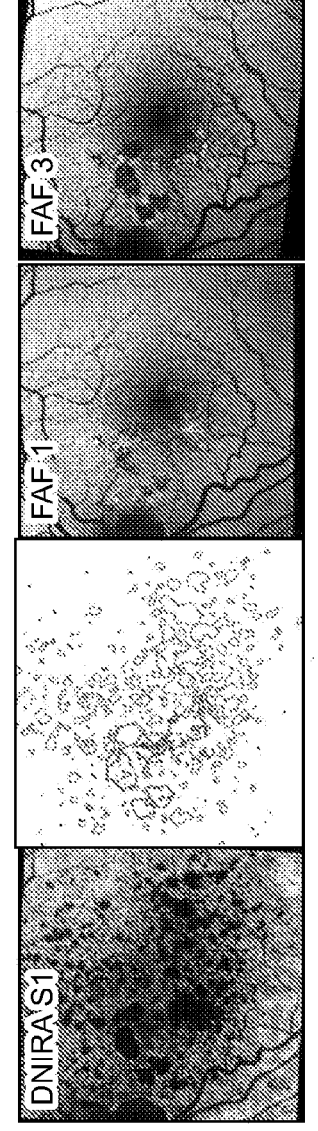
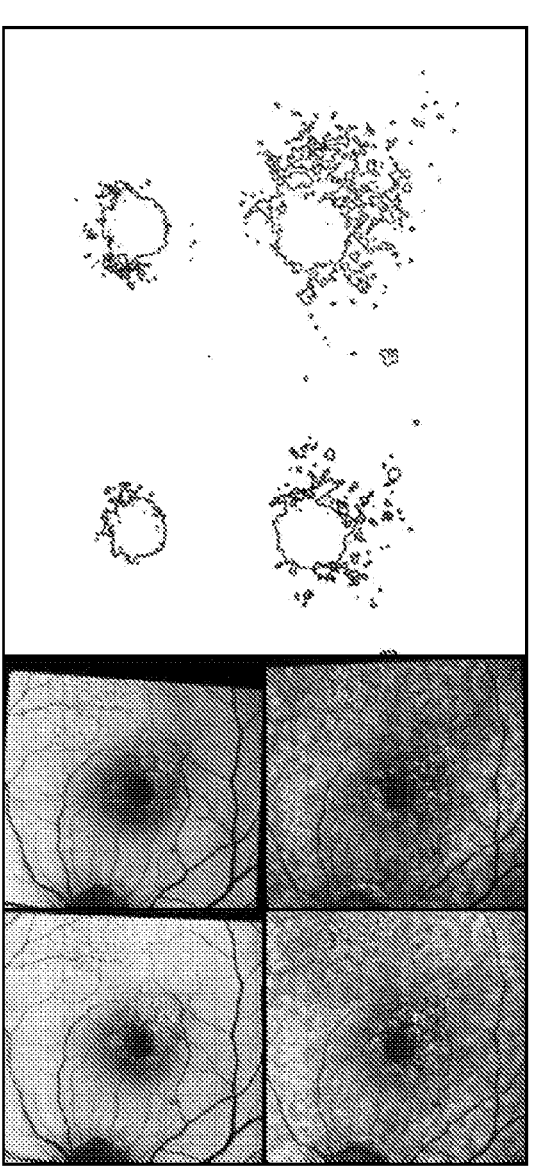
FIG. 30

Tiled low power montage

Blue = nuclei  Red = Iba1 (macrophages)  Green = RPE65 (RPE)

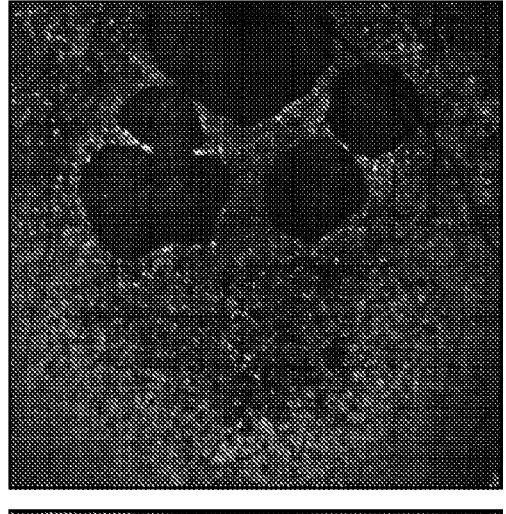
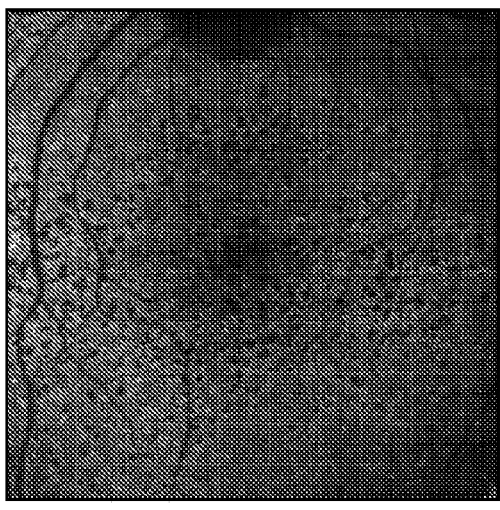
FIG. 34A

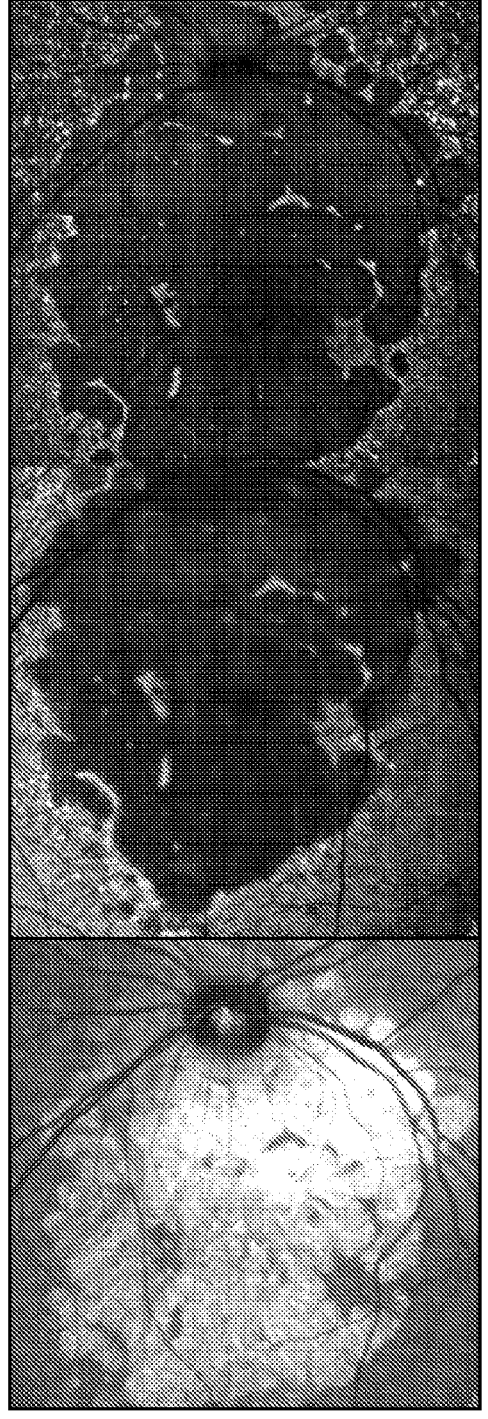
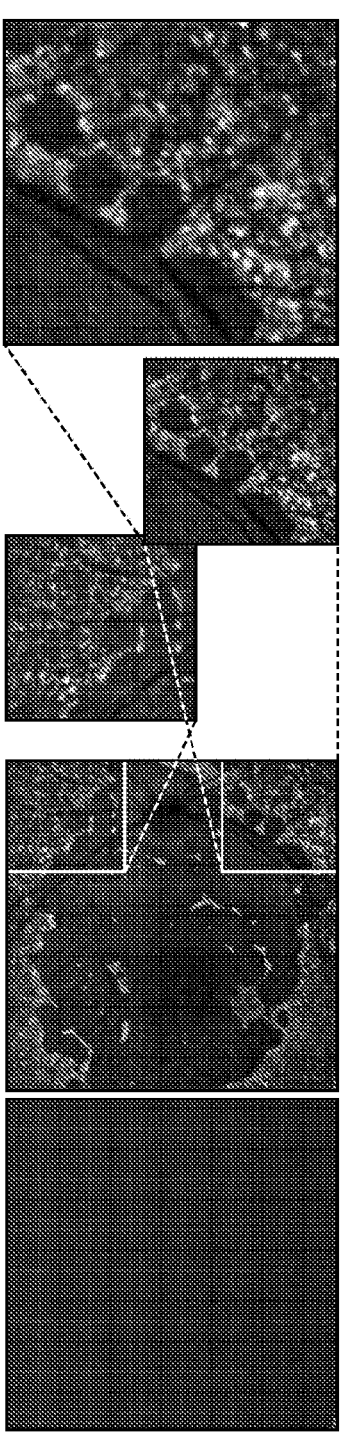
FIG. 37

S1

S2

S3

S4

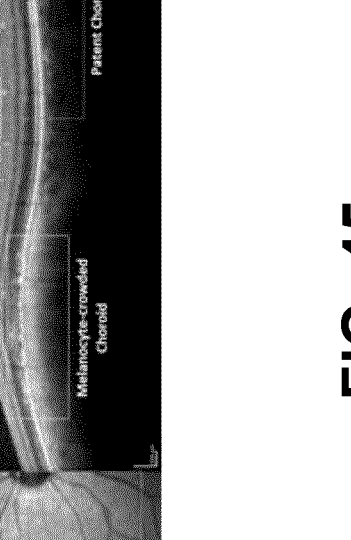
FIG. 45

1402                    1404

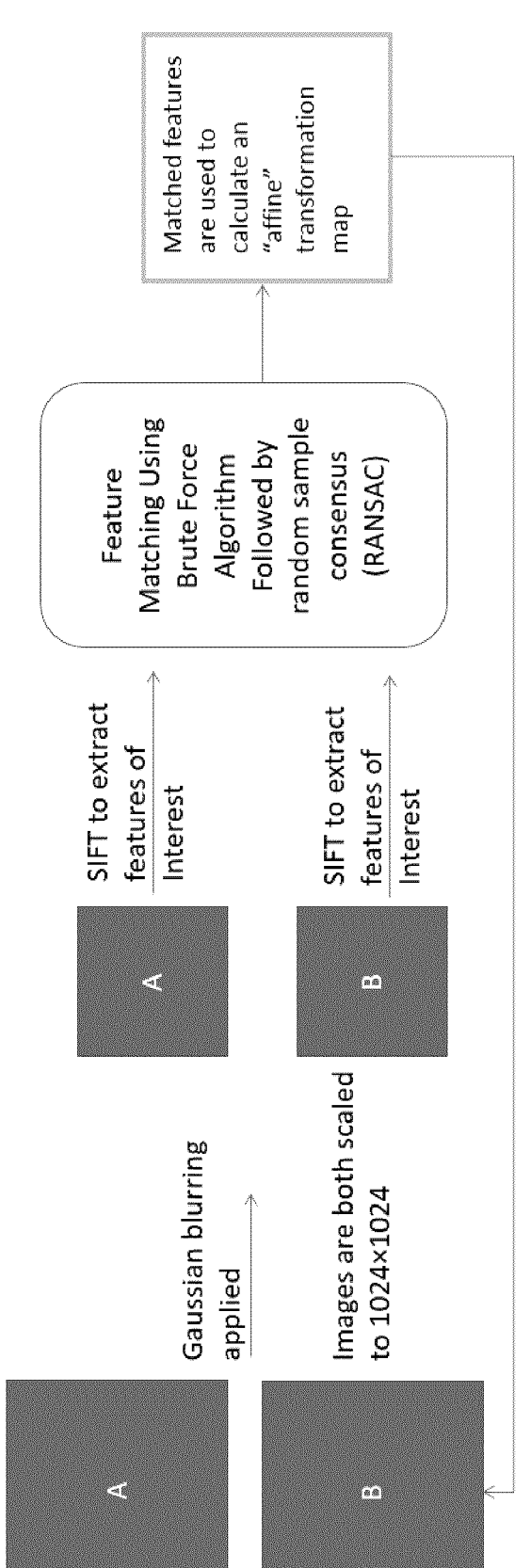

Scale Invariant Feature Transform (SIFT) Based Image Registration
Images Registration has been performed for images acquired using cSLO Confocal scanning laser ophthalmoscopy (cSLO) images are saved in RGB format
Intensity levels are equal in all three channels
Images are stored in 1536x1536 pixel format
Generally the size of each image is about 8x8 mm Registration is performed using python. Image processing , feature extract and feature matching uses Open Computer Vision (OpenCV) implementation in Python Gaussian blurring applied Images are both scaled to 1024×1024

SIFT to extract features of Interest

A

SIFT to extract features of Interest

B

Feature Matching Using Brute Force Algorithm Followed by random sample consensus (RANSAC)

Matched features are used to calculate an "affine" transformation map

Inverse transformation applied back to B to register it to A

Reference IR                    OCT Slice
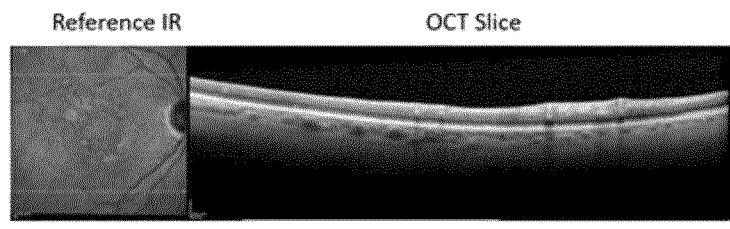
Extracted Reference IR
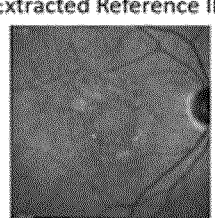
FIG. 57

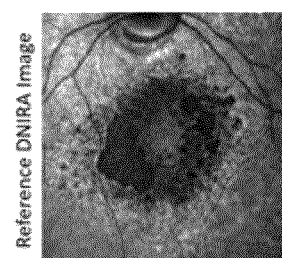
OCT scans are performed in the Near IR channel then the pipeline would us the DNIRA image as a reference
Reference DNIRA Image
FIG. 59

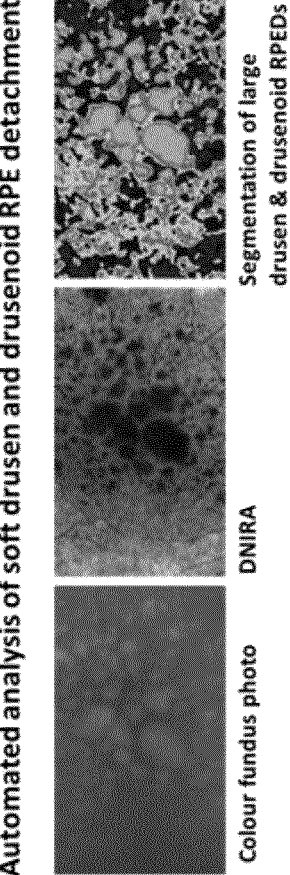
Automated analysis of soft drusen and drusenoid RPE detachments
Colour fundus photo     DNIRA     Segmentation of large drusen & drusenoid RPEDs
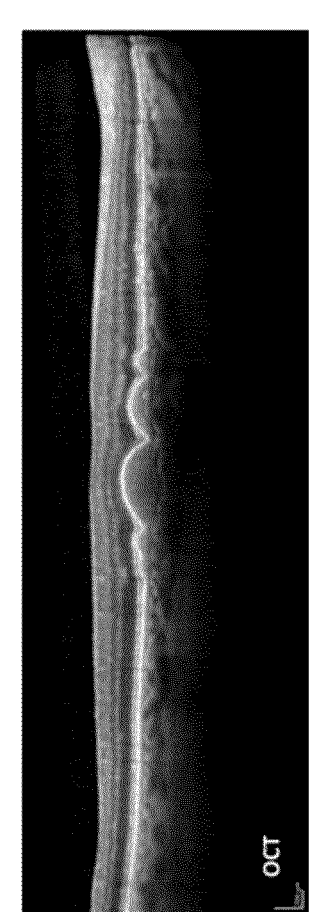
OCT
FIG. 65

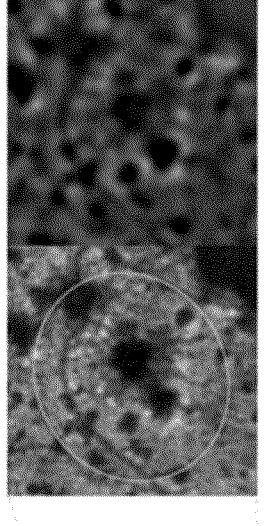
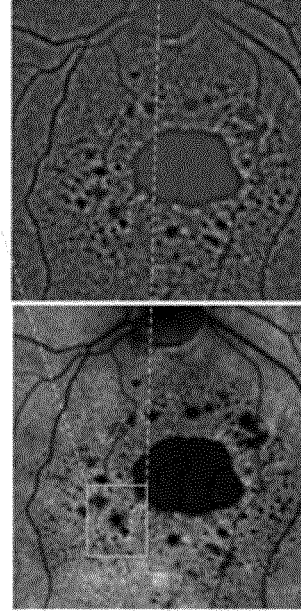
FIG. 73

DETECTION, PREDICTION, AND CLASSIFICATION FOR OCULAR DISEASE

FIELD

This generally relates to computer systems for ocular imaging and disease evaluation.

BACKGROUND

Because ocular biopsy and the evaluation of systemic (e.g., non-ocular) samples such as blood or urine are not part of routine eye care, ophthalmologists and vision specialists rely on in vivo imaging for the diagnosis, classification and stratification of disease, patient management, and clinical trial design.

However, for many potentially blinding eye diseases, it is presently not possible to adequately characterize disease features or complex phenotypes using image-based bio-markers. As such, it is often not possible to adequately diagnose, stage, grade, prognosticate, monitor or predict response to treatments or interventions, or to predict safety of those treatments or interventions. New image-based, computer-based analytic tools offer such opportunities.

By way of non-limiting example, it is presently not possible to readily identify patients at imminent risk of progressing from early to late blinding Age Related Macular Degeneration (AMD) so studies aimed to reduce the onset of geographic atrophy (GA) or choroidal neovascularization (CNV) (e.g., to progress from early to late disease) are not feasible. Further, because central visual acuity is not a suitable endpoint for studies of dry AMD, Phase III clinical trial design is limited to the enrollment of patients with pre-existent patches of geographic atrophy (GA), typically of a defined size range, and prospectively measuring and comparing the rates of geographic atrophy expansion in study eyes and control eyes. Such endpoints address disease only after the late complications develop. Similarly by way of non-limiting example, it is presently not possible to readily predict patients with pre-existent GA who are likely to expand quickly versus those who will expand showly.

SUMMARY

There is a clear unmet need to develop better methods to classify patients with blinding eye diseases using image-based biomarkers, both qualitatively (e.g. describing new phenotypes) and quantitatively (measuring for example, the extent, quantity, en face 2-dimensional (2D) area, cross-sectional 2D area or 3-dimensional (3D) volume of disease features and the dynamic change in these features over time). There is also a clear unmet need to develop methods to predict future changes in disease (e.g. progression for early to late, expansion of pre-existent GA) using image-based biomarkers, and improved classification schemes (phenotypes). Further, there is a clear unmet met to provide functional testing to evaluate the impact of disease and disease treatment on patient outcomes. Unfortunately, most imaging is structural, while most functional tests are both time-consuming and unreliable owing to variable levels of effort and cognitive capacity of the individual being tested. There is also clearly an unmet need to provide a functional imaging method that relies on normal tissue physiology for the acquisition of the image. Such a functional imaging method may permit better biomarkers for clinical trial enrollment, outcome measure, and for the evaluation of patient performance in response to such treatments in the clinical course of care.

Disclosed herein are computing systems for storage and analysis of a plurality of ocular images. In some embodiments, the computing system can comprise a computer processor. In some embodiments, the computing system can comprise a communications interface configured to import the plurality of ocular images, which plurality of ocular images corresponds to a plurality of different imaging modalities. In some embodiments, the computing system can comprise a database configured to store the plurality of ocular images. In some embodiments, the computing system can comprise a computer memory comprising a computer program. In some embodiments, the computer program can be executable by a computer processor to perform one or more of: (i) controlling the communications interface to import the plurality of ocular images, (ii) processing the plurality of ocular images, and (iii) controlling the database to store the plurality of ocular images. In some embodiments, the plurality of different imaging modalities can comprise delayed near-infrared analysis (DNIRA). In some embodiments, the plurality of different imaging modalities can comprise one or more of, by way of non-limiting example: infra-red reflectance (IR), infra-red autofluorescence (IR-AF), near-infra-red autofluorescence (NIR-AF), confocal scanning laser ophthalmoscopy (cSLO), fundus autofluorescence (FAF), color fundus photography (CFP), optical coherence tomography (OCT), OCT-angiography (OCT-A), fluorescence life-time imaging ophthalmology or fluorescence lifetime imaging (FLI), and multispectral detection, and polarized fluorescence imaging.

In some embodiments, the plurality of different imaging modalities can comprise by way of non-limiting example, those able to detect ocular manifestations of central nervous system (CNS) or brain diseases, for the ocular detection of amyloid. In some embodiments, the plurality of different imaging modalities can comprise a functional modality. In some embodiments, the functional imaging modality can comprise, by way of non-limiting example, microperimetry, visual field testing, electroretinography (ERG), dark adaptometry (DA), or low luminance visual acuity testing. In some embodiments, the plurality of ocular images can comprise a plurality of different file formats. In some embodiments, the database can comprise a local storage unit. In some embodiments, the database can comprise an external storage unit communicatively coupled to the computer processor over a computer network. In some embodiments, the plurality of ocular images can be acquired from a subject during a single clinical visit. In some embodiments, the plurality of ocular images can be acquired from a subject during a plurality of clinical visits. In some embodiments, the plurality of ocular images can be acquired from a plurality of subjects. In some embodiments, the processing can comprise generating image metadata for each of the plurality of ocular images. In some embodiments, the image metadata can comprise a time stamp and a tag for future reference. In some embodiments, the processing can comprise generating composite images from the plurality of ocular images. In some embodiments, the processing can comprise generating pseudo-composite images from the plurality of ocular images. In some embodiments, the computer program can comprise a graphical user interface (GUI) configured to allow user selection of a plurality of analytical modules. In some embodiments, the plurality of analytical modules can perform image analysis on the plurality of ocular images. In some embodiments, the plurality of analytical modules can control the database to store the plurality of ocular images. In some embodiments, the plurality of analytical modules can comprise a preprocessing module configured to normalize and register the plurality of ocular images, thereby generating a plurality of preprocessed ocular images. In some embodiments, the plurality of analytical modules can comprise a segmentation module configured to perform segmentation analysis of the plurality of preprocessed ocular images. In some embodiments, the segmentation analysis can be based on one or more features selected from the group consisting of, by way of non-limiting example: circularity, granularity, area, location relative to fovea, location relative to optic nerve head, location relative to periphery, number, clustering, thickness, degree of hyper-fluorescence or hypofluorescence, degree of hypo-reflectance or hypo-reflectance, softness or hardness of edges, confluence between or joining of individual features, and presence or absence of known features in other modalities. In some embodiments, the known features in other modalities can comprise, by way of non-limiting example, features selected from the group consisting of: blood or blood vessels, fluid, small hard drusen, medium drusen, large drusen, confluent drusen, serous, drusenoid or hemorrhagic RPE detachments, regions of geographic atrophy, active or quiescent choroidal neovascularization, nascent geographic atrophy, geographic atrophy, collapsed pigment epithelial detachment, basal laminar deposits, basal linear deposits, subretinal hyper-reflective material, hyper-reflective material, hypo-fluorescent FAF, hyper-fluorescent FAF, hypo-reflective IR or hyper-reflective IR-AF, hypo-fluorescent or hyper-fluorescent NIR-AF, and scarring. In some embodiments, the segmentation analysis can be mapped and/or masked on ocular images of a subject acquired at subsequent clinical visits. In some embodiments, the segmentation analysis can be used to quantify changes in size in ocular images of a subject acquired at subsequent clinical visits. In some embodiments, the segmentation analysis can comprise storing the segmented ocular images in the database. In some embodiments, the segmentation analysis can comprise displaying the segmented ocular images. In some embodiments, the plurality of analytical modules can comprise a delta module configured to perform a delta analysis of the plurality of preprocessed ocular images. In some embodiments, the delta analysis can comprise determining changes between preprocessed ocular images acquired from a single subject during different clinical visits. In some embodiments, the delta analysis can comprise determining changes between preprocessed ocular images acquired from a single subject corresponding to a plurality of different imaging modalities. In some embodiments, the delta analysis can comprise generating subtracted ocular images representative of changes between preprocessed ocular images. In some embodiments, the delta analysis can comprise storing the subtracted ocular images in the database. In some embodiments, the delta analysis can comprise displaying the subtracted ocular images. In some embodiments, the subtracted ocular images can be displayed as an overlay on preprocessed ocular images acquired at earlier clinical visits. In some embodiments, the plurality of analytical modules can comprise a broad image analytics module configured to perform a broad image analysis of the plurality of preprocessed ocular images, and the plurality of ocular images can be acquired from a plurality of subjects. In some embodiments, the broad image analysis can comprise aggregating quantitative features extracted from the plurality of preprocessed ocular images. In some embodiments, the aggregated quantitative features can be used to identify and quantify a burden of a degenerative eye disease. In some embodiments, the aggregated quantitative features can be used to identify, characterize, treat or prevent the onset of reversible or irreversible eye tissue loss caused by an eye disease. In some embodiments, the prevention can comprise performing an ocular or systemic (non-ocular) administration of one or more of: a delivery of gene therapy, a cell-based therapy, a laser-based therapy, and a pharmacological or biological therapy. In some embodiments, the aggregated quantitative features can be processed by a cognitive technology configured to perform one or more of: (i) cognitive analysis of phenotyping, genotyping, and/or epigenetics, (ii) biomarker identification, (iii) estimating a probability of an eye disease, (iv) estimating a probability of effectiveness of a treatment for an eye disease, (v) estimating a probability for recommending a treatment for an eye disease, and (vi) estimating a probability for recommending a clinical trial enrollment, (vii) estimating the likelihood of responding to a treatment for an eye disease, (viii) estimating the safety of a treatment of an eye disease.

In some embodiments, the plurality of analytical modules can comprise an analysis of unstructured data, configured to perform analysis of the plurality of ocular images. In some embodiments, the analysis of unstructured data, or non-segmentable data, can be based on selected and unselected features. These may include, by way of non-limiting example: circularity, granularity, area, location relative to fovea, location relative to optic nerve head, location relative to periphery, number, clustering, thickness, degree of hyper-fluorescence or hypofluorescence, degree of hypo-reflectance or hypo-reflectance, softness or hardness of edges, confluence between or joining of individual features, complex en face patterns, arrays, distributions, and the presence or absence of known features in other modalities. Methods may include pattern recognition, signal processing, statistical analysis, deep learning, cognitive computing, convolutional neural network (CNN) and artificial intelligence. In some embodiments, the computational image analysis is semi-automated, fully automated, supervised or unsupervised. In some embodiment it may with known features in other modalities can comprise, by way of non-limiting example, features selected from the group consisting of: blood or blood vessels, fluid, small hard drusen, medium drusen, large drusen, confluent drusen, serous, drusenoid or hemorrhagic RPE detachments, regions of geographic atrophy, active or quiescent choroidal neovascularization, nascent geographic atrophy, geographic atrophy, collapsed pigment epithelial detachment, basal laminar deposits, basal linear deposits, subretinal hyper-reflective material, hyper-reflective material, hypo-fluorescent FAF, hyper-fluorescent FAF, hypo-reflective IR or hyper-reflective IR-AF, hypo-fluorescent or hyper-fluorescent NIR-AF, and scarring. In some embodiments, the segmentation analysis can be mapped and/or masked on ocular images of a subject acquired at subsequent clinical visits. In some embodiments, the segmentation analysis can be used to quantify changes in size in ocular images of a subject acquired at subsequent clinical visits. In some embodiments, In some embodiment it may not align with known features in other modalities can comprise, by way of non-limiting example, features selected from the group consisting of: blood or blood vessels, active choroidal neovascularization, non-exudative neovascularization, quiescent neovascularization, fluid, small hard drusen, medium drusen, large drusen, confluent drusen, serous, drusenoid or hemorrhagic RPE detachments, regions of geographic atrophy, nascent geographic atrophy, RORA, geographic atrophy, collapsed pigment epithelial detachment, basal laminar deposits, basal linear deposits, subretinal hyper-reflective material, hyper-reflective material, hypo-fluorescent FAF, hyper-fluorescent FAF, hypo-reflective IR or hyper-reflective IR-AF, hypo-fluorescent or hyper-fluorescent NIR-AF, and scarring. In some embodiments, the segmentation analysis can be mapped and/or masked on ocular images of a subject acquired at subsequent clinical visits. In some embodiments, the segmentation analysis can be used to quantify changes in size of image based features in ocular images of a subject acquired at subsequent clinical visits.

Also disclosed herein are computer-implemented methods for storing and analyzing a plurality of ocular images. In some embodiments, the methods can comprise importing, using a computer processor, a plurality of ocular images corresponding to a plurality of different imaging modalities. In some embodiments, the methods can comprise processing, using the computer processor, the plurality of ocular images. In some embodiments, the methods can comprise storing, using the computer processor, the plurality of ocular images in a database. In some embodiments, the plurality of different imaging modalities can comprise delayed near-infrared analysis (DNIRA). In some embodiments, the plurality of different imaging modalities can comprise, by way of non-limiting example, one or more of: infra-red reflectance (IR), infra-red autofluorescence (IF-AF), near-infra-red autofluorescence (NIR-AF), confocal scanning laser ophthalmoscopy (cSLO), fundus autofluorescence (FAF), color fundus photography (CFP), optical coherence tomography (OCT), and OCT-angiography (OCT-A), fluorescence lifetime imaging (FLI), multispectral detection, and polarized fluorescence imaging. In some embodiments, the plurality of different imaging modalities can comprise, by way of non-limiting example, those able to detect ocular manifestations of central nervous system (CNS) or brain diseases, for the ocular detection of amyloid. In some embodiments, the plurality of different imaging modalities can comprise a functional modality. In some embodiments, the functional modality can comprise, by way of non-limiting example, microperimetry, visual field testing, electroretinography (ERG), or dark adaptometry (DA), or low luminance visual acuity testing. In some embodiments, the plurality of ocular images can comprise a plurality of different file formats. In some embodiments, the database can comprise a local storage unit. In some embodiments, the database can comprise an external storage unit communicatively coupled to the computer processor over a computer network. In some embodiments, the plurality of ocular images can be acquired from a subject during a single clinical visit. In some embodiments, the plurality of ocular images can be acquired from a subject during a plurality of clinical visits. In some embodiments, the plurality of ocular images can be acquired from a plurality of subjects. In some embodiments, the processing can comprise generating image metadata for each of the plurality of ocular images. In some embodiments, the image metadata can comprise a time stamp and a tag for future reference. In some embodiments, the processing can comprise generating composite images from the plurality of ocular images. In some embodiments, the processing can comprise generating pseudo-composite images from the plurality of ocular images. In some embodiments, the methods can further comprise using a graphical user interface (GUI) to select from a plurality of analytical processes. In some embodiments, the analytical processes can perform image analysis on the plurality of ocular images. In some embodiments, the analytical processes can control the database to store the plurality of ocular images. In some embodiments, the plurality of analytical processes can comprise a preprocessing, which preprocessing can comprise normalizing and registering the plurality of ocular images, thereby generating a plurality of preprocessed ocular images. In some embodiments, the plurality of analytical processes can comprise a segmentation analysis of the plurality of preprocessed ocular images. In some embodiments, the segmentation analysis can be based on one or more features selected from the group consisting of, by way of non-limiting example: circularity, granularity, area, location relative to fovea, location relative to optic nerve head, location relative to periphery, number, clustering, thickness, degree of hyperfluorescence or hypofluorescence, degree of hyper-reflectance or hypo-reflectance, softness or hardness of edges, confluence between or joining of individual features, and presence or absence of known features in other modalities. In some embodiments, the known features in other modalities can comprise features selected from the group consisting of: blood or blood vessels, fluid, small hard drusen, medium drusen, large drusen, confluent drusen, serous, drusenoid or hemorrhagic RPE detachments, regions of geographic atrophy, active or quiescent choroidal neovascularization, nascent geographic atrophy, geographic atrophy, collapsed pigment epithelial detachment, basal laminar deposits, basal linear deposits, subretinal hyper-reflective material, hyper-reflective material, hypo-fluorescent FAF or hyper-fluorescent FAF, hypo-reflective IR or hyper-reflective IR, hypo-reflective IR or hyper-reflective NIR, and scarring. In some embodiments, the segmentation analysis can be mapped and/or masked on ocular images of a subject acquired at subsequent clinical visits. In some embodiments, the segmentation analysis can be used to quantify changes in size in ocular images of a subject acquired at subsequent clinical visits. In some embodiments, the segmentation analysis can comprise storing the segmented ocular images in the database. In some embodiments, the segmentation analysis can comprise displaying the segmented ocular images. In some embodiments, the plurality of analytical processes can comprise a delta analysis of the plurality of preprocessed ocular images. In some embodiments, the delta analysis can comprise determining changes between preprocessed ocular images acquired from a single subject during different clinical visits. In some embodiments, the delta analysis can comprise determining changes between preprocessed ocular images acquired from a single subject corresponding to a plurality of different imaging modalities. In some embodiments, the delta analysis can comprise generating subtracted ocular images representative of changes between preprocessed ocular images. In some embodiments, the delta analysis can comprise storing the subtracted ocular images in the database. In some embodiments, the delta analysis can comprise displaying the subtracted ocular images. In some embodiments, the methods can further comprise displaying the subtracted ocular images as an overlay on preprocessed ocular images acquired at earlier clinical visits. In some embodiments, the plurality of analytical processes can comprise a broad image analysis of the plurality of preprocessed ocular images, and the plurality of ocular images can be acquired from a plurality of subjects. In some embodiments, the broad image analysis can comprise aggregating quantitative features extracted from the plurality of preprocessed ocular images. In some embodiments, the methods can further comprise identifying and quantifying burden of a degenerative eye disease using the aggregated quantitative features. In some embodiments, the methods can further comprise preventing the onset of reversible or irreversible eye tissue loss caused by an eye disease using the aggregated quantitative features. In some embodiments, the prevention can comprise performing an ocular or systemic (non-ocular) administration of one or more of: a delivery of gene therapy, a cell-based therapy, and a pharmacological or biological therapy. In some embodiments, the methods can further comprise processing the aggregated quantitative features by a cognitive technology to perform one or more of: (i) cognitive analysis of phenotyping, genotyping, and/or epigenetics, (ii) biomarker identification, (iii) estimating a probability of an eye disease, (iv) estimating a probability of effectiveness of a treatment for an eye disease, (v) estimating a probability for recommending a treatment for an eye disease, and (vi) estimating a probability for recommending a clinical trial enrollment, (vii) estimating the likelihood of responding to a treatment for an eye disease, (viii) estimating the safety of a treatment of an eye disease.

Also disclosed herein are methods of detecting an ocular disease in a subject. In some embodiments, the methods can comprise administering systemically to the subject a fluorescent agent. In some embodiments, the fluorescent agent can be internalized by, or accumulated within, a cell, cell layer or tissue layer from the subject having the ocular disease. In some embodiments, the internalized agent can produce a fluorescent emission within the cell, cell layer or tissue layer, thereby producing an image data. In some embodiments, the methods can comprise analyzing the fluorescent emission using an algorithm. In some embodiments, the algorithm can comprise detecting a pattern of fluorescence from the image data from the subject. In some embodiments, the algorithm can comprise comparing the pattern of fluorescence from the image data from the subject to a pattern of fluorescence from a control subject, or a subject with a differing eye disease. In some embodiments, the algorithm can comprise detecting the ocular disease if the image data from the subject has a greater or lesser degree of fluorescence than the image data from the control subject, or a subject with differing eye disease. In some embodiments, the cell or cell layer can be localized in ocular tissue of the subject. In some embodiments, the cell can be a phagocytic cell. In some embodiments, the cell can be an immune cell or antigen presenting cell, retinal pigment epithelial cell, or photoreceptor. In some embodiments, the cell can be a macrophage. In some embodiments, the cells can be a resident or circulating macrophage. The macrophage can be an inflammatory macrophage, perivascular macrophage, parenchymal macrophage, microglial cell, dendritic cell, or other antigen-presenting cell. In some embodiments, the internalized agent can produce a fluorescent emission at least about 2 hours, 6 hours, 12 hours or 24 hours after the administering. In some embodiments, the internalized agent can produce a fluorescent emission less than about 7 days or 14 days after the administering. In some embodiments, the pattern of fluorescence can comprise hyperfluorescence. In some embodiments, the pattern of fluorescence can comprise hypofluorescence. In some embodiments, the fluorescent agent can be a near-infrared dye. In some embodiments, the near-infrared dye can be indocyanine green. In some embodiments, the administering can be ocular, intraocular, intravitreal, suprachoroidal, penocular, sub-tenons, intravenous, intraarterial, transdermal, oral, intranasal, intramuscular, subcutaneous, sublingual, buccal, or suppository. In some embodiments, the ocular disease can be an ocular disorder selected from the group consisting of dry age-related macular degeneration (AMD), wet AMD, reticular pseudodrusen, late onset retinal degeneration, and any combination thereof. In some embodiments, the ocular disease can be any affecting the retinal pigment epithelium (RPE), photoreceptors, macrophages and cells of the immune system. In some embodiments, the ocular disease can be central serous retinopathy (CSR), adult vitelliform disease, uveitis, both primary and secondary to systemic disease (e.g. by way of non-limiting example, sarcoid, rheumatoid disease, the arthritidities, etc.), the white dot syndromes (to include MEWDS (multiple evanescent white dot syndrome), serpiginous choroidopathy, AMPPE (acute multifocal posterior placoid epitheliopathy), POHS (presumed ocular histoplasmosis), or Serpiginous Chorioretinopathy. In some embodiments, the disease can be a maculopathy or cone dystrophy such as, by way or non-limiting example, Stargardt disease. In some embodiments, the disease can be an inherited degenerative disease such as Retinitis Pigmentosa (RP). In some embodiments, the ocular disease can be an ocular melanoma, an ocular tumor or an infiltrating tumor. In some embodiments, the algorithm can further comprise segmenting the image data based on one or more features to form a segmented image data. In some embodiments, the one or more features can be selected from, by way of non-limiting example, circularity, granularity, area, location relative to fovea, location relative to optic nerve head, location relative to periphery, number, clustering, thickness, degree of hyperfluorescence or hypofluorescence, degree of hyper-reflectance or hypo-reflectance, softness or hardness of edges, confluence between or joining of individual features, complex 2-dimensional (2D) pattern, and presence or absence of known features in other modalities. In some embodiments, the one or more features can comprise a hyperfluorescent dot. In some embodiments, the methods can further comprise comparing the segmented image data to a second segmented image data generated at a subsequent clinical visit. In some embodiments, the methods can further comprise comparing the segmented image data to a second segmented image data generated at a prior clinical visit. In some embodiments, the methods can further comprise comparing the segmented image data to a patient risk factor, an additional imaging modality, a functional modality, or an epigenetic factor. In some embodiments, the methods can further comprise comparing the segmented image data to a patient risk factor. The patient risk factor can be selected from, by way of non-limiting example, drusen, pseudodrusen, RPE detachments, pigment, hyper-reflective material, basal laminar deposits, basal linear deposits, hypofluorescent FAF, hyper-fluorescent FAF, geographic atrophy, choroidal neovascularization, genetic single nucleotide polymorphisms (SNPs), copy number variants (CNV), genome wide associative studies (GWAS), exome sequencing, full genome sequencing, genomics, proteomics, transcriptomics, ocular biomarkers, systemic (blood, urine, tissue) biomarkers, environmental risk factors, or any combination thereof. In some embodiments, the methods can further comprise comparing the segmented image data to an additional (vs, "a second") imaging modality. In some embodiments, the comparing the segmented image data can comprise a delta analysis of the segmented image data. In some embodiments, the delta analysis can comprise determining changes between the segmented image data acquired from the subject during different clinical visits. In some embodiments, the delta analysis can comprise determining changes between the segmented image data acquired from the subject corresponding and a plurality of different imaging modalities. In some embodiments, the delta analysis can comprise generating a subtracted ocular image representative of changes between segmented image data. In some embodiments, the second imaging modality can be selected, by way of non-limiting example, from infra-red reflectance (IR), infra-red autofluorescence (IR-AF), near-infra-red autofluorescence (NIR-AF), confocal scanning laser ophthalmoscopy (cSLO), fundus autofluorescence (FAF), color fundus photography (CFP), optical coherence tomography (OCT), and OCT-angiography (OCT-A). In some embodiments, the methods can further comprise comparing the segmented image data to a functional modality. The functional modality can be selected, by way of non-limiting example, from microperimetry, electroretinography (ERG), visual field testing, dark adaptometry (DA), and low luminance visual acuity testing. In some embodiments, the methods can further comprise comparing the segmented image data to an epigenetic factor. The epigenetic factor can be selected from smoking, age, body mass index, obesity index, dietary intake, dietary vitamin consumption, lipid panel, cholesterol levels, blood pressure, family history, concurrent medications, or a pre-existing condition. In some embodiments, the algorithm can further comprise a process for transforming image data for display. In some embodiments, the methods can further comprise preprocessing the image data by a registration and a normalization of the image data. In some embodiments, the methods can further comprise post-processing the image data. In some embodiments, post processing the data can comprise transforming the image data to generate an output image data. In some embodiments, post processing the data can comprise displaying changes in segments of the image data over time. In some embodiments, post processing the data can comprise generating a graphical user interface of visual elements representative of the image output data. In some embodiments, the algorithm further comprises disease diagnosis, risk stratification, monitoring, prognosis, or a selection and prediction of a treatment and its response. In some embodiments, the imaging method can be used as a surrogate biomarker for diagnosis, prognosis, disease progression, treatment selection and prediction of a treatment response or clinical trial design, or any combination thereof. In some embodiments, the imaging method can be used as a companion diagnostic for detection and treatment of the ocular disease or clinical trial enrollment or exclusion. In some embodiments, the methods can further comprise administering a treatment to the subject. In some embodiments, the treatment can comprise administering a drug or pharmaceutically acceptable salt thereof to the subject. In some embodiments, the administering can be ocular, intraocular, pen-ocular, intravitreal, suprachoroidal, intravenous, intraarterial, transdermal, oral, intranasal, intramuscular, subcutaneous, sublingual, buccal, or suppository. In some embodiments, the methods can further comprise communicating a result via a communication medium.

According to an aspect, there is provided computer system comprising: a processor; a memory in communication with the processor, the memory storing instructions that, when executed by the processor cause the processor to: at a training phase, receive training data corresponding to a plurality of ocular images; perform feature extraction and feature selection to generate features based on the training data to build a pattern recognition model; at a classification phase, receive a plurality of ocular images corresponding to a plurality of imaging modalities; classify features of the plurality of ocular images using the pattern recognition model.

In some embodiments, the pattern recognition model is at least one of a convolutional neural network, machine learning, decision trees, logistic regression, principal components analysis, naive Bayes model, support vector machine model, and nearest neighbor model.

In some embodiments, the feature extraction generates a masked image of defined shapes.

In some embodiments, the feature selection is based on at least one of focality of the defined shapes, a number of focal points per unit area of the defined shapes, and a square root of an area of the defined shapes.

In some embodiments, the features are defined by areas of black or hypofluorescence.

In some embodiments, the features are defined by areas of hyperfluorescence.

In some embodiments, the plurality of ocular images of the training data correspond to a plurality of imaging modalities.

In some embodiments, the training phase further comprises building a pattern recognition model for each of the plurality of imaging modalities.

In some embodiments, the plurality of ocular images comprises a cross-section image.

In some embodiments, the plurality of ocular images comprises an en face image.

In some embodiments, the training phase further comprises registering the plurality of ocular images to a common coordinate system.

In some embodiments, the training phase further comprises cross-modal fusion of the plurality of ocular images to a common coordinate system.

In some embodiments, the plurality of imaging modalities comprises at least one of delayed near-infrared analysis (DNIRA), infra-red reflectance (IR), confocal scanning laser ophthalmoscopy (cSLO), fundus autofluorescence (FAF), color fundus photography (CFP), optical coherence tomography (OCT), OCT-angiography, fluorescence lifetime imaging (FLI).

In some embodiments, the memory stores further instructions that, when executed by the processor cause the processor to: generate a cross-section segmentation map corresponding to an en face region of an eye, each segment of the cross-section segmentation map corresponding to a cross-section image at that region of the eye; classifying each segment of the cross-section segmentation map as a phenotype of one of normal, drusen, retinal pigment epithelium detachments (RPEDs), pseudodrusen geographic atrophy, macular atrophy, or neovascularization based at least in part on classification of the cross-section image corresponding to that segment using the pattern recognition model.

In some embodiments, the plurality of ocular images comprises multiple cross-section images corresponding to multiple time points and the memory stores further instructions that, when executed by the processor cause the processor to: generate, for each of the multiple time points, a cross-section segmentation map corresponding to an en face region of an eye, each segment of the cross-section segmentation map corresponding to a cross-section image at that region of the eye; classify each segment of each cross-section segmentation map as a phenotype of tissue state of one of normal, drusen, retinal pigment epithelium detachments (RPEDs), pseudodrusen geographic atrophy, macular atrophy, or neovascularization, based at least in part on classification of the cross-section image corresponding to that segment using the pattern recognition model; and generate a time series data model based on the cross-section segmentation map at each of the multiple time points.

In some embodiments, the time series data model is based at least in part on identified changes in the cross-section segmentation maps over time.

In some embodiments, the time series data model visualizes disease progression.

In some embodiments, the time series data model is based at least in part on elapsed time between the multiple time points.

In some embodiments, the features selected comprise phenotypes of a user associated with the plurality of ocular images.

In some embodiments, the memory stores further instructions that, when executed by the processor cause the processor to: correlate the features with stage or grade variants of binding eye disease including Age Related Macular Degeneration (AMD), monogenic eye disease, inherited eye disease and inflammatory eye disease.

In some embodiments, the memory stores further instructions that, when executed by the processor cause the processor to: correlate the features with stage or grade variants of central nervous system (brain) disease, such as dementia and Alzheimer's disease.

According to another aspect, there is provided a computer-implemented method for detecting a phenotype, comprising: receiving a plurality of ocular images corresponding to a plurality of imaging modalities; registering the plurality of ocular images to a common coordinate system; classifying features of each of the plurality of ocular images using a pattern recognition model; identifying features of the image as one or more phenotypes.

In some embodiments, the pattern recognition model is a convolutional neural network built based on training data corresponding to a plurality of ocular images and feature extraction and feature selection is performed to generate features from the training data.

In some embodiments, the feature extraction generates a greyscale image of defined shapes.

In some embodiments, the defined shapes include at least one of leopard spots, loose weave, grey smudge, and fingerling potatoes.

In some embodiments, the computer-implemented method further comprises correlating one or more of the defined shapes with the presence of phagocytic immune cells such as macrophages.

In some embodiments, the computer-implemented method further comprises generating one or more descriptors of characteristics of the identified phenotype, such as location, size, quantity and colour.

According to a further aspect, there is provided a computer-implemented method for predicting tissue loss, comprising: receiving a plurality of ocular images corresponding to a plurality of imaging modalities; registering the plurality of ocular images to a common coordinate system; classifying features of each of the plurality of ocular images using a pattern recognition model; predicting tissue loss based at least in part on the features.

In some embodiments, the plurality of imaging modalities comprises at least one of delayed near-infrared analysis (DNIRA), infra-red reflectance (IR), confocal scanning laser ophthalmoscopy (cSLO), fundus autofluorescence (FAF), color fundus photography (CFP), optical coherence tomography (OCT), OCT-angiography and fluorescence lifetime imaging (FLI).

In some embodiments, the plurality of imaging modalities includes cross-section images and en face images.

In some embodiments, the pattern recognition model is a convolutional neural network built based on training data corresponding to a plurality of ocular images and feature extraction and feature selection performed to generate features from the training data.

In some embodiments, the feature extraction generates a masked image of defined shapes.

In some embodiments, the feature selection comprises one or more of an area of geographical atrophy, a square root of area of geographical atrophy, focality of geographical atrophy, focality index of geographical atrophy, and rate of geographical atrophy expansion.

In some embodiments, the predicting tissue loss is based on time series forecasting to predict tissue loss based on a time series data model.

In some embodiments, the time series data model is generated based on multiple cross-section segmentation maps generated for each of multiple time points and corresponding cross-section images, each of the cross-section segmentation maps corresponding to an en face region of an eye, and each segment of the cross-section segmentation map corresponding to a cross-section image at that region of the eye classified as a phenotype of one of pseudodrusen, normal, drusen, or geographical atrophy, based at least in part on classification of the cross-section image corresponding to that segment using a convolutional neural network.

In some embodiments, the features selected comprise phenotypes of a user associated with the plurality of ocular images.

In some embodiments, the computer-implemented method further comprises identifying the phenotypes as risk factors by correlating the phenotypes with a rate of tissue loss over time.

In some embodiments, the predicting tissue loss is based at least in part on non-image based biomarker data.

In some embodiments, the non-image based biomarker data comprises characteristics of a user associated with the plurality of ocular images, the characteristics including at least one of age, genetics, sex, smoker, diet, health parameters, concurrent illness and concurrent medications and therapies.

In some embodiments, the predicting tissue loss comprises predicting a rate of tissue loss.

In some embodiments, the predicting tissue loss comprises predicting whether tissue loss has previously occurred.

In some embodiments, the predicting tissue loss comprises predicting whether tissue loss will occur in the future.

In some embodiments, the predicting tissue loss comprises predicting regions of disease progression and rate of disease progress.

In some embodiments, the predicting tissue loss comprises predicting progression from early to late dry Age Related Macular Degeneration (AMD).

In some embodiments, the computer-implemented method further comprises predicting a response of a patient to an intervention based at least in part on the features.

According to another aspect, there is provided a computer-implemented method for predicting neovascularization, comprising: receiving a plurality of ocular images corresponding to a plurality of imaging modalities; registering the plurality of ocular images to a common coordinate system; classifying features of each of the plurality of ocular images using a pattern recognition model; predicting neovascularization based at least in part on the features.

In some embodiments, the plurality of imaging modalities comprises at least one of delayed near-infrared analysis (DNIRA), infra-red reflectance (IR), confocal scanning laser ophthalmoscopy (cSLO), fundus autofluorescence (FAF), color fundus photography (CFP), optical coherence tomography (OCT), OCT-angiography and fluorescence lifetime imaging (FLI).

In some embodiments, the plurality of imaging modalities including cross-section images and en face images.

In some embodiments, the pattern recognition model is a convolutional neural network built based on training data corresponding to a plurality of ocular images and feature extraction and feature selection performed to generate features from the training data.

In some embodiments, the feature extraction generates a masked image of defined shapes.

In some embodiments, the feature selection comprises one or more of an are of intra-retinal, subretinal or sub-retinal pigment epithelium fluid using OCT, or dye leakage using angiography.

In some embodiments, the predicting neovascularization is based on time series forecasting to predict tissue loss based on a time series data model.

In some embodiments, the time series data model is generated based on multiple cross-section segmentation maps generated for each of multiple time points and corresponding cross-section images, each of the cross-section segmentation maps corresponding to an en face region of an eye, and each segment of the cross-section segmentation map corresponding to a cross-section image at that region of the eye classified as a phenotype of one of normal, drusen, retinal pigment epithelium detachment, geographic atrophy, macular atrophy or neovascularization, based at least in part on classification of the cross-section image corresponding to that segment using a convolutional neural network.

In some embodiments, the features selected comprise phenotypes of a user associated with the plurality of ocular images.

In some embodiments, the computer-implemented method further comprises identifying the phenotypes as risk factors by correlating the phenotypes with a rate of tissue loss over time.

In some embodiments, the predicting neovascularization is based at least in part on non-image based biomarker data.

In some embodiments, the non-image based biomarker data comprises characteristics of a user associated with the plurality of ocular images, the characteristics including at least one of age, genetics, sex, smoker, diet, health parameters, concurrent illness and concurrent medications or therapies.

In some embodiments, the predicting neovascularization comprises predicting a onset of neovascularizaton.

In some embodiments, the predicting neovascularization comprises predicting whether neovascularization has previously occurred.

In some embodiments, the predicting neovascularization comprises predicting whether neovascularization will occur in the future.

In some embodiments, the predicting neovascularization comprises predicting regions of disease progression and rate of disease progress.

In some embodiments, the predicting neovascularization comprises predicting progression from early to late dry Age Related Macular Degeneration (AMD).

In some embodiments, the computer-implemented method further comprises predicting a response of a patient to an intervention based at least in part on the features.

In accordance with another aspect, there is provided a compound, such as a macrophage modulator, in particular 2-((1-Benzyl-1H-indazol-3-yl)methoxy)-2-methylpro-panoic acid and its derivatives and formulations, for use in treating Age Related Macular Degeneration selected using DNIRA-based features or phenotypes, made distinguishable using a DNIRA based classifier or a DNIRA-based PRE-DICTOR as described herein.

In accordance with another aspect, there is provided a compound, such as a macrophage modulator, in particular 2-((1-Benzyl-1H-indazol-3-yl)methoxy)-2-methylpro-panoic acid and its derivatives and formulations, for use in treating Age Related Macular Degeneration, comprising assaying the eye with DNIRA-based features or phenotypes, made distinguishable using a DNIRA based classifier or a DNIRA-based PREDICTOR as described herein, and administering a therapeutically effective amount of a mac-rophage modulator to the patient if a DNIRA-based feature or phenotype is present.

BRIEF DESCRIPTION OF THE DRAWINGS

Novel features of exemplary embodiments are set forth with particularity in the appended claims. A better under-standing of the features and advantages will be obtained by reference to the following detailed description that sets forth illustrative embodiments, in which the principles of the disclosed systems and methods are utilized, and the accom-panying drawings of which:

FIG. 14 depicts a representative DNIRA image of a patient with central GA observed on FAF (left). The DNIRA image (right) shows greater number of hypofluorescent signals, a greater total area of hypofluorescence, and greater amount of perimeter/border of hypofluroescence. The difference between these two images represents the "delta" portion of the signal.

FIGS. 19A-19J depicts the analysis of Tumor Associated Macrophages (TAMs) using DNIRA. DNIRA images were assembled into composites and correlated to other modalities including fundus imaging, FAF, and OCT. Regions of interest were selected and analyzed using imaging and quantification techniques, compared in patients with melanomas, indeterminate lesions or benign nevi. ANOVA and Bonferroni multiple comparisons analysis of regional dot densities were analyzed across groups.

FIGS. 27A and 27B depict representative examples of DNIRA Features to Distinguish Diseases of Similar Clinical Appearance to Assist with Diagnostic Accuracy (Diagnostic Biomarker).

FIGS. 28A and 28B depict representative examples of DNIRA Features Identify Inherited Monogenic Disorders and Disease that May Not Yet Be Diagnosed (NYD).

FIG. 30 depicts a representative example of DNIRA Feature to Monitor Disease Progression, Comparing Within and Across Modalities and Other Imaging Biomarkers Over Time (Monitoring and Prognostic Biomarker).

FIG. 34A-34D depict representative examples of DNIRA to Detect Multiple Types of Hyperfluorescent Dot Signals (Predictive Biomarkers).

FIG. 37 depicts representative example of DNIRA to detect Two Populations of Bright Hyperfluoerscent Dots in Diffuse-Tricking AMD (Diagnostic, Prognostic Biomarkers).

FIG. 45 depicts a representative example of a DNIRA signal in black (arrow) where the tumour cells are blocking the flow of dye-labeled blood in the choroid.

FIG. 53 depicts image registration, exemplary of an embodiment.

FIG. 57 depicts a representative example of en face OCT using IR image reference to determine position of cross-section.

FIG. 59 depicts OCT scans performed in the near IR channel, exemplary of an embodiment.

FIG. 65 depicts a representative example of a graphical representation of using DNIRA to detect and quantify known risk factors for disease progression.

FIG. 73 depicts macrophages as detected by an embodiment of a detector.

DETAILED DESCRIPTION

Overview

Figure 1:
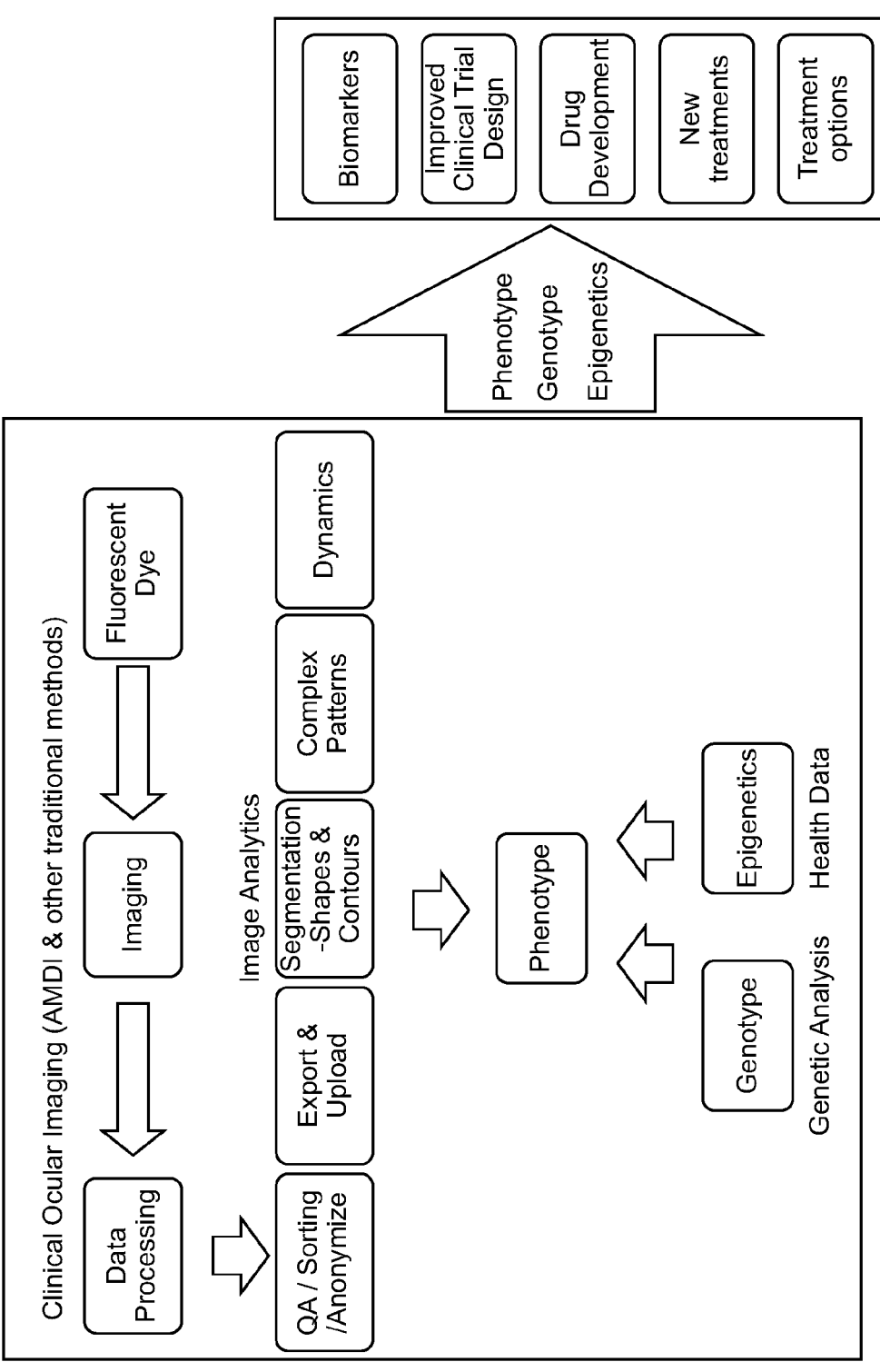
FIG. 1 is a schematic diagram of a system for processing, storage and retrieval of ocular images. Image acquisition is followed by cloud-based image analysis to generate a com-plex subject phenotype. Together with genetic and epigen-etic data, this subject phenotype may feed the downstream steps of biomarker development, improved clinical trial design, drug development, new treatments and ultimately, the selection of specific treatments for individualized medi-cine from a menu of options. (QA=quality assurance).

Ocular diseases or disorders, which may reduce or eliminate one's sight, among other effects, are a major medical concern. For instance, age-related macular degeneration (AMD) is a leading cause of ocular dysfunction, including irreversible blindness, especially in subjects over 50 years old. All subjects start with early non-exudative, so-called, "dry" AMD. At the early stage, dry AMD is characterized by deposits known as drusen, or in some cases pseudodrusen, that can be seen clinically in the posterior pole of the eye known as the macula. Advanced AMD can take two forms— late "wet" or late "dry". The primary treatment option for advanced "wet" AMD is regular intra-ocular injections of antiangiogenic drugs. These injections are given after pathological new blood vessels grow beneath or into the central retina, where they leak, bleed or cause tissue damage and scarring. By contrast, there are no treatments for early or late dry AMD. Late dry AMD is characterized by death or atrophy of the photoreceptors and their associated "nurse" cell layer, the retinal pigment epithelium (RPE). Patches of irreversible RPE and photoreceptor tissue loss are known as "geographic atrophy" (GA). GA can occur centrally, in the fovea, robbing subjects of their central vision early in disease (measured as a decrease in visual acuity), or can accumulate extra- or juxta-foveally, leaving central visual acuity intact in the face of significant disease. These non-foveal scotoma, or blind spots, cause significant disability particularly with respect to reading speed, tracking and text and detecting or identifying non-central objects. This means that visual acuity (e.g., reading the eye chart) is not a suitable endpoint for clinical trial, nor a suitable measure for clinical trial enrichment.

Because ocular biopsy and the evaluation of systemic (e.g., non-ocular) samples such as blood or urine are not part of routine eye care, ophthalmologists and vision specialists rely on in vivo imaging for the diagnosis, classification and stratification of disease, patient management, and clinical trial design. Fundus Autofluorescence (FAF) is a standard current method imaging dry AMD, and relies on the non-invasive detection of endogenous fluorophores such as lipo-fuscin pigments within the RPE monolayer that, when stimulated with fluorescent light in the blue spectrum, pro-vide a diffuse homogenous ground-glass glow in the normal eye. In regions where RPE is lost (e.g., in regions of GA) so too is the autofluorescent FAF signal. By virtue of their profoundly hypofluorescent, often black signal with sharp borders, the 2-dimensional (2D) areas of GA can be readily quantified. These black signals contrast sharply against the remainder of the image which exhibits variable shades of grey (grey-scale) and therefore cannot be reliably measured, both between patient visits and between patients. Newer methods of Optical Coherence Tomography (OCT), when reconstructed to form a slab, may be viewed en face to demonstrate regions of GA. However, at present, no imaging method other than FAF provides readily quantifiable regions of profoundly hypofluorescent, or black, signal to charac-terize AMD or other ocular diseases or disorders.

It follows, in the absence of other suitable measures of disease, that the quantification of GA and its rate of expan-sion over time may be used to drive clinical trial design, serving for example as inclusion criterion or endpoint, respectively. However, the detection of GA by FAF identi-fies areas of RPE and photoreceptor loss after tissue already missing, and thus when it cannot be rescued or recovered. It does not provide a measure of tissue at risk for future loss, provide an indication of tissue suitable for therapeutic protection, identify who may be at imminent risk of devel-oping GA (progressing from early to late dry AMD), nor does it provide insight into disease pathogenesis and sub-types of disease. Therefore, there is a paucity of methods to characterize and quantify the features of early and late dry AMD.

Accordingly there is a need for new, or at least alternate, ophthalmic imaging methods for ocular diseases or disor-ders, including AMD. Such methods can be independent of patient fixation (which may be lost with central GA), may not rely on prolonged or intense activity (that often wanes dues to patient fatigue), and may not require significant cognitive ability (which can decline in the elderly, particu-larly amongst patients with neurodegenerative disease). There is also a need for new and alternative imaging techniques and a system for processing, storage and retrieval of ocular images from multiple imaging modalities. Addi-tionally, there is a move for personalized medicine, image-guided medicine, and biomarker discovery, to accelerate/automate drug discovery, and optimize health care and medical solutions for patients. In this way, scarce resources can be better distributed during drug development stages, minimizing variability during clinical trials. To do so, there is an immense need for machine learning, deep learning, artificial intelligence, healthcare analytics and cloud com-puting systems.

Disclosed herein are methods, systems and compositions that can be useful for the diagnosis, treatment, or prevention of an ocular disease or disorder, including the use of in vivo imaging methods, image processing methods, and genera-tion of graphical representations using the output from the image processing, as part of an integrated platform.

Described herein is a novel functional imaging method, Delayed Near-Infrared Analysis (DNIRA) that has generated unprecedented images of the retina (the film of the eye) that include both known and unknown phenotypes of disease. These complex images can be compared against an indi-vidual's genetic makeup (their genotype) and their concur-rent illnesses, medications, and lifestyle history (their epi-genetics). This imaging can be used as a diagnosis tool and to help identify particular subjects that may benefit from certain clinical trials and drug development programs, and ultimately guiding clinical trial design and treatment out-comes. In some aspects, when DNIRA is used specifically for imaging subjects with AMD, it is referred to as AMD Imaging (AMDI). In some aspects, when DNIRA is used to image tumor associated macrophages (TAMs) in ocular melanoma subjects DNIRA is referred to as Tumor Associ-ated Macrophage Imaging (TAMI). However, as the meth-odology has utility in multiple ocular disorders, it can also be generally referred to by its broad, inclusive name, DNIRA.

Accordingly, described herein are methods for detecting an ocular disease or disorder or its late blinding complica-tion(s), comprising administering to a subject in need thereof an effective amount of an agent capable of enhancing optical detection of the RPE, photoreceptors or other com-ponent of the retina or associated tissue including cells of the immune system, based on the presence of endogenous fluorophores, chromophores or chemiluminescent com-pounds, or based on, but not limited to, the physiological uptake, processing, activation or accumulation of exogenous fluorphores, chromophores or chemiluminescent com-pounds that may be provided locally or systemically and differentially handled or metabolized by those tissues.

In some aspects, described herein are methods of detect-ing and imaging the physiological uptake, processing, acti-vation or accumulation of a systemically administered dye, comprising administering to a subject a systemic dye such as indocyanine green (ICG) or its derivatives, and photograph-ing using specialized imaging equipment, its presence in the hours and days thereafter using appropriate excitation and emission filters or optical systems, without further admin-istration of dye.

In some aspects, described herein are systems for pro-cessing the images obtained using such methods to generate graphical representations of output data. In some aspects, described herein are systems that can provide a logical, hardware and software unit for analyzing, quantifying quali-tatively representing the images obtained using such meth-ods. In some aspects, described herein are methods that provide an integrated platform for image acquisition, processing, and output. The platform can store and retrieve imaging data and generate graphical representations of the imaging data. In some aspects, described herein are methods that provide a graphical user interface (GUI) with dynamic graphical representations of imaging data from the images obtained using the methods described herein. In some aspects, described herein are systems provide a centralized or networked image processing platform for processing, storage and retrieval of ocular images from multiple imaging modalities and/or a cloud server.

In various aspects, systems described herein can relate to AMDI (AMD Imaging), which is comprised of the clinical application of delayed near infrared analysis (DNIRA) along with the logical processes, hardware and software units and an integrated platform for its analysis, interpretation, dissemination, application and integration with other imaging and non-imaging modalities used to evaluate subjects with AMD or RPD, other potentially blinding diseases, and other ocular abnormalities where macrophage are present.

In various aspects, systems described herein can relate to TAMI (Tumor Associated Macrophage Imaging), which is comprised of the clinical application of DNIRA along with the logical processes, hardware and software units and an integrated platform for its analysis, interpretation, dissemination, application and integration with other imaging and non-imaging modalities used to evaluate subjects with ocular melanoma, ocular tumors, and other ocular abnormalities where macrophages are present.

Aspects described herein further relate to the use of DNIRA/AMDI/TAMI as entrance inclusion or exclusion criteria, or endpoint analysis for clinical trial design. Some aspects can comprise the development and application of a complementary biomarker for clinical trial design and drug development. Some aspects can comprise the use of DNIRA/AMDI/TAMI as a marker for diagnosis and/or prognosis and/or progression of an ocular disease or disorder (including, without limitation AMD and RPD, Ocular Melanoma, Diabetic Retinopathy, Inherited Retinal Disease, Uveitis, and others).

Also described herein are methods and compositions that can be useful for the diagnosis, treatment, or prevention of an ocular disease or disorder, including the use of in vivo imaging methods, their outputs, their processes, and management, as part of an integrated system for computer assisted analysis and diagnosis (CAAD). The system can use as inputs images of the eye (macula/posterior retina) from various imaging modalities for comparative processing and provide as output graphical representations of a plurality of measures including prognostic and diagnostic scores upon which to base personalized treatments for diseases of the eye. The images may include standard clinical macular images as well as the novel imaging types as described herein.

The system can use as input data images from multiple modalities and user configurations or parameters. The system implements image processing to obtain measurements and other reporting data for the images. The system has one or more processing components to register the images, segment objects of interest from the images, define patterns of segmented objects and/or intensity texture of the images. The information can be aggregated by the system into a feature vector for each subject. The subject's data can be used as input for statistical models to generate diagnostic and prognostic scores which can be either categorical or continuous in nature. The system can rely on expert users to provide training or configuration information for image processing and to the review the outputs from the image processing to provide a feedback loop to check the suitability of the results.

Also described herein are systems for image processing and display comprising: an image acquisition device to capture image data; data storage to store and retrieve the image data; a processor configured with a preprocessing unit, a post-processing unit, and broad analytics unit to transform the image data to generate output image data, the data storage storing the output image data; and a client application to connect to a display device to generate and update a graphical user interface (GUI) of visual elements representative of the image output data. In some aspects, the preprocessing unit can be configured to register and normalize the image data. In some aspects, the preprocessing unit can be configured to register the image data using registration parameters that are dynamically adjusted using a feedback loop of control commands to verify, approve and adjust the registration parameters. In some aspects, the post-processing unit can be configured to segment the image data and feature extract from the segmented image data. In some aspects, the broad analytics unit is configured to comparatively process the image data to generate comparative image data as a portion of the output image data.

In some aspects, a system described herein can have a delta image unit to cross reference and compare segments of the image data over a time period, and across modalities to automatically monitor the image data for changes to features of the segments of the image data. In some aspects, a first segment of the image data at a first time point can be mapped or masked on subsequent segments of the image data at subsequent time points. In some aspects, the system can have a delta image unit to compare a first image segment to a second image segment to generate difference image data, and a client application to generate visual elements of the different image data to visualize a level of change between the image segments.

Also described herein are devices for image processing and display comprising: a data storage to store and retrieve image data; processor configured with a preprocessing unit, a post-processing unit, and broad analytics unit to transform the image data to generate output image data, the data storage storing the output image data; and a client application to connect to a display device to generate and update a graphical user interface of visual elements representative of the image output data. In some aspects, the preprocessing unit is configured to register and normalize the image data. In some aspects, the preprocessing unit can be configured to register using registration parameters that are dynamically adjusted using a feedback loop of control commands to verify, approve and adjust the registration parameters. In some aspects, the post-processing unit can be configured to segment the image data and feature extract from the segmented image data. In some aspects, the broad analytics unit can be configured to comparatively process the image data to generate comparative image data as a portion of the output image data. In some aspects, the device can have a delta image unit to cross reference and compare segments of the image data over a time period and across modalities to automatically monitor the image data for changes to features of the segments of the image data. In some aspects, a first segment of the image data at a first time point can be mapped or masked on subsequent segments of the image data at subsequent time points. In some aspects, the device can have a delta image unit to compare a first image segment to a second image segment to generate difference image data, the client application to generate visual elements of the different image data to visualize a level of change between the image segments.

Also disclosed herein are processes for transforming image data for display comprising: preprocessing image data by registration and normalization of the image data; post-processing image data by, transforming the image data to generate output image data, showing changes in segments of the image data over time; and generating and updating a graphical user interface of visual elements representative of the image output data. In some aspects, a process can comprise comparing features detected using computer algorithms/analytics to subject genetic risk factors and epigenetics.

Various example details are set forth in the accompanying description below. Methods and materials similar or equivalent to those described herein can be used in the practice or testing of various aspects. Illustrative methods and materials are described by way of example. Other features, objects, and advantages will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art.

In some cases, a method described herein can comprise an administration of a fluorescent dye, for example, ICG, an agent long used for evaluation of the ocular (retinal and choroidal) vasculature, that can be detected within phagocytic cells such as RPE and macrophages in the hours, days and weeks after systemic vascular administration with the appropriate optical imaging system without further injection of dye. This method is distinct from autofluorescence that relies on endogenous fluorophores without provision of dye, and distinct from angiography that is used to evaluate the anatomy and patency of the blood vessels, performed during the transit and recirculation phases of dye, and in the minutes or hours immediately thereafter. Such a method, DNIRA, can enhance visualization of the rodent RPE, thereby making patches of GA-like RPE and photoreceptor loss visible, similar to the method of FAF described for subjects with late dry AMD. Accordingly, some aspects can comprise a method for enhancing visualization of the RPE/photoreceptor layer in subjects.

In some cases, a method can comprise visualizing (via generated graphical representations), detecting, quantifying the ability of RPE/retinal cells to internalize/incorporate exogenous dyes as a measure of cellular viability, thus providing for the first time, an image-based measure of cellular activity, metabolism and/or dysfunction. In some aspects, a method can comprise visualizing, detecting, and or quantifying the burden of disease. In some aspects, a method can comprise detecting tissue at risk of imminent loss. In some aspects, a method can comprise identifying subjects suitable for clinical investigation or treatment for the secondary prevention of GA amongst those with early AMD.

In some cases, immune cells, particularly those capable of internalizing/incorporating (through, by non-limiting example, ingestion, or passive influx, membrane incorporation) exogenous dyes, fluorophores, chromophores or chemiluminescent compounds, can be detected in vivo in the eyes of subjects. The data can extend the observations of ImmunoD and Pulsed DNIRA. Thus, in some aspects, a method can comprise visualizing, for the first time, phagocytic immune cells in the human eye, including by way of non-limiting example, microglia, macrophages, monocytes, dendritic cells. In some aspects, a method can comprise co-localization of immune cells with advancing disease, and thus can suggest their role in disease progression. Such disease can include diseases of innate immune dysfunction.

Also disclosed herein are logical algorithms that can distinguish DNIRA from other known imaging methods such as FAF, infra-red, or other enface methods in any wavelength of light, or cross-sectional methods such as optical coherence tomography (OCT).

Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which may depend in part on how the value is measured or determined, e.g., the limitations of the measurement system. For example, "about" can mean plus or minus 10%, per a practice in the art. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

The terms "subject", "patient" or "individual" as used herein can encompass a mammal and a non-mammal. A mammal can be any member of the Mammalian class, including but not limited to a human, a non-human primates such as a chimpanzee, an ape or other monkey species; a farm animal such as cattle, a horse, a sheep, a goat, a swine; a domestic animal such as a rabbit, a dog (or a canine), and a cat (or a feline); a laboratory animal including a rodent, such as a rat, a mouse and a guinea pig, and the like. A non-mammal can include a bird, a fish and the like. In some aspects, a subject can be a mammal. In some aspects, a subject can be a human. In some instances, a human can be an adult. In some instances, a human can be a child. In some instances, a human can be age 0-17 years old. In some instances, a human can be age 18-130 years old. In some instances, a subject can be a male. In some instances, a subject can be a female. In some instances, a subject can be diagnosed with, or can be suspected of having, a condition or disease. In some instances a disease or condition can be cancer. A subject can be a patient. A subject can be an individual. In some instances, a subject, patient or individual can be used interchangeably.

The terms "treat," "treating," "treatment," "ameliorate" or "ameliorating" and other grammatical equivalents as used herein, can include alleviating, or abating a disease or condition symptoms, inhibiting a disease or condition, e.g., arresting the development of a disease or condition, relieving a disease or condition, causing regression of a disease or condition, relieving a condition caused by the disease or condition, or stopping symptoms of a disease or condition. The term "preventing" can mean preventing additional symptoms, ameliorating or preventing the underlying metabolic causes of symptoms, and can include prophylaxis.

The terms "Age-Related Macular Degeneration Imaging" (AMDI) and "Delayed Near InfraRed Analysis" (DNIRA) can be used interchangeably to describe a method of ocular imaging as described herein.

The term "connected" or "coupled to" may include both direct coupling (in which two elements that are coupled to each other contact each other) and indirect coupling (in which at least one additional element is located between the two elements).

FIG. 1 is a flow diagram for processes that are involved in obtaining, identifying, processing DNIRA images, and using them in downstream applications. Following image acquisition, cloud-based image analysis is used to generate a complex subject phenotype. Together with genetic and epigenetic data, this subject phenotype may feed the downstream steps of biomarker development, improved clinical trial design, drug development, new treatments and ultimately, the selection of specific treatments for individualized medicine from a menu of options. (QA=quality assurance).

Imaging System

Devices, systems and methods described herein may be implemented in a combination of both hardware and software. Various aspects may be implemented on programmable computers, each computer including at least one processor, a data storage system (including volatile memory or non-volatile memory or other data storage elements or a combination thereof), and at least one communication interface.

Although exemplary aspects may represent a single combination of inventive elements, all possible combinations of the disclosed elements can be envisaged and are within the scope of the disclosure provided herein. For example, if one aspect comprises elements A, B, and C, and a second aspect comprises elements B and D, then the scope of the disclosure provided herein can include other remaining combinations of A, B, C, or D, even if not explicitly disclosed.

Program code can be applied to input data to perform the functions described herein and to generate output information. The output information is applied to one or more output devices. In some instances, a communication interface may be a network communication interface. In some instances, elements may be combined. For example, a communication interface may be a software communication interface, such as those for inter-process communication. In some instances, there may be a combination of communication interfaces implemented as hardware, software, and combination thereof.

Throughout the discussion, numerous references may be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution described herein may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods described herein.

Methods described herein can be implemented by physical computer hardware, including computing devices, servers, receivers, transmitters, processors, memory, displays, and networks. The methods described herein can include useful physical machines and particularly configured computer hardware arrangements for execution of the method. In some aspects, electronic machines and methods implemented by electronic machines adapted for processing and transforming electromagnetic signals which represent various types of information are contemplated.

Figure 2:
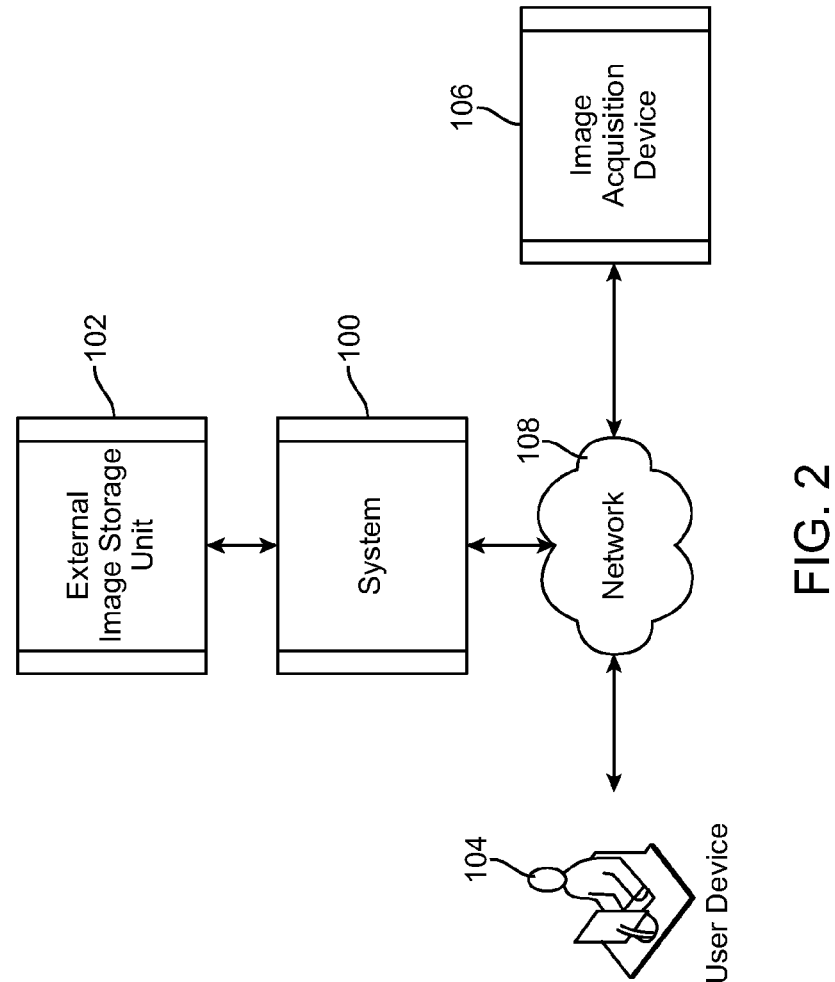
FIG. 2 is a schematic diagram of a system for processing, storage and retrieval of ocular images. The system 100 connects to an image acquisition device 106 to receive ocular images of one or more modalities. The system 100 also connects to an external image storage unit 102 to access ocular images of one or more modalities. The system 100 processes the images to generate output data. In particular, the system 100 generates graphical representations (of visual elements) of the output data for display on user device 104. The user device 104 can also provide user configurations and parameters to system 100 to provide feedback and input data, as well as dynamically control the display to update the graphical representations based on timing and subject data.

FIG. 2 is a schematic diagram of a device for processing, storage and retrieval of ocular images according to some aspects. System 100 can connect to an image acquisition device 106 to receive ocular images of one or more modalities. System 100 can also connect to an external image storage unit 102 to access ocular images of one or more modalities. System 100 can process the images as described herein to generate output data. In particular, system 100 can generate graphical representations (of visual elements) of the output data for display on user device 104. The user device 104 can also provide user configurations and parameters to system 100 to provide feedback and input data, as well as dynamically control the display to update the graphical representations based on timing and subject data.

System 100 can connect to other components in various ways including directly coupled and indirectly coupled via a network 108. Network 108 (or multiple networks) is capable of carrying data. Network 108 can involve wired connections, wireless connections, or a combination thereof. Network 108 may involve different network communication technologies, standards and protocols, such as for example Global System for Mobile Communications (GSM), Code division multiple access (CDMA), wireless local loop, WiMAX, Wi-Fi, Bluetooth, Long Term Evolution (LTE) and so on. Network 108 may involve different physical media such as coaxial cable, fiber optics, transceiver stations and so on. Example network types include the Internet, Ethernet, plain old telephone service (POTS) line, public switched telephone network (PSTN), integrated services digital network (ISDN), digital subscriber line (DSL), and others, including any combination of these. Network 108 can be a local area network or wide area network.

Figure 3:
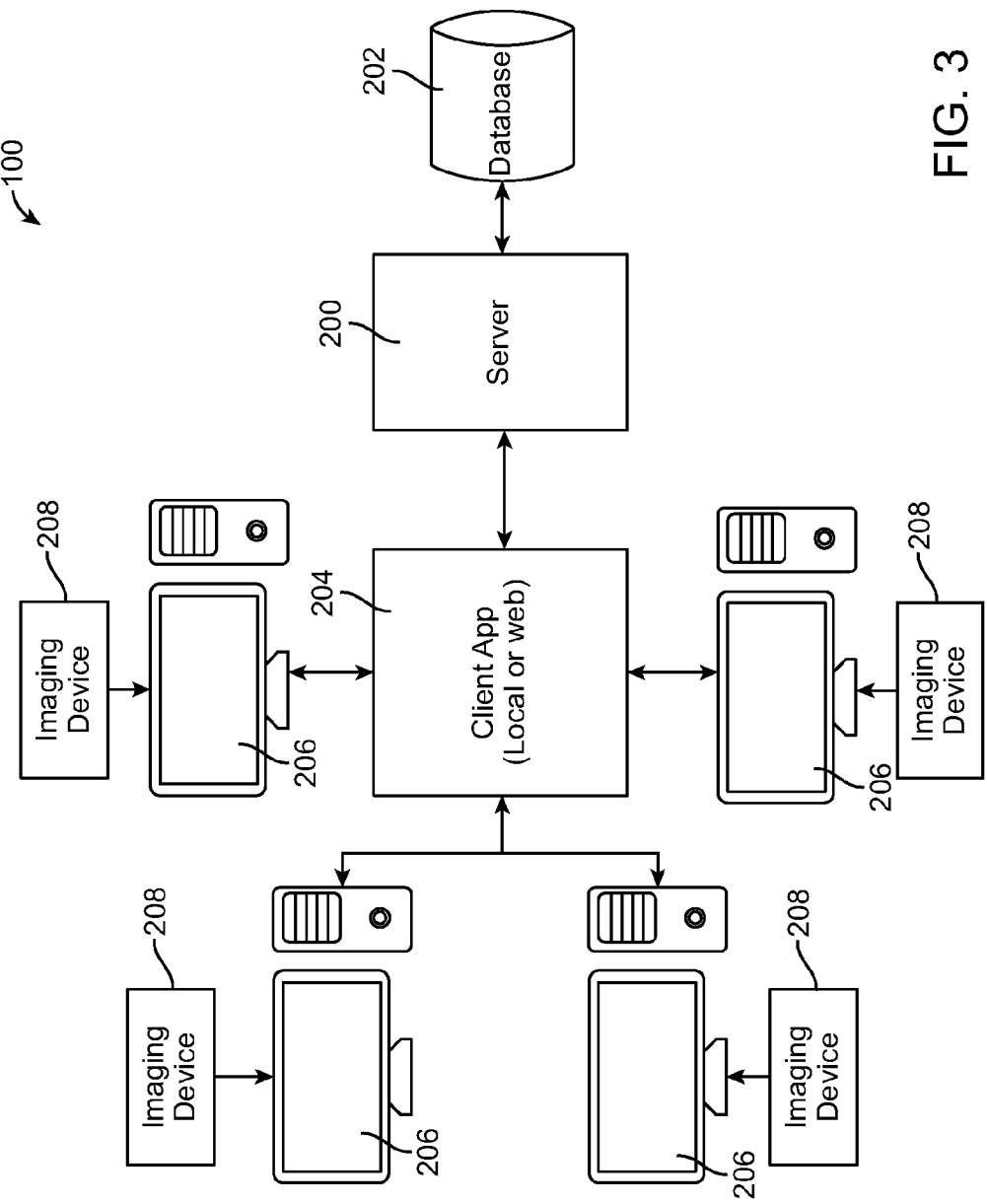
FIG. 3 is a flow diagram of a method for processing, storage and retrieval of ocular images. System 100 includes a server 200, database 202, client application 204, user devices 206, and imaging devices 208.

FIG. 3 is a schematic diagram of a system 100 for processing, storage and retrieval of ocular images according to some aspects. System 100 includes a server 200, database 202, client application 204, user devices 206, and imaging devices 208. System 100 may be useful for the diagnosis, treatment, or prevention of an ocular disease or disorder. System 100, and in particular imaging devices 208, can use in vivo imaging methods to generate output data. System 100 provides an integrated platform for computer assisted analysis and diagnosis (CAAD). System 100 receives images of the eye (macula) from various imaging modalities (captured by imaging devices 208) for comparative processing and provides as output graphical representations of a plurality of measures including prognostic and diagnostic scores upon which to base personalized treatments for diseases of the eye. The images can include standard clinical macular images as well as the novel imaging types as described herein.

System 100 can include a client application 204 to exchange data between server 200 and user devices 206 and imaging devices 108. Server 200 uses as input data images from multiple modalities captured by imaging devices 108 and user configurations or parameters received by user device 206. Server 200 implements image processing to obtain measurements and other reporting data for the images. Server 200 has one or more processing components to register the images, segment objects of interest from the images, define patterns of segmented objects and/or intensity texture of the images. The information can be aggregated by the server 200 into a feature vector for each subject. The subject's data can be used as input for statistical models to generate diagnostic and prognostic scores which can be either categorical or continuous in nature. System 100 can interact with expert users via user device 206 to provide training or configuration information for image processing and to the review the outputs from the image processing to provide a feedback loop to check the suitability of the results Client Application 204 can be either web-based or downloaded and can run locally on a specified computing machine (user device 206). The user device 206 displays a of a graphical user interface (GUI) controlled and generated by client application 204. The GUI can display various graphical representations of the output data and receive control commands to update image processing. Client Application 204 contains a set of processing and analytical tools that provides a platform for image analysis and storage of ocular images.

Figure 4:
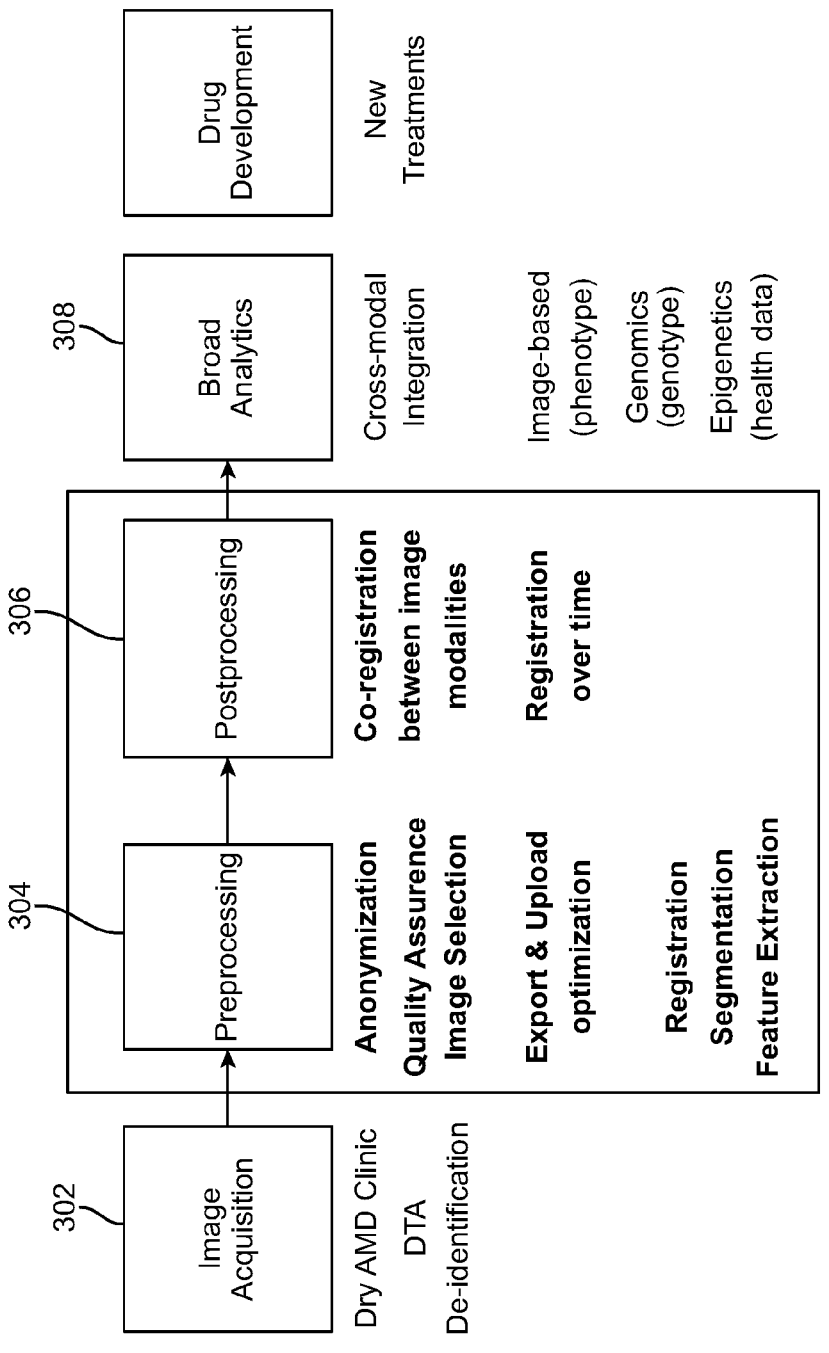
FIG. 4 is a schematic diagram of a system for processing steps, analytics, and the end-use of image data for drug development of new treatments. The diagram depicts the flow of data from the clinical setting, through the compu-tational steps, integration with other modalities, including phenotypes, genome data and epigenetics, and ultimately to an end user for treatment development.

The images, once imported, undergo a preprocessing module/stage. Preprocessing may be implemented using a suitable computer system via a local client application or web-based application. Images may be automatically normalized and registered. This is a process that is performed image by image to produce a new set of images (replicates) that have been successfully normalized and registered. Given the inherent variability across images acquired over time, in cases where images are not processed well (normalization and/or registration failure) the clinician or diagnostician may be prompted or images may be tagged to for assessment by the clinical professional at a later date. FIG. 4 is a flow diagram of a method 300 for processing, storage and retrieval of ocular images according to some aspects. At 302, system 100 acquires ocular images in various modalities. System 100 can acquire images using imaging device 208 or from database 202.

In some aspects, system 100 can acquire ocular images in various modalities from an external image storage unit 102 or an image acquisition device 106. At the image acquisition stage, system 100 can acquire images using various ocular imaging equipment. Once acquired images are stored locally in a database or on a dedicated local server 200 or externally on image storage unit 102. From there clinicians and diagnosticians can use the user device 104, 206 to import acquired images to the client application 204 for further processing and analysis. The images can be imported by various ways and in different formats. The images can be sequenced in time for a specific subject seen by a diagnostician (e.g., an ophthalmologist) over a period of time. The clinician or diagnostician can use user device 104, 206 to import and process images as they are acquired on per subject visit basis or import a tranche of images extending over a period of time for multiple subjects. Image metadata may establish the appropriate sequential time frame of images and to create a tag for future reference. At 304, system 100 can implement preprocessing of the ocular images. The preprocessing may generally involve registration and normalization of the ocular images. At 306, system 100 can implement post-processing of the ocular images. The post-processing may generally involve segmentation and feature extraction of the ocular images. At 308, system 100 can implement broad analytics of the ocular images to generate output data. The broad analytics may generally involve comparative processing, and/or report generation. Server 200 generates graphical representations of the output data for display on user device 206. Server 200 stores and retrieves image data and the output data, along with configuration and parameter related data. Database 202 can store historical and comparative data sets for machine learning and pattern matching by server 200 in generating the output data. For example, aspects of the workflow may be implemented by server 200, client application 204, or a combination thereof.

Figure 5:
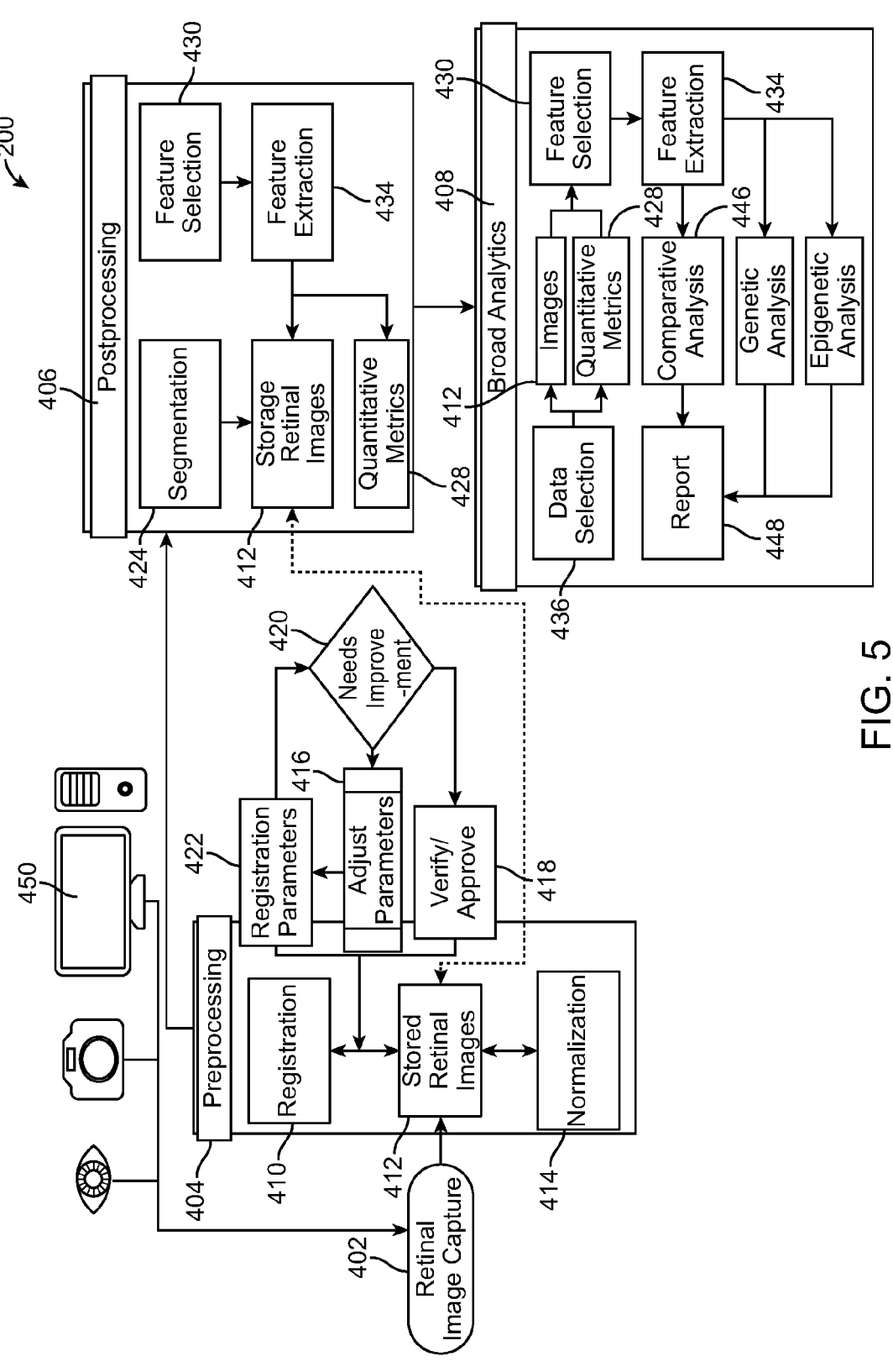
FIG. 5 is a schematic diagram of a system for processing, storage and retrieval of ocular images. System 100 has a retinal image capture unit 402, a display device 450, and a server 200. Server 200 includes various hardware and soft-ware units, including, preprocessing unit 404, post-process-ing unit 408, and a broad analytics unit 408. Server 200 stores ocular images received from retinal image capture unit 402. Server 200 integrates analysis from components 406 and 408. Server 200 generates graphical representations of output data for display as part of GUI on display device 450. Server 200 receives commands, configurations and parameters from display device 450. Server 200 displays processed images on display device 450.

FIG. 5 is a schematic diagram of a system 100 for processing, storage and retrieval of ocular images according to some aspects. System 100 can have a retinal image capture unit 402, a display device 450, and a server 200. Server 200 can include various hardware and software units, including, preprocessing unit 404, post-processing unit 408, and a broad analytics unit 408. Server 200 can store ocular images received from retinal image capture unit 402. Server 200 can generate graphical representations of output data for display as part of GUI on display device 450. Server 200 can receive commands, configurations and parameters from display device 450. Server 200 can display processed images on display device 450. Preprocessing unit 404 generally involves registration 410 and normalization 414 of the stored ocular images 412.

Registration 410 can transform different sets of image data into a target image space, domain or coordinate system, for example. Image data may be in multiple modalities, data from different image devices, times, depths, or viewpoints. Registration 410 can provide the ability to compare or integrate the image data obtained from different modalities, formats, and measurements. Registration 410 can receive registration parameters 422 to transform different sets of image data from the stored ocular images 412 from a reference image space to a target image space using transformation models. The transformation models can receive the registration parameters 422 as input. Feedback can be received to indicate whether or not the registration parameters 422 need improvement 420. Preprocessing unit 404 adjusts parameters 416 if control commands or data processing indicates that they need improvement 420. Registration 410 receives verification or approval 418 before updating the stored ocular images 412 with the registered image data.

Normalization 414 can be a process that can change the range of pixel intensity values of the stored ocular images 412. Once registered and normalized, post-processing unit 460 further processes the stored retinal images 412 to generate unique information regarding the stage and progression of various ocular diseases. The additional processing features can be implemented on a stand-alone basis or sequentially.

Segmentation unit 404 detects and segments regions of the retinal images 412. Ocular images inherently possess several characteristic features, such as vessels, that are unlikely to change over time. Ocular images can be used to generate visualizations of physiological changes resulting from biological implications. By segmenting areas and features of interest on an ocular image the segmented region can be automatically monitored over time for changes, such as shape or size. For example, in the case for a single subject with 4 image acquisitions 1-2 months apart, segmentation unit 404 can segment regions of the image and features of interest in the image acquired in the first visit to serve as the baseline for size and shape of feature. When comparatively analyzing a sequence of images, the original segmentation can be mapped and/or masked on subsequent images. Additionally, the segmented region in the first image can be used to quantify changes in size in later images.

Feature selection 430 can be used to select and identify features in images 412 and segments of the images 412. Feature extraction 434 can extract features intended to be informative and non-redundant, facilitating subsequent learning and generalization steps. Feature extraction 430 can be related to dimensionality reduction. Feature selection 430 may facilitate transforming large amounts of image data to a reduced set of features (e.g. a features vector). The selected features contain the relevant information from the input data, so that the comparative processing can be performed by using this reduced representation instead of the complete initial data.

Broad Image Analytics 408 can be used to derive output values based on comparative processing of images. As images 412 are processed for subjects on multiple visits, quantitative information 428 can be generated and stored throughout the process. If a clinician or diagnostician were interested in compiling and analyzing major characteristic changes over several subjects over time, the data can be selected, pooled and reprocessed to yield aggregate quantitative results 428. For example, if a clinician were interested in analyzing changes in geographic atrophy for a subject pool undergoing a common therapeutic treatment for a specific disease, they can aggregate subject results over the course of their visits to yield quantitative measurements and information regarding the pool of subjects.

Quantitative metrics 428 can generate different output data values. An example quantitative metric 428 is delta. A function of the system 100 can be the ability to analyze images, cross reference and compare characteristic features across different modalities over time. Feature selection 430 and feature extraction 430 are tools to isolate features from segments of images 412.

Comparative analyses 446 for feature differences can be performed between two images taken sequentially in time within the same modality, but it can also be used to observe and measure differences over images separated by multiple intervening imaging time points (e.g. Time point 1 vs Time point 4) and it can be extended to compare images taken from different modalities, such as fundus auto-fluorescence (FAF), infrared (IR), or DNIRA. Report unit 448 can generate graphical representations of output data for display on display device 450 as part of GUI. Data selection 436 selects and isolates data sets for comparison or for use by report generation 448.

Figure 6:
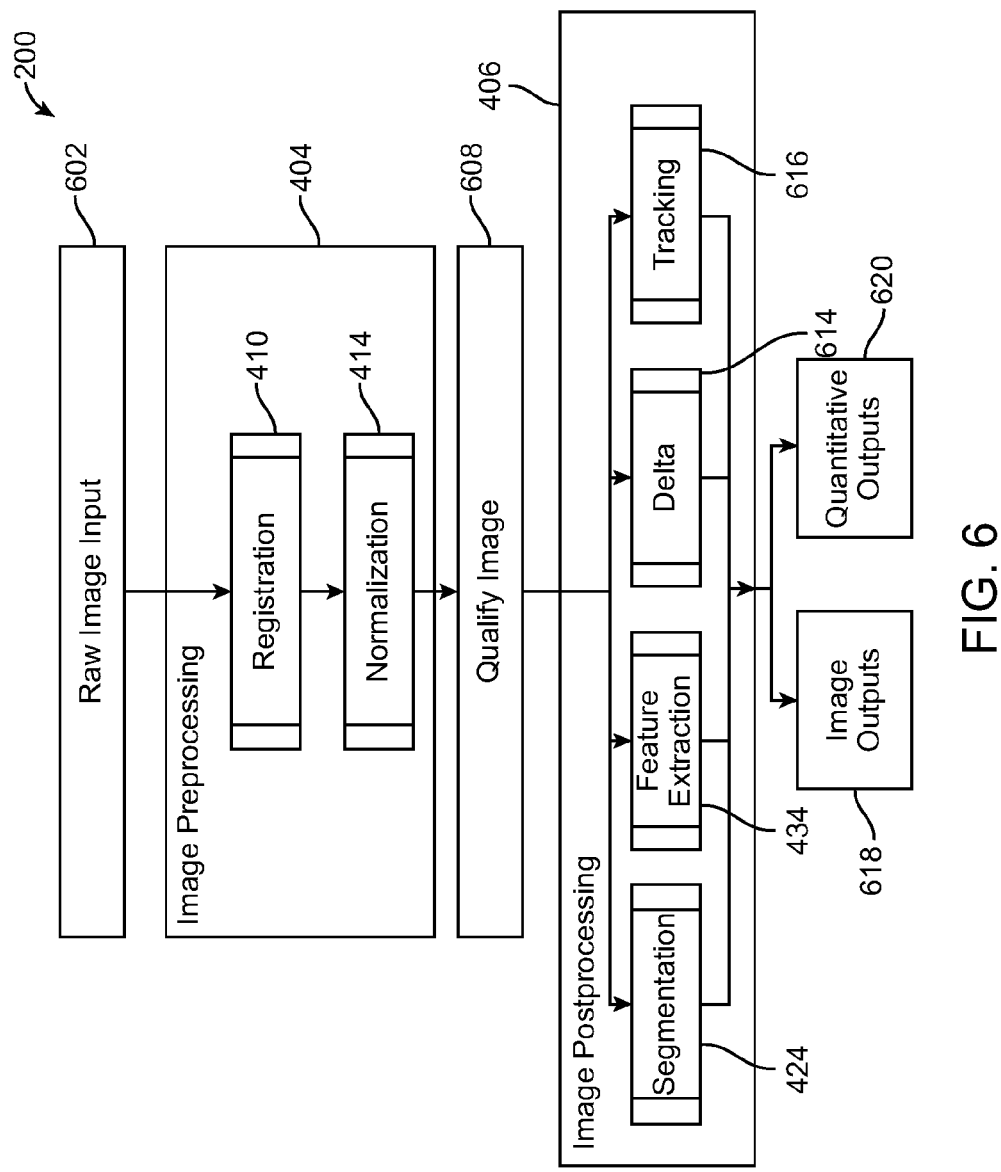
FIG. 6 is a schematic diagram of a system for the key steps of processing ocular DNIRA images. Raw image input 602 is provided to an image preprocessing unit 404 to generate qualified image data 608 by the steps of registration 410 and normalization 414. Image post-processing unit 406 further transforms and processes the qualified image data 608 using segmentation 424 and feature extraction 434. Delta unit 614 generates delta images as output data. Outputs include image outputs 618 and quantitative outputs 620.
Figure 7:
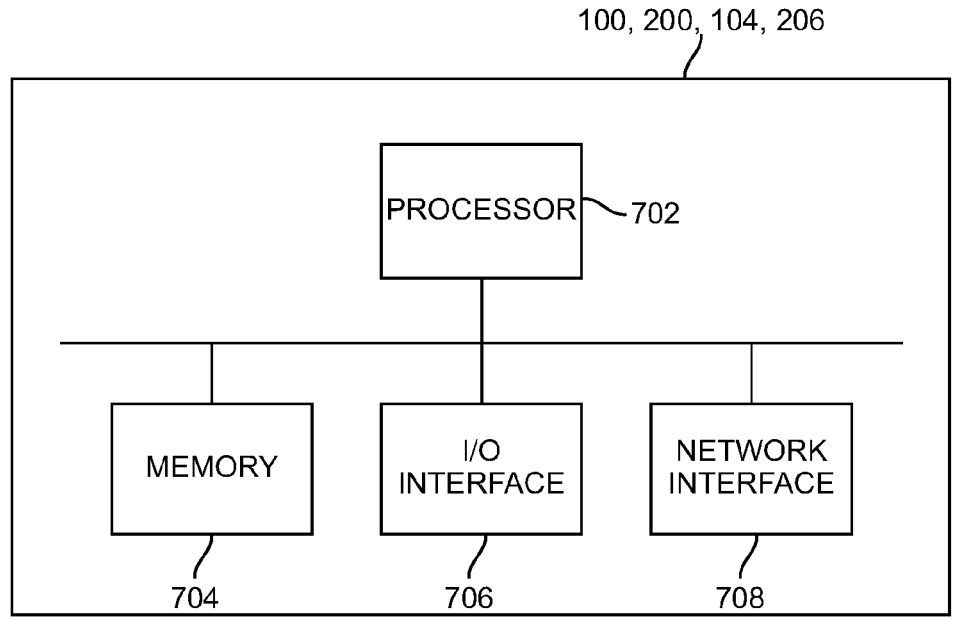
FIG. 7 is a schematic diagram of a computing device to implement aspects of systems for processing, storage and retrieval of ocular images. Depicted is system 100 (including server 200 or user device 104, 206) for processing, storage and retrieval of ocular images. The system includes processor 702, memory 704, I/O interface 706, and network interface 708.

FIG. 6 depicts various units and applications of devices and methods described herein. Exemplary device configuration consistent with FIG. 5 are depicted in FIG. 6 and FIG. 7. FIG. 6 is a schematic diagram of a system for processing, storage and retrieval of ocular images according to some aspects. As shown, in some aspects, server 200 may or may not include aspects of broad analytics 408. FIG. 6 is a schematic diagram of a system for processing, storage and retrieval of ocular images according to some aspects. Raw image input 602 can be provided to an image preprocessing unit 404 to generate qualified image data 608. Image postprocessing unit 406 further transforms and processes the qualified image data 608 using segmentation 424 and feature extraction 434.

Delta unit 614 can generate delta images as output data. A function of the system 100 can be the ability to process images to cross reference and compare characteristic features of the images across different modalities over time. Feature selection 430 and feature extraction 430 can be tools to isolate features from segments of images 412.

Comparative analyses for feature differences can be done between two images taken sequentially in time within the same modality. Comparative analyses can also be used to observe and measure differences over images separated by multiple intervening imaging time points (e.g. Time point 1 vs Time point 4) and it can be extend to compare images taken from different modalities, such as fundus auto-fluorescence (FAF), OCT, fundus photos, red-free, infrared (IR), angiography or DNIRA.

The image differencing or delta process 614 makes use of statistical and algorithmic processes to compare two, or more than two, preprocessed images with one another and determine or visualize the level of change between them. Differences can also be quantified at a pixel-by-pixel, or region of pixels, level. In general, two images 412 are compared with one another by subtracting one from the other to generate a difference image. This difference image can be an example output data that can be used to generate visual representations for GUI and display device 450.

Delta image generation unit 614 is configured to generate a sequence of delta image outputs linked to a comparative time reference, between the images, either image-by-image or with reference to a common, baseline image. The selection of images for this delta generation process 614 may be automated and may also involve manual input. A clinician or diagnostician can configure the analysis to compare a single, or a sequence of images, to a baseline reference and assemble the difference data in such a way as to highlight major changes over time.

The output Delta images (quantitative outputs 620 and image outputs 618) can be created and stored (either locally or externally). Delta image outputs can be viewed and processed through an integrated viewer as part of GUI and displayed on display device 450. When visualized in an integrated format, the difference images may be overlaid in different colors so a user can observe how the changes have manifested themselves over time. Delta image analysis can also present an overlaid formatting where each image is superimposed over the previous one in the visual representation. By allowing for the image differences to be displayed on the display device relative to the eye structures, the user can be afforded an opportunity to see how the differences compare to the structure of the eye, making diagnosis of diseases easier.

FIG. 7 is a schematic diagram of a computing device to implement aspects of system 100 (including server 200 or user device 104, 206) for processing, storage and retrieval of ocular images according to some aspects. For simplicity only one computing device is shown but the system may include more computing devices operable by users to access remote network resources and exchange data. The computing devices may be the same or different types of devices. The computing device may comprise at least one processor, a data storage device (including volatile memory or non-volatile memory or other data storage elements or a combination thereof), and at least one communication interface. The computing device components may be connected in various ways including directly coupled, indirectly coupled via a network, and distributed over a wide geographic area and connected via a network (which may be referred to as "cloud computing").

In some aspects, a computing device may be a server, network appliance, set-top box, embedded device, computer expansion module, personal computer, laptop, personal data assistant, cellular telephone, smartphone device, imaging device, display terminal, and wireless hypermedia device or any other computing device capable of being configured to carry out the methods described herein. Computing device (e.g. system 100, server 200 or user device 104, 206) can include at least one processor 702, memory 704, at least one I/O interface 706, and at least one network interface 708.

Each processor 702 may be, for example, any type of general-purpose microprocessor or microcontroller, a digital signal processing (DSP) processor, an integrated circuit, a field programmable gate array (FPGA), a reconfigurable processor, or any combination thereof. Memory 704 may include a suitable combination of any type of computer memory that is located either internally or externally such as, for example, random-access memory (RAM), read-only memory (ROM), compact disc read-only memory (CD-ROM), electro-optical memory, magneto-optical memory, erasable programmable read-only memory (EPROM), and electrically-erasable programmable read-only memory (EE-PROM), Ferroelectric RAM (FRAM) or the like.

Each I/O interface 706 enables computing device to interconnect with one or more input devices, such as a keyboard, mouse, camera, touch screen and a microphone, or with one or more output devices such as a display screen and a speaker. Each network interface 708 enables computing device to communicate with other components, to exchange data with other components, to access and connect to network resources, to serve applications, and perform other computing applications by connecting to a network (or multiple networks) capable of carrying data. A Computing device can be operable to register and authenticate users (using a login, unique identifier, and password for example) prior to providing access to applications, a local network, network resources, other networks and network security devices. Computing devices may serve one user or multiple users.

Figure 8:
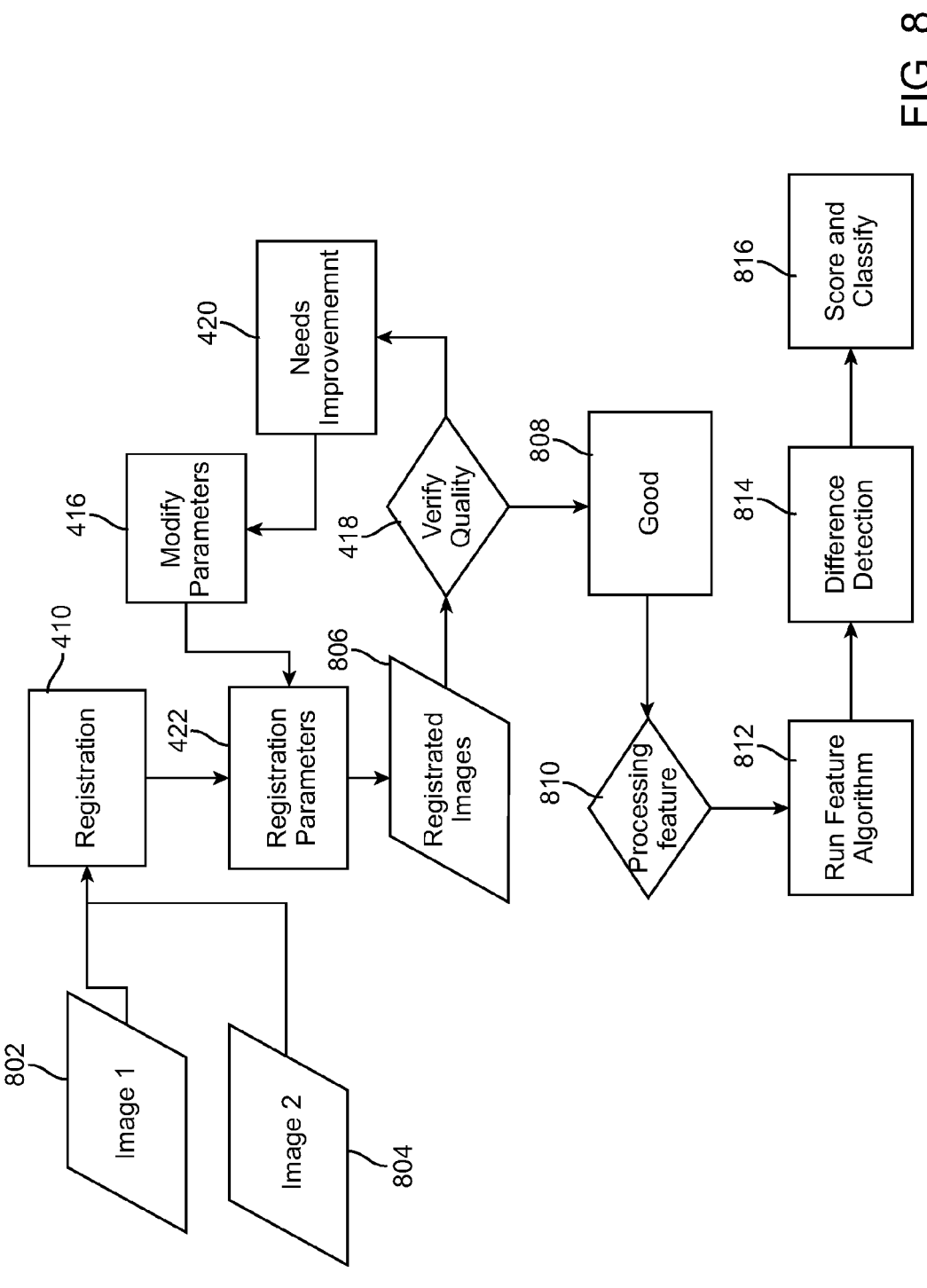
FIG. 8 is a flow diagram of a method for processing, storage and retrieval of ocular images involving different components described herein. The diagram shows analysis of 2 images simultaneously 802, 804 including components of registration 410, which is improved through cycles of modification until sufficient quality is reached, feature extraction 810 using algorithms developed for the uniquely identified disease-associated features 812, comparison of the 2 images 814, and classification 816.
Figure 9:
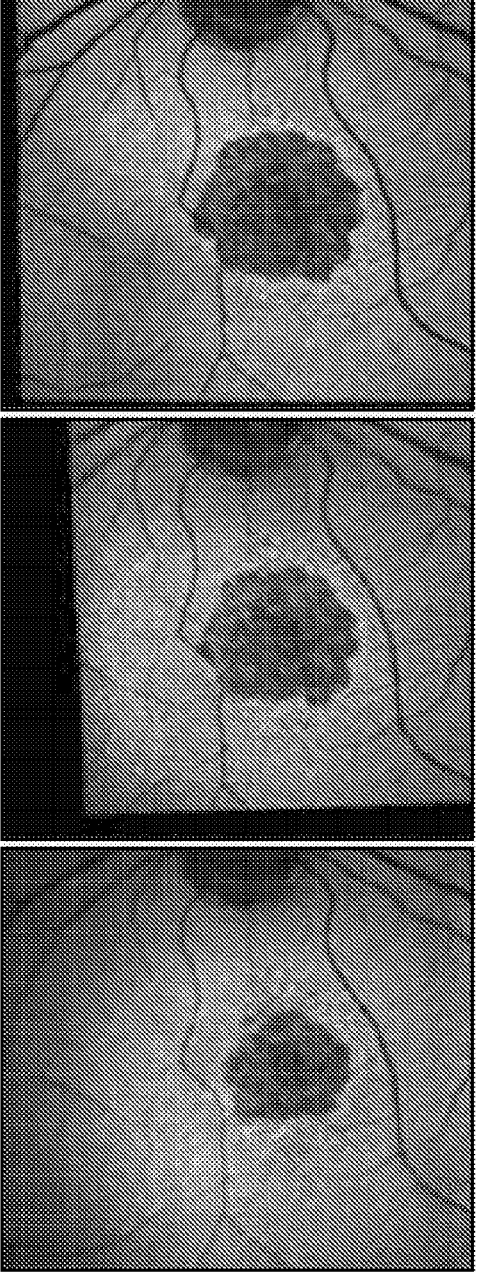
FIG. 9 depicts the importance of image registration in serial ophthalmic imaging and analysis. Registration allows to accommodate for slight changes in alignment, tilt, skew, magnification and any other parameters that may vary across each patient visit. Example is shown using FAF images. Further this figure demonstrates the expansion of central GA on FAF, showing only regions where the tissue has died and the damage is irreversible.

FIG. 8 depicts an exemplary flow diagram of a method for processing, storage and retrieval of ocular images. The process uses as input a first image 802 and a second image 804 (and additional images) to compare features of the images over time. The process generates as output visual elements or representations for a GUI to show changes to the features over the time period.

In some aspects, the process can provide for the comparative analysis of images within and between various imaging modalities. The method can provide for registration 410 two or more images 802, 804 with one another by establishing point correspondences between the images or a target image space. The registration 410 is performed so as to visualize and address characteristic differences between images taken at a specific point in time or over a period of time within an imaging modality, such as individual DNIRA images, or between images of different modalities, such as DNIRA alongside FAF, OCT, fundus photo, red free, Infrared (IR), angiography, and OCTA images. An example of registration is depicted in FIG. 8. The process of registration 410 maps each point in one image onto the corresponding point in each of the other images. In certain aspects, registration 410 may be accomplished by determining the registration parameters 422 using correlation and/or feature location matching. The images may then be registered with each other via the registration function 410. Alternatively, a mechanical deformation model may be used for the registration 410. Different registration methods may be employed to register the images with one another before comparing the images for differences or changes. This includes fully automatic registration as well as computer assisted manual registration, or different registration approaches using varying degrees of manual intervention. To register more than two images, the images may be registered in pairs. For example, if a first image and a second image are registered, and, separately, the second image and a third image are registered, then by the composition of the registration functions, the first and third images are effectively registered. This concept can extend to any number of images. Thus, using a pairwise registration 410 process, one can register any number of images. Additionally, registration 410 processes that simultaneously register more than two images may also be employed by the present technique.

In some instances, registration 410 may be based on landmark extraction or feature-based. The registration 410 of images may be accomplished by modeling the large-scale motion and local distortion of the anatomy. In some instances, registration parameters 422 of the model that defines these motions are estimated and selected. A search is then performed to find the parameter values that produce the best alignment of the images within and between modalities over time. The quality of this alignment may be based on a comparison of corresponding points in the original images.

In some aspects of a system described herein, pixel intensities may vary significantly between images, both within and between imaging modalities, potentially obscuring valuable characteristics in the image. Normalization 414 of the images can correct for variable intensities between images. Registration 410 can transform images to a target image space for comparison to other images in the common target image space.

Hypofluorescent Signal Processing

Disclosed herein is an en face functional imaging system and method for evaluation of an ocular disease or disorder such as non-exudative (dry) Age Related Macular Degeneration (AMD) capable of identifying both tissue loss (structural damage) and "sick" or abnormal tissue (functional damage). This method may be referred to herein as AMD Imaging (AMDI) or Delayed Near InfraRed Analysis (DNIRA). By way of illustration the DNIRA method can be compared to Fundus Autofluorescence (FAF). DNIRA, like FAF, can generate images that are readily-quantifiable using structured computer learning based on the detection of regions of profound hypofluorescence (black) in otherwise grey-scale images. FAF may be capable only of quantifying advanced, late dry AMD with Geographic Atrophy (GA) only after irreversible loss of the retinal pigment epithelium (RPE) and photoreceptors.

An imaging system to can be used to register, segment and provide inter-modal comparison between DNIRA and any other imaging methods capable of generating readily quantifiable images. For example, an imaging system can register, segment and provide intra-modal comparison of DNIRA over time to any other imaging modality over time. In some aspects, an imaging system to register and provide inter- and intra-modal comparison of DNIRA and FAF against any other en face or cross-sectional imaging modalities capable of generating ophthalmic images. In some aspects, an imaging system to register and provide inter- and intra-modal comparison of DNIRA and FAF against any functional modalities that can generate information about the state/health of the fundus. By way of non-limiting examples, such methods could include microperimetry, low luminance visual acuity, and dark apaptometry.

Imaging system described herein can register and provide inter- and intra-modal comparison of DNIRA, FAF and other imaging modalities, against other presently-used non-imaging modalities such genetic analysis, not limited by example, comparing to single nucleotide polymorphisms in genes such as CFH, C2, C3, C5, C6, C7, C8, C9, CFI, CFD, MCP-1, MCP-2, MCP-3, ARMS2/HTRA1, TIMP3, SLC16A8, COL4A3, COL8A1, CETP, LIPC, APOE, VEGFA, VEGFC, ABCA1, ABCA4, MMP9, VTN, NFkap-paB. Alternatively images may be compared against genetic analysis of copy number variation, for example, without limitation, of any of the above genes.

Furthermore, imaging systems described herein can register and provide inter- and intra-modal comparison of DNIRA, FAF and other imaging modalities against other factors, such as analysis of concurrent disease, for example, but not limiting to, cardiovascular disease, such as coronary artery disease, atherosclerosis or stroke; neurodegenerative disease, such as Alzheimer's disease, Parkinson's disease, multiple sclerosis, Huntington's disease, Amyotrophic lateral sclerosis and neurological trauma; inflammatory disease, such as rheumatoid arthritis, osteoarthritis, ankylosing spondylitis, systemic lupus erythematosus, celiac disease, Crohn's disease, Behcet's disease; pulmonary disease, such as asthma, chronic obstructive pulmonary disease (COPD) including emphysema and allergies; as well as chronic kidney disease. In some aspects, an imaging system can register and provide inter- and intra-modal comparison of DNIRA and FAF against intraocular and systemic biomarkers, for example, but not limited to, monocyte chemoattractant proteins (MCPs) such as MCP-1, MCP-2, MCP-3, interleukins (ILs) such as IL-6, IL-8, vascular endothelial growth factors (VEGFs), such as VEGF-A, tumor necrosis factors (TNFs) such as TNFa, nitric oxide synthases (NOSs) such as NOS-2, complement components, such as C1-C9, complement regulators, such as CFD, CFH, CFI, apolipoproteins (Apos) such as ApoE, ApoB, C-reactive protein, and eotaxins, such as eotaxin-1. In some exemplary aspects, an imaging system can register and provide inter- and intramodal comparison of DNIRA, FAF and other imaging modalities, against environmental/epigenetic risk factors such as smoking, obesity, blood pressure, body mass index, waist to hip ratio, cholesterol levels, lipid panel, family history, age and dietary vitamin intake and medications.

Aspects described herein can provide two iteratively-improved data analytical processes for testing. A beta version 1 may be configured for non-cognitive image analysis with iterative improvements based on novel biology with clinician input; to also include multi-modal image comparisons. A beta version 2 may be configured for cognitive and non-cognitive image analysis with iterative improvements for large data analytics, cloud-based analysis; for multi-modal image-based comparisons, and for intra-modal comparisons with other subject-centered databases (e.g. genetics, concurrent disease, medications, diet).

Aspects described herein can provide an imaging system to implement the following: image output from acquisition device; registration of native images; segmentation of image regions; feature extraction specific disease-relevant observations (to be compared against other modalities, and over time); inter-modal image analysis and generation of delta image data (for example DNIRA subtracting another imaging modality data such as FAF); and segmentation over time.

When the system 100 generates image output from acquisition device there may be challenges in the selection of "best" subject images, slow conversion to non-proprietary image output format, long directory names, and a need to be suitable for downstream batch processing. A purpose for generating image output from the acquisition device is for selection of suitable images for device-independent (agnostic) downstream analysis. The system 100 can be suitable for doctor use, for example, by way of an image-based, interactive GUI interface rendered and updated on user device 104, for example.

When the system 100 implements registration of native images there may be challenges due to the spherical shape of human eye which can introduces tilt, skew, subtle magnification changes between images, and human features potentially introduce significant differences over time (e.g. cataract). A purpose for registration of native images is inter-modal and temporal image comparison. This permits detection of image-based features that occur in one or more modalities, and that increase, decrease or remain unchanged in size (area) over time. A computational requirement is the identification of branch points on retinal blood vessels; visualization of optic nerve head (ONH). An optimization may be that images are processed in concentric rings/zones including: a) outer ring discarded due to distortion; b) center ring not used owing to regions of Interest (RoI) and paucity of medium to large blood vessels. An optimization may be that images are iteratively reviewed with doctors or experts providing feedback regarding acceptable and unacceptable differences as training input for the machine learning processes. An optimization may be for batch processing by way of a threshold value such as of >85% of all images (e.g., to reject <15% for manual registration).

Figure 17A:
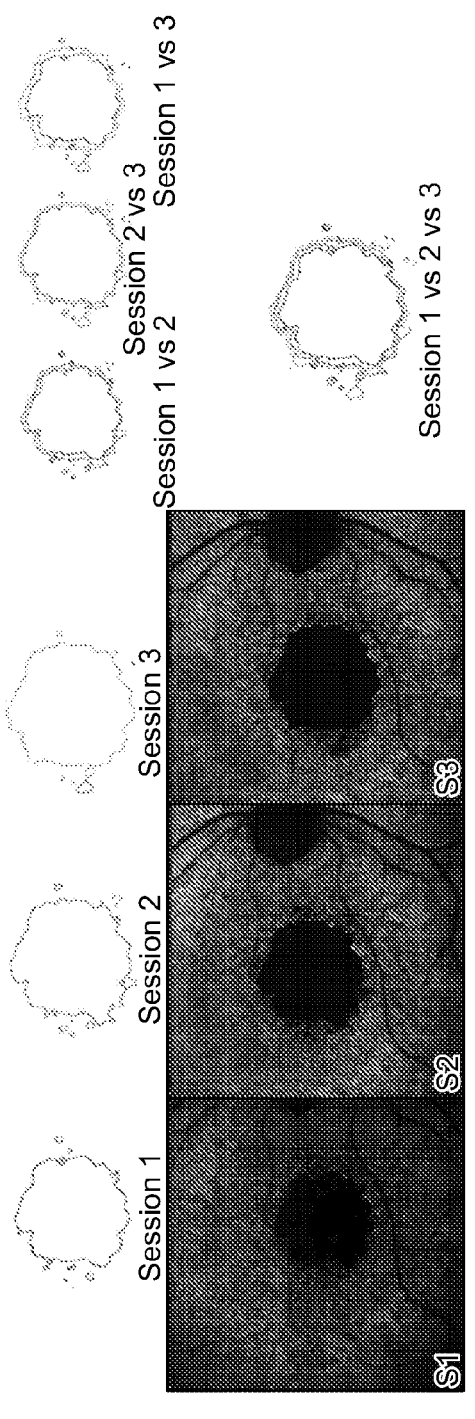
FIGS. 17A and 17B depict representative image of quantification of total hypofluorescent DNIRA area as a marker of progressive or dynamic change, and comparison of DNIRA signal across multiple timepoints/sessions to observe changes associated with increasing or decreasing DNIRA signal.
Figure 17B:
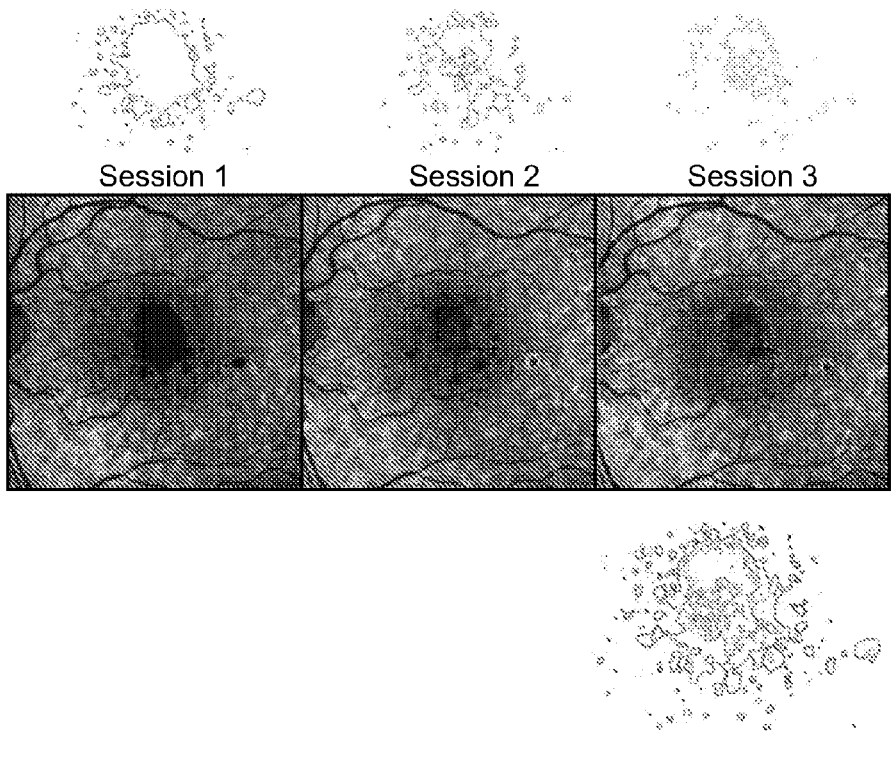

An optimization may be registration of three images, using vascular markings (images taken at three separate time points). More or fewer images may be used in various aspects. FIGS. 17A and 17B show image output data as a visual representation of three images at three separate time points. The output of registration of native images may be a stack of registered images for downstream manipulation and processing. The system 100 can be suitable for doctor input for iterative improvements to the parameters. The system 100 can be suitable export-ready cloud-based processing for a large data analytical platform.

When the system 100 implements segmentation of the images there may be challenges after registration to distinguish regions of black from grey-scale background. After registration, regions of black should exclude constant features such as blood vessels and ONH. A purpose for segmentation is for identification and quantification of high-contrast features, identified as profoundly hypofluorescent (black). For example, using FAF techniques areas of black correspond to regions of irreversible tissue loss. FIG. 17A shows progressive, irreversible loss of tissue as visualized by FAF imaging. Over time, areas of black increase in size or remain the same (e.g., no regression or reduction in black is observed).

DNIRA provides a quantifiable, functional readout of tissue function. Using DNIRA, system 100 can detect areas of black in the images that correspond to regions of irreversible tissue loss and to abnormal or sick tissue. Over time, areas of black can remain the same, increase or decrease in size. System 100 can implement a determination of "baseline DNIRA" images. The system 100 can obtain the baseline DNIRA image by subtracting signal from pre-dye NIR images from post-dye NIR images.

When the system 100 implements feature extraction there may be challenges relating to the identification and quantification of features of disease other than tissue loss. This process presently relies on manual interpretation of multimodal images, including 4 en face methods, and 1 cross-sectional method. The system 100 can automate aspects of this process using techniques described herein. A purpose of feature extraction is to identify disease-relevant features that assist with subject diagnosis, staging, risk-stratification, and ultimately with clinical trial design and monitoring response to treatment. A purpose of feature extraction is to make readily possible the quantification and classification of drusen, RPE detachments (RPED), and other disease features using image processing. A purpose of feature extraction is to make possible the observation and quantification of dynamic changes of disease using graphical representations and visual elements in a GUI displayed on a user device 104. For example, the identification of the following en face features informs doctors of disease severity and subject risk (based on clinical examination and imaging methods): a) small hard drusen; b) medium drusen; c) large drusen; d) confluent drusen; e) RPE detachments (e.g. drusenoid, serous); f) regions of geographic atrophy (GA); g) blood. System 100 implementing DNIRA offers the potential to identify and quantify clinically-relevant features (beyond just GA) using structured computational processes. This may detect in image data the following: a) small black dots, <65 μm diameter, with circularity of 0.8 or more; b) small black dots, 65-125 μm diameter, with circularity of 0.8 or more; c) large black dots, >125 μm diameter, with circularity of 0.8 or more; d) oblong, oval or round structures deemed to arise from the confluence of drusen (for example, resembling a shape of "fingerling potatoes"), >125 μm in one dimension, with circularity >0.2; e) large black areas >200 μm in diameter, circularity >0.5; f) regions of black, seen in both DNIRA and FAF; g) blood.

The system 100 implements inter-modal image analysis and generates delta image data (DNIRA subtracting FAF). The delta image, defines, at any imaging session the regions of black DNIRA that correspond with black GA (and so represent GA), versus the black DNIRA that is in excess of the black FAF (so represents potential damaged or abnormal tissue, present outside of GA), for example. En face segmentation-suitable methods include DNIRA and FAF. The system 100 implements inter-modal image analysis and generates delta image data to identify disease-relevant features in registered and segmented images, both between modalities (FAF & DNIRA only) and over time. The system 100 implements inter-modal image analysis and generates delta image data for the identification of en face features informs doctors of disease severity and subject risk based on FAF, including for example regions of geographic atrophy (GA). DNIRA offers the potential to identify and quantify GA using structured computational processes. For example regions >200 μm, or alternatively measured relative to the diameter of the ONH, that appear black using DNIRA and are equal or larger in area to black regions also observed on FAF in the same spatial location. The output can be Delta Image data which is "DNIRA minus FAF" image data to identify regions of corresponding black signal.

The identification of en face features is not presently known to doctors and may inform them of abnormal RPE/PhR physiology in regions outside of GA (e.g., the extent of diseased tissue, not dead tissue), including for example regions of abnormal cellular physiology that do NOT include GA. Discrete regions >200 μm (or measured relative to the ONH) that appear black using DNIRA may not be evident on FAF which provides an improvement. Delta Image data includes "DNIRA minus FAF" image data to identify regions of black signal that extend beyond the borders of GA, or exist in different spatial areas.

En face grey-scale methods include: InfraRed (IR) Reflectance, Red Free (RF) Color, Color (RGB), Color (CNYK), angiography [useful for wet AMD; but may be less useful for dry AMD], en face Optical Coherence Tomography (OCT) and OCT angiography (OCTA). A purpose of inter-modal image analysis is to identify disease-relevant features in registered images, both between modalities and over time, in grey-scale images. The inter-modal image analysis may implement the identification of the following en face features informs MDs of disease severity and subject risk on examination and in currently available en face imaging methods (excluding FAF): a) small hard drusen; b) medium drusen; c) large drusen; d) confluent drusen; e) RPE detachments (drusenoid, serous, hemorrhagic); f) blood; g) regions of geographic atrophy (GA). inter-modal image analysis can use unstructured computational processes (e.g. cognitive computing), to generate output data and transform image data.

Cross-sectional methods include: Optical Coherence Tomography (OCT) and OCT angiography (OCTA). The inter-modal image analysis may implement the identification of the following cross-sectional features, detected on OCT, informs MDs of disease severity and subject risk: a) presence and number of drusen in RPE/sub-RPE space; b) drusenoid RPE detachments; c) pseudodrusen in subretinal space; d) geographic atrophy (loss of RPE/PhR with greater OCT signal in deeper tissues), e) drusen volume, f) areas of drusen regression, g) outer nuclear layer (ONL) thickness and volume, h) hyper-reflective OCT foci, i) presence of nascent GA, j) presence of quiescent CNV k) sub-foveal choroidal thickness, l) collapsed pigment epithelial detachment En face DNIRA or other modality imaging can be compared against OCT using single cross-sections or 3D reconstructions that generate graphical representations of the cross-sectional imaging.

The system 100 can implement segmentation over time where different feature that are selected and extracted are followed over time (e.g. to determine if it is increasing, remaining the same, or deceasing in area or number). The system 100 can implement segmentation and, followed over time, FAF can enable doctors to quantify regions of GA and measure their rates of expansion over time. This step can permit identification of subjects with highest rates of GA expansion, and may be useful for clinical trial enrollment and endpoint analysis. However it may not follow changes before irreversible tissue loss. Further, the quantification of GA suggests that disease is unidirectional (e.g. that features accumulate but do not regress) which may be false. Three main parameters can be assessed: A. change in total black DNIRA (beyond GA); B. change in total drusen; C. change in RPE detachments. A purpose of segmentation over time may be to quantify clinically-relevant feature of disease (e.g. drusen, RPEDs, etc.) and determine their change over time. including Areas of GA; Total area beyond GA (as potential measure of disease burden); and Areas of subsegmented features of disease (e.g. small, med, large drusen, RPEDs, etc). Data confirms that regions of black DNIRA not only increase, but can decrease over time, confirming the dynamic features of disease observed most typically in color photos (for example drusen regression). This may be drusen regression. The system 100 implements segmentation over time to generate Delta Time (DNIRA) which can be measured as a decrease of black DNIRA signal over time in small, medium or large. The system 100 implements segmentation over time to generate the following output a) Changes in total black DNIRA over time; b) Changes in "Delta DNIRA minus FAF" over time; c) Changes in specifically segmented features, for example: changes in small drusen, changes in medium drusen, and changes in large drusen.

The change in disease burden (outside of GA) may not be detected using known approached. To identify total diseased or dysfunctional tissue this parameter could provide a measure of the burden of disease and support clinical trial enrollment. The output of "Delta Image=DNIRA minus FAF" can indicate regions that increase in size (area) over time.

The system 100 implements segmentation over time to quantify the extent of diseased or dysfunctional tissue. The output "Delta Image=DNIRA minus FAF" indicate regions that remain unchanged in size (area) over time. The output "Delta Inage=DNIRA minus FAF" indicate regions that decrease in size (area) over time.

The change in drusen accumulation over time may be difficult to identify and even more difficult to quantify. Drusen are not uniformly detected on FAF or other en face methods. DNIRA may be used to detect and quantify dynamic changes in drusen accumulation & regression. It is widely held that the accumulation of drusen (number, area or 3D volume) is proportionate to disease. The output "Delta Image=DNIRA minus FAF" indicate regions that increase in size (area) over time. The output "Delta Image=DNIRA minus FAF" indicate regions that remain unchanged in size (area) over time.

Drusen regression (often seen in color photos or by number, area or 3D volume) can be a sign of progressing disease. Drusen loss can herald late AMD, with GA or CNVM. The output "Delta Inage=DNIRA minus FAF" indicate regions that decrease in size (area) over time.

Drusen may be detected using OCT, with 3D slab analysis. It is held that the accumulation of drusen (number, area or 3D volume) can be proportionate to disease. The output "Delta DNIRA minus FAF" indicate regions that increase in size (area) over time which may be used for comparing against OCT.

The change in RPE detachment (RPED) size (area, height, volume) over time may be difficult to identify and difficult to quantify. The system 100 can detect and quantify dynamic changes in RPED size (area) and number. It is held that the resolution of RPEDs, [particularly the drusenoid variety] suggests risk for progression to late, blinding GA. The output "Delta Image=DNIRA minus FAF" indicate regions of RPED that increase in size (area) over time. The output "Delta Image=DNIRA minus FAF" indicate regions that remain unchanged in size (area) over time. The output "Delta Inage=DNIRA minus FAF" indicate regions that decrease in size (area) over time.

Although the accumulation of drusen reflects ongoing disease, regions of drusen regression (often seen in color photos, or by number, area or 3D volume) is a sign of progressing disease. Drusen loss can herald late AMD, with GA or CNVM. In some aspects, AMDI can detect regression of drusen, allowing determination of progression of AMD.

In some aspects, AMDI images can be compared against other imaging methods such as OCT-Angiography (OCT-A). Such a comparison allows identification of regions of pathological blood flow (either decreased flow through the choriocapillaris or other layers of the choroid) or potentially increased flow into areas of leaking or non-leaking neovascularization (choroidal neovascularization) or vascular pathology (such as choroidal plexus, polyps, aneurysms, anastomose).

Exemplary Output Data

Figure 11A:
FIGS. 11A-11D, depict representative DNIRA images of diseased retinas. Arrows indicate hypofluorescent regions. Yellow lines indicate the boundaries of hypofluorescent regions.
Figure 11B:
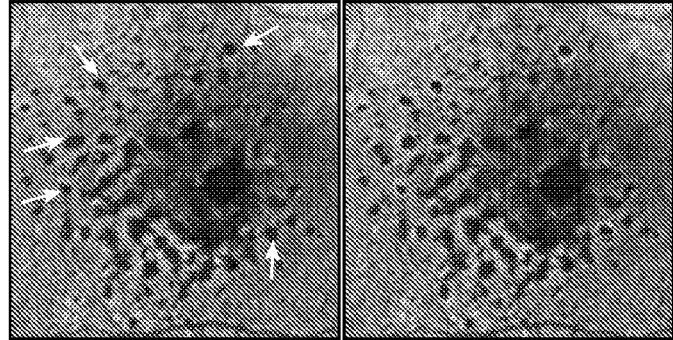

FIGS. 11A-11D depict exemplary demonstrations of visual representations that can be visualized using a system described herein. FIG. 11A shows image output data as a visual representation of multiple small and medium black dots (<65 μm and 65-125 μm). FIG. 11B shows image output data as a visual representation of a large drusen (>125 μm).

Figure 11C:
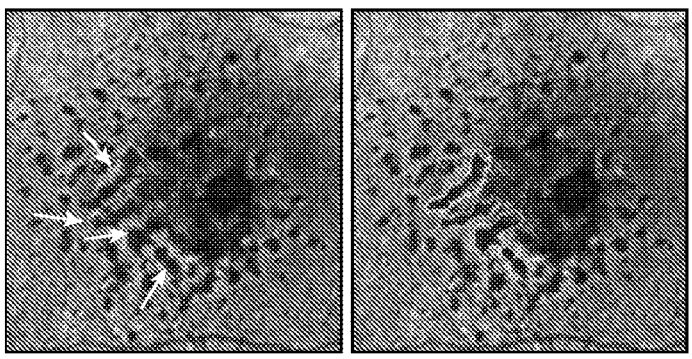
Figure 11D:
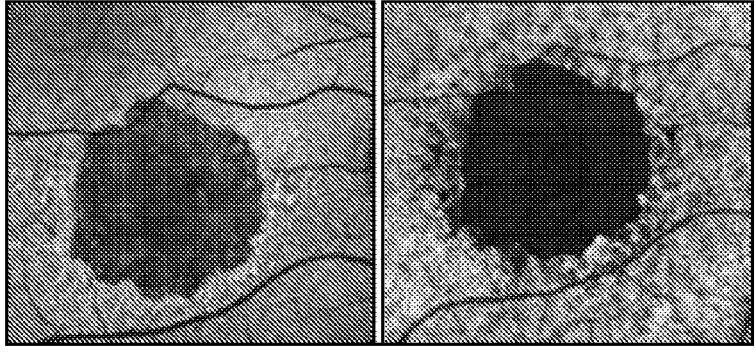

FIG. 11C shows image output data as a visual representation of confluent drusen. FIG. 11D shows image output data as a visual representation of GA.

Figure 12:
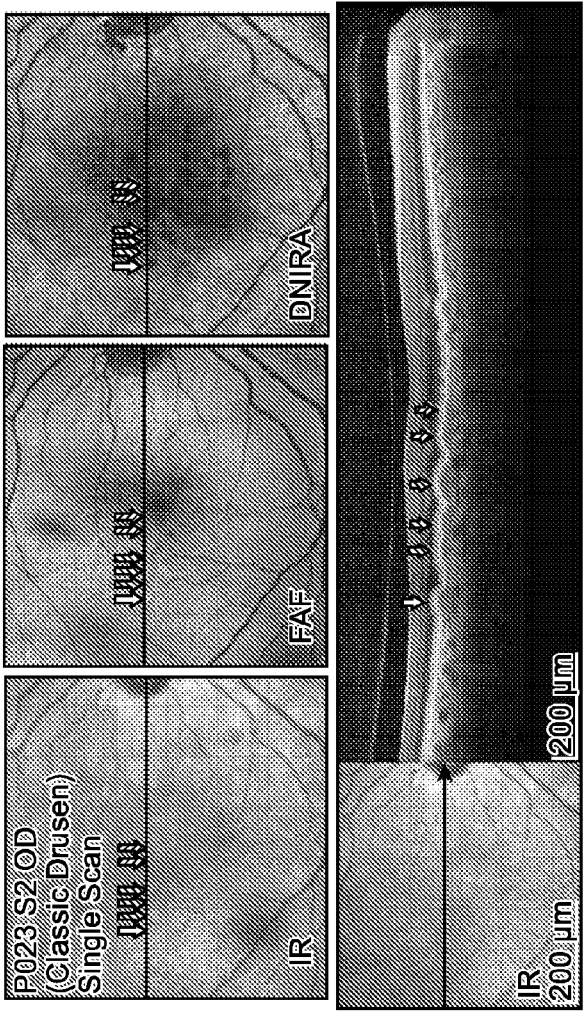
FIG. 12 depicts representative DNIRA images compared to corresponding IR, FAF and OCT images. The left panel is an IR, the middle is an FAF image, and the right panel is a DNIRA image. The bottom panel shows the corresponding OCT.
Figure 13:
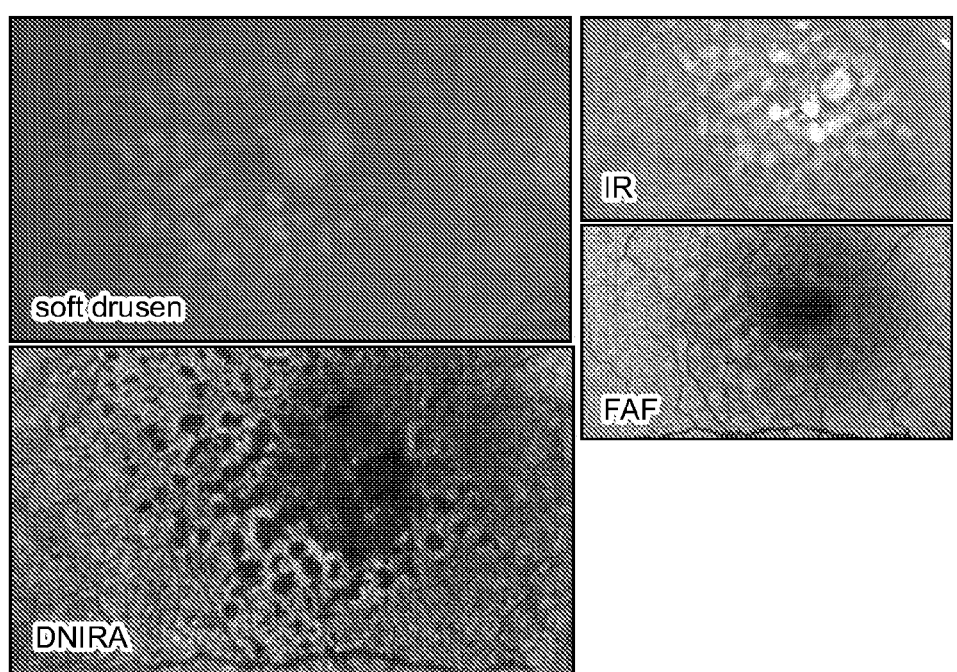
FIG. 13 depicts representative DNIRA images compared to corresponding IR, FAF and fundus photo. The top left is a fundus photo showing drusen, the bottom left the corresponding DNIRA image showing regions of black where the drusen are. The right panel shows IR (top) and FAF (bottom) where drusen are typically mode difficult to detect.

In some cases, output data can be depicted as multiple black dots as represented in FIGS. 12 and 13. Unlike FAF, the DNIRA signal is black where RPE is separated from BM & choroid by structures such as drusen (arrows overlaid on the DNIRA image show representative drusen). As depicted in FIG. 13, soft confluent drusen demonstrate oblong footprints that are profoundly hypofluorescent (black) using DNIRA. Soft drusen are typically defined by colour fundus photography. They are grey-scale, and hence not quantifiable in other wavelengths.

In some cases, output image data obtained by DNIRA can be compared output image data obtained by other methods to elucidate features of the image pair that would not necessarily be apparent when analyzing the images in isolation. For example, FIG. 12 depicts comparative retinal images obtained by IR, FAF, DNIRA, and OCT imaging. Arrows indicate the location of drusen visible in the DNIRA image. These drusen are not readily visible in the corresponding IR or FAF images. FIG. 14 also shows differences between images acquired using DNIRA with images acquired by FAF. FIG. 14 depicts a representative DNIRA image of a patient with central GA observed on FAF (left). As depicted in FIG. 14, image output data from FAF imaging (left) shows less black (GA) while a DNIRA image (right) shows more black. The DNIRA image (right) shows greater number of hypofluorescent signals, a greater total area of hypofluorescence, and greater amount of perimeter/border of hypofluroescence. The difference between these two images represents the "Delta" portion of the signal. The Delta Image data can be "Area of DNIRA black—(minus) Area of FAF black" which is the area of diseased or dysfunctional tissue, in absence of GA.

Figure 15A:
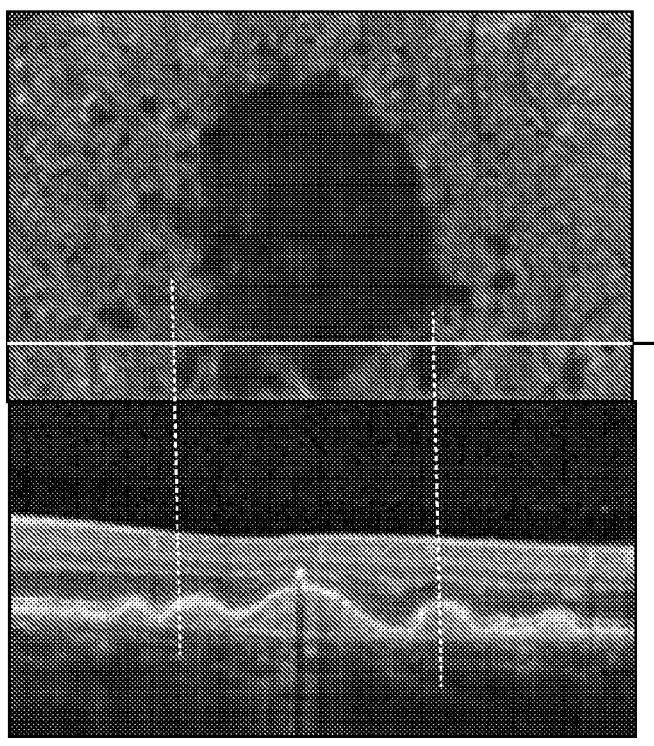
FIGS. 15A and 15B show representative output data as a visual representation comparing DNIRA to lower image representing an RPE detachment on OCT.
Figure 15B:
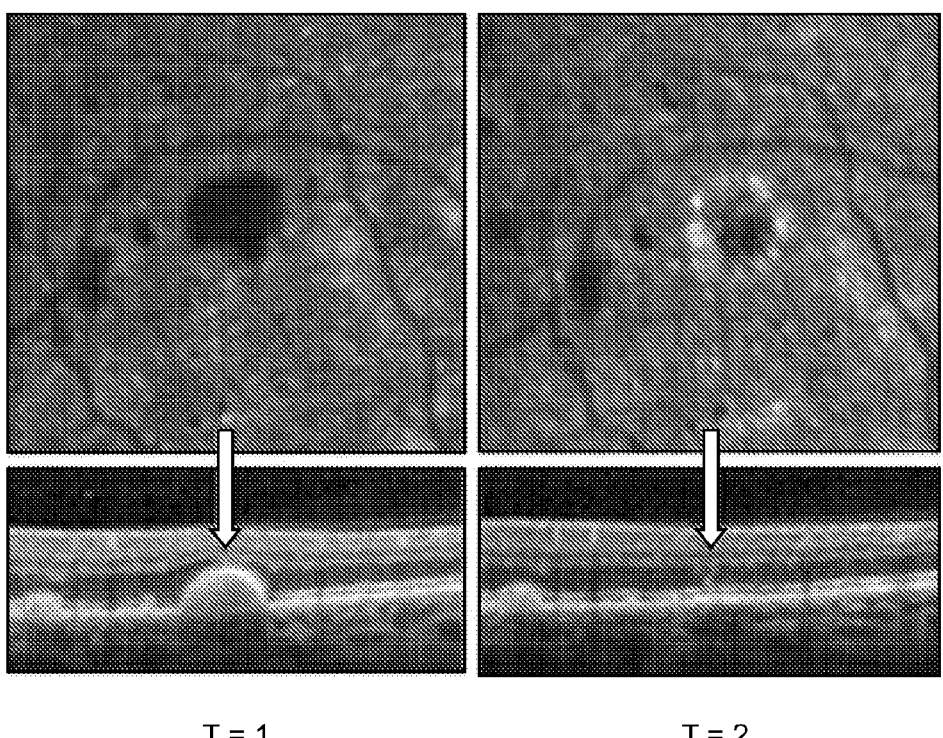

FIG. 15A shows image output data as a visual representation with an upper image representing a large RPE detachment appears black using DNIRA and a lower image representing OCT shows elevation of RPE layer (elevated thick white line). Blue horizontal line indicates level at which OCT cross-section was obtained. FIG. 15B shows image output data as a visual representation with a left image having an upper portion for DNIRA that shows region of black and a lower portion for OCT that shows small drusenoid RPE detachment (definition >200 μm). A right image has an upper for DNIRA that shows some remaining black signal and a lower portion for OCT that shows resolution of RPE detachment. Note that the right image also shows association of bright dots with RPED suggesting the presence of macrophages.

Figure 16:
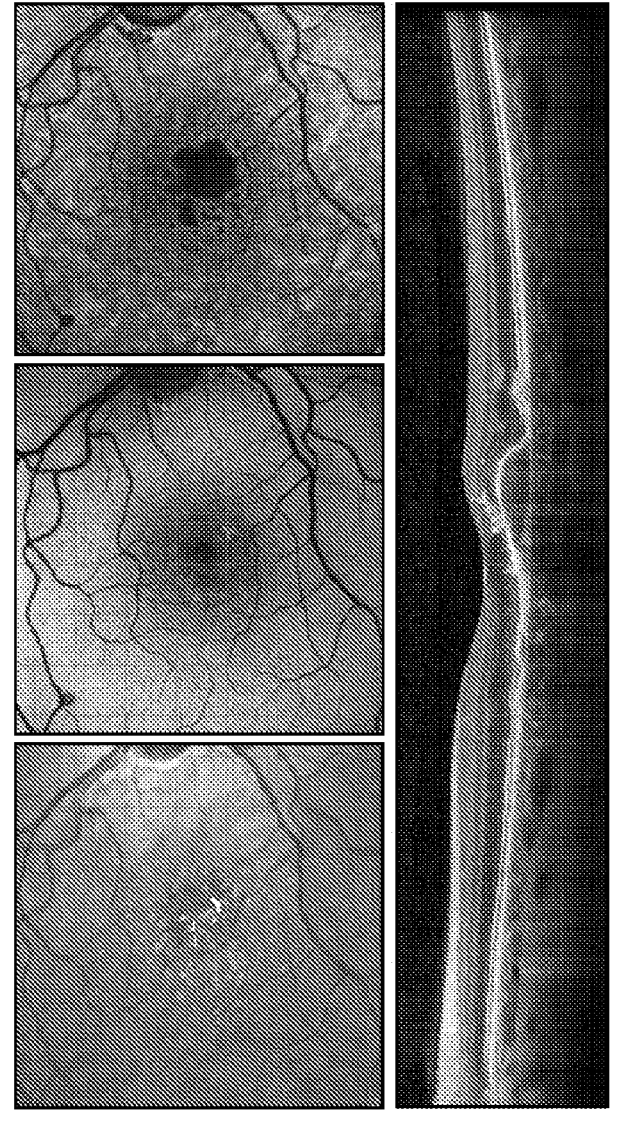
FIG. 16 shows image output data as a visual representation comparing IR, FAF and OCT with DNIRA.

In some aspects, analysis of image data from multiple imaging methods can be used to visualize features of an RPE. FIG. 16 shows image output data as a visual representation with the left image for IR, the middle image for FAF, and the right image for DNIRA. Hypofluorescent (black) regions indicate loss of RPE.

In some instances, images can be collected as a function of time in order to elucidate changes in a disease state or condition. For example, FIG. 17A shows image output data as a visual representation of a left image a time t=1, a middle image at t=2, and a right image at time t=3 (all 4 months apart). The region of black is greater in first image than the second, indicating that feature is decreasing. FIGS. 18 and 19A-19J show assembly of TAMi composites can allow for correlation of the disclosed imaging method with current clinical modalities. Fundus autofluorescence (FAF, FIG. 19B) and TAMi composites (FIG. 19C) were assembled as an overlay on color photographs (FIG. 19A). Multi-modal analysis allowed identification of regions of interest (FIG. 19F) including the tumor region (i), areas of current or previous fluid (ii), and peripheral (extra-lesional) regions (iii). Region area in mm² was determined using ImageJ measurements and used in hyperfluorescent dot density calculations (FIG. 19H). These were compared across patients with melanomas, indeterminate lesions, or benign nevi, as determined by clinician ground truth. Mean dot density is shown as number of dots/mm2±SEM. One-way ANOVA and post hoc multiple comparisons (FIG. 19I) show significantly higher dot densities in melanoma arms when considering lesion and fluid regions, but not in peripheral regions. (FIG. 19J) Multiple comparisons of dot density in each region within risk group's fond melanoma had significantly higher dot density in lesion and fluid regions when compared to peripheral areas. This was not observed in other risk groups.

Hypofluorescent DNIRA Signal

In some aspects, a method can comprise identifying discrete regions of the eye, for example within the macula, where a dye, fluorophore, chromophore or chemiluminescent molecule that should otherwise be internalized, taken up, processed or accumulated, cannot be, (or can to a lesser extent) thus precluding or reducing its detection. This may occur within particular layers or tissues such as, by way of non-limiting example, discrete regions of the RPE monolayer. Such regions, made visible by their hypofluorescent/black signal, can be identified and quantified by DNIRA/AMDI, both within a single image and their rate of change calculated across multiple images over time.

Similar observations have been made using for example FAF, in which regions of absent signal correspond spatially with regions of RPE/photoreceptor loss, as occurs with Geographic Atrophy. FAF detects an endogenous fluorophore produced by the photoreceptors and accumulated within RPE, and so too when RPE is lost, the FAF signal is lost. Because regions of GA cannot regress, e.g., become smaller in size, area of profoundly hypofluorescent/black FAF either remain the same or increase in size over time.

Aspects described herein relate in part to the temporal changes in DNIRA images that demonstrate expansion over time. Without wishing to be limited by theory, such increases in the areas of hypofluorescent/black DNIRA could represent increased burden of disease. As such these regions could represent areas where abnormal or damaged RPE/photoreceptors are not able to internalize dye. Again, without wishing to be limited by theory, such increases could (i) represent regions where changes in tissue anatomy preclude or reduce dye uptake in the presence of otherwise normal RPE/photoreceptor cells or (ii) represent regions where the anatomy is normal, but the cellular physiology is abnormal.

In some aspects, temporal changes in DNIRA images can be employed to demonstrate reduction of profoundly hypofluorescent/black areas over time. Without wishing to be limited by theory, such decreases in the areas of hypofluorescent/black DNIRA could represent decreased, improved, or lessened burden of disease. As such these regions could represent areas where abnormal or damaged RPE/photoreceptors are better able to internalize dye. Again, without wishing to be limited by theory, such reductions in hypofluorescent/black signal could also represent regions where changes in tissue anatomy are improved, thereby facilitating uptake of dye in the presence of otherwise normal RPE/photoreceptor cells. As example, such reduction could occur with resolution of an RPE detachment (RPED) that permits the RPE layer to re-appose itself with its underlying Bruch's membrane, and so facilitate transfer and uptake of dyes such as ICG from the underlying choroidal vasculature. Such reduction in the size of hyperfluorescent/black regions is not reported using FAF or other imaging modalities. As such, these features demonstrate the dynamic quality of DNIRA, distinguishing it further from FAF and other static imaging modalities.

Figure 10:
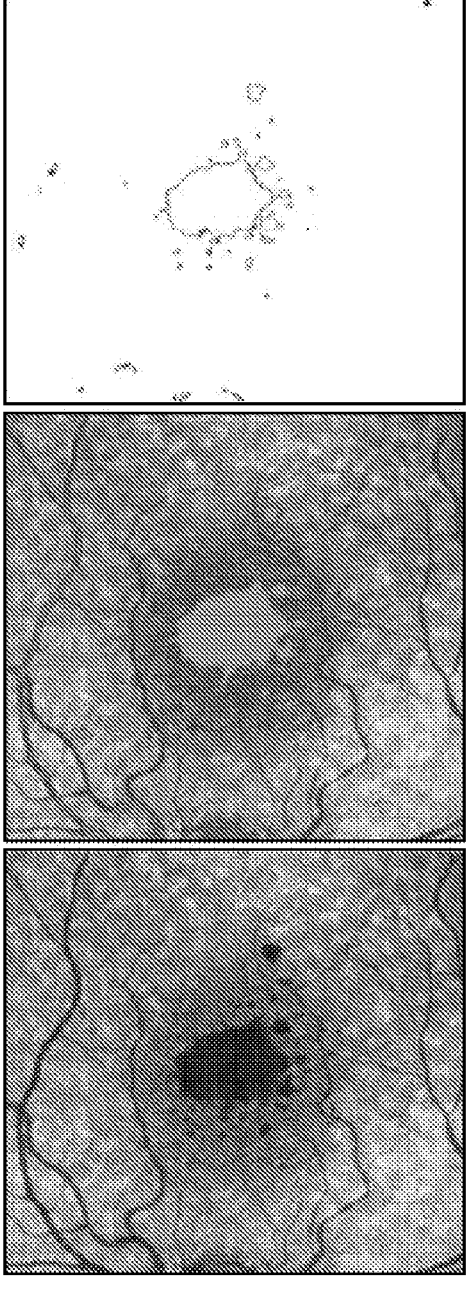
FIG. 10 depicts segmentation and feature extraction of a DNIRA image. In the left panel, DNIRA identifies regions of profound hypofluorescence (central black region). In the middle panel identification of the region of DNIRA hypofluorescence is shown. In the right panel segmentation is used to select regions of hypofluorescent DNIRA signal, enabling for further feature extraction and quantification.

Aspects described herein can relate to temporal changes in DNIRA/AMDI that demonstrate the persistence of profoundly hypofluorescent/black regions that remain unchanged over time. When coincident with profoundly hypofluorescent/black regions of FAF, they are hypothesized to reflect regions of RPE/photoreceptor loss, after it is dead and gone. By contrast, other regions of profoundly hypofluorescent/black regions of DNIRA may reflect, without wishing to be bound by theory, anatomical areas that preclude the uptake of dyes such as ICG from the underlying choroidal vasculature and that they remain largely unchanged. For example, in addition to RPE detachments that separate the RPE/photoreceptors from the underlying choroidal vasculature, the interposition of small deposits known as drusen, basal laminar deposits or basal linear deposits, could also preclude uptake of dye (FIG. 10). As such, the presence of profoundly hypofluorescent/black dots, measured to be consistent in size and location with drusen observed in other imaging modalities (e.g. IR, red free, color fundus photography, OCT, angiography, OCTA), could provide a novel method for measuring total drusen area. Without wishing to be bound by theory, drusen volume is considered an overall measure of the burden of disease, but their quantification is difficult owing to their grey-scale nature using imaging methods such as IR or FAF, and the need for 3-dimensional (3D) volumetric reconstruction in other methods such as OCT. In this aspect, the ability to quantify small, profoundly hypofluorescent/black dots in a given size range, for example larger than a droplet (a small non-pathological aging deposit) and smaller than a drusenoid RPED (e.g. 200 to 250 µm) could provide an entirely novel method of quantifying the burden of disease.

Mid-Grey Hypofluorescent Signal

In some instances, AMDI identifies regions of mid-tone grey—neither profoundly hyperfluorescent/black nor brightly hyperfluorescent. These 2D regions occur in some but not all subjects, and may occur in the presence or absence of pre-existent GA (as determined by FAF for example). Unlike the profoundly hypofluorescent/black regions, no structural abnormality (e.g. no drusen, no RPE detachments, no GA) was observed. Instead, RPE cells and the retina appear anatomically normal both using other en face modalities (e.g. IR, FAF, red-free, color, angiography, OCTA and others) and in cross-section (e.g. OCT). These cells may be physiologically deranged, damaged, or genetically distinct from normal cells, as so are unable to internalize dyes such as ICG. As such, in some aspects, AMDI can be used to identify and quantify dysfunctional RPE/retina.

Figure 20:
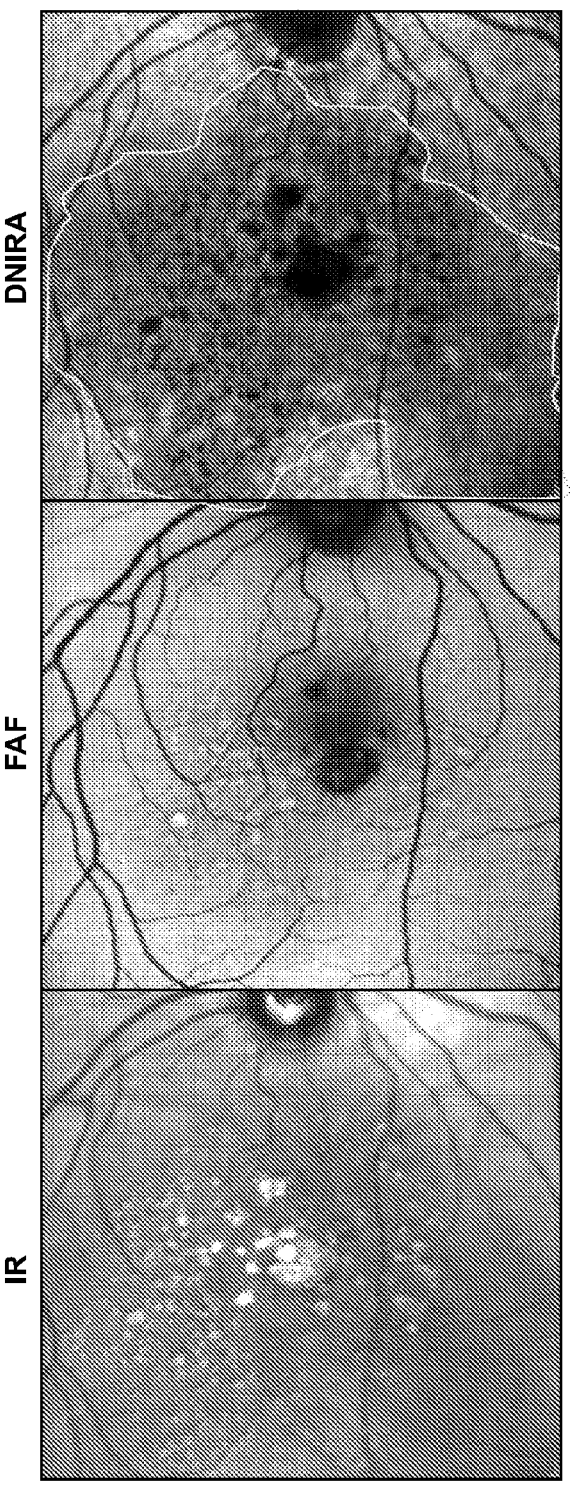
FIG. 20 shows comparative retinal images obtained by IR, FAF, and DNIRA imaging to detect intermediate grey signal in the DNIRA image. Unlike FAF, the DNIRA image reveals abnormal or "sick" RPE as a darker grey.
Figure 21B:
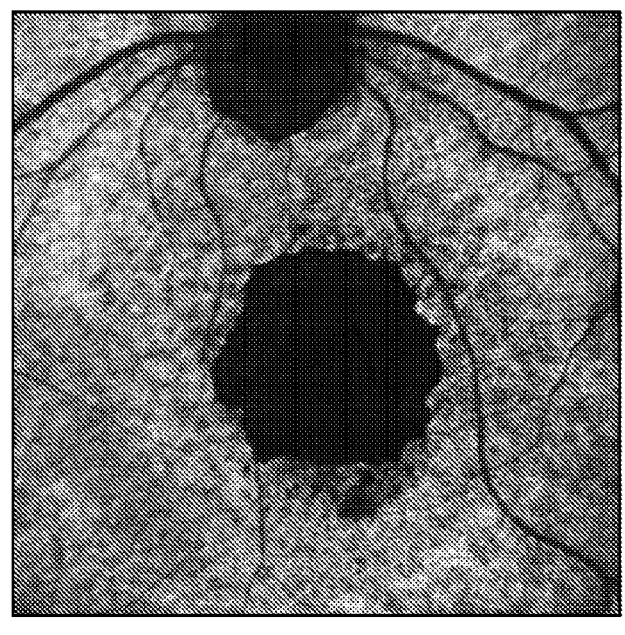
FIGS. 21A-21E depicts examples of patterns that have an interwoven, lacy, reticular or spot-like configuration. In some instances are observed patterns that are more coarse (wider) in aspect or finer (tighter) in aspect. These patterns may be indicative of different subtypes of AMD and therefore different response to therapeutic options.
Figure 21A:
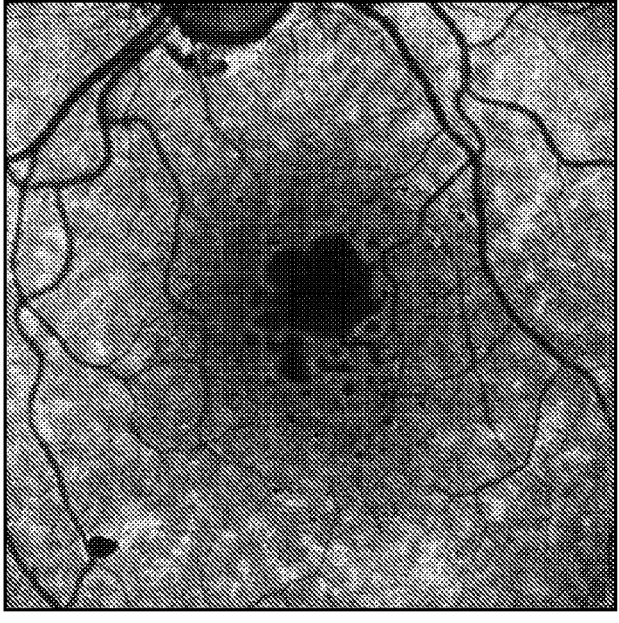
Figure 21E:
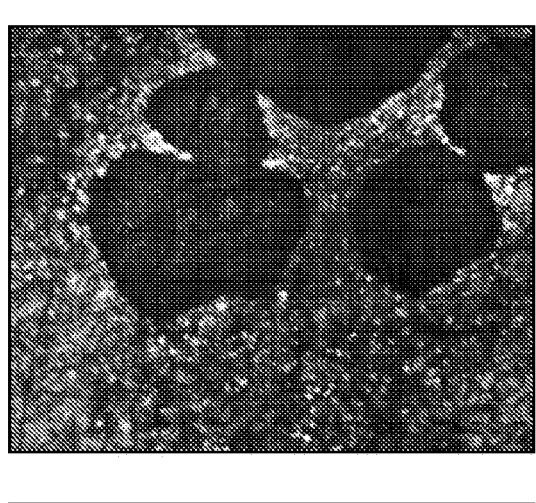
Figure 21D:
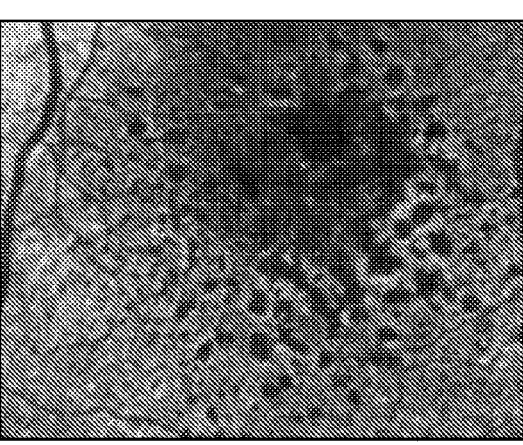
Figure 21C:
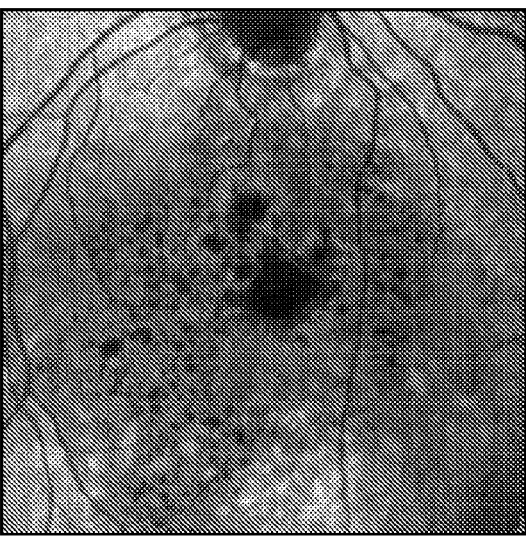

FIG. 20 shows comparative retinal images obtained by IR, FAF, and DNIRA imaging. Unlike FAF, regions of apparently "normal" RPE appear an intermediate grey in the DNIRA image. Unlike FAF, the DNIRA image reveals abnormal or "sick" RPE as a darker grey (highlighted by the yellow line) against an intermediate grey background.

Hyperfluorescent Signal Processing

In some aspects described herein, an in vivo functional imaging method can be employed for the detection of phagocytic immune cells, e.g. macrophages or microglia (collectively macrophages), in the eyes of subjects with an ocular disease or disorder. The system 100 implementing DNIRA identifies presumptive macrophages in the eyes of subjects with intra-ocular tumors and AMD, placing these potentially aggressive cells in proximity to regions of tissue damage and inflammation. Further, complex 2D patterns of hyper-, normo- and hypo-fluorescent are identified for the first time using DNIRA—these grey-scale images may be used by system 100 to implement cognitive computing for their analysis and interpretation.

At present, there may be no method for detecting immune cells in the living human eye, and because tissue biopsy is not a viable option, no method for providing clinico-pathological correlation between in vivo findings and post-mortem histopathology exists.

In some cases, system 100 can implement the following: 1) using registered DNIRA images, to identify the spatiotemporal distribution of presumptive macrophages; 2) using registered DNIRA images, to identify the co-distribution of presumptive macrophages with high-risk and late-stage features of disease; 3) using registered DNIRA images, to identify the change in the spatiotemporal distribution and co-distribution of macrophages and high-risk and late-stage features of disease over time; 4) to identify novel complex patterns of disease phenotype; and 5) to compare DNIRA images against other en face and cross-sectional modalities over time. System 100 can generally implement image output processing from the image acquisition unit; registration of native images; and segmentation of images. System 100 can generally implement image output processing from the image acquisition unit. There may be challenges relating to a) selection of "best" subject images; b) slow conversion to non-proprietary image output format; c) long directory names; and d) need to be suitable for downstream batch processing. System 100 can generally implement image output processing for selection of suitable images for device-independent (agnostic) downstream analysis and processing. System 100 can generally implement registration of native images.

System 100 can generally implement segmentation of images. There may be challenges as after registration. Individual bright dots may be distinguished from areas of surrounding black and grey-scale background. Further bright presumptive macrophage dots may be quantified over time. System 100 can generally implement segmentation of image to identify spatiotemporal distribution of bright macrophages. Macrophages are believed to be associated with disease activity. System 100 can generally implement segmentation of image for selecting regions of interest "ROIs". System 100 can generally implement segmentation of image for thresholding bright signal to separate from otherwise greyscale background. System 100 can generally implement segmentation of image for identifying appropriate dot size. System 100 can generally implement segmentation of image for quantifying numbers of bright DNIRA macrophages in ROIs. System 100 can generally implement segmentation of image to -indicate range of allowable error for thresholding to capture bright signal. System 100 can generally implement segmentation of image to indicate range of allowable error for capturing dot size.

System 100 can generally implement segmentation of image to correlate distribution of bright macrophages with regions of high-risk disease features. High risk features of disease can predict disease progression; therefore correlating macrophages to these high risk features may provide another biological predictor of disease and increase the predictive power. System 100 can generally implement segmentation of image for selecting ROIs in areas of disease activity. System 100 can generally implement segmentation of image for quantifying numbers of bright DNIRA macrophages in ROIs using processes described herein.

System 100 can generally implement segmentation of images to identify the change in the spatiotemporal distribution and co-distribution of macrophages and high-risk and late-stage features of disease over time. Macrophages are highly plastic and dynamic cells that change spatially and temporally based on their tissue environment, therefore their changes can further help predict future disease activity. System 100 can generally implement segmentation of images for thresholding bright signal to separate from otherwise greyscale background. System 100 can generally implement segmentation of images for identifying appropriate dot size. System 100 can generally implement segmentation of image for capturing bright dots in ROI to quantify. System 100 can generally implement segmentation of images for comparing bright dots in ROI from one timepoint to the next which may indicate a change in quantity (increase/decrease over time), or a change in localization within the same ROI (no increase/decrease but spatial change).

System 100 can generally implement segmentation of images to identify complex patterns of disease phenotype. Imaging macrophages in vivo in the subject eye has never been reported before, and disclosed herein are methods that identify new patterns that have not been previously identified and need to be characterized. System 100 can generally implement segmentation of images for thresholding bright signal to separate from otherwise greyscale background. System 100 can generally implement segmentation of image for identifying appropriate dot size. System 100 can generally implement segmentation of image for identifying clusters of grouped dots. System 100 can generally implement segmentation of image for identifying commonality in clusters of dots to depict distinct patterns that share features across subjects. For example, a similar numbers of grouped dots, similar distances between clusters, and similar patterns of localization may provide an indication.

System 100 can generally implement segmentation of image to compare DNIRA images against other en face and cross-sectional modalities over time. DNIRA provides features that are unprecedented by other ophthalmic modalities, and by comparing to other modalities can increase the power associated with DNIRA, but also help identify potential features in those modalities, the biology of which has been unknown before. Example comparisons include DNIRA vs FAF, DNIRA vs OCT, DNIRA vs IR, DNIRA vs NIR-AF, DNIRA vs RF, DNIRA vs angiography, DNIRA vs OCTA.

The following provides an example of registration and analysis with reference to FIG. 20 which provides an example graphical representation of image data. The system 100 can register each timepoint using the linear stack alignment with SIFT plugin with the following (mostly default) settings (determined through trial-and-error): Initial Gaussian blur: 1.60 pixels, Steps per scale octave: 3 pixels, Feature descriptor size: 4 pixels, Feature descriptor orientation bins: 8, Closest/next closest ratio: 0.92, Maximal alignment error: 25 pixels, Inlier ratio=0.05. The expected transformation may be Affine. The system 100 can subtract a blurred version of each image from the original image. This should remove most of the image background, but the contrast may be low as a result. A blurred image provides a Gaussian blur with sigma=50 µM. The system 100 can subtract remaining background using "Subtract Background" plugin with rolling ball radius=4 µM. This helps remove last vestiges of background. The system 100 can enhance contrast, saturating 0.2% of pixels, and normalize the histogram. The system 100 can stretch histogram of timepoint 2 to mimic pixel intensity of timepoint 1 using the "Bleach Correction" plugin. This is done because differences in averaging number, shadows, and more can alter relative brightness of dots between two timepoints. Since a threshold may be applied, dots may be similarly bright in both images. This plugin was originally intended to compensate for diminishing signal intensity when imaging sensitive fluorophores over long periods of time. The system can apply "Intermodes" thresholding algorithm, and convert to mask. In this step, anything above a threshold intensity value as determined in the "intermodes" algorithm can be captured, and everything else can be removed. In theory, this should select only the brightest signals. In some aspects, this selects all of the dots.

Furthermore, system 100 can despeckle, watershed and dilate (despeckle to remove noise, watershed algorithm to separate close-together dots, prevents the program from wrongly identifying a cluster of dots as a single large dot). The system 100 can use "image calculator" feature to go pixel-by-pixel, selecting for "max" and "min" brightness values between two timepoints with an explanation for this is outlined in the next slide. The system 100 can subtract a "max" image from a "min" image. System 100 can analyze particles with following settings Size <400 $\mu M^2$, circularity=0.50-1.00. Back-calculating, 400 $\mu M^2$ leads to a diameter of 22 $\mu M$. This is reaching macrophage territory in terms of size, but this also reaches the current resolution limit of DNIRA. The blur associated with the point-spread function means that the dots in DNIRA are likely larger than the source of said dots. System 100 can use appropriate means to conduct a Manders co-localization test. This is a co-localization test commonly used for IHC, but is now being applied to test the system's ability to identify static vs dynamic dots.

Hyperfluorescent DNIRA Signal

In some aspects, DNIRA can identify small hyperfluorescent dots in the eyes of subjects. Surprisingly, some of these dots are stationary between subject visits, while others are dynamic, being present at some timepoints and not at others, residing at different locations. Without wishing to be bound by theory, these small hyperfluorescent dots identified using DNIRA may represent phagocytic immune cells, such as macrophages, that migrate, divide, appear or disappear over time. It was previously demonstrated preclinically using DNIRA and two variants of DNIRA—ImmunoD-NIRA and Pulsed-DNIRA—that cells such as macrophages can internalize ICG and be visualized thereafter in the living eye using excitation/emission filters coincident with the spectral characteristics of the dye. Disclosed herein is the unprecedented finding that the stationary or dynamic population of dots identified in the eyes of subjects with AMD are of appropriate size and shape to be immune cells such as macrophages.

Figure 18:
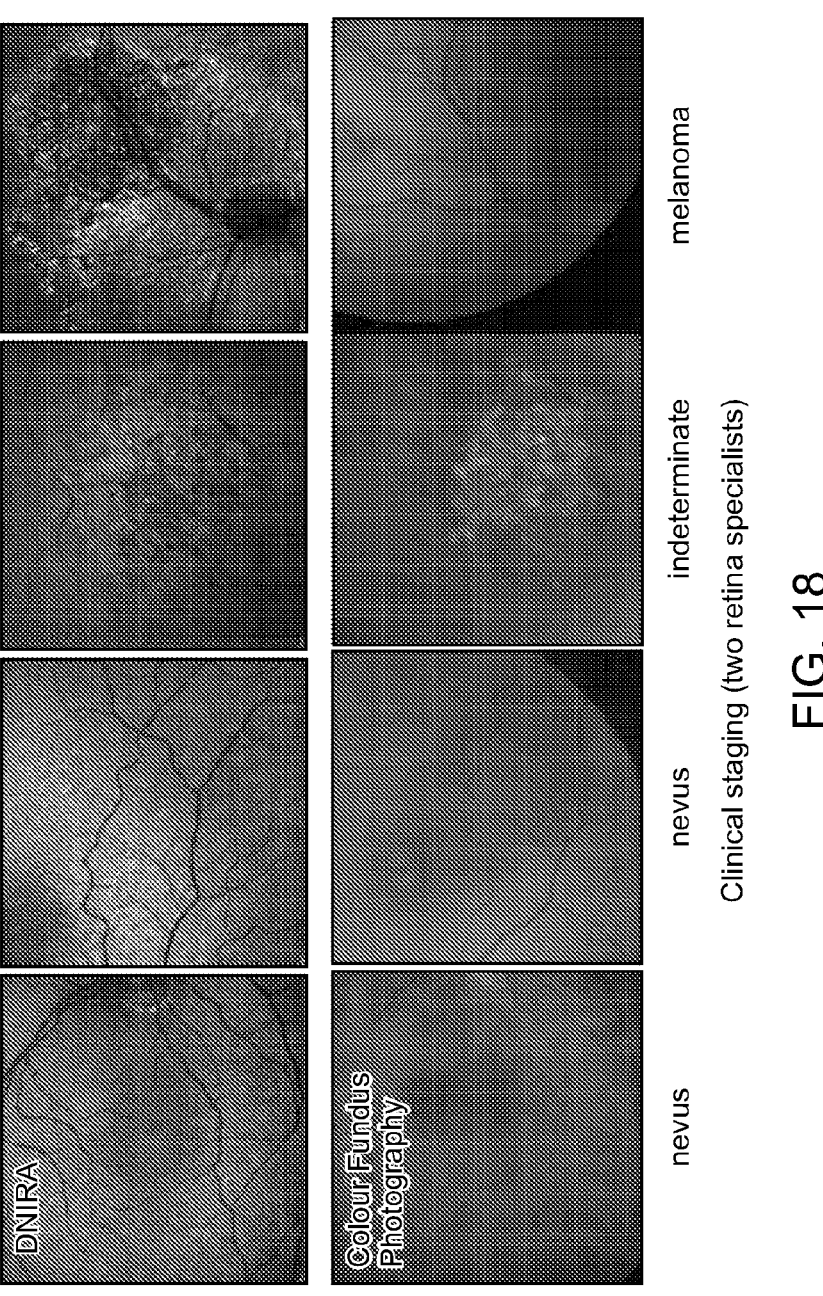
FIG. 18 depicts a comparison of DNIRA vs colour photos & clinical grading of uveal melanoma examples.
Figures 19A, 19B, 19C, 19D, 19E, 19F, 19G:
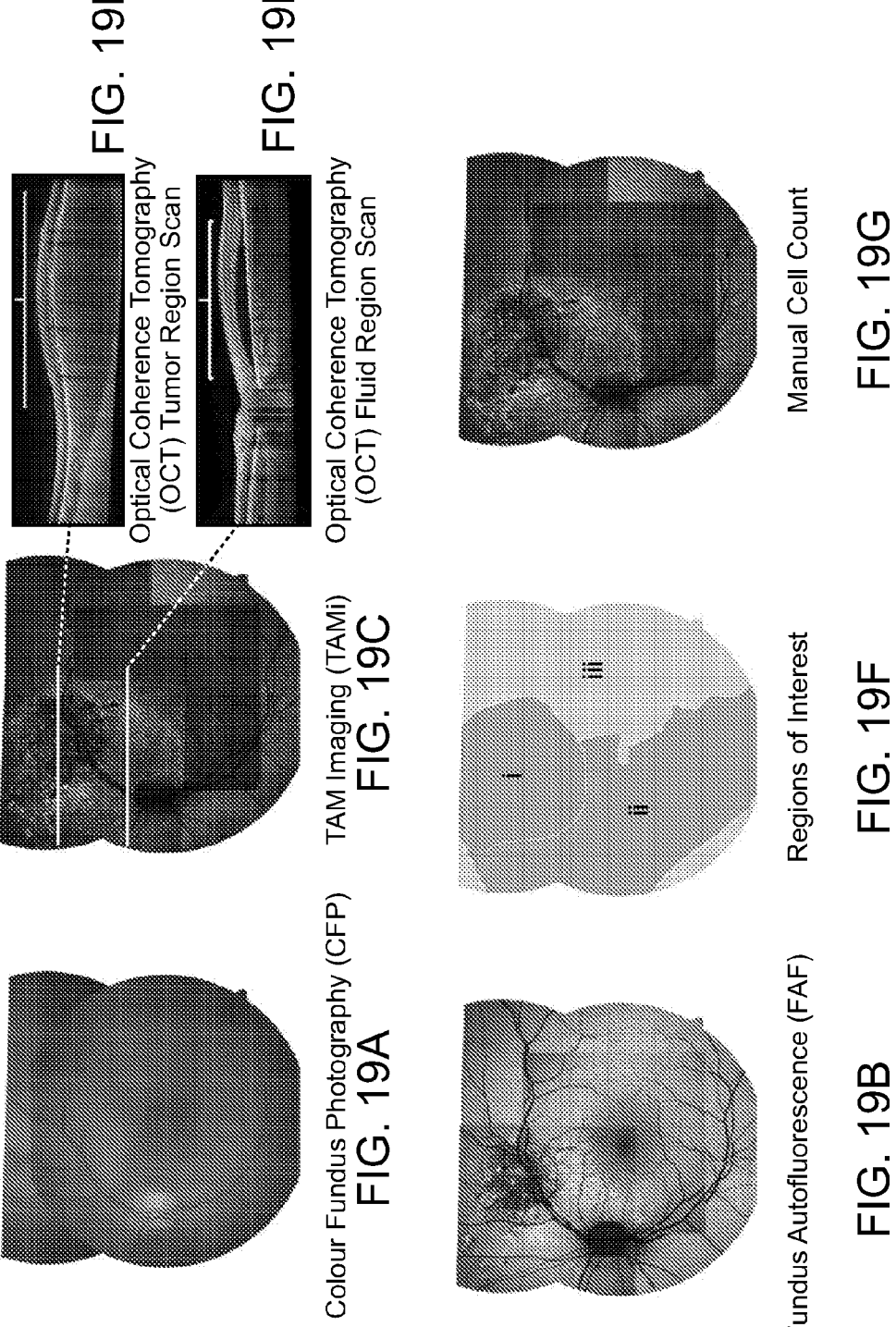
Figure 19H:
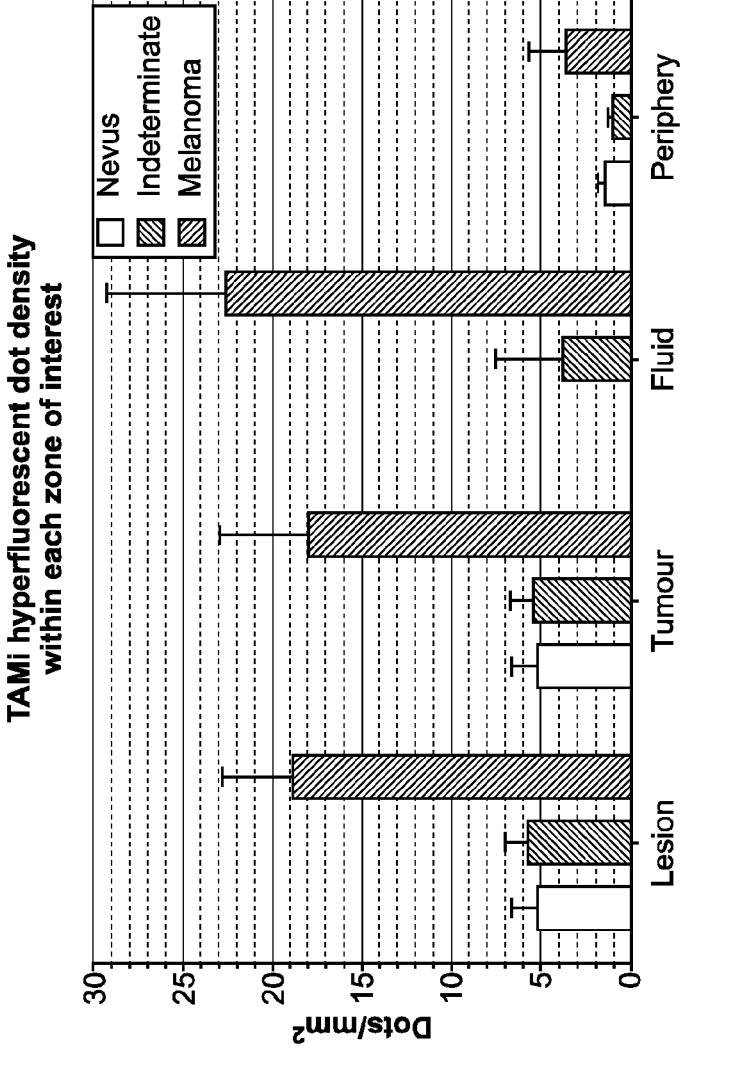

With reference to FIGS. 18, and 19, by way of proof-of-concept, it is also observed that similarly-size hyperfluorescent dots are present in eyes with uveal melanoma or high-risk indeterminate melanocytic lesions. They are absent from nevi and low-risk indeterminate lesions. Inflammation is a hallmark of cancer, and pathological specimens of uveal melanoma, particularly those of high-grade (chromosome 3 monosomy) are associated with high numbers of macrophages while nevi are not. This correlation is confirmed in vivo using DNIRA to visualize Tumor Associated Macrophages (TAMs) by way of the method termed "TAMI" (TAM Imaging). Using TAMI it is confirmed that regions of interest can be segmented based on their presence or absence of hyperfluorescent DNIRA labelled dots. These regions correspond to differences in the concentrations of bright dots, which can be quantified. Hyperfluorescent dots may be identified by number, density, concentration, size or radius, fluorescent intensity, or location. The quantification of dots correlates significantly with burden of disease, as regions with larger amounts of dots correlate to incidence of melanoma, compared to indeterminate lesions or benign nevi.

2D Patterns of DNIRA Signal

In some aspects, early studies described herein applying DNIRA/AMDI to subjects have identified a novel two-dimensional (2D) grey-scale pattern, as observed in FIGS. 21A-21E. These can occur centrally within the macula, or more peripherally in the macula or the mid-retina. These patterns often have an interwoven, lacy, reticular or spot-like configuration. In some instances are observed patterns that are more coarse (wider) in aspect or finer (tighter) in aspect. Without any precedent, in some cases these are termed "loose weave" (FIG. 21A) or "tight weave" (FIG. 21B), respectively. These patterns may be indicative of different subtypes of AMD and therefore different response to therapeutic options, as depicted in Example 7.

It therefore follows, that in some aspects, logical and software algorithms may be used to identify and categorize or stratify subjects by their 2D patterns observed using DNIRA/AMDI. As these patterns are not readily described by conventional software programming (e.g. registration and segmentation), unstructured computational algorithms are applied to refine their description.

Delta—Comparing FAF and DNIRA

In some aspects, there is provided a method for distinguishing regions of profoundly hypofluorescent/black signal in FAF (where RPE/photoreceptors are dead and gone) from regions that are profoundly hyperfluorescent/black in DNIRA. Compared against FAF, DNIRA images always have the same or greater amounts of profoundly hypofluorescent/black areas than does FAF, enabling us to calculate the difference, or delta, as depicted in FIG. 14. This delta may represent RPE/photoreceptors with abnormal physiology rather than their loss. Thus, in some aspects, DNIRA can detect regions of disease.

Some aspects can relate to the changes in DNIRA images compared against other imaging modalities (for example, FAF, IR, color, red free, segmented or non-segmented cross-sectional or en face OCT, OCTA providing the difference between the two modalities, delta).

It additionally relates to the temporal changes of DNIRA over time compared against the temporal changes of FAF over time. For example, and without wishing to be limited by theory, regions of profoundly hypofluorescent/black DNIRA seen at timepoint 1 may precede, and be predictive of changes seen in other modalities such as FAF at a later time. As such, DNIRA can be seen as a method for detecting early change. It therefore follows, that in some aspects, DNIRA can identify regions of RPE/photoreceptor damage before its loss and before the onset of profoundly hypofluorescent/black regions of RPE/photoreceptor loss detected using FAF. Accordingly, DNIRA/AMDI can therefore be used to identify subjects at risk of developing GA, e.g., progressing from early to late dry AMD. As such, DNIRA provides a novel method of identifying subjects for enrollment in clinical trials to prevent the onset of GA, or for treatment should one arise.

Logical Biology-Driven Hardware and Software for Image Processing

Aspects described herein relate to the logical algorithms used to drive software and hardware design. These include, but are not limited to those described above, e.g. temporal changes in DNIRA and cross-modality difference between DNIRA and other methods, and the temporally-related cross-modality changes. AMDI has not previously been reported. Exemplary data disclosed herein are derived from the first application of DNIRA to the clinical setting. Accordingly, each of these observations is novel. In some cases, systems described herein can comprise software modules that implement the logical processes described herein. Furthermore, a system described herein can comprise an integrated image processing, image analysis and image output platform.

In some aspects, such logical and software algorithms can identify, quantify and align regions of profoundly hypofluorescent/black DNIRA over time and between modalities. In some aspects, such logical and software algorithms can identify, quantify and align hyperfluorescent dots, evaluating their numbers, size and location. Such logical and software algorithms can identify, quantify and align bright hyperfluorescent dots relative to regions of profoundly hypofluorescent/black DNIRA over time and between modalities. Without wishing to be bound by theory, spatiotemporal localization of presumptive immune cells such as macrophages in proximity to areas of RPE/photoreceptor loss, implicates phagocytic activity with RPE/photoreceptor loss. Co-localization is described herein. As such, DNIRA could be used to identify subjects suited to immunomodulatory therapies.

In some aspects, the ocular disease or disorder can be one or more of dry AMD, RPD, white-dot syndromes (e.g. serpiginous chorioretinopathy, serpiginous retinopathy, acute posterior multifocal placoid pigment epitheliopathy (APMPPE), multiple evanescent white dot syndrome (MEWDS), acute zonal occult outer retinopathy (AZOOR), punctate inner choroidopathy (PIC), diffuse subretinal fibrosis (DSF)), late onset retinal degeneration (LORDs; e.g. Q1qTNF5 deficiency), and central serous retinopathy (CSR). In some aspects, the ocular disease or disorder can be Lecithin Retinol Acyltransferase (LRAT) deficiency, which is optionally associated with: lrat-related leber congenital amaurosis, and retinal dystrophy, early-onset, severe. In some aspects, the ocular disease or disorder can be fundus albipunctatus, which may be associated with one or more of the following genetic locations: 3q22.1 (Retinitis punctata albescens, RHO); 6p21.1 (Retinitis punctata albescens, PRPH2); 12q13.2 (Fundus albipunctatus, RDH5); 15q26.1 (Retinitis punctata albescens, RLBP1); and 15q26.1 (Fundus albipunctatus, RLBP1). In some aspects, the ocular disease or disorder can be one or more of dry AMD and RPD disease. In some aspects, the presence of phagocytic immune cells is measured by DNIRA.

In some aspects, the ocular disease or disorder can be one or more of a diabetic eye disease (for instance, diabetic retinopathy and DME), Vogt-Kayanagi-Harada disease (VKH); Sarcoid uveitis; Ocular histoplasmosis and/or Presumed Ocular Histoplasmosis Syndrome; idiopathic uveitis, Autoimmune uveitis; Uveitis associated with systemic diseases, e.g. lupus, Crohn's disease, rheumatoid arthritis, and other diseases of known immune origin; Posterior uveitis (including that which may not yet be diagnosed); Anterior uveitis (e.g. iritis); Bechet's disease; Polyarteritis nodosa; and Wegener granulomatosis. This is depicted in Example 21, and FIG. 39.

In some aspects, the RPD disease can be identifiable by the presence of one or more areas of distinct patterns of retinal imaging in the eye of a subject. The retinal imaging can be one or more of white light, red-free light, blue light, FAF, near infra-red (NIR), infra-red (IR), angiography, and DNIRA and/or the presence of one or more areas of abnormally-fluorescent FAF in the eye of a subject and/or an increase (including a transient increase) in permeability across the subject's epithelial barrier between a choroid and a retina relative to an undiseased state and/or a presence of phagocytic immune cells across the subject's RPE relative to an undiseased state.

In some aspects, a method can determine whether an ocular disease or disorder in a subject is responsive to treatment with an agent that inhibits or modifies the function of a subject's immune cells, comprising detecting a presence, detecting an absence, or measuring an amount of immune cells in the subject's eye, wherein the subject's eye fluoresces in response to light having a wavelength of about 600 nm to about 900 nm. In some aspects, the light can have a wavelength of about 400 nm to about 900 nm A method described herein can further comprise administering to the subject an effective amount of a fluorescent compound, wherein the detecting or measuring occurs at least one day after the administration of the fluorescent compound. In some aspects, the detecting or measuring can occur at least one day after administering to the subject an effective amount of a fluorescent compound. In some aspects, the methods described herein can further comprise the step of detecting or measuring FAF in the eye of the subject. In some aspects, the methods described herein can further comprise the step of correlating an FAF pattern to the presence, absence, or amount of immune cells in the subject's eye. In some aspects, the detecting or measuring can comprise performing cSLO, FAF, DNIRA, OCT, or OCTA, and correlating these modalities to the presence, absence of amount of immune cells in the subject's eye. In some aspects, the immune cells can be cells of the subject's innate immune system and/or macrophage and/or microglial cells, dendritic cells, monocytes, mononuclear phagocytes, phagocytic immune cells.

DNIRA

In various aspects, system 100 can use optical imaging, using various techniques. For example, such techniques include, but are not limited to fundus photography, cSLO, FAF, angiography, OCT, OCTA, including three dimensional reconstructions of such. In various aspects, exposing an eye to light comprises performing cSLO, FAF, DNIRA, angiography or OCT. In various aspects, the imaging is DNIRA. In various aspects, combinations of any of the above techniques may be used.

The inventor previously demonstrated that following systemic delivery of sodium iodate, patches of hypofluorescent FAF are not observed in vivo in areas of RPE loss (in the non-clinical setting, i.e., non-human eye) as would be predicted from clinical investigation (data not shown). However, by pre-labeling the RPE with a fluorescent dye, such as the near infra-red (NIR) dye indocyanine green (ICG), a technique called Delayed Near InfraRed Analysis (DNIRA), the RPE is made visible using cSLO imaging. Once labeled, areas of RPE loss become apparent as quantifiable patches of hypofluorescence similar to those observed clinically. In various aspects, NaIO3, FAF and DNIRA may be used together to show, by way of example, the relationship between RPE loss, macrophages, macrophage polarization, and regulation of the M1 response.

For DNIRA, a compound suitable for fluorescence detection including a near-infrared (NIR) dye, such as, ICG when given at non-toxic doses, can label the RPE and therefore make it visible when viewed using the ICG excitation/emission filters in the days or weeks thereafter. Importantly, this visualization in the days and weeks thereafter may be without re-administration of dye. Accordingly, in some aspects, a central component of the DNIRA technique lies in its timing. This is distinct from the present usage of ICG or other angiographic dyes that are viewed immediately after injection, during the transit phase, or in the immediate minutes to hours following injection, to determine the intravascular localization of dye and its immediate extravasation.

In some aspects, DNIRA can be used in a laboratory animal. In one aspect, DNIRA may involve administration of a compound suitable for fluorescence detection, by way of non-limiting example, ICG (and, optionally, angiography) at about one or more days prior to administration with a toxin or other agent that causes patchy geographic areas of RPE loss (e.g. NaIO$_3$) and optionally followed by, at about 1 or more days (or about one week, or about one month, or about three months), an additional amount of NaIO$_3$ or another agent that causes expansion of the areas of patchy RPE loss. For example, the other challenge that causes geographic atrophy expansion (e.g. as an initial, or second, or third, or fourth administration) may be a modulator of cell survival, cell death, survival, autophagy, proliferation, regeneration, and the like.

In various aspects, the DNIRA technique can be used in a human subject. For example, DNIRA in a human subject may not comprise the use of a toxin. DNIRA in a human subject may comprise the evaluation of normal or disease-associated changes in the eye, using a fluorescent dye, with the excitation/emission filters in place but no angiography and following a delay of hours or days after dye administration.

Expansion of geographic atrophy is a U.S. Food and Drug Administration (FDA) acceptable primary outcome for clinical trial design. Accordingly, methods and systems as described herein can make possible observation of geographic atrophy, in particularly the expansion of geographic atrophy, in an animal model, thus permitting correlation between pre-clinical disease models and clinical trial design. The inability to clearly identify the geographic atrophy, or expansion of geographic atrophy, in an eye of an animal has precluded direct correlation between pre-clinical studies and clinical observation. Further, in some aspects, a system as described herein can allow for clinical evaluation of the size and rates of expansion of geographic atrophy, including the expansion of geographic atrophy, in a human subject.

In some aspects, the compound suitable for fluorescence detection can be suitable for imaging with various wavelengths of fluorescence. In some aspects, these wavelengths range from visible light to infrared, e.g., 390 nm to 1 mm, including, for example, blue light, white light, and near-infrared. In some aspects, the dye is a near-infrared dye. In some aspects, the dye is ICG.

In some aspects, DNIRA can be performed (and/or delayed near infrared fluorescence (DNIRF) is observed) at about 6 hours, 12 hours, 24 hours, or about 2 days, or about 3 days, or about 4 days, or about 5 days, or about 6 days, or about 7 days, or about 10 days, or about 14 days, or about 21 day after the administration. In some aspects, the DNIRA can be performed at least 1 day after the administration, or at least 2 days, or at least 3 days, or at least 4 days, or at least 5 days, or at least 6 days, or at least 7 days, or at least 10 days, or at least 14 days, or at least 21 days after the administration. In some aspects, the DNIRA can be performed at least about 2 hours, 4, hours, 8 hours, 24 hours, or at least about 7 days, or at least about 30 days, or at least 60 days, or at least 90 days after administering. In some aspects, the DNIRA may not performed during the transit stage (e.g. the first passage of dye as it flows through the ocular blood vessels and into the ocular tissue) or minutes thereafter. In some aspects, angiographic imaging may not be required, thus further distinguishing current dye-based imaging systems from DNIRA.

In some aspects, the visualization can be effected using a cSLO. In some aspects, the visualization can be effected using white light and appropriate filters. In some aspects, the ICG excitation/emission filters can be 795 nm (excitation)/810 nm (emission) filters. In some cases, the visualization can be effected using a fundus camera or other ocular imaging device with appropriate spectra.

The RPE is a critical epithelial monolayer that serves a "nurse-cell" function for an eye's specialized photoreceptors, the rods and cones. Ocular diseases or disorders, such as, for example, AMD and RPD, are, without wishing to be bound by theory, causally linked in part to abnormalities of the RPE. DNIRA makes it possible to clearly identify the RPE layer in vivo in an eye of an animal. Further, the leading technique used to detect the RPE in the human eye, FAF, is ineffective or poorly effective in the rodent eye (by way of non-limiting example), possibly owing to a relative paucity of fluorophores such as lipofuscin. FAF imaging in the human eye is performed using the blue spectrum of non-coherent light in the presence of stimulation/emission filters, or coherent blue light, and can identify areas of absent RPE (e.g. hypo-fluorescent signal) or abnormal RPE (e.g. hyper-fluorescent signal). The inability to clearly identify the RPE in an eye of an animal, in the absence of DNIRA, has precluded direct correlation between pre-clinical studies and clinical observation.

Accordingly, in various aspects, methods to make visible the RPE layer, such as, for example, DNIRA, in an eye of an animal for pre-clinical investigation of ocular diseases or disorders are provided. Further, as described herein, DNIRA, or variations thereof, can allow for visualization of fluorescent immune cells in the eyes of an animal. Further, as described herein, DNIRA, or variations thereof, can allow for visualization of fluorescent immune cells in the eyes of human subject. In some aspects, the practicing of a method described herein with a human subject may not comprise toxin administration.

In some aspects, DNIRA can be used in the identification of an agent that is effective for treating an ocular disease or disorder. In some aspects, DNIRA can be used as a method to evaluate a subject that has, or may have, an ocular disease or disorder (including, without limitation AMD and RPD). In some aspects, DNIRA can be a surrogate biomarker for diagnosis and/or prognosis and/or progression of an ocular disease or disorder (including, without limitation AMD and RPD). For example, DNIRA may be used to identify patterns, including lacy, reticular or leopard-like pattern of alternating hyper- and hypo-fluorescent DNIRA that is not seen in other imaging modalities, that are indicative of a ocular disease state (without limitation AMD and RPD). DNIRA may also be used to identify, and quantify, areas of hyper- and hypo-fluorescent DNIRA.

In various aspects, DNIRA can be used to identify hypo-fluorescent features of an eye. For instance, these areas appear black when imaged and therefore allow for easy quantitation (in contrast to ICG imaging, or in contrast to hyperfluorescent signal, which is grey-scale rather than black/white). Detection of hypofluorescent DNIRA, in some aspects, can be predictive of damaged or dead RPE. For example, hypofluorescent DNIRA may indicate one or more of an absence of RPE, abnormal/unhealthy RPE (which is unable to uptake ICG dye), RPE that does not lie in contact with Bruch's Membrane (and so are no longer in a position to take up ICG dye from the choroidal vasculature), and the presence of lipid that could be located either between the RPE and BM (thus blocking ICG uptake), or could be internal to the RPE (thus blocking the RPE signal).

In various aspects, DNIRA can be used to identify hyper-fluorescent features of an eye. For instance, these areas appear light when imaged and therefore allow for easy quantitation. Detection of hyperfluorescent DNIRA, in some aspects, is predictive of macrophages, including M1 and/or M2 macrophages.

In various aspects, DNIRA can be used biomarker for diagnosis of an ocular disease state (without limitation AMD and RPD) and prompts further evaluation and/or treatment with one of more agents, including without limitation those described herein. In various aspects, DNIRA can be used as a biomarker for prognosis of an ocular disease state (without limitation AMD and RPD) and prompts further evaluation and/or treatment with one of more agents, including without limitation those described herein. In various aspects, DNIRA can be used to improve identification of suitable subjects for study recruitment and to evaluate progression of disease. In various aspects, DNIRA can be used to monitor disease progression.

In various aspects, DNIRA can be used to identify regions of disease that may be amendable to gene therapies, stem/progenitor or other cell therapies, or combined gene/cell therapies. By way of non-limiting example, regions suitable for rescue by cell replacement or trophic factor support, can be identified and targeted for therapy In various aspects, DNIRA can be used as a companion diagnostic to any of the agents described herein. In various aspects, DNIRA can be used to evaluate subject response to any of the agents described herein (including evaluating the effectiveness of any of the agents described herein and/or the likelihood of response to any of the agents described herein). In various aspects, the use of DNIRA can entail entrance inclusion or exclusion criteria, or endpoint analysis for clinical trial design.

In various embodiments, the present relates to methods for evaluating a binding eye disease using the systems and methods described herein. For instance, in various embodiments, there is provided a method for evaluating a subject's eye using DNIRA (e.g. using the systems and methods described herein). In various embodiments, there is provided a method for evaluating subject's eye by administering a fluorescent compound, such as is indocyanine green (ICG), which is ingested by one or more cells (including, without limitation, retinal pigment epithelial (RPE) cells and cells of immune system such as macrophages) and exposing the eye to light having a wavelength of about 600 nm to about 900 nm, wherein the exposing occurs at least 24 hours (e.g. about 24 hours, 36 hours, or about 2 days, or about 3 days, or about 4 days, or about 5 days, or about 6 days, or about 7 days, or about 2 weeks, or about one month) after administering the fluorescent compound; and evaluating the fluorescent pattern in the eye for one or more features indicative of a binding eye disease or stage thereof. The features indicative of a binding eye disease may be selected and/or identified based on analysis of a cohort of patients (e.g., comprising an experimental group having the binding eye disease or stage thereof and a comparator group that does not have the blinding eye disease). Features may be selected and/or identified using pattern recognition and/or cluster analysis. The presence of the features in the subject's images may be determined using a classifier algorithm, which may be trained using the images and analysis from the cohort(s).

Such methodology allows for binning or classifying of subject fluorescent pattern information in a manner that guides clinical trial design, e.g. directing enrollment or exclusion of patients into therapeutic studies of a binding eye disease. For instance, such methodology, in various embodiments, allows for discriminating between a subject having a binding eye disease and a subject not having a binding eye disease. Further, in various embodiments, such methodology allows for discrimination among or between subjects having a blinding eye disease, e.g. for disease stage or progression, disease subtype, related molecular genetics, pathobiology, drug response, etc. Such discrimination and resultant direction of clinical trial decision-making is described further elsewhere herein. Such discrimination and direction of clinical treatment are consistent with custom-ized or personalized clinical trial design or personalized medicine.

Further, in the presence of potential or various treatments, such methodology allows for binning or classifying of subject fluorescent pattern information in a manner that guides clinical decision-making, e.g. directing treatment of a blinding eye disease, if necessary. For instance, such methodology, in various embodiments, allows for discrimi-nating between a subject having a blinding eye disease and a subject not having a blinding eye disease. Further, in various embodiments, such methodology allows for dis-crimination among or between subjects having a blinding eye disease, e.g. for disease stage or progression, disease subtype, related molecular genetics, pathobiology, drug response, etc. Such discrimination and resultant direction of clinical decision-making is described further elsewhere herein. Such discrimination and direction of clinical treat-ment are consistent with personalized medicine.

In various embodiments, the present methods allow for a comparison between eyes in a test group and eyes in a control group (e.g. not having the blinding eye disease) to train an algorithm for classifying a subject's images for the presence of a binding eye disease or the status or stage of the binding eye disease (e.g., as progressing or regressing in response to therapy (in cases where the method is being used for monitoring)). For instance, in various embodiments, the present methods allow for the assembly of a database of various patterns or features of eyes in a cohort, such a cohort comprising groups selected from diseased, non-diseased, early-stage disease, late-stage disease, disease subtypes, etc. Accordingly, in various embodiments, the images are com-pared to allow for feature or pattern extraction, which can form the basis of the classifier. In various embodiments, pattern recognition using a machine learning methodology is used to continually enhance the power of the classifier as further images are analyzed, and which can provide for continual improvement of the power to discriminate condi-tions for clinical decision-making (e.g. by providing objec-tive decision support tools to assist medical professionals in diagnosis and prognosis of blinding eye conditions, and to assist researchers in clinical trial design.

In various embodiments, an image profile of the various eyes, when analyzed, allows for extraction of various fea-tures which are informative about, for instance, the presence, absence, extent, subtype, etc. of a blinding eye disease. Image profile analysis and/or feature extraction can employ any suitable algorithm. Such an algorithm may classify a sample between blinding eye disease-afflicted and non-afflicted groups. For example, samples may be classified on the basis of imaging features as described herein, e.g. in subjects having a blinding eye disease, or suspected of having a blinding eye disease, versus a non-blinding eye disease population (e.g., a cohort from the general population or a patient cohort with diseases other than a blinding eye disease) or versus other blinding or non-blinding eye disease populations (e.g. a cohort with a particular blinding eye disease compared against a distinct binding or non-blinding eye disease). Various classification schemes are known for classifying samples between two or more groups, including Decision Trees, Logistic Regression, Principal Components Analysis, Naive Bayes model, Support Vector Machine model, and Nearest Neighbor model. Further, several different algorithms may be utilized for analysis of the eye imaging data. The algorithms may include, for example, a machine learning single class classifier or an anomaly detector algorithm. As shown above, detection algorithms may be based on a support vector data description (SVDD). Additional algorithms may include a support vector machine (SVM), a relevance vector machine (RVM), a neural network, neural analysis, a large margin classifier, a kernel based classifier, a classifier based on a probability density function (PDF) estimator, a classifier based on a Parzen PDF estimator, a Bayesian classifier, a Constant False Alarm Rate (CFAR) detector, a fuzzy logic based classifier, and/or similar detection algorithms. In addition, the predictions from multiple models or algorithms can be combined to generate an overall prediction.

In various embodiments, the present methods of evaluation employ machine learning and computational intelligence techniques, such as deep neural networks, and combinations of supervised, semi-supervised and unsupervised learning techniques. Such machine learning and computational intelligence techniques provide, in various embodiments, image classification, image analysis, computer-aided diagnosis and prognosis, and/or pattern recognition information.

In various embodiments, the present methods of evaluation employ a supervised algorithm (by way of non-limiting example, linear region, random forest classification, decision tree learning, ensemble learning, bootstrap aggregating, and the like). In various embodiments, the present methods of evaluation employ a non-supervised algorithm (by way of non-limiting example, clustering or association).

In various embodiments, the present systems and methods enable the pattern recognition, e.g. of various features of relevance to blinding eye diseases as described herein.

In various embodiments, discriminant analysis and/or classification analysis allows for the binning of patients so as to inform on an eye status (e.g. presence or absence of disease, severity of disease, identity of disease, and the like).

In various embodiments, the present systems and methods are useful in the interpretation of various eye features as shown elsewhere herein.

In various embodiments, the present systems and methods are useful in the detection of hypofluorescent patterns including presence, absence, or extent of, by way of non-limiting example, regions of profound hypofluorescence (PHoF), intermediate hypofluorescence (IHoF), low hypofluorescence (LHoF) (e.g. such levels of hypofluorescence may be assessed relative to image standards, e.g. a reduction of fluorescence to about 90% or more of the hypofluorescence measured at the optic nerve head (ONH) (e.g. 60-90% of the ONH, 20-60% of the ONH), that may have sharp (readily delineated) borders or soft (blurry or fuzzy) borders, and complex fluorescent patterns.

In some embodiments, systems and methods described herein detect and identify and classify hypofluorescent patterns and regions having various hypofluorescent shapes. The detection of hypofluorescent patterns may include, by way of example: detection and classificiation of a region of repeating hypofluroescent shapes into classes, which may be pre-defined or generated automatically by way of a learning algorithm. Such classes may correspond, for example, to various observed patterns. Such patterns may includes, for example, in a "loose weave" pattern; a region of concentrated repeating hypofluorescent shapes, for example, in a "tight weave" pattern; patterns of generally elliptical, oval or oblong shaped hypofluorescent regions, for example, hypofluroescent shapes resembling "fingerling potatoes"; patterns of generally round or rosette shaped hypofluorescent regions, for example, hypofluorescent shapes resembling "leopard spots"; and regions of intermediate hypofluroescence (IHoF) or low hypofluorescence (LHoF), for example, resembling a "grey smudge".

In various embodiments, the present systems and methods are useful in the detection of hyperfluorescence patterns including presence, absence, or extent of, by way of non-limiting example, regions of profound hyperfluorescence (PHrF), intermediate hyperfluorescence (IHrF), low hyperfluorescence (LHrF), that may have sharp (readily delineated) borders or soft (blurry or fuzzy) borders or of "bright dots", "bright spots", "large bright spots" and various complex patterns including "haloes".

In various embodiments, the present systems and methods are useful in the detection of complex 2D patterns, by way of non-limiting example, labeled "tight weave", "loose weave", "grey smudge", "oil stains", "bullet holes", etc.

In various embodiments, the present systems and methods allow for the detection of the transition from the presence of drusen or pseudodrusen in the absence of geographic atrophy, macular atrophy (MA), or choroidal neovascularization, to the presence of drusen or pseudodrusen in the presence of geographic atrophy, macular atrophy, or choroidal neovascularization. In various embodiments, the present systems and methods allow for the detection of drusen regression (e.g. a reduction of drusen by about 25%, or about 50%, or about 75%, or about 100%).

In various embodiments, the present systems and methods allow for the detection of ocular tissue loss (e.g. a reduction of ocular tissue loss by about 25%, or about 50%, or about 75%, or about 100%).

In various embodiments, the present systems and methods allow for detection of presence, absence, or extent of drusen, pseudodrusen, picsiform lesions, inflammatory infiltrates, subretinal fluid, variably shaped hyper- or hypo-pigmented regions (e.g. bull's eye lesion) in the absence of geographic atrophy, macular atrophy, or choroidal neovascularization, to the presence of drusen, pseudodrusen, picsiform lesions, inflammatory infiltrates, subretinal fluid, variably shaped hyper- or hypo-pigmented regions (e.g. bull's eye lesion) in the presence of any of any tissue loss, geographic atrophy, macular atrophy, or choroidal neovascularization.

Figure 40:
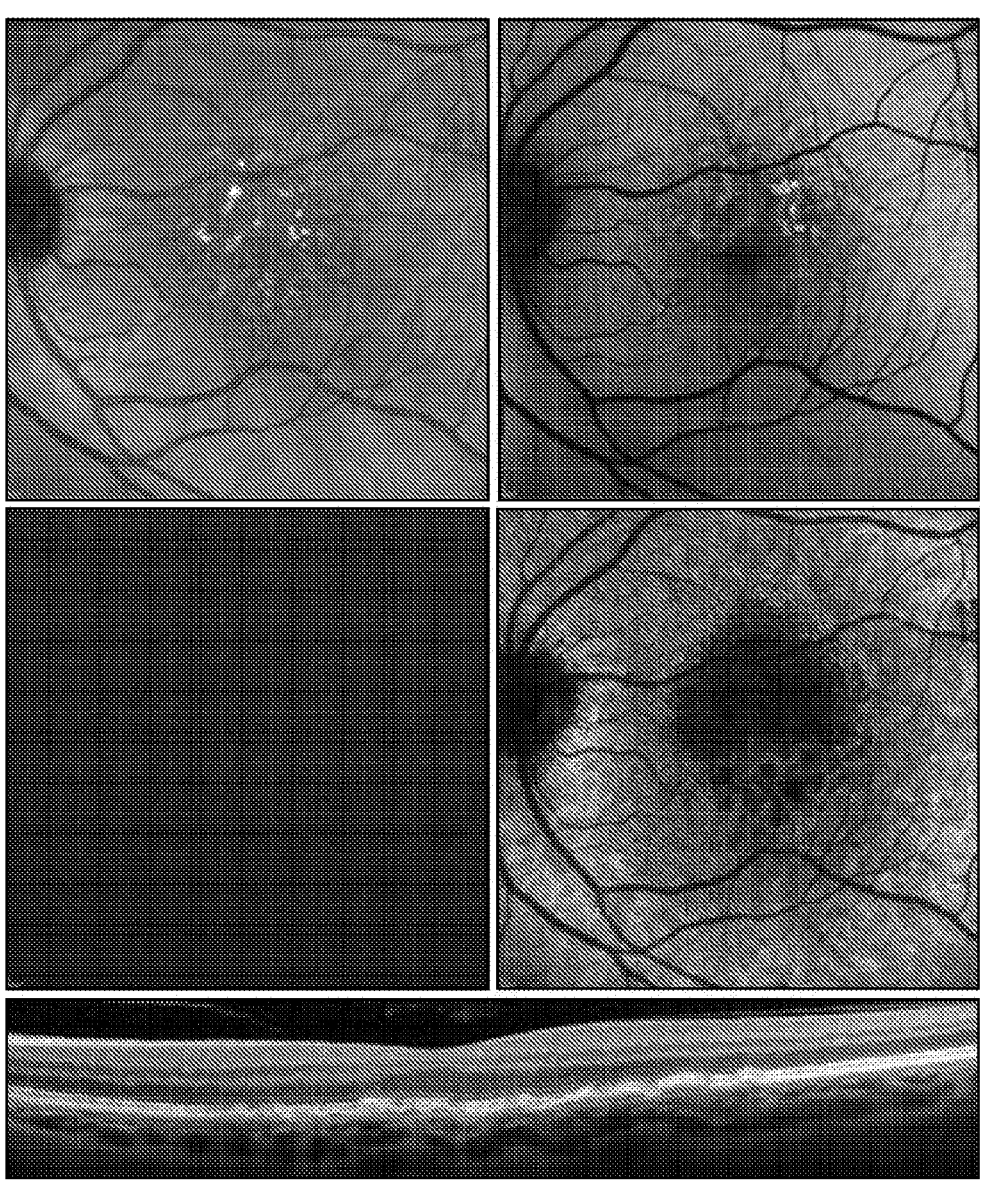
FIG. 40 depicts the use of DNIRA as a marker of high risk AMD features to identify progression from early to late disease.
Figure 41:
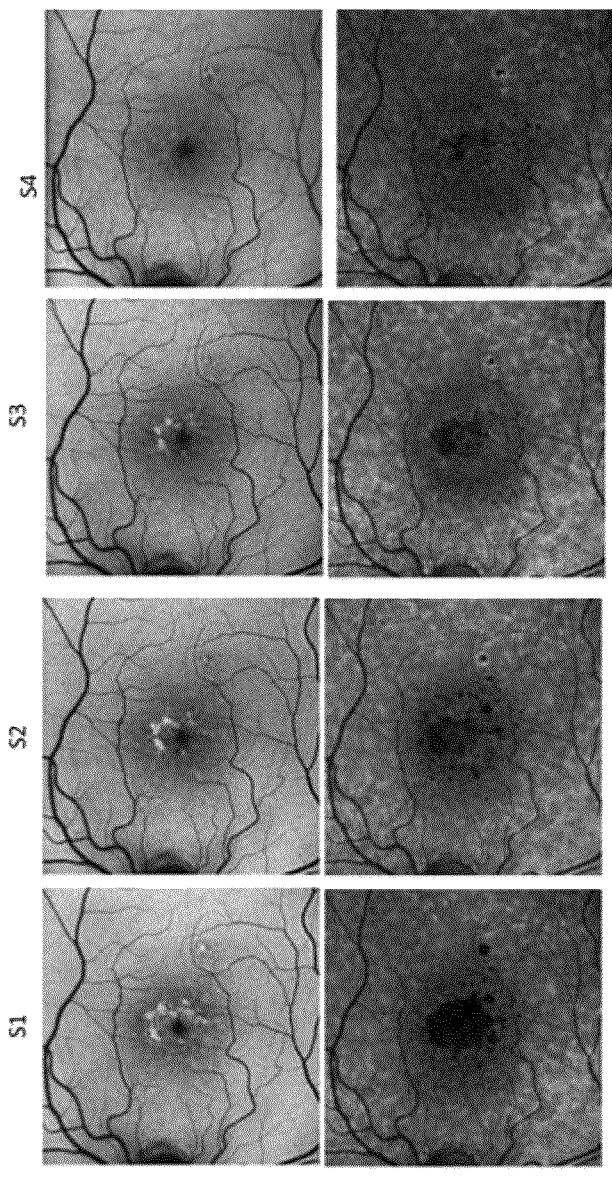
FIGS. 41-44 depict representative examples of a sequence of DNIRA images and OCT images of a patient's eyes obtained over four sessions.
Figure 42:
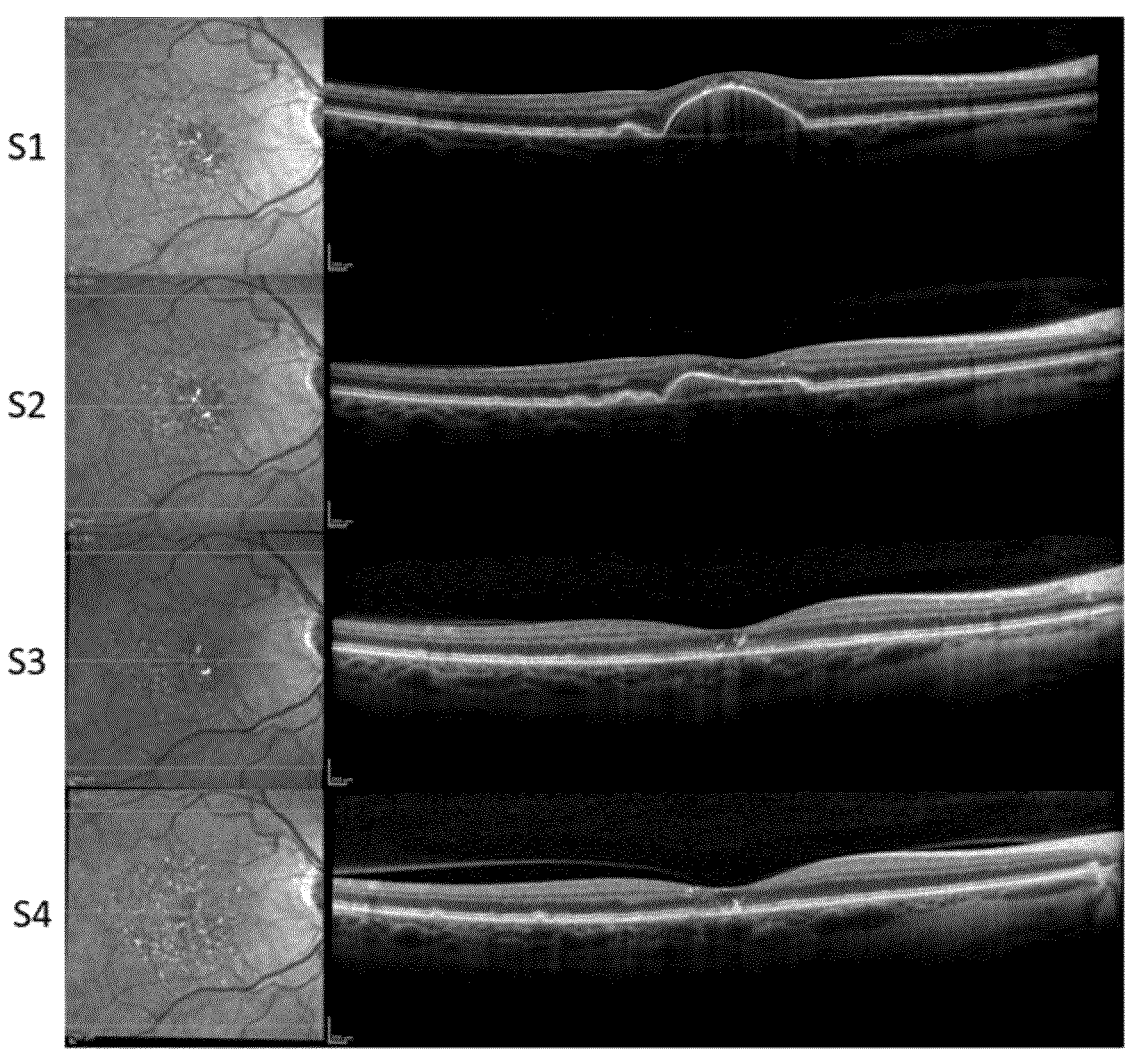
Figure 43:
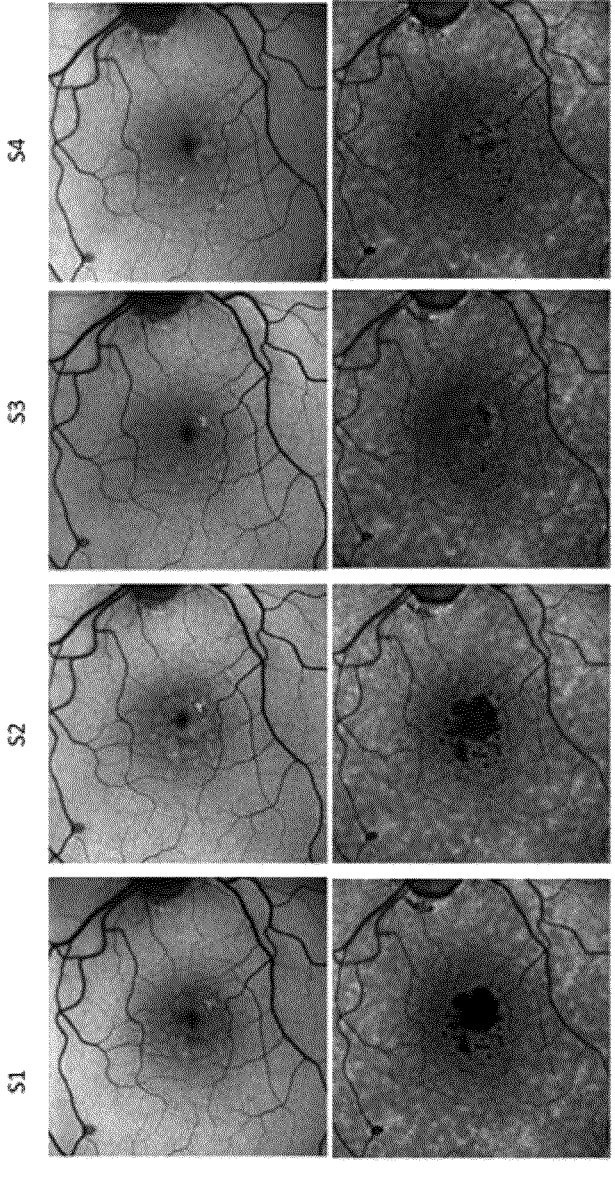
Figure 44:
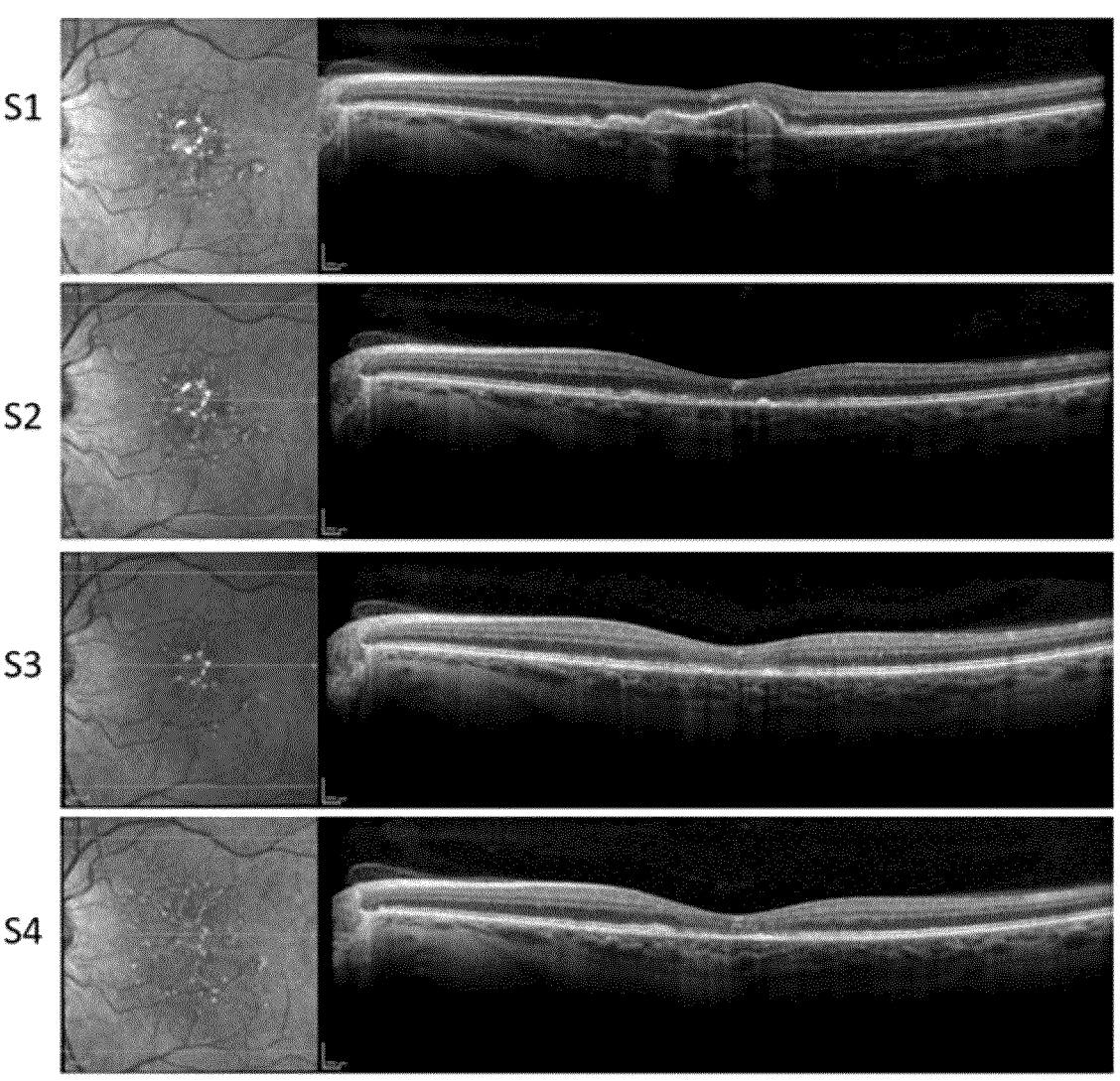

In various embodiments, the present systems and methods allow for detection of the total number of drusen, the size of drusen, the presence of soft confluent drusen, hyperpigmentation, RPE detachments, hypopigmentation, hypo-reflective subretinal material, hyper-reflective dots, subretinal basal laminar and/or basal linear deposits as depicted in Example 22 and FIG. 40.

In various embodiments, the present systems and methods allow for detection of the extent (utilizing by way of non-limiting example, the area, square root of the area, perimeter, diameter of best-fit circle) of regions of hypofluorescent DNIRA signal that coincide with high-risk features such as the total number of drusen, the size of drusen, the area of drusen, the volume of drusen, the border of drusen, the presence of soft fuzzy drusen, the presence of soft confluent drusen, hyperpigmentation, RPE detachments, hypopigmentation, hypo-reflective subretinal material, hyper-reflective dots, subretinal basal laminar or basal linear deposits, and the like. An illustration of this is exemplified in FIG. 40 and depicted in Example 22.

In some embodiments, the methods provide for pattern recognition in the fluorescence of the RPE and outer retinal layer in a subject, including patterns based on the loss of fluorescence of the RPE and outer retinal layer. RPE and outer retinal layer fluorescent patterns can be used for training classifier algorithm for evaluating blinding eye disease.

Accordingly, in various embodiments, the present provides ophthalmic image-based biomarkers to allow for eye evaluation. In some embodiments, such ophthalmic image-based biomarkers are to be used alone or in conjunction with other ophthalmic image-based biomarkers (such as but not limited to color, FAF, IR, NIR, OCT, OCT-A, angiography) or non-image-based biomarkers (such as, but not limited to, genomics, tissue biochemistry, functional measures of disease, and other outcomes measures such as QALY (Quality Adjusted Life Years)) to enhance the diagnosis of disease, to identify previously known and unknown subtypes of disease, to identify patients likely to develop disease, to identify patients likely to suffer disease progression, to identify patients likely or not to respond to a particular intervention (e.g. therapy), and/or to identify patients whose future outcome or whose safety may be compromised by disease progression, disease intervention or environmental influence.

In various embodiments, the present provides methods for identifying patients with blinding eye disease earlier in a disease course/progression. If detected early, earlier intervention may be pursued. Alternatively, the present provides methods for identifying patients with blinding eye disease later in a disease course/progression. If detected later, less burdensome intervention may be pursued.

In various embodiments, the present provides methods of detecting patients more likely to progress from earlier disease to later disease (e.g. prognostic biomarker)

In various embodiments, the present provides method for measuring or monitoring the rate of disease progression or the effect of an intervention over time (e.g. disease response) to one or more therapeutic agents (e.g. a prognostic, predictive or monitoring biomarker)

In various embodiments, the present provides a method of determining patient prognosis, e.g., to identify the likelihood of a clinical event, disease recurrence, or disease progression in patients who have blinding eye disease such as AMD, RPD, maculopathy, central serous retinopathy, uveitis, inherited retinal degeneration and the other disease mentioned elsewhere herein.

In various embodiments, the present provides a method for predicting the response of a patient or group of patients to an intervention (e.g. a therapy) to identify individuals who are more likely than similar individuals without the biomarker to experience a favorable or unfavorable effect from exposure to a medical product or an environmental agent. For instance, such methods predict that a patient may be a responder to a therapy. If so, in various embodiments, such a patient may be directed to receive treatment with the therapy. Alternatively, such methods predict that a patient may not respond to a therapy. If so, in various embodiments, such a patient may be directed to not receive treatment the therapy and, therefore, may be directed to alternative therapies. (E.g. a prognostic, predictive, monitoring or safety biomarker).

In various embodiments, the present provides a method for demonstrating that a biological response has occurred in an individual who has been exposed to a medical product or an environmental agent. (e.g. a predictive or safety biomarker)

In various embodiments, the present provides a complimentary biomarker to drive clinical trial design. In various embodiments, the present provides a companion biomarker to drive clinical trial design. In various embodiments, the present systems and methods allow for the selection of patients likely to respond to a clinical trial drug or other clinical trial intervention and therefore allow recruitment of a suitable population for a clinical trial.

In various embodiments, the present provides a method for personalized drug development or personalized medicine. For instance, the present methods allow, in various embodiments, interventions and/or products being tailored to the individual patient based on their predicted response or risk of disease.

By way of illustration, in various embodiments, the present methods provide for diagnostic biomarkers or methods. For example, the present methods and systems identify complex 3D patterns of reduced hypofluorescent signal in patients with a family history of a blinding eye disease (e.g. AMD) but without a personal clinical diagnosis. As such, DNIRA may enable the early diagnosis of patients, or a subset of patients, likely to develop disease. By contrast, patients with no known family or personal history do not have the same pattern of hypofluorescence. Such information directs ready intervention. In various embodiments, the present diagnostic biomarkers or methods may enable the early diagnosis of patients which have family or personal history of a blinding eye disease (e.g. AMD) but lack knowledge of such. Accordingly, such methods may direct early treatment in patients that would otherwise not be treated.

In various embodiments, the present methods inform treatment with one or more therapeutic agents, such as, without limitation, an anti-VEGF agent, an ACE inhibitor, a PPAR-gamma agonist or partial agonist, a renin inhibitor, a steroid, and an agent that modulates autophagy, as well as a semapimod, a MIF inhibitor, a CCR2 inhibitor, CKR-2B, a 2-thioimidazole, CAS 445479-97-0, CCX140, clodronate, a clodonate-liposome preparation or gadolinium chloride.

Non-limiting examples of anti-VEGF agents useful in the present methods include ranibizumab, bevacizumab, aflibercept, KH902 VEGF receptor-Fc, fusion protein, 2C3 antibody, ORA102, pegaptanib, bevasiranib, SIRNA-027, decursin, decursinol, picropodophyllin, guggulsterone, PLG101, eicosanoid LXA4, PTK787, pazopanib, axitinib, CDDO-Me, CDDO-Imm, shikonin, beta-, hydroxyisovalerylshikonin, ganglioside GM3, DC101 antibody, Mab25 antibody, Mab73 antibody, 4A5 antibody, 4E10 antibody, 5F12 antibody, VA01 antibody, BL2 antibody, VEGF-related protein, sFLT01, sFLT02, Peptide B3, TG100801, sorafenib, G6-31 antibody, a fusion antibody and an antibody that binds to an epitope of VEGF. Additional non-limiting examples of anti-VEGF agents useful in the present methods include a substance that specifically binds to one or more of a human vascular endothelial growth factor-A (VEGF-A), human vascular endothelial growth factor-B (VEGF-B), human vascular endothelial growth factor-C (VEGF-C), human vascular endothelial growth factor-D (VEGF-D) and human vascular endothelial growth, factor-E (VEGF-E), and an antibody that binds, to an epitope of VEGF.

In some embodiments, the anti-VEGF agent is the antibody ranibizumab or a pharmaceutically acceptable salt thereof. Ranibizumab is commercially available under the trademark LUCENTIS. In another embodiment, the anti-VEGF agent is the antibody bevacizumab or a pharmaceutically acceptable salt thereof. Bevacizumab is commercially available under the trademark AVASTIN. In another embodiment, the anti-VEGF agent is aflibercept or a pharmaceutically acceptable salt thereof. Aflibercept is commercially available under the trademark EYLEA. In one embodiment, the anti-VEGF agent is pegaptanib or a pharmaceutically acceptable salt thereof. Pegaptinib is commercially available under the trademark MACUGEN. In another embodiment, the anti-VEGF agent is an antibody or an antibody fragment that binds to an epitope of VEGF, such as an epitope of VEGF-A, VEGF-B, VEGF-C, VEGF-D, or VEGF-E. In some embodiments, the VEGF antagonist binds to an epitope of VEGF such that binding of VEGF and VEGFR are inhibited. In one embodiment, the epitope encompasses a component of the three dimensional structure of VEGF that is displayed, such that the epitope is exposed on the surface of the folded VEGF molecule. In one embodiment, the epitope is a linear amino acid sequence from VEGF.

In various embodiments, the present methods inform treatment with one or more therapeutic agents, not limited to, a vitamin supplement, a complement inhibitor or activator, a visual cycle modulator, an amyloid blocker or inhibitor, a neuroprotectant, an autophagy inhibitor, an anti-inflammatory, a modulator of macrophage behavior or activity, a modulator of CD36, a tyrosine kinase inhibitor, an RNA modulator, gene therapy or cell therapy. Examples of these include APL-2, Eculizumab, LFG316, Sirolimus, Fluocinolone acetonide (Illuvien), Fenretinide, Emixustat, Trimetazidine, Alprostadil, Moxaverine, Sildenafil, MC-1101 (MacuClear), OT551, Tandospirone, GSK933766, Lampalizumab, ARC-1905, RNG6, Oracea, Brimonidine Tartrate, FMX-103, CLG-561, BIO-201, BIO-203, tesidolumab, unoprostone isopropyl, GS-030, ICR-14967, methotrexate, ONL-1204, RST-001, TT-231, KSI-401, OCU-100, RC-1 alpha, ACU-02, ACU-3223, alprostadil, AVT-2, HMR-59, INO-6001, INO-6002, MCT-355, NT-501, SIR-1046, SIR-1047, SIR-1076, zinc monocysteine, EBI-028, EG-30, RNA-144101.

In various embodiments, the present methods inform treatment with one or more therapeutic agents, such as, a complement inhibitor or activator, a visual cycle modulator, an amyloid blocker or inhibitor, a neuroprotectant, an autophagy inhibitor, an anti-inflammatory, and a modulator of macrophage behavior or activity.

In various embodiments, the present methods provide for identification of disease subtypes, e.g. amongst patients with a known diagnosis of a blinding eye disease (e.g. AMD).

Presently, the classification of AMD is limited to early (drusen), late (which can be wet (neovascular) or dry (with GA)). The co-existence of variably sized drusen (small, medium and large) and pigment, seen in clinical examination and color fundus photography, can further stratify early disease into subcategories of Low Risk and Intermediate Risk (or high-risk Early). However, given the multigenicity of AMD, with over 30 genes and 200 SNPs, this represents significant simplification and precludes the development of broad, targeted or subtype-specific, e.g. customized therapies (through over-inclusive clinical trial design) and ultimately personalized therapies. Further, novel, rich image obtained using DNIRA, serving as image-based biomarkers with defined and ill-defined features are particularly well-suited to the use of cognitive computing for novel AI-derived pattern recognition. Coupled with genetic, epigenetic and lifestyle data, DNIRA provides previously unknown correlations that point to efficient, customized clinical trial design and personalized therapeutics.

By way of example, subtypes in the context of wet AMD include segregation by location of CNV (e.g. subfoveal, juxtafoveal, extrafoveal, and peripapillary) and/or traditional classifications (e.g. wholly classic, predominantly classic, minimally classic, and occult no classic).

In various embodiments, the present methods find use in distinguishing (e.g. differentiating, discerning, perceiving) diseases of similar clinical appearance to assist with diagnostic accuracy and new diagnostic classification. For instance, the present methods reveal complex image-based patterns that are absent in patients with ocular conditions other than AMD, or frequently misdiagnosed as AMD. Reciprocally, the present methods can lead to correct diagnosis of certain diseases that otherwise would be diagnosed as AMD, e.g. but not limited to, Stragardt disease, Adult Vitelliform disease, Bietti's crystalline dystrophy, pattern dystrophy, and others. These other conditions can be included in comparator cohorts to increase the power of discrimination. Accordingly, in various embodiments, the present methods allow for improved diagnostic accuracy, enriched clinical trial enrollment, and directed, and a more appropriate, personalized therapeutic plan for an individual patient.

In various embodiments, the present methods find use in monitoring progression of a blinding eye disease and/or the effect of a treatment over time. Accordingly, in various embodiments, the present methods find use as a monitoring biomarker. For example, by way of illustration, the ability to measure dark (e.g. hypofluorescent) regions using the present methods makes it useful monitoring biomarker. Assessed serially over time the present methods detect and measure the presence, status, or extent of a blinding eye disease such as AMD, or provide evidence of an intervention effect or exposure, including exposure to a medical product or an environmental agent.

In various embodiments, the present methods find use in quantifying or better qualitatively describing aspects of disease known to predict progression (prognostic biomarker). In various embodiments, the present methods identify and quantify known high-risk features of disease such as large, soft and confluent drusen. The AREDS 1 and 2 clinical studies identified risk factors that correlate with increased risk of progression from early to late AMD, and amongst these the most powerful predictor of progression is the presence of large, soft, confluent drusen, with or without pigmentary change. Soft drusen can be identified during clinical examination and are documented using color fundus photography, but by nature has indistinct or "fuzzy" borders precluding their precise quantification even with alternative imaging methods such as Optical Coherence Tomography (both cross-sectional and en face). The present methods make detection and quantification of risk features such as soft drusen possible and as such, can identify patients at risk, stratify risk of progression, and instruct which patients to enlist in clinical trials (particularly trials aiming to prevent late disease, either choroidal neovascularization, geographic atrophy, or macular atrophy).

In various embodiments, the present methods are used to quantify aspects of disease currently hypothesized to predict progression (predictive biomarker). In various embodiments, the present methods identify, quantify and follow over time the spatiotemporal changes in disease features predicted to correlate with disease but currently not quantifiable and hence not demonstrated. For example, in various embodiments, the present methods can quantify total drusen load, change in the same over time, and the like.

Further, over time, For example, while large and medium drusen confer disease risk and risk of progression, their dynamic changes are difficult to observe. The present methods permit the establishment of a Dynamic Drusen Index (DDI) that can calculate total drusen burden at single or multiple timepoints, or can calculate the change in particular drusen subtypes. Relying on the current classification of drusen, the DDI is defined as: Total DDI (for all drusen types), Large Confluent Dynamic Drusen Index (LC-DDI), Large Dynamic Drusen Index (L-DDI), Medium Dynamic Drusen Index (M-DDI), and Small Dynamic Drusen Index (S-DDI). In various embodiments, DDI instructs which patients to preferentially enlist in particular clinical trials.

In various embodiments, the present methods identify presumptive macrophages in the eyes of patients with diseases such as, without limitation, the disease described herein (e.g. AMD, RPD, inflammatory disease, inherited maculopathies, retinal degeneration, and ocular tumors), thus identifying individuals who are more likely than similar individuals without the biomarker to experience a favorable or unfavorable effect from exposure to a medical product such as macrophage modulating therapy or environmental agent. For example, there are presently no therapies available for the treatment of dry AMD despite the current understanding that it is a disease of the innate immune system: no Phase III studies targeting the complement cascade have yet been successful. In various embodiments, the present methods allow for investigating the cellular arm of the innate immune system, e.g. the macrophage population (collectively all phagocytic immune cells including but not limited to perivascular macrophages, microglia, resident parenchymal macrophages, dendritic cells and circulating monocytes) and/or the a quantification of a number of macrophages over time, or with versus without treatment, etc.

In various embodiments, the present methods provide a method for demonstrating that a biological response has occurred in an individual who has been exposed to a medical product such as, but not limited to, bindarit, its derivatives and related compounds, macrophage modulating agents, methotrexate, IkBa inhibitors and NFkB inhibitors, complement modulators, other anti-inflammatory compounds or environmental agents, alone or in combination In various embodiments, the present methods are used to both qualitatively evaluate and quantify the pharmacodynamic response to such treatment, thereby being useful to establish proof-of-concept that a drug or other therapeutic produces the desired pharmacologic response in humans thought to be related to clinical benefit, and to guide dose-response studies. In various embodiments, the present methods can further provide evidence of target engagement.

In various embodiments, the present methods are used to both qualitatively evaluate and quantify the pharmacodynamic response to stem cell therapy—e.g. as a possible beneficial effect of macrophage modulation in their survival and/or in use to restore damaged or missing RPE.

In various embodiments, illustrative blinding eye diseases relevant to the present evaluation methods include, for example, dry AMD, wet AMD, reticular pseudodrusen (RPD), LORDs (late onset retinal degeneration), retinal degeneration associated with c1qTNF5 deficiency or its corresponding gene mutation, or another maculopathy, including, but not limited to, Stargart disease, pattern dystrophy, as well as retinitis pigmentosa (RP) and related diseases. In one embodiment, the maculopathy is inherited. In other embodiments, the blinding eye disease relevant to the present evaluation methods is an idiopathic disorder that may, without wishing to be bound by theory, be characterized by retinal inflammation, with or without accompanying macular degeneration, including, but not limited to, white-dot syndromes (e.g. serpiginous chorioretinopathy, serpiginous retinopathy, acute posterior multifocal placoid pigment epitheliopathy (APMPPE), multiple evanescent white dot syndrome (MEWDS), acute zonal occult outer retinopathy (AZOOR), punctate inner choroidopathy (PIC), and diffuse subretinal fibrosis (DSF)). In other embodiments, the blinding eye disease relevant to the present evaluation methods is central serous retinopathy (CSR). In other embodiments, the blinding eye disease relevant to the present evaluation methods is a retinopathy, including diabetic retinopathy.

In various embodiments, the present evaluation methods find use in evaluation of a tumor of the eye. For instance, in some embodiments, the present methods allow for the detection of macrophages, e.g. tumor-associated macrophages. For instance, the present methods allow the detection of hyperfluorescent bright dots and/or a quantification of hyperfluorescent bright dot density. Such dot density correlates with clinical classification (e.g. as determined by the observation/grading of a clinician) and always for standardization of diagnosis and a less subjective classification scheme. In various embodiments, the present methods allow for detection or prediction of ocular tumor-associated fluid, height of ocular tumor, and the like.

In various embodiments, the present evaluation methods find use in evaluation of a tumor of the eye, such as tumor being one or more of (e.g. a metastasis to the eye of) a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoprol iterative disorder (PTLD), as well as abnormal vascular proliferation associated with phakomatoses, edema (e.g. that associated with brain tumors), and Meigs' syndrome.

In various embodiments, the present evaluation methods find use in evaluation of a tumor of the eye, such as a primary intraocular cancer (e.g., without limitation, intraocular melanoma or primary intraocular lymphoma). In various embodiments, the present evaluation methods find use in evaluation of retinoblastoma or medulloepithelioma.
Image Analysis Platform and Output Systems described herein can provide output in the form of either raw images for user analysis, or processed images for end-user (consumer) utilization. The output may be represented as visual elements on a GUI display. In one aspect, the output can be comprised of raw images derived from the application of DNIRA to subjects with AMD and/or other blinding diseases prior to their registration, alignment, enhancement, adjustment, segmentation, or any other relevant image processing, provided as single or composite images, randomly or serially-arranged.

In some aspects, the output can be comprised of processed imaged derived from the application of DNIRA to subjects with AMD and/or other blinding diseases after initial processing, that could include any or all of registration, alignment, enhancement, adjustment, segmentation, or any other relevant image processing, provided as single or composite images, randomly or serially-arranged.

Systems and devices described herein can provide for image utilization by independent users and/or for users through a centralized image analysis center or platform. Independent users include, but are not limited to, physicians, vision care specialists, ophthalmic technical staff, vision scientists, contract research organizations, the drug development sector and those involved in clinical trial design and execution. Centralized image platforms could include, by way of non-limiting example, cloud-based systems, web-based systems, network-based systems, and locally active network (LAN) based systems.

Systems and devices described herein can provide independent users, and/or centralized users with a graphical user interface (GUI) compatible with multiple systems for desktop, lap-top, or hand-held devices. Systems and devices described herein can provide centralized users with DNIRA image software for further analysis. DNIRA image software can be implemented for such analysis. A DNIRA image software can capable of, but not limited to processes such as registration, alignment, contrast adjustment, sharpening, segmentation for structured analysis of pre-defined features, such as areas of hypofluorescent signal, hyperfluorescent signal, hyperfluorescent dots, complex 2-dimensional patterns.

Systems and devices described herein can provide provides centralized users with DNIRA image software capable of, but not limited to processes such as registration, alignment, contrast adjustment, sharpening, segmentation for unstructured analysis of undefined or complex features other than those addressed by structured analysis.
Graphical User Interface Systems described herein can provide an iteratively-improved graphic user interface (GUI), intended to optimize day-to-day and specialized user-guided image manipulation and analysis. Such GUIs could be made available on hand-held devices, iPads, laptops, and other personalized computing systems. Such GUIs could be embedded in commercially available imaging equipment or purpose-specific devices optimized for DNIRA.

In an aspect, the GUI can comprise a series of visual elements that dynamically update based on control commands and image output data as described herein. The GUI may include for example, an image carousel, tiled array with enlarged images, grid or tiled array without enlargements.
Software-Embedded Chips and/or Software Programs for Dissemination In some aspects, device-independent software programs can be developed that can process DNIRA images acquired from any suitable imaging system (e.g. cSLO or non-cSLO based). In some aspects, the software program can be made available for incorporation into current or future devices; in another, the software program is made available to current device and software manufacturers for post-acquisition image analysis.
Centralized Software System for Data Analysis and Iterative Program Development In some aspects, a system described herein can comprise centralized image processing, that could be for example, without limitation, be cloud-based, internet-based, locally accessible network (LAN)-based, or a dedicated reading center using pre-existent or new platforms.

In some aspects, the software would rely on structured computation, for example providing registration, segmentation and other functions, with the centrally-processed output made ready for downstream analysis. In this case, output could be a single or series of adjusted images (e.g. registration, contrast, sharpness, etc. . . . ), provided to the user in random or non-random order, for subsequent use.

In a variation of this aspect, the software would rely on structured computation, with the output pre-analyzed for the user and compared against relevant modifiable or non-modifiable risk factors for disease. In this case, output could be a single or series of adjusted images (e.g. registration, contrast, sharpness, etc.), provided to the user with a qualitative or quantitative description of the image content(s).

In some aspects, the software would rely on unstructured computation, artificial intelligence or deep learning, such that in addition to readily-defined features (such as profoundly hypofluorescent/bright areas or hyperfluorescent dots), regions of variable grey-scale would be iteratively analyzed using layered or multi-layered processing. As unstructured computation benefits from large and increasing numbers of images, unstructured DNIRA analysis would be particularly well-suited to a cloud-based, networked or reading center-based platform.

In a variation of this aspect, the software would rely on unstructured computation, such that regions of high complexity could be iteratively analyzed using layered or multi-layered processing. By way of non-limiting example, these can include complex 2D patterns of varying grey-scale density. Output could be a single or series of adjusted images (e.g. registration, contrast, sharpness, etc. . . . ), provided to the user with a qualitative or quantitative description of the image content(s), potentially over time, and, for example, with and without treatment.

In a further variation of this aspect, the software would rely on unstructured computation, so-called "artificial intelligence" or "deep learning", such that in addition to readily-defined features (such as profoundly hypofluorescent/bright areas or hyperfluorescent dots), regions of variable grey-scale would be iteratively analyzed using layered or multi-layered processing, however, in this case, output could be provided to the user with a qualitative or quantitative description of the image content(s), potentially over time, and, for example, with and without treatment.

AMDI Phenotyping and Genotyping

Present systems for categorizing or describing subjects with AMD are limited. For example, in a commonly-used system based on clinical examination and/or color fundus photographs, subjects are classified as either early or late. All subjects with early disease are considered "dry", and are commonly diagnosed by the presence of 5 or more drusen larger than "droplets" (<10 μm). Late AMD can be exudative (neovascular, or "wet"), or non-exudative (atrophic, or "dry"), and both are associated with vision loss; both forms of late disease can co-exist. Late "wet" AMD can co-exist with early dry or late dry.

A commonly used system uses a so-called "simple score" to identify subjects at high-risk of progressing from early to late disease (either exudative or non-exudative). Accordingly, the presence of 2 or more large drusen (>125 μm) in one eye, or pigment clumps in one eye yields a score of 1 each; the presence of both in both eyes therefore yields a score of 4. Subjects with scores of 3 or more are more likely to progress from early to late AMD. In some systems these subjects are categorized as "high-risk early" or in some systems, as "intermediate" AMD.

In contrast to these simple classifications, AMD is known to be a complex multigenic disorder with over 20 associated mutations/SNPs that can be inherited alone or in combination. Disease expression is further modified by epigenetic risk factors such as smoking, diet and nutrient supplementation.

FAF can be a standard method for analysis of dry AMD, and regions of profoundly hypofluorescent/dark signal indicate the presence of GA and therefore late disease. Complex 2D patterns of hyperfluorescent FAF can also be observed and some, when found in conjunction with patches of GA, are associated with increased rates of patch expansion. These include, for example, the banded and diffuse (speckled) patterns. To date, there has been no definitive correlation between the genetics (genotype) of AMD and the clinical patterns (phenotype) determined by clinical examination or specialized imaging such as FAF or OCT.

AMDI can identify previously unknown image-based patterns of disease, e.g., provides novel phenotypic description of individual subjects. Accordingly, there is a need for image-based systems that can stratify subjects into different subtypes of disease that may differ according to rates of progression, susceptibility to epigenetic risk, response to different therapies and ultimately to rates of vision loss. AMDI can dramatically increase an ability to define these groups. As AMDI provides unprecedented description of different patterns or subtypes of disease, the results of a centralized imaging platform, iteratively improved used structured and unstructured learning, can then be compared against GWAS analysis, epigenetic status, and other medical or demographic information.

Biology of DNIRA

Figure 22:
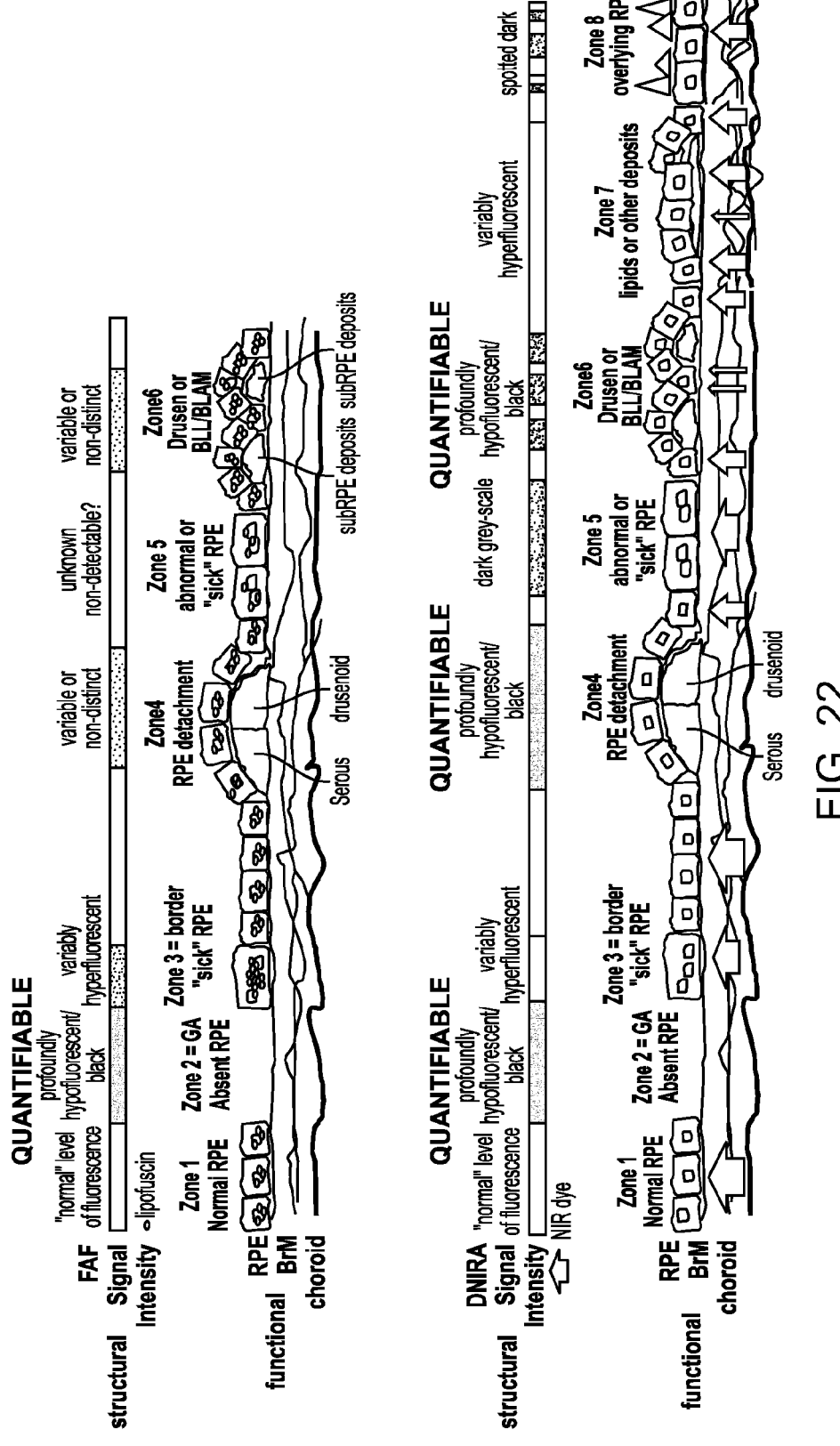
FIG. 22 depicts structural and functional aspects of DNIRA signal in RPE. Upper panel shows the relative intensity of DNIRA signal relative to corresponding tissue change in the lower panel. In the lower panel, the normal RPE, Bruch's membrane (BrM) and choroidal vasculature is illustrated, along with commonly observed changes that occur in dry AMD. Hypofluorescence is observed in association with GA, RPE detachments, and drusen or other sub-RPE deposits (basal linear, basal laminar deposits). A mid-grey signal is illustrated in regions where RPE are in their correct anatomical position relative to the choroidal blood vessels but where cell metabolism is surmised to be abnormal.
Figure 23:
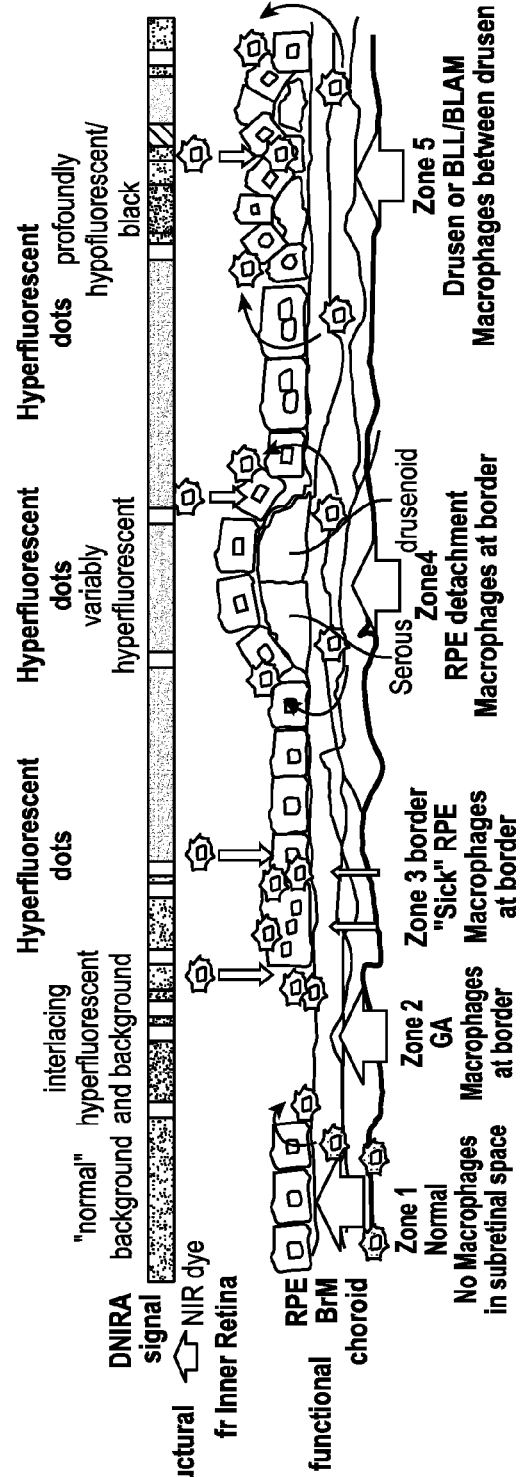
FIG. 23 depicts structural and functional aspects of DNIRA signal in macrophages. Relative intensity of DNIRA signal is shown in the upper panel relative to corresponding tissue change in the lower panel. Hyperfluorescent dots (of a particular size, shape and motility) that are associated with DNIRA signal are identified as phagocytic immune cells, namely macrophages. Green arrows indicate movement/uptake of ICG dye from choroidal circulation to retinal/RPE complex. In the lower panel, presence of phagocytic macrophages that have taken up dye is illustrated.

FIGS. 22 and 23 are graphical illustrations of biology of DNIRA signal in RPE and macrophages respectively. FIG. 22 depicts structural and functional aspects of DNIRA signal in RPE, where profoundly hypofluorescent/black signal occurs in associations with several pathological changes. Green arrows indicate movement/uptake of ICG dye from choroidal circulation to RPE monolayer. "Normal" levels of DNIRA signal are illustrated as light green cells capable of internalizing dye. In the lower panel the normal RPE, Bruch's membrane (BrM) and choroidal vasculature is illustrated, along with commonly observed changes that occur in dry AMD. Hypofluorescence is observed in association with GA, RPE detachments, and drusen or other sub-RPE deposits (basal linear, basal laminar deposits). A mid-grey signal is illustrated in regions where RPE are in their correct anatomical position relative to the choroidal blood vessels but where cell metabolism is surmised to be abnormal. FIG. 23 depicts structural and functional aspects of DNIRA signal in macrophages. Hyperfluorescent dots (of a particular size, shape and motility) can appear in conjunction with the signals obtained in FIG. 22. Green arrows indicate movement/uptake of dye from choroidal circulation to retinal/RPE layer where tissue macrophages are capable of internalizing it. In addition to the fact that macrophages may internalize the dye directly in the circulation before the cells themselves influx into the retinal/RPE tissue. During inflammation, increased phagocytic activity may correlate with increased dye uptake and the generation of brightly fluorescent dots. Normally situated deep in the choroid (macrophages) or in the inner retina (microglia), their recruitment to the sites of RPE and photoreceptor damage would also suggest the presence of bright DNIRA dots.

DNIRA can identify previously unknown image-based patterns of disease, e.g., provides novel phenotypic description of individual subjects. Accordingly, there is a need for image-based systems that can stratify subjects into different subtypes of disease that may differ according to rates of progression, susceptibility to epigenetic risk, response to different therapies and ultimately to rates of vision loss. DNIRA can dramatically increase an ability to define these groups. As DNIRA provides unprecedented description of different patterns or subtypes of disease, the results of a centralized imaging platform, iteratively improved used structured and unstructured learning, can then be compared against GWAS analysis, epigenetic status, and other medical or demographic information.

DNIRA as Functional Imaging

Without wishing to be limited by theory, it is understood that the pathogenesis of AMD derives in part from the inability to adequately transport oxygen and nutrients from the underlying choroidal blood vessels to the RPE/photoreceptor (RPE/PhR) complex, which may be exacerbated as drusen or other deposits (e.g., lipids, basal laminar deposits, etc. . . . ) accumulate or as Bruch's membrane (the specialized basement membrane of both the choroidal endothelium and RPE monolayer) thickens. Likewise, the removal of metabolic waste from the RPE/PhR complex may also be impeded. A disturbance of this normal physiological exchange is believed to underlie some aspects of disease. DNIRA represents the first measure of this transport system, and so represents the first functional imaging method. Other imaging methods to date are structural and do not rely on such dye uptake.

DNIRA relies on the circulation of systemically delivered dye through the choroidal vasculature, its passage through Bruch's membrane and its active uptake into the retinal pigment epithelium (RPE) layer. A reduction in dye uptake can therefore be caused in several ways: through interposition of material between the choroid and the RPE (such as drusen or basal linear or basal laminar deposits, or deposits of unspecific composition), the separation of the RPE from its basement membrane (such as an RPE detachment, which may be serous, drusenoid, haemorrhagic or other), the localized loss of the choroidal blood vessels (as occurs when tumours infiltrate the choroid) or, by a general dysfunction of the RPE/Bruch's membrane complex that is unable, or of lessened ability, to transport the dye from the choroidal circulation to the RPE/photoreceptor complex. If this ability is completely lost, regions of DNIRA appear black. If this ability is partially lost, areas of DNIRA may appear grey. Such grey regions may be a sensitive indicator of decreased RPE health.

In the following two examples, the DNIRA signal is reduced when a small group of choroidal tumour cells preclude blood flow in a small region. In the second example, regions of black DNIRA recover as an initially large RPED resolves.

In one example of DNIRA as a functional imaging method, FIGS. 41-44 show a sequence of DNIRA images and OCT images of a patient's eyes obtained over four sessions. Recovery of functionality can be observed as the patient recovered from large RPE detachment and soft drusen diminished, with recovery in functionality corresponding to signal recovery (decrease in black pitch) in the DNIRA images over time.

A striking feature seen in FIGS. 41-44 is the reduction in 2D area of the regions of black, hypofluorescent DNIRA. This is not observed using FAF, the current gold standard, wherein regions of black, hypofluorescence correspond with region of atrophy, and so, in the absence of any available interventions, can only enlarge over time. In this instance, concurrently acquired and registered OCT images show that the return to normal levels of DNIRA fluorescence corresponds to a reduction, or flattening, of the retinal pigment epithelium detachment (RPED) and concurrent resolution of drusen.

Significantly, DNIRA images can reveal aspects of dynamic functional behavior of retinal tissue and thus be used as a form of functional imaging. In contrast, conventional imaging modalities such as FAF do not provide dynamic functional behavior of retinal tissue as signal loss is observed when tissue is dead and no recovery is available.

As a form of functional imaging, DNIRA can be used to measure treatment response in clinical trials, such as trials of pharmacotherapy, nutraceutical, thermal therapy, light-based therapy, stem cell therapy, gene therapy, or the like.

As a form of functional imaging, DNIRA can be used to follow the course of disease in a clinical (medical) setting In another example of DNIRA as a functional imaging method, FIG. 45 illustrates a DNIRA signal in black (as indicated by the arrow) where the tumour cells are blocking the flow of dye-labeled blood in the choroid, so precluding its uptake into the overlying RPE and photoreceptor tissue.

Taken together, the data in FIGS. 41-45 may suggest that DNIRA, the features of DNIRA, the constellation of DNIRA features that make up a phenotype, the DNIRA classifier and DNIRA predictor can serve as biomarkers to drive precision drug development and personalized medicine. This is of particular importance in jurisdictions where functional endpoints are required for late phase clinical trial.

Dyes

While reference has been made to ICG dye, in some aspects, other fluorescent compounds are substituted for ICG and are included in any of the aspects described above. Such fluorescent compounds can be suitable for imaging with various wavelengths of fluorescence. In some aspects, these wavelengths range from visible light to infrared, e.g., 390 nm to 1 mm, including, for example, blue light, white light, and near-infrared. In some aspects, the dye can be a near-infrared dye. Further, while specialists in eye disease, particularly retinal disease have used ICG, and other dyes such as fluorescein, for the purposes of angiography, angiography is not required for DNIRA.

Angiography, by definition "the study of blood vessels", requires the intra-vascular injection of dye and evaluation of the changes that occur in the dye distribution thereafter, starting within seconds and extending to the minutes and hours thereafter, described by those versed in the art as leakage or staining, within defined time frames such as circulation phase, transit phase, and re-circulation or late phase. As DNIRA does not evaluate blood vessels or their integrity, dyes can be provided by other routes of administration, such as oral and imaging performed thereafter in hours or days or weeks.

In some aspects, the fluorescent compound can absorb light at a wavelength of about 600 nm to about 900 nm and/or emits light at a wavelength of about 750 nm to about 950 nm. In some aspects, fluorescent compound can have the following features: about 795 nm (excitation) and about 810 nm (emission).

Grey-Scale Feature Extraction

In some embodiments, processing of DNIRA images may including extracting features using a Gray Level Co-occurrence Matrix (GLCM) analysis. In accordance with GLCM, a matrix is constructed by counting the number of co-occurrences for a pixel value at different distances. This matrix is then be used to extract statistical coefficients which are generally referred to as GLCM features, which include energy, entropy, contrast, homogeneity, correlation, shade, and prominence.

Classifier

As noted above, the computer systems described herein may be adapted to provide a computer system that processes ophthalmic image data, such as ocular images, to automatically classify data samples into one or more groups. Each of such special purpose computer systems may be referred to as a "classifier" herein.

In some embodiments, a classifier may be configured to distinguish, stage, or grade variants of binding eye disease such as, but not limited to, as Age Related Macular Degeneration (AMD), monogenic eye disease, inherited eye disease, inflammatory eye disease, CSR, serpiginous, ocular tumours or the like.

In some embodiments, a classifier may be configured to distinguish, stage, or grade variants of central nervous system (brain) disease, such as dementia, Alzheimer's disease, or the like, wherein aspects or components of the disease concurrently exist in eye and brain, such as the deposition of amyloid.

In some embodiments, a classifier may be configured to classify particular regions of eye by tissue state such as, but not limited to, normal tissue, drusen, pseudodrusen, or GA. In some embodiments, a map of tissue state across the eye is generated by sampling eye image data at a plurality of regions and classifying the tissue state of each region. Such a map may be used for visualizing disease state, e.g., upon presentation to a graphic user interface. Maps generated at different time periods for the same eye may be used to visualize disease progression.

The maps may also be used as input data to other classifiers or configured to classify a patient, subject, or eye by, for example, extent of tissue loss, disease stage or grade. The input data may be used for such classifiers at a training phase or a classification phase. The maps may also be used as input data to a predictor, as detailed below, for predicting an area of disease progression (e.g., tissue loss or neovascularization) or a rate of disease progression or disease expansion.

Figure 46A:
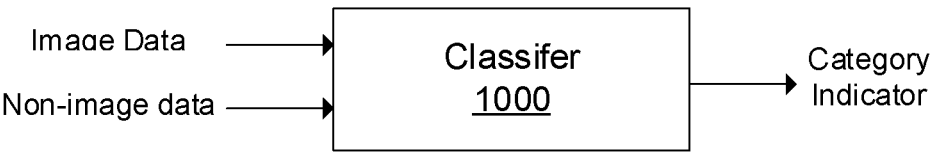
FIG. 46A depicts a classifier exemplary of an embodiment.

FIG. 46A depicts a classifier 1000 exemplary of an embodiment. As depicted, classifier 1000 may receive image data and non-image data as inputs and processes these data to produce a category indicator, namely, a digital indicator of the computed category, as an output. In one example, the category indicator may, for example, be indicative of a pre-defined category. The classification indicator may, by way of non-limiting example, categorical, continuous, binary, or descriptive.

Image Data

The image data input to classifier 1000 may include multi-modal image data as described herein. In one embodiment, the image data includes data produced at image acquisition 302 (FIG. 4). In another embodiment, the image data includes data produced at preprocessing 304 (FIG. 4). In another embodiment, the image data includes data produced at postprocessing 306 (FIG. 4). Classifier 1000 may implement some or all of the preprocessing and postprocessing functions such as registration, segmentation, feature extraction, etc.

Imaging modalities of image data that is input to classifier 1000 may be at least one of delayed near-infrared analysis (DNIRA), infra-red reflectance (IR), confocal scanning laser ophthalmoscopy (cSLO), fundus autofluorescence (FAF), color fundus photography (CFP), optical coherence tomography (OCT), OCT-angiography, fluorescence lifetime imaging (FLI), multispectral detection, and polarized fluorescence imaging.

DNIRA image generation may be performed as described herein. Briefly, images are acquired using a commercially available confocal scanning ophthalmoscope (e.g., Spectralis, Heidelberg Engineering, Germany) or other capable imaging device, before and at a suitable time after the systemic administration of ICG dye. Additional images are also obtained in the red-free, FAF (488/500 nm excitation/emission), IR reflectance channel (830 nm) and ICG fluorescence channels (795/810 nm excitation/emission), along with optical coherence tomography (OCT), optical coherence tomography angiography (OCT-A), fluorescence lifetime imaging (FLI), color fundus photography, multispectral detection, and polarized fluorescence imaging. Fluorescein or ICG angiography may or may not be performed.

Non-Image Data

The non-image data input to classifier 1000 may include other data reflective of the biology or health of the patient including, for example, age, height, weight, body mass index, blood pressure, measures of bodily tissue or fluids, or to measures of their visual function, evaluated using methods such as visual acuity (VA), low luminance visual acuity (LLVA), delta LLVA, microperimetry, dark adaptometry, reading speed, preferential looking tests, electroretinography, patient demographic data, concurrent illness, medications, allergies, smoking status, or the like. The non-image data may be particular to a specific patient or may be data reflective of a particular group of patients. The non-image data may include record data automatically retrieved from a database storing patient health records.

The non-image data may be particular to a specific patient or may be data reflective of a particular group of patients. The non-image data may include record data automatically retrieved from a database storing patient health records.

Non-image data input to classifier 1000 may include data related to systemic biomarkers. Such biomarker samples may include blood or cell samples (e.g., buccal) for genetic testing, genomic testing, or may include blood sampling for, by way of non-limiting example, cellular analysis, protein analysis, proteomics, metabolomics, transcriptomics analysis, or may include samples of other bodily tissues such as gum and periodontal sampling or urine or stool sampling, for by way of non-limiting example, evaluation of oral or gut microbiome The non-image data input to classifier 1000 may also include parameters of a pattern recognition model. For example, when classifier 1000 is implemented as a CNN, such parameters may include the CNN's kernels, template, window size, or the like.

Data Transfer

During data transfer, for example, during preprocessing and prior to input to classifier 1000, data may be handled in compliance with privacy rights regulations, such as the Personal Health Information Protection Act (PHIPA) in Ontario, or other regions globally. Input data, including both image and non-image data, may be de-indentified and anonymized multimodal images with or without metadata and exported using proprietary (e.g., Heyex, Heidelberg Engineering, Heidelberg, Germany) or non-proprietary software to local drives, network drives, distributed networks, or a cloud computing service.

Data Storage

In some embodiments, storage of data that may be used as input for classifier 1000 follows a hierarchical tree representation. Each tree branch contains information about session number, imaging modality, wavelength/dye used for that modality and finally the filename. The file name follows a specific pattern which contain the patient number session number and whether the image is for the left eye 'OS' (short for oculus sinster) or right eye 'OD' (oculus dextrus, right eye).

Figure 47:
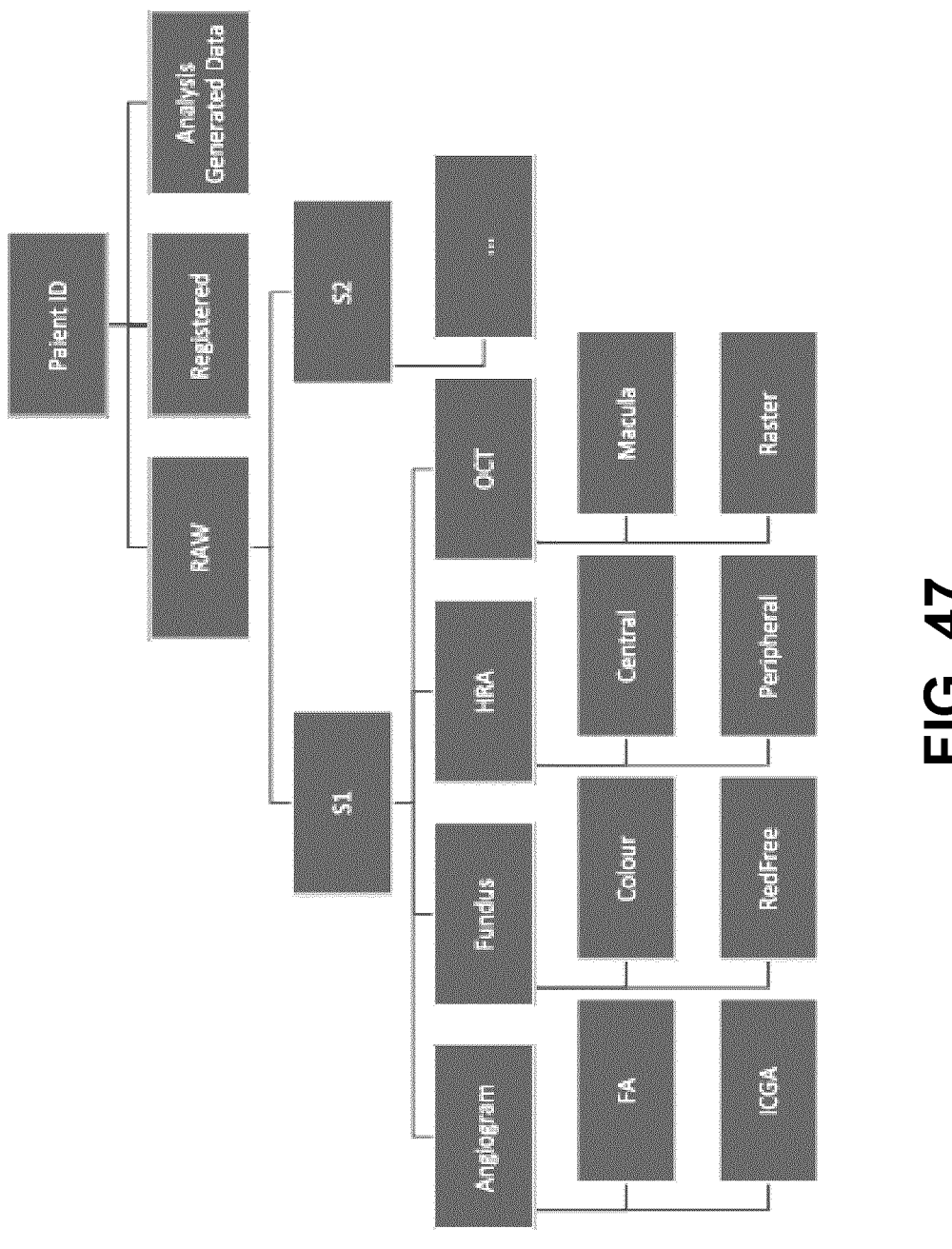
FIG. 47 depicts a data structure for storing multimodal retinal images, exemplary of an embodiment.

In one specific embodiment, the image data may be input to classifier 1000 in the form of a data structure as depicted in FIG. 47, for storing multimodal retinal images.

A tree representation of data storage is illustrated in FIG. 47. Each patient is supplied with an identification (ID) number which forms parent branch in the data storage path. Within each patient branch the data can be stored in the RAW, registered or further analysis data folder. Within each of these folders the images are stored into a new branch indicating their visit session number denoted by "S". For each session, multiple images are acquired. The images are further divided into "Angiogram", "Fundus", "HRA", and "OCT"; based on the modality of acquisition.

The modality tree can branch further, for instance an angiogram branch contains images related to angiography which are used to investigate the flow of blood in the back of the eye. Angiography can be performed using different agents such as ICG (ICGA) or Fluorescein (FA). The angiogram branch is then divided to two new branches indicating the type of dye used.

At the end of each branch, images are labelled using a precise pattern which contains information about the ID, visit number, imaging wavelength and eye id. Both the hierarchical tree and the file name may be used to easily identify and retrieve the needed images from a data server. For example, to retrieve the central fundus autofluorescence (FAF) image for patient 1 for the left eye, from their first visit, the following path may be generated: 001>RAW>S1>Fundus>HRA>Central>P008_S1_FAF_OD.tif In some embodiments, for single or multi-site studies, data may be configured using a forest.

Machine Learning

In some embodiments, classifier 1000 may be configured to automatically identify important features or phenotypes, or combinations of features or phenotypes during a training stage, as detailed below.

In some embodiments, classifier 1000 can train a pattern recognition model 1002 that is one or more of a convolutional neural network (CNN), decision trees, logistic regression, principal components analysis, naive Bayes model, support vector machine model, and nearest neighbor model.

A neural network may include, for example, three layers of neurons: an input layer, a hidden layer and an output layer. The hidden layer is a linear combination of the input x and a bias (e.g., z=Wx+b). Neurons at each layer may be activated via some nonlinearity (e.g., a=tanh (z)). The output layer is configured to generate an assessment of input layer (e.g., normal/GA), and errors are corrected via back propagation.

Convolutional neural networks may be used for image classification, and scan across an image with filters that pick out different patterns. Each successive layer picks out more complex patterns.

A convolutional neural network may be composed of two parts, feature extraction part and class identifier. The convolutional layers are known as feature extractors. The first layers extract simple features such as lines and edges while the following layers create combinations of these features. In the final layers of a feature extraction part, a more abstract features representation is created by a chain of combination of combinations of features. The second part of the convolutional neural network, the class identifier, identifies to which class these abstract representations belong.

Figure 48:
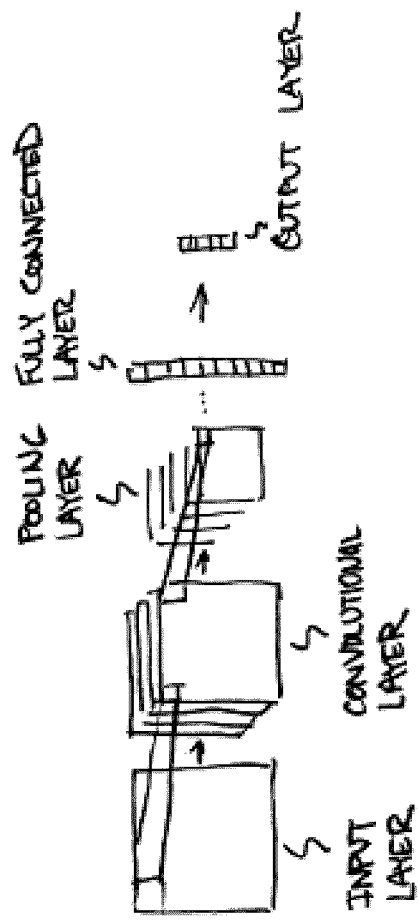
FIG. 48 depicts convolutional neural network architecture exemplary of an embodiment.

An example convolutional neural network architecture is shown in FIG. 48. An input layer receives input data. A convolutional layer applies a convolution operation to the input (emulating the response of an individual neuron to visual stimuli), passing the result to the next layer. A pooling layer reduces the dimensions of the data by combining the outputs of neuron clusters at one layer into a single neuron in the next layer. A fully connected layer connects every neuron in one layer to every neuron in another layer. The flattened matrix goes through a fully connected layer to classify the images. An output layer outputs, for example, a classification.

A trained classifier identifies important features or combination of features (phenotypes) that help it learn a particular class. During a training phase, classifier 1000 attempts to use many different iterations of features combination until it identifies important sets of features, that may be a single feature or a plurality of features, that it uses to determine the class.

In some embodiments, features may be clinically identified, such as generally elliptical shaped hypofluorescent regions resembling "fingerling potatoes". For example, the classifier may process input image data corresponding to a greyscale region and, upon performing classification, generate a classifier indicator in form of a category label such as "fingerling potato", "loose weave", "tight weave", "leopard spots", and the like, as described herein.

Furthermore, examining the different layers of the CNN, may allow for identification a new set of features or phenotypes, and their importance may be examined in identifying the classes.

In some embodiments, a pattern recognition model may be implemented as a U-Net model built and trained, by way of non-limiting example, using Keras with TensorFlow backend.

In Use

Figure 49:
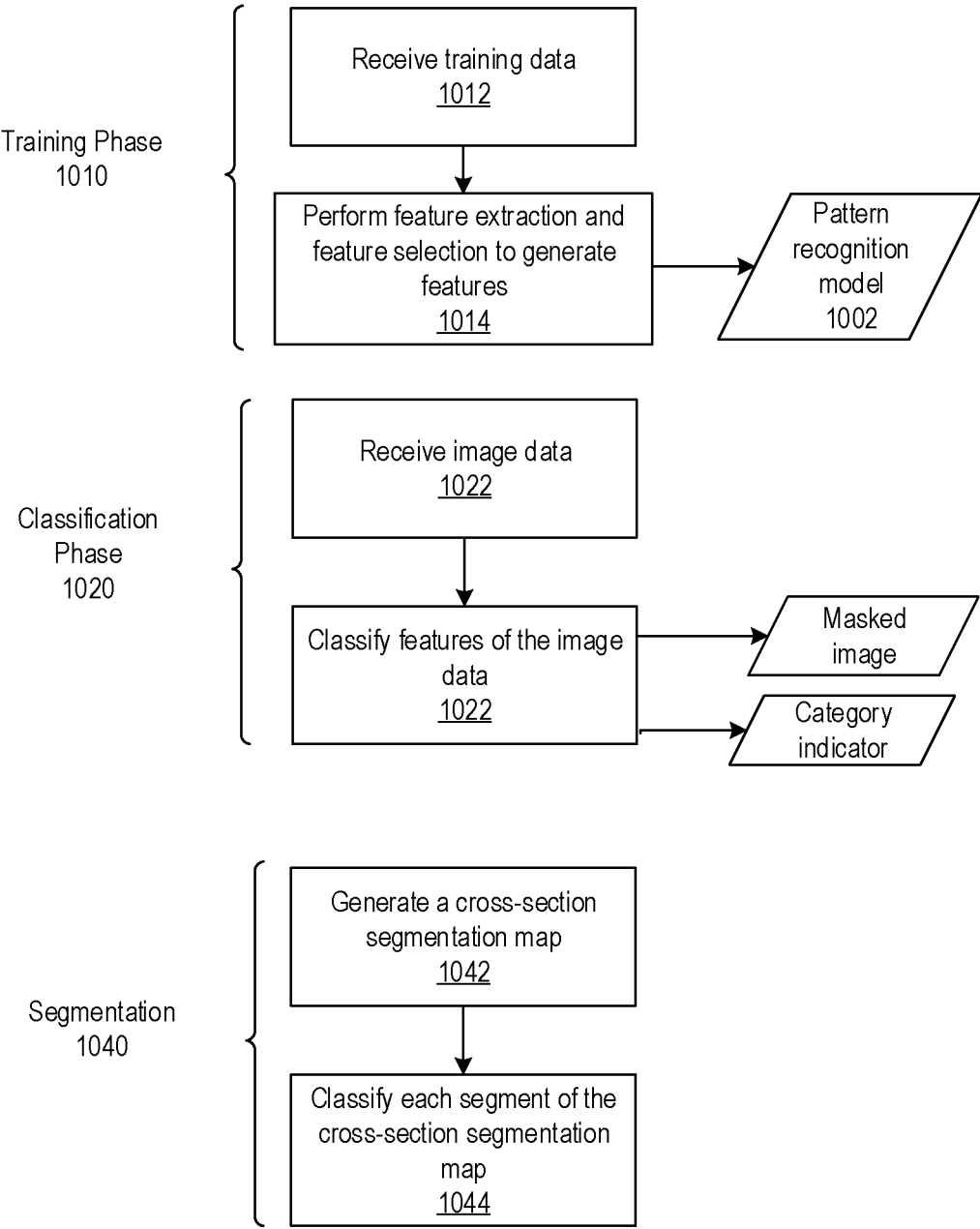
FIG. 49 depicts operation of the classifier of FIG. 46A, exemplary of an embodiment.

The operation of classifier 1000 is described with reference to the flowchart of FIG. 49.

At a training phase 1010, at block 1012 classifier 1000 may receive training data corresponding to image data and non-image data, as described herein. In an example, training data may be image data corresponding to a plurality of ocular images.

In some embodiments, the plurality of ocular images includes en face images and cross-section images.

In some embodiments, the plurality of ocular images of the training data correspond to a plurality of imaging modalities.

In some embodiments, the plurality of imaging modalities may be at least one of delayed near-infrared analysis (DNIRA), infra-red reflectance (IR), confocal scanning laser ophthalmoscopy (cSLO), fundus autofluorescence (FAF), color fundus photography (CFP), optical coherence tomography (OCT), OCT-angiography, fluorescence lifetime imaging (FLI), multispectral detection, and polarized fluorescence imaging.

In some embodiments, input to classifier 1000 may be en face images from the central macular region, or multiple en face images from adjacent or extra-macular areas, which may or may not be acquired, assembled or stitched into a composite image.

At block 1120, classifier 1000 may perform feature extraction and feature selection to generate features based on the training data to build a pattern recognition model 1002.

In some embodiments, a pattern recognition model may be built for each of the plurality of imaging modalities.

At a classification phase 1020, at block 1022 classifier 1000 may receive image data, for example, a plurality of ocular images corresponding to a plurality of imaging modalities.

At block 1024, classifier 1000 may classify features of the image data using pattern recognition model 1002. Classifier 1000 may then output, for example, a segmented image such as a masked image illustrating the identified features, and a category indicator for one or more of the classified features.

Figure 50:
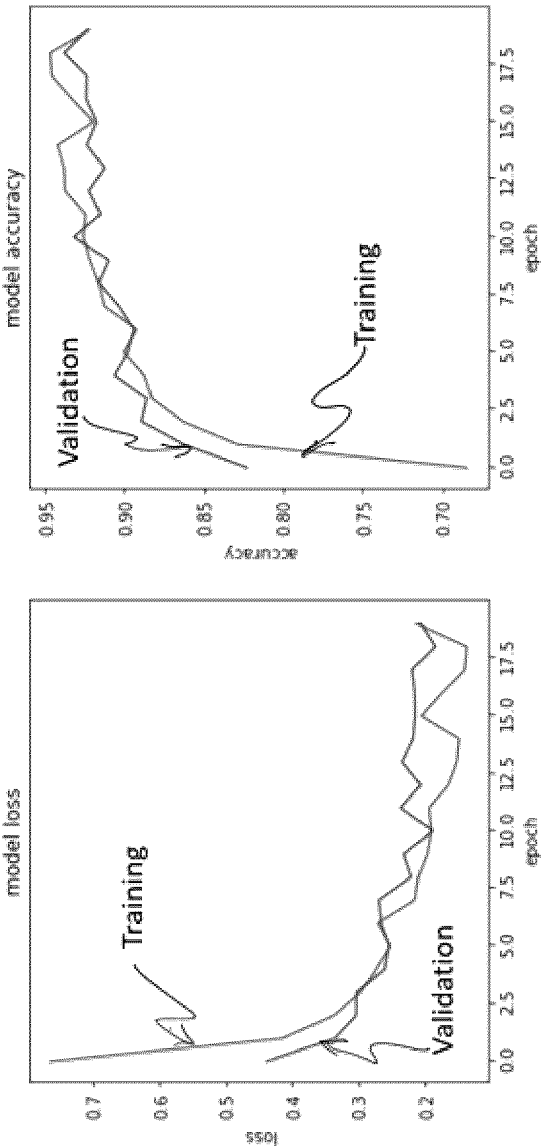
FIG. 50 depicts a representative example plots of model loss and model accuracy on training and validation datasets over training epochs.

In experimental work to date, performance of an example embodiment of pattern recognition model 1002 as a CNN has been evaluated. Using a CNN similar to pattern recognition model 1002 described herein, training and validation were performed. FIG. 50 shows plots of model loss and model accuracy on training and validation datasets over training epochs.

A dataset was generated of 13,324 images of cross-section regions of interest (ROIs).

CNN training was performed on a training dataset of 10754 regions of interest (80% of the total available dataset) and validation was performed with the remaining 2570 regions of interest (20% of the total available dataset).

As seen in FIG. 50, the model has comparable performance on both training and validation datasets, as the plots converge.

Image Segmentation

Classifier 1000 is configured to perform segmentation of unprocessed high-resolution DNIRA images to generate a segmented image. A segmented image may be a masked image, shown for example in a masked image 1404 shown in FIG. 51.

Image segmentation refers to a process of identifying a set of pixels in an image belonging to an object or feature of interest. In particular, in some embodiments classifier 1000 segments retinal images and identifies areas where retinal tissue changes have occurred.

Figure 51:
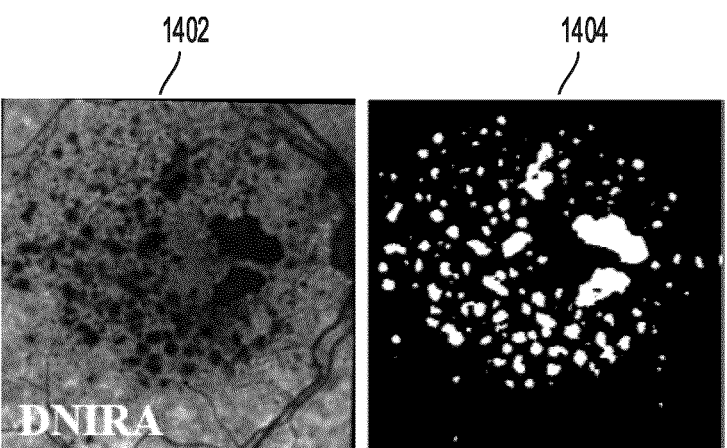
FIG. 51 depicts a representative example of an input and output of a classifier, exemplary of an embodiment.

By way of example, regions of hypofluorescent/black DNIRA can be segmented, as shown in FIG. 51, illustrating an input 1402, a DNIRA en face ocular image, to classifier 1000, and a masked image 1404 of defined shapes generated by classifier 1000.

In some embodiments, features generated by classifier 1000 include defined areas of hypofluorescence (that identify regions of absent fluorescence signal), or areas of hyperfluorescence, as illustrated in masked image 1404.

Input images may be evaluated by classifier 1000 at a single timepoint and regions of profoundly hypofluorescent/black DNIRA signal identified and quantified.

Input 1402 illustrates a raw image of a patient with late dry AMD, with regions of hypo/black DNIRA.

Output 1404 illustrates an automatically segmented image, or mask, derived using classifier 1000.

Figure 52:
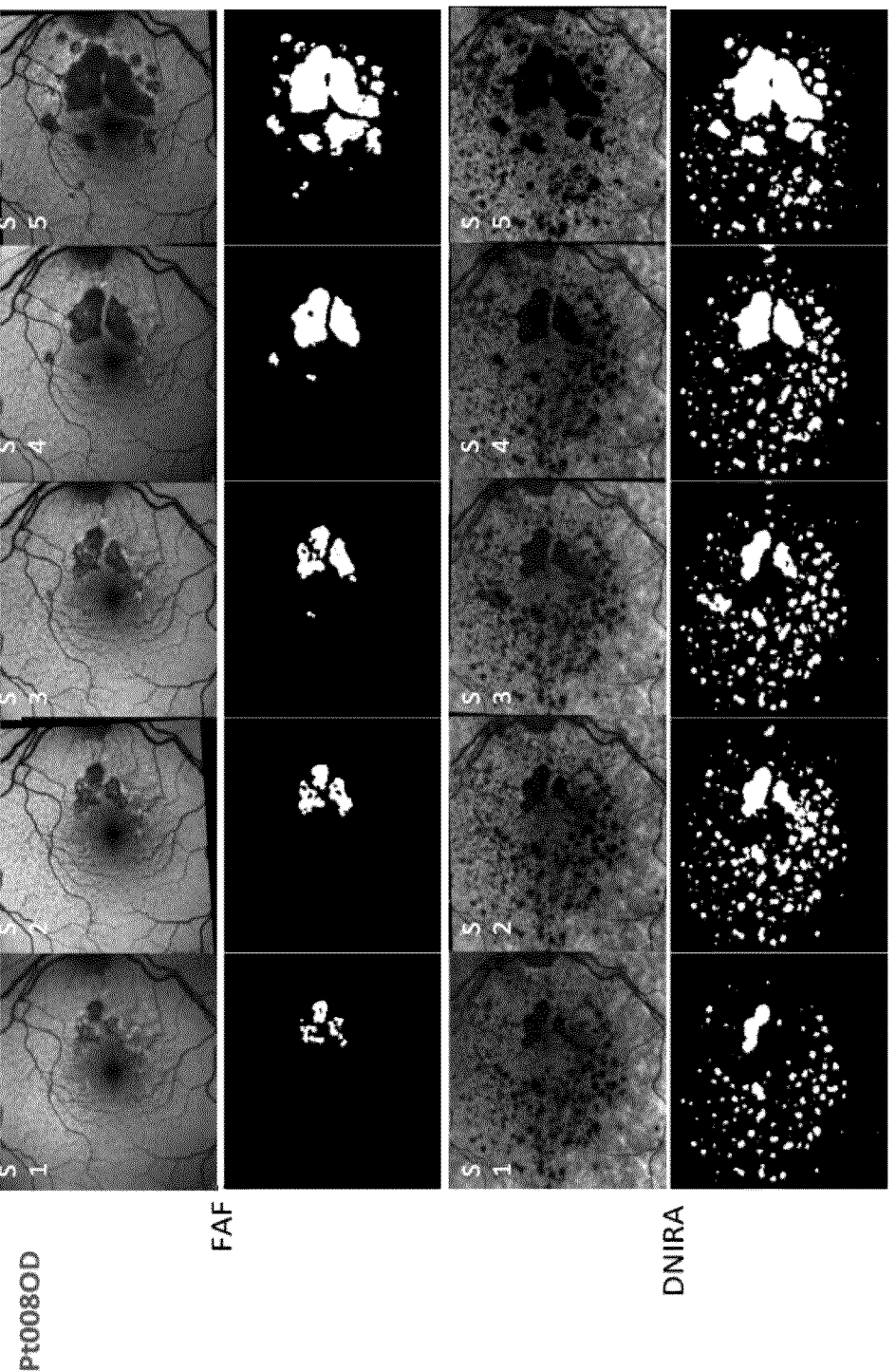
FIG. 52 depicts an example sequence of masked images from four timepoints.

Images may be obtained at a single timepoint, or over multiple timepoints for processing by classifier 1000. Regions of profoundly hypofluorescent/black DNIRA signal may be identified and quantified, and the difference, or delta, identified. FIG. 52 shows an example sequence of masked images from four timepoints. As shown, the mask images may be generated for multi-modal image input, e.g., FAF and DNIRA images.

In an embodiment of pattern recognition model 1002, U-Net convolutional networks may be utilized to segment 2D FAF and DNIRA images and extract areas where signal loss has occurred.

The U-Net convolutional network works by using convolutional layers to produce a low-dimensionality representation of the image. The U-Net convolutional network then creates a new representation of the image by going through de-convolutional layers. The de-convolutional network suppresses undesired features in the image.

In some embodiments, implementation of the U-Net architecture uses batch normalization. Batch normalization refers to normalizing the output of different layers in neural networks. This may improve information flow from one layer to the next, which may allows the algorithm to converge faster.

Image segmentation may be performed using a classical machine learning approach, or a deep learning based approach.

In an example classical machine learning approach:

1. Construct a training set by selecting regions with hypofluorescent DNIRA (class 1) and regions where non-hypofluorescent DNIRA (class2, normal DNIRA signal and/or hyperfluorescent DNIRA).
2. Extract a set of predetermined features (mean, variance, entropy, texture features, wavelet features) for both regions.
3. Train an algorithm to distinguish between class1 and class2. These algorithms are generally based on decision trees such as random forest trees.
4. Define window size that slides across the image.
5. At each window step extract same set of features as in step 2.
6. Use trained algorithm in step 3 to decide whether this region is hyperfluorescent DNIRA or not.
7. Decision map is now a segmentation map used to extract hypofluorescent regions.

In an example deep learning based approach:

1. Use multi-level threshold create binary maps of DNIRA. At each level identify regions where hyperfluorescent DNIRA outline has been identified. Combine these regions and set create a binary mask where 1 indicates pixel belongs to hypofluorescent region (class 1) and 0 indicates that pixel belongs to class 2.
2. Save images and masks in separate folders. Both the image and the mask should have the same name identifier.

3. Build a large data bank containing many examples of manually generated masks which will be used to train deep learning algorithms.
4. Use deep learning based segmentation algorithm using generated data bank in step 3. (https://ieeexplore.ieee-.org/document/7749007).
5. Store weights for trained algorithm on disk.
6. Load algorithm and training weights and pass new image through the algorithm.
7. Algorithm outputs probability map for the likelihood that a certain pixel belongs to class A or B. to generate a binary mask a probability threshold is applied (in our case we use a 50% as the threshold).

In some embodiments, image segmentation may be performed using image processing algorithms such as edge detection or principal component analysis, alone or in combination with techniques described herein.

In some embodiments, training makes use of boot-strapping to improve the quality of segmentation algorithms. In boot-strapping masks can be generated using the classical machine learning approach which are then manually examined and improved to be used as part of the training bank for deep learning based approaches.

Feature Classification

The features classified by classifier 1000 may be phenotypes of a user associated with the plurality of ocular images.

In some embodiments, the features may distinguish between different phenotypes and biomarkers.

In some embodiments, the features may be correlated with stage or grade variants of blinding eye disease including Age Related Macular Degeneration (AMD), monogenic eye disease, inherited eye disease and inflammatory eye disease.

In some embodiments, the features may be correlated with stage or grade variants of central nervous system (brain) disease, such as dementia and Alzheimer's disease.

In some embodiments, the features may be correlated with other measures of disease or health.

In some embodiments, the features may be correlated with biomarkers, by way of non-limiting example such as those for diagnosis, prognosis, monitoring, and those applied to determine treatment efficacy or safety.

The output of classifier 1000 may be, by way of non-limiting example, categorical, continuous, binary, or descriptive.

Registration

In some embodiments, ocular images may be registered to a common coordinate system before classification. In some embodiments, ocular images may be registered following classification.

In some embodiments, registration may be cross-modal fusion of the plurality of ocular images to a common coordinate system.

In some embodiments, registration may be done using elastic or non-elastic transformation.

As illustrated in FIG. 53, in some embodiments, image registration is performed by first scaling the images, such as unprocessed high-resolution DNIRA images, and applying a Gaussian filter. Scale Invariant Feature Transform (SIFT, included in OpenCV) is used to find features across multiple images. The main features of interest in an example may be blood vessels. The corresponding feature pairs between two images are determined using brute force algorithm (BF) followed by random sample consensus (RANSAC) to calculate an affine transformation map. The inverse of the affine matrix is applied to the second image to register it to the first image.

Multi-modal registration may be used to align images of the same modality, or between DNIRA and images of other modalities.

Segmentation Map

Returning to FIG. 49, in some embodiments, classifier 1000 may perform segmentation 1040 based on input cross-section images. At block 1042, cross-section segmentation map is generated corresponding to an en face region of an eye, each segment of the cross-section segmentation map corresponding to a cross-section image at that region of the eye.

At block 1044, each segment of the cross-section segmentation map is classified as a phenotype such as a tissue state, for example, one of pseudodrusen, normal, drusen, retinal pigment epithelium detachment, geographical atrophy, macular atrophy or neovascularization based at least in part on classification of the cross-section image corresponding to that segment using pattern recognition model 1002.

Figure 54:
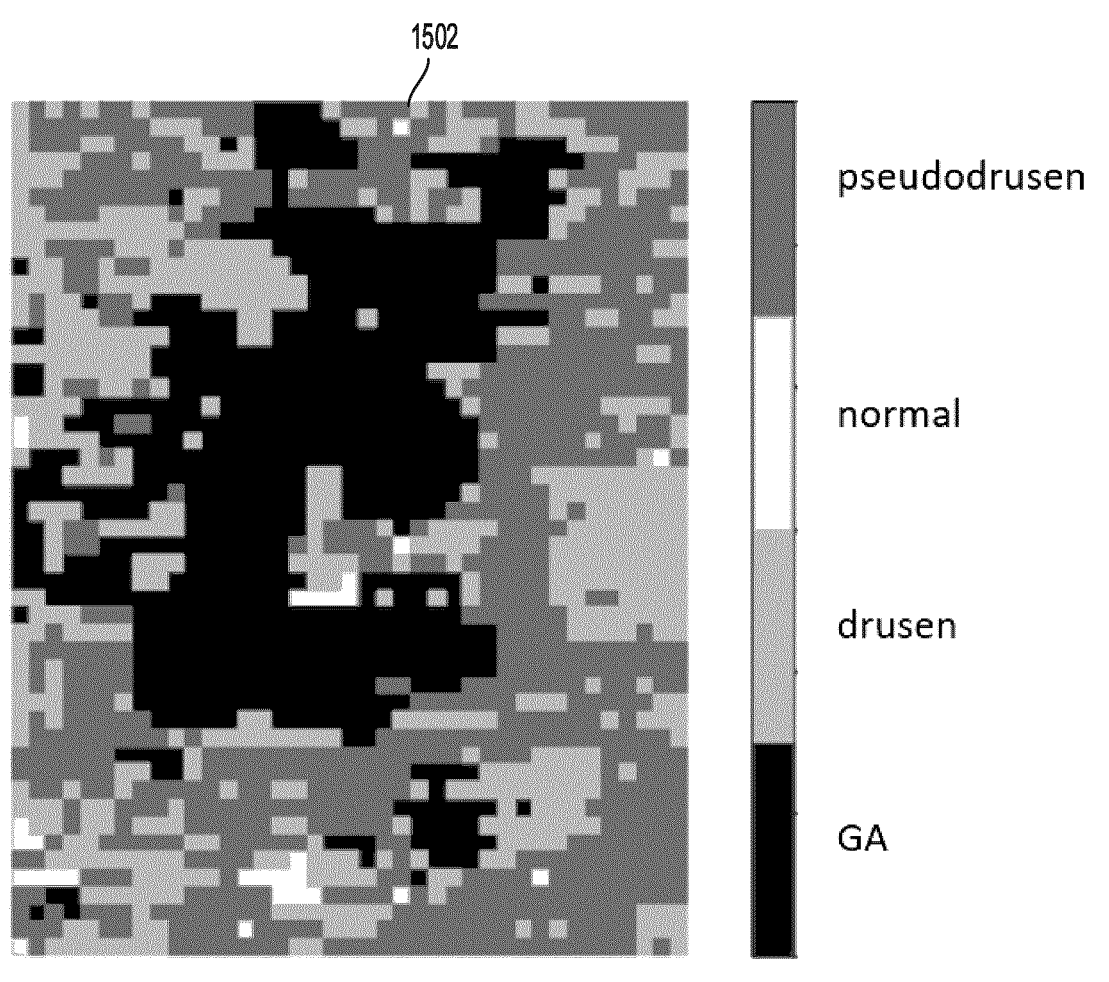
FIG. 54 depicts a representative example of a classified cross-section segmentation map.

FIG. 54 illustrates an example classified cross-section segmentation map 1502, with the classifications of tissue state phenotypes identified in the legend as psuedodrusen, normal, drusen or GA (geographical atrophy).

Steps of segmentation 1040 may be performed to generate a cross-section segmentation map for each of the multiple time points. A time series data model may then be generated based on the cross-section segmentation map at each of the multiple time points.

Figure 55:
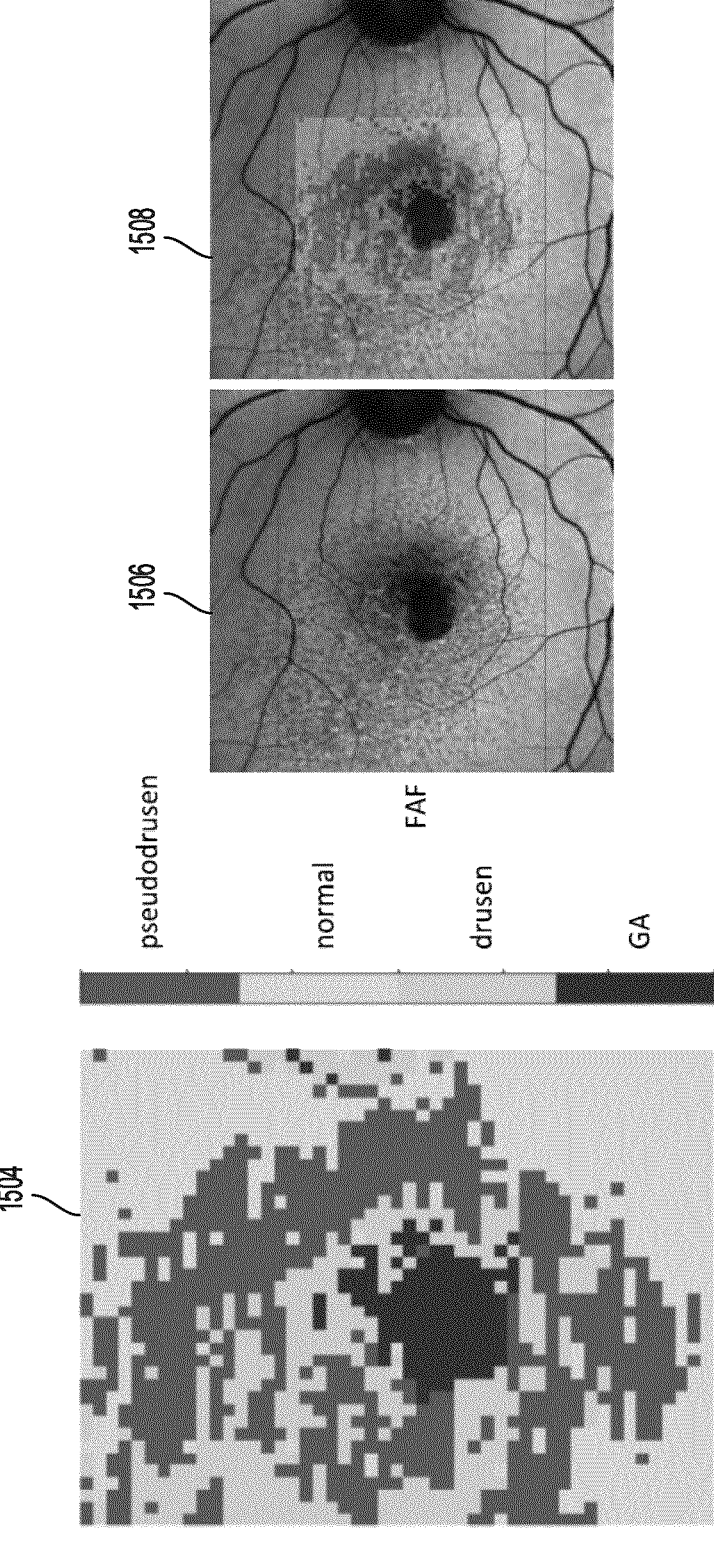
FIG. 55 depicts a representative example of a classified cross-section segmentation map registered to an en face FAF image.

As shown in FIG. 55, in some embodiments, a classified cross-section segmentation map 1504 may be registered to a common coordinate system with an en face FAF image 1506, illustrated by registered image 1508.

Conveniently, cross-section segment information on a eye, such as a tissue state, may be mapped to the corresponding en face region to visualize cross-section information on an en face image, providing further insights on the health of an eye.

Time Series

Figure 56:
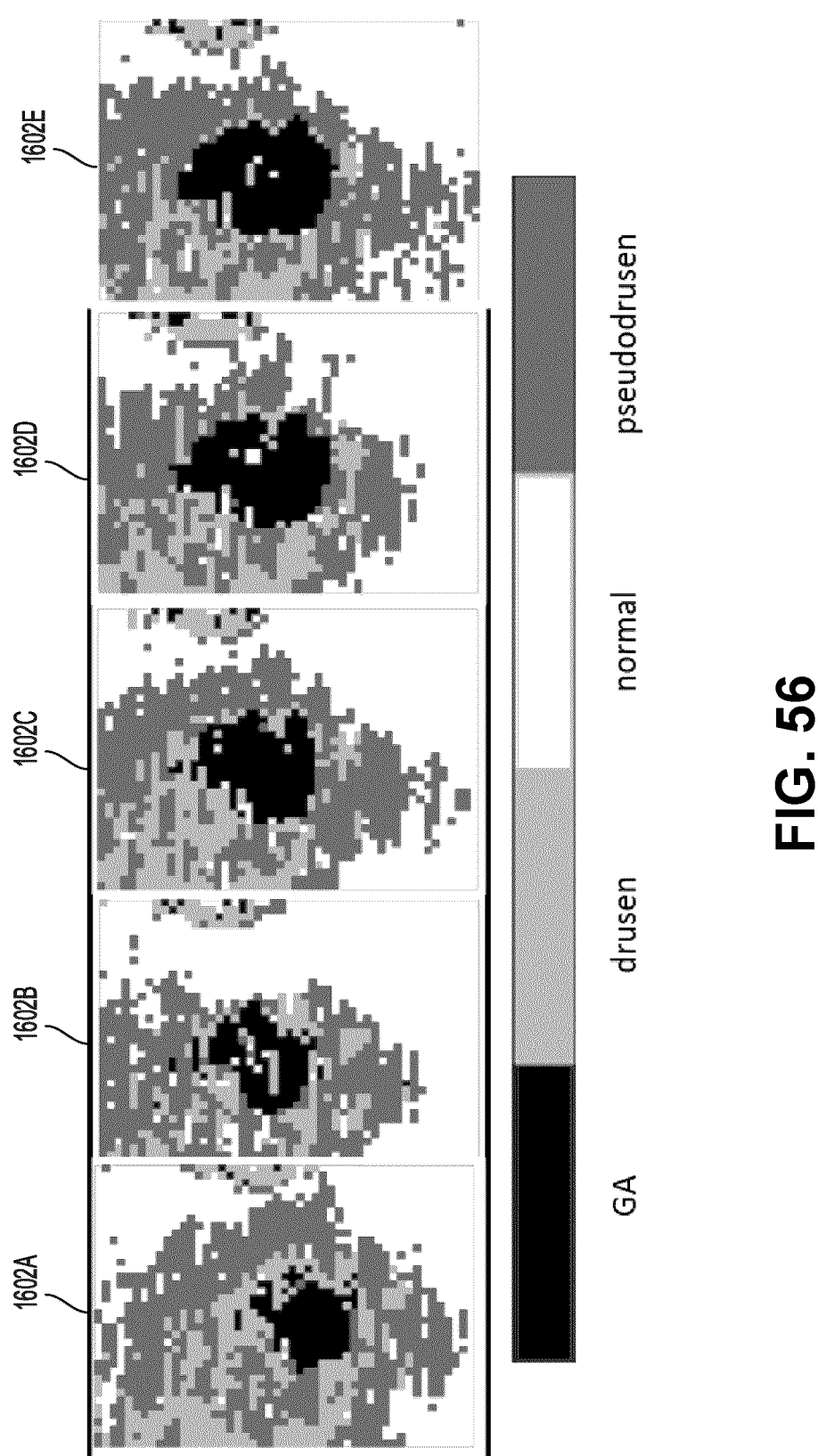
FIG. 56 depicts a representative example of classified cross-section segmentation maps, each associated with a time point.

FIG. 56 illustrates classified cross-section segmentation maps 1602A, 1602B, 1602C, 1602D and 1602E, each associated with a corresponding time point. Classified cross-section segmentation maps 1602A-1602B are generated based on cross-sections of ocular images, illustrating a progression or change in eye tissue over time. Classifications of tissue state phenotypes identified in the legend illustrated in FIG. 56 as psuedodrusen, normal, drusen or GA (geographical atrophy). In some embodiments, a time series of segmentation maps such as those shown in FIG. 56 may be used to train a predictor, for example, a time series model, to predict whether tissue loss has occurred or will occur within a given time period. Different time scales may be used for training examples, for example, across one or more of the maps 1602A-1602E. Thus, the presence of certain features (such as a region of particular size, shape and tissue type) may be used to predict tissue loss, for example, future rates of geographical atrophy expansion, based on such a time series model.

In some embodiments, the time series data model is based at least in part on identified changes in the cross-section segmentation maps over time.

In some embodiments, the time series data model visualizes disease progression.

In some embodiments, the time series data model is based at least in part on elapsed time between the multiple time points.

Multi-Sessional Image Registration

Retinal imaging of a patient population may be used to keep track of retinal tissue loss in time, and patients come back for multiple imaging sessions. Temporal analysis of the rate of tissue loss in time is a quantifiable observation and key requirement when performing medical trials. Thus, image registration may also be applied for the multisession images for each individual patient.

A registration pipeline used in some embodiments to perform multimodal image acquisition for multiple sessions includes registering en face images to the cross-sectional images. Cross-sectional OCT images may be acquired using the Infrared (IR) wavelength and the En face OCT registered to the IR confocal image. The reference IR image may be used to register the other modalities, thus allowing multi-modal registration of OCT to other 2D images.

FIG. 57 illustrates an example of en face OCT using IR image reference to determine position of cross-section. This IR reference is used to register other modalities to the OCT.

Figure 58:
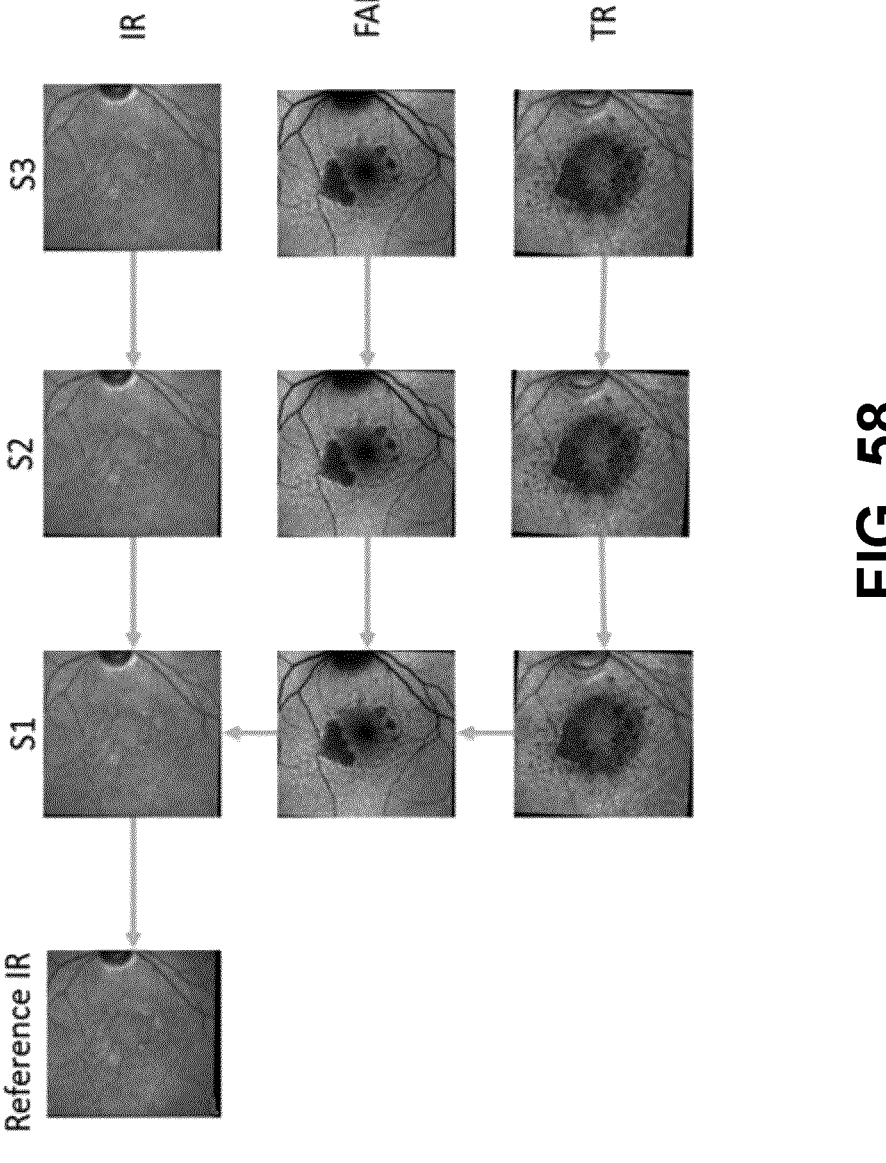
FIG. 58 depicts multi-modal image registration for multiple sessions, exemplary of an embodiment.

FIG. 58 illustrates multi-modal image registration for multiple sessions. The IR image used by the OCT in the first session (S1) is used to register images in all the sessions (S1, S2 and S3).

As shown by way of example in FIG. 58, the confocal IR image in the first session (S1) is used as the reference to register all the other images. FAF in S1 is registered to IR in S1. DNIRA in S1 is registered to FAF in S1. For imaging sessions beyond S1, each image is registered to its corresponding modality. For example, DNIRA in S2 is registered to DNIRA in S1. DNIRA in S3 is registered to the "now registered" DNIRA in S2. This registration path may result in a high level of consistency between extracted features from one session to the other. Conveniently, this may provide a better overall registration performance.

Figure 60:
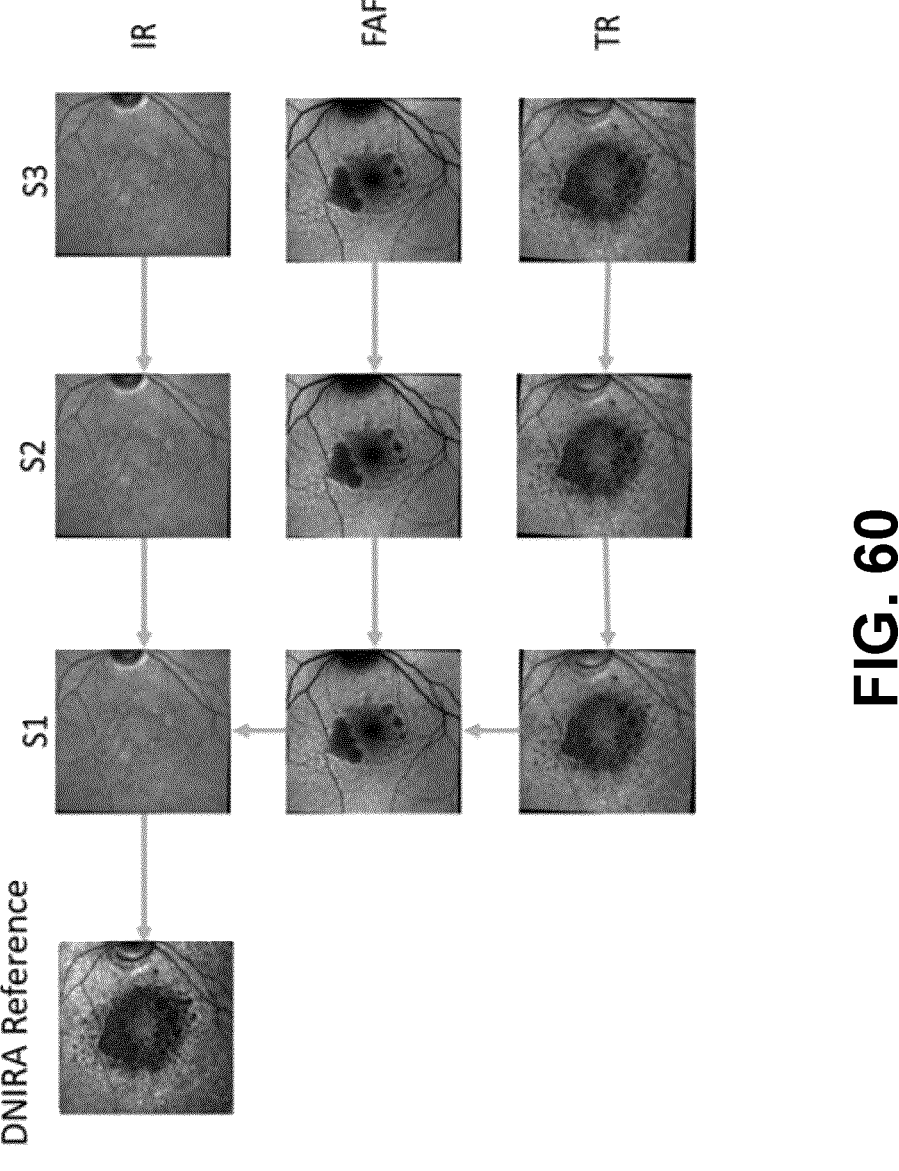
FIG. 60 depicts multi-modal image registration for multiple sessions, using a DNIRA image as a reference, exemplary of an embodiment.

In another example, OCT scans may be performed in the near IR channel, as shown in FIG. 59 and the pipeline may use the DNIRA image as a reference, as shown in FIG. 60.

FIG. 60 illustrates multi-modal image registration pipeline for multiple sessions. The DNIRA image used by the Near IR OCT in the first session (S1) is used to register images in all the sessions (S1, S2 and S3).

Detector

The computer systems described herein may also be adapted to provide a computer system that processes ophthalmic image data to automatically detect the presence of image-based phenotypes, and disease features, eye structures, or other features of interest. Each of such special purpose computer systems may be referred to as a "detector" herein.

In some embodiments, a detector may be configured to detect presence of one or more of the features shown in FIGS. 21A-21E, namely, according to pre-defined descriptive labels "loose weave", "tight weave", "leopard spots", "grey smudge", "fingerling potatoes" or the like.

As described further herein, features may include hypofluorescent patterns such as: a region of repeating hypofluorescent shapes, for example, in a "loose weave" pattern; a region of concentrated repeating hypofluorescent shapes, for example, in a "tight weave" pattern; patterns of generally elliptical, oval or oblong shaped hypofluorescent regions, for example, hypofluroescent shapes resembling "fingerling potatoes"; patterns of generally round or rosette shaped hypofluorescent regions, for example, hypofluorescent shapes resembling "leopard spots"; and regions of intermediate hypofluroescence (IHoF) or low hypofluorescence (LHoF), for example, resembling a "grey smudge".

In some embodiments, a detector may be configured to detect the presence phagocytic immune cells such as macrophages.

Optionally, the detector may generate one or more descriptors of the characteristics of the detected phenotype or feature, such as location, size, quantity, color.

Figure 46B:
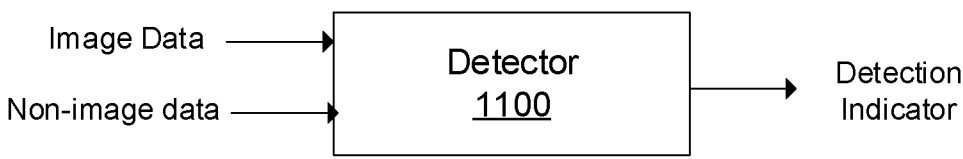
FIG. 46B depicts a detector exemplary of an embodiment.

FIG. 46B depicts a detector 1100 exemplary of an embodiment. As depicted, detector 1100 may receive image data and non-image data as inputs and processes these data to produce a detection indicator, namely, a digital indicator of whether a particular feature or phenotype was detected, as an output.

The detection indicator may be, by way of non-limiting example, continuous, binary, or descriptive.

The image data input to detector 1100 may include some or all of the types of data described in association with classifier 1000.

The non-image data input to detector 1100 may include some or all of the types of data described in association with classifier 1000.

In some embodiments, detector 1100 may be configured to perform detection using solely image data input.

Figure 61:
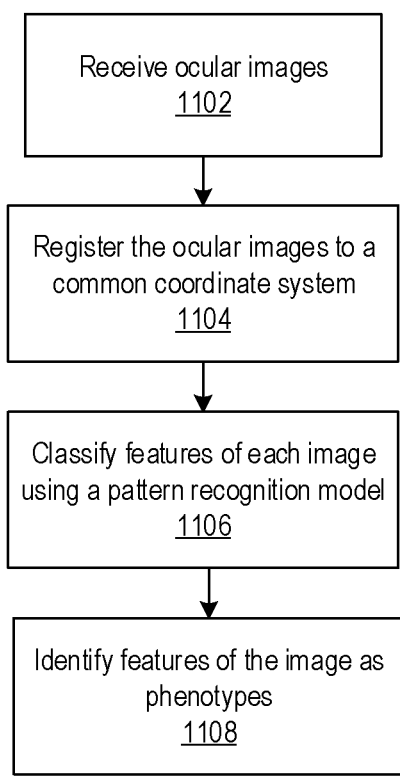
FIG. 61 depicts operation of the detector of FIG. 46B, exemplary of an embodiment.

The operation of detector 1100 to detect a phenotype is described with reference to the flowchart of FIG. 61.

At block 1102, input image data, for example, ocular images corresponding to a plurality of imaging modalities, is received.

The imaging modalities may include, for example, delayed near-infrared analysis (DNIRA), infra-red reflectance (IR), confocal scanning laser ophthalmoscopy (cSLO), fundus autofluorescence (FAF), color fundus photography (CFP), optical coherence tomography (OCT), OCT-angiography, fluorescence lifetime imaging (FLI), multispectral detection, and polarized fluorescence imaging.

At block 1104, the ocular images are registered to a common coordinate system, for example, using registration techniques as described herein.

At block 1106, features of each of the ocular images are classified, using a pattern recognition model.

In some embodiments, the pattern recognition model may be pattern recognition model 1102, as described herein. For example, the pattern recognition model may be a convolutional neural network built based on training data corresponding to a plurality of ocular images and feature extraction and feature selection is performed to generate features from the training data.

In some embodiments, the feature extraction generates a greyscale image of defined shapes. The defined shapes may include at least one of patterns labelled as "leopard spots", "loose weave", "grey smudge", and "fingerling potatoes", as described further herein.

For example, defined shapes may include hypofluorescent patterns such as: a region of repeating hypofluroescent shapes, for example, in a "loose weave" pattern; a region of concentrated repeating hypofluorescent shapes, for example, in a "tight weave" pattern; patterns of generally elliptical, oval or oblong shaped hypofluorescent regions, for example, hypofluroescent shapes resembling "fingerling potatoes"; patterns of generally round or rosette shaped hypofluorescent regions, for example, hypofluorescent shapes resembling "leopard spots"; and regions of intermediate hypofluroescence (IHoF) or low hypofluorescence (LHoF), for example, resembling a "grey smudge".

At block 1108, features of the image are identified as phenotypes.

In some embodiments, detector 1100 may further correlate one or more of the defined shapes with the presence of phagocytic immune cells such as macrophages.

In some embodiments, detector 1100 may further generate one or more descriptors of characteristics of the identified phenotype, such as location, size, quantity and colour.

Predictor

The computer systems described herein may also be adapted to provide a computer system that processes ophthalmic image data to automatically predict future changes in a patient, e.g., regions of disease progression, rate of disease progress. Each of such special purpose computer systems may be referred to as a "predictor" herein.

In some embodiments, a predictor may be configured to predict an area of tissue loss, or a rate of tissue loss. In some embodiments, a predictor may be configured to predict progression from early to late dry AMD. In some embodiments, a predictor may be configured to predict the response of a patient or group of patients to an intervention (e.g., a therapy). In some embodiments, a predictor may be configured to predict future onset of new GA. In some embodiments, a predictor may be configured to predict neovascularization.

In some embodiments, a predictor may compute one or more metrics reflective of a confidence level of a particular prediction.

Figure 46C:
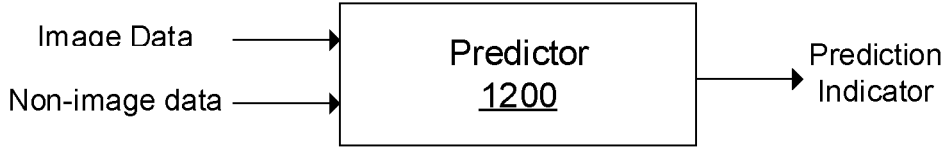
FIG. 46C depicts a predictor exemplary of an embodiment.

FIG. 46C depicts a predictor 1200 exemplary of an embodiment. As depicted, predictor 1200 may receive image data and non-image data as inputs and processes these data to produce a prediction indicator, namely, a digital indicator of a computed prediction, as an output.

The image data input to predictor 1200 may include some or all of the types of data described in association with classifier 1000.

The non-image data input to predictor 1200 may include some or all of the types of data described in association with classifier 1000.

Figure 62:
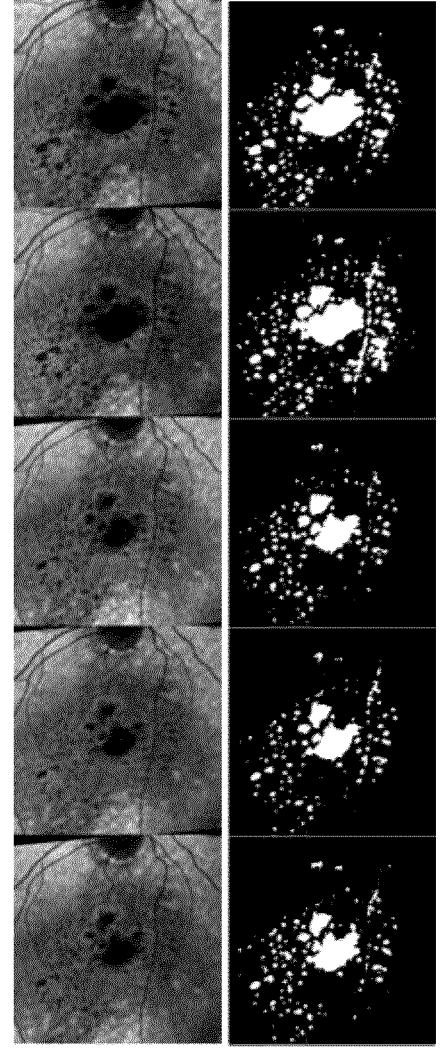
FIG. 62 depicts a representative example of images taken of a particular subject's eye over five sessions.

The image data input to predictor 1200 may include image data for images obtained at a single time point (a single session) or over multiple time points (multiple sessions). Predictor 1200 may be trained using image data for multiple time points to learn trends in features or phenotypes. For example, FIG. 62 illustrates images taken of a particular subject's eye over five sessions, showing an increase in hypofluorescent/black in the DNIRA image over that time.

In some embodiments, predictor 1200 may generate a prediction indicator reflective of a predicted change over time, either for an individual subject or a group of subjects. The change may be expressed in a variety of units, for example, the change in total area, the changes in the square root of the total area, the change in focality, the change in the focality index, or the like. Other examples include Circularity, Equivalent Diameter, Solidty, Eccentricity, Extent, Aspect Ratio. Spatial moment analysis may also be applied to these patterns, known as Hu invariants. The prediction indicator may be, by way of non-limiting example, categorical, continuous, binary, or descriptive.

Figure 63:
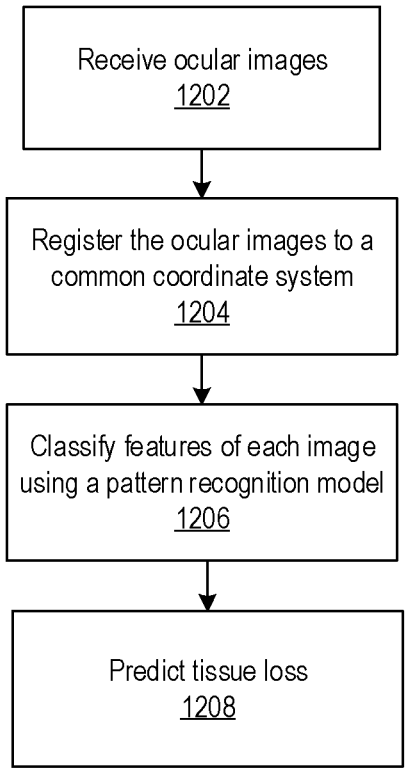
FIG. 63 depicts operation of the predictor of FIG. 46C, exemplary of an embodiment.

The operation of predictor 1200 to predict tissue loss is described with reference to the flowchart of FIG. 63.

At block 1202, input image data, for example, ocular images corresponding to a plurality of imaging modalities, is received.

The imaging modalities may include, for example, delayed near-infrared analysis (DNIRA), infra-red reflectance (IR), confocal scanning laser ophthalmoscopy (cSLO), fundus autofluorescence (FAF), color fundus photography (CFP), optical coherence tomography (OCT), and OCT-angiography.

The imaging modalities may include cross-section images and en face images.

At block 1204, the ocular images are registered to a common coordinate system, for example, using registration techniques as described herein.

At block 1206, features of each of the ocular images are classified, using a pattern recognition model.

In some embodiments, the pattern recognition model may be pattern recognition model 1002, as described herein. For example, the pattern recognition model may be a convolutional neural network built based on training data corresponding to a plurality of ocular images and feature extraction and feature selection is performed to generate features from the training data.

At block 1208, tissue loss may be predicted based at least in part on the features. In some embodiments, choroidal neovascularization (CNV) may be predicted, based at least in part on the features.

In some embodiments, the features selected comprise phenotypes of a user associated with the plurality of ocular images.

In some embodiments, tissue loss prediction may include identifying the phenotypes as risk factors by correlating the phenotypes with a rate of tissue loss over time.

In some embodiments, the predicting tissue loss is based on time series forecasting to predict tissue loss based on a time series data model, such as time series data model as generated by classifier 1000 as described herein.

For example, the time series data model may be generated based on multiple cross-section segmentation maps generated for each of multiple time points and corresponding cross-section images, each of the cross-section segmentation maps corresponding to an en face region of an eye, and each segment of the cross-section segmentation map corresponding to a cross-section image at that region of the eye classified as a phenotype of one of pseudodrusen, normal, drusen, retinal pigment epithelium detachment, geographical atrophy, macular atrophy or neovascularization based at least in part on classification of the cross-section image corresponding to that segment using a convolutional neural network.

In some embodiments, predicting tissue loss is based at least in part on non-image based biomarker data. Non-image based biomarker data may include characteristics of a user associated with the plurality of ocular images, the characteristics including at least one of age, genetics, sex, smoker status, and diet.

Predicting tissue loss may include one or more of predicting a rate of tissue loss, predicting whether tissue loss has previously occurred, and predicting whether tissue loss will occur in the future.

In some embodiments, predicting tissue loss comprises predicting regions of disease progression and rate of disease progress, such as progression from early to late dry Age Related Macular Degeneration (AMD).

In some embodiments, predictor 1200 may predict choroidal neovascularization (CNV) which indicates that the patient has converted from dry to wet AMD. In some embodiments, predicting neovascularization comprises predicting a onset of neovascularizaton. In some embodiments, predicting neovascularization comprises predicting whether neovascularization has previously occurred. In some embodiments, predicting neovascularization comprises predicting whether neovascularization will occur in the future.

In some embodiments, two or more classifiers 1000, detectors 1100, and predictors 1200 operate in concert to produce a category indicator, a detection indicator, or a prediction indicator. In one particular example, a detection indicator indicating the presence of a particular feature or phenotype (e.g., a macrophage) may be included within non-image data inputted to a predictor 1200. In this way, for example, a prediction of disease progression may be made based on the detection of a macrophage. In another particular example, a detection indicator indicating the presence of a particular feature or phenotype may be included within non-image data inputted to a classifier 1100. In another particular example, a classifier indicator may be included within non-image data inputted to a detector 1000. In another particular example, a classifier indicator may be included within non-image data inputted to a predictor 1200. In another particular example, a prediction indicator may be included within non-image data inputted to a classifier 1000. In another particular example, a prediction indicator may be included within non-image data inputted to a detector 1100.

Other combinations of classifiers 1000, detectors 1100, and predictors 1200 will be readily apparent to one of ordinary skill in the art in view of the present disclosure.

In some embodiments, the output of a particular classifier 1000, detector 1100, and predictor 1200 may be used to train that particular classifier 1000, detector 1100, or predictor 1200. Such training may be supervised, partially supervised, or unsupervised. In some embodiments, the output of one or more classifiers 1000, detectors 1100, and predictors 1200 may be used to train others of classifiers 1000, detectors 1100, and predictors 1200.

Some embodiments of the classifiers 1000, detectors 1100, and predictors 1200 disclosed herein may have therapeutic value. In one example embodiment, a classifier 1000, detector 1100, or predictor 1200 using image data including DNIRA image data may be used in a method for determining a potential treatment or intervention will be useful in treating Age Related Macular Degeneration or other diseases as described herein. For example, a classifier 1000, detector 1100, or predictor 1200 may generate or use one or more features or phenotypes corresponding to a biomarker in a method for determining a potential treatment or intervention will be useful in treating Age Related Macular Degeneration or other diseases. In one specific example, the treatment or intervention may be one that targets macrophages.

In another example embodiment, a classifier 1000, detector 1100, or predictor 1200 using image data including DNIRA image data may be used in a method for determining that compound may be useful in treating Age Related Macular Degeneration or other diseases, the method comprising assaying the eye with DNIRA-based feature or phenotypes, made distinguishable using the classifier 1000, and administering a therapeutically effective amount of the compound to the patient if a DNIRA-based feature or phenotype is present. For example, a classifier 1000, detector 1100, or predictor 1200 may generate or use one or more features or phenotypes corresponding to a biomarker in for determining that compound may be useful in treating Age Related Macular Degeneration or other diseases, the method comprising assaying the eye with DNIRA-based feature or phenotypes, made distinguishable using the classifier 1000, detector 1100, or predictor 1200, and administering a therapeutically effective amount of the compound to the patient if a DNIRA-based feature or phenotype is present. In one specific example, the compound may be particular to a compound that targets macrophages.

Figure 64:
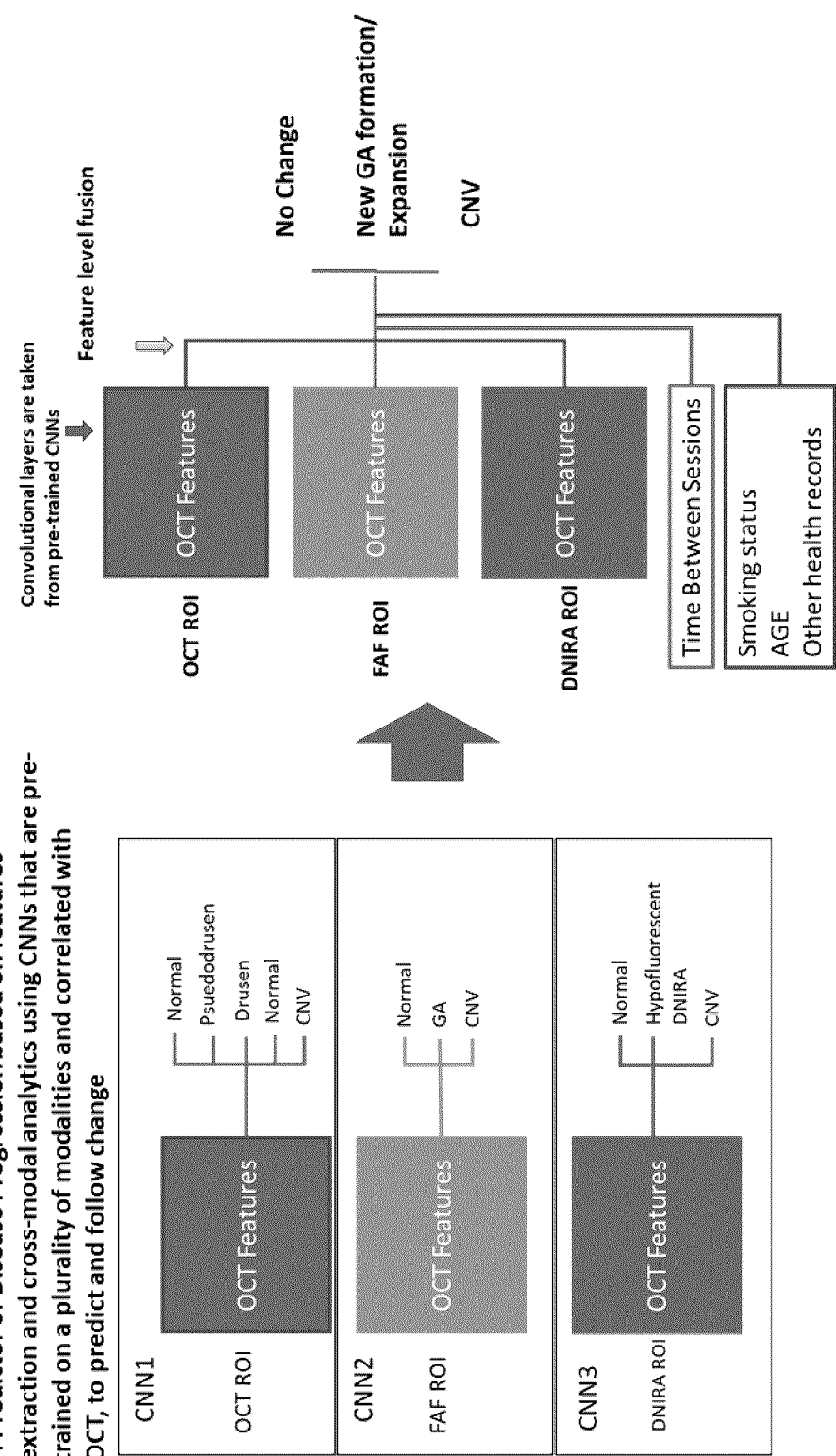
FIG. 64 depicts an embodiment of predictor to predict disease progression.

FIG. 64 illustrates an embodiment of predictor 1200 to predict disease progression based on feature extraction (for example, performed by classifier 1000) and cross-modal analytics using CNNs that are pre-trained on a plurality of image modalities, and correlated (or registered) with OCT images, to predict and follow changes to tissue.

FIG. 64 illustrates an example of a technique for detecting a feature such as a soft drusen (in a colour picture where they are identified) then performing cross-modal analysis and training of a CNN to confirm using the OCT that it is in fact a class drusen or drusenoid RPE detachment, and from that information, feed this into the OCT segmentation maps, as described herein.

Multimodal images and divide them into small regions of interest (ROIs). Each modality may contain different information about the tissue anomaly. Predictor 1200 combines this information and determines and outputs if there is no change, GA formation/expansion has occurred within a given time frame, and/or CNV.

The classifier may utilize different features from different imaging modalities. Each CNN may be trained a simpler task the convolutional layers used as input for the prediction stage.

For the case of OCT, a first CNN model, CNN1, is trained to determine whether tissue anomaly is normal, pseudodrusen, drusen or GA. For FAF, a second CNN model, CNN2, is trained to determine whether there is GA or no GA in the ROI. For DNIRA, a third CNN model, CNN3, is trained to determine whether this is normal tissue or hypofluorescent.

The pre-trained convolutional layers are then used to extract features from multimodal ROI images. Those features are combined (feature level fusion) along with other features about the patient health status (for example, age and smoking states). The predictor is also fed information about the time difference between the two session.

Predictor 1200 then outputs a prediction of no change, new GA formation/expansion, and/or CNV.

As noted above, predictor 1200, using image data including DNIRA image data, may be used in determining that a potential treatment or intervention will be useful in treating diseases. In some embodiments, this may include evaluating or determining whether an agent is effective for the treatment of an ocular disorder as described herein.

In some embodiments, the agent is an immunomodulatory agent (optionally selected from a Monocyte Chemoattractant Protein (MCP)-modulating agent, inclusive of MCP-1, MCP-2, and MCP-3-modulating agents, including a compound of Formula I (2-((1-benzylindazol-3-yl) methoxy)-2-methyl propionic acid), such as bindarit (sometimes referred to herein as TMi-018), methotrexate, PPAR gamma modulator, migration inhibitory factor (MIF) inhibitor, and chemokine receptor 2 (CCR2) inhibitor (e.g., Maraviroc, cenicriviroc, CD192, CCX872, CCX140, 2-((Isopropylaminocarbonyl)amino)-N-(2-((cis-2-((4-(memylthio)benzoyl) amino)cyclohexyl)amino)-2-oxoethyl)-5-(trifluoromethyl)-benzamide, vicriviroc, SCH351125, TAK779, Teijin, RS-504393, compound 2, compound 14, or compound 19 (Plos ONE 7(3): e32864)).

In some embodiments, the agent is a complement factor. In some embodiments, the agent is an anti-factor D antibody (e.g. lampalizumab (Genentech)), an anti-amyloid (anti-Aβ) antibody (e.g. GSK933776 (GSK)), a corticosteroid (e.g. fluocinolone acetonide), MC-1101 (MacuCLEAR), a CD34+ stem cell therapy, an anti-VEGF antibody (e.g. Ranibizumab), brimonidine (Alphagan), an anti-C5 complement antibody (e.g. LFG316 (Novartis), doxycycline (ORACEA), emixustat hydrochloride, sirolimus (RAPAMUNE), and glatiramer acetate (COPAXONE).

In some embodiments, the agent is a nucleoside reverse transcriptase inhibitor (NRTIs), by way of non-limiting example zidovudine, didanosine, zalcitabine, stavudine, lamivudine, abacavir, emtricitabine, and entecavir. In some embodiments, the agent is acyclovir.

The agent may also be, in various embodiments, an anti-vascular endothelial growth factor (VEGF) agent (e.g., Ranibizumb (LUCENTIS), Bevizumab (AVASTIN) or Aflibercept (EYLEA)), an angiotensin-converting enzyme (ACE) inhibitor, a peroxisome proliferator-activated receptor (PPAR)-gamma agonist (e.g., rosiglitazone (AVANDIA), pioglitazone (ACTOS), troglitazone (REZULIN), netoglitazone, rivoglitazone, ciglitazone, rhodanine), a renin inhibitor, a steroid, and an agent that modulates autophagy. In some embodiments, the agent is a modulator of the complement cascade (e.g. a modulator of C3, C5, complement factor D, or complement factor B).

In still another embodiment, an agent is a modulator of macrophage polarization. Illustrative modulators of macrophage polarization include peroxisome proliferator activated receptor gamma (PPAR-g) modulators, including, for example, agonists, partial agonists, antagonists or combined PPAR-gamma/alpha agonists.

In some embodiments, the PPAR gamma modulator is a full agonist or a partial agonist. In some embodiments, the PPAR gamma modulator is a member of the drug class of thiazolidinediones (TZDs, or glitazones). By way of non-limiting example, the PPAR gamma modulator may be one or more of rosiglitazone (AVANDIA), pioglitazone (ACTOS), troglitazone (REZULIN), netoglitazone, rivoglitazone, ciglitazone, rhodanine. In some embodiments, the PPAR gamma modulator is one or more of irbesartan and telmesartan. In some embodiments, the PPAR gamma modulator is a nonsteroidal anti-inflammatory drugs (NSAID, such as, for example, ibuprofen) and indoles. Known inhibitors include the experimental agent GW-9662. Further examples of PPAR gamma modulators are described in WIPO Publication Nos. WO/1999/063983, WO/2001/000579, Nat Rev Immunol. 2011 Oct. 25; 11(11):750-61, or agents identified using the methods of WO/2002/068386, the contents of which are hereby incorporated by reference in their entireties.

In some embodiments, the PPAR gamma modulator is a "dual," or "balanced," or "pan" PPAR modulator. In some embodiments, the PPAR gamma modulator is a glitazar, which bind two or more PPAR isoforms, e.g., muraglitazar (Pargluva) and tesaglitazar (Galida) and aleglitazar.

In another embodiment, an agent is semapimod (CNI-1493) as described in Bianchi, et al. (March 1995). Molecular Medicine (Cambridge, Mass.) 1 (3): 254-266, the contents of which are hereby incorporated by reference in their entireties.

In still another embodiment, an agent is a migration inhibitory factor (MIF) inhibitor. Illustrative MIF inhibitors are described in WIPO Publication Nos. WO 2003/104203, WO 2007/070961, WO 2009/117706 and U.S. Pat. Nos. 7,732,146 and 7,632,505, and 7,294,753 7,294,753 the contents of which are hereby incorporated by reference in their entireties. In some embodiments, the MIF inhibitor is (S,R)-3-(4-hydroxyphenyl)-4,5-dihydro-5-isoxazole acetic acid methyl ester (ISO-1), isoxazoline, p425 (J. Biol. Chem., 287, 30653-30663), epoxyazadiradione, or vitamin E.

In still another embodiment, an agent is a chemokine receptor 2 (CCR2) inhibitor as described in, for example, U.S. Patent and Patent Publication Nos.: U.S. Pat. Nos. 7,799,824, 8,067,415, US 2007/0197590, US 2006/0069123, US 2006/0058289, and US 2007/0037794, the contents of which are hereby incorporated by reference in their entireties. In some embodiments, the CCR2) inhibitor is Maraviroc, cenicriviroc, CD192, CCX872, CCX140, 2-((Isopropylaminocarbonyl)amino)-N-(2-((cis-2-((4-(me-mylthio)benzoyl)amino)cyclohexyl)amino)-2-oxoethyl)-5-(trifluoromethyl)-benzamide, vicriviroc, SCH351125, TAK779, Teijin, RS-504393, compound 2, compound 14, or compound 19 (Plos ONE 7(3): e32864).

In various embodiments, an agent is one or more of CKR-2B, a 2-thioimidazole, CCR2 Antagonist (CAS 445479-97-0), and CCX140.

In various embodiments an agent is an anti-VEGF agent. Non-limiting examples of anti-VEGF agents useful in the present methods include ranibizumab, bevacizumab, afliber-cept, KH902 VEGF receptor-Fc, fusion protein, 2C3 anti-body, ORA102, pegaptanib, bevasiranib, SIRNA-027, decursin, decursinol, picropodophyllin, guggulsterone, PLGlO1, eicosanoid LXA4, PTK787, pazopanib, axitinib, CDDO-Me, CDDO-Imm, shikonin, beta-, hydroxyisovaler-ylshikonin, ganglioside GM3, DC101 antibody, Mab25 anti-body, Mab73 antibody, 4A5 antibody, 4E10 antibody, 5F12 antibody, VA01 antibody, BL2 antibody, VEGF-related pro-tein, sFLTO1, sFLTO2, Peptide B3, TG100801, sorafenib, G6-31 antibody, a fusion antibody and an antibody that binds to an epitope of VEGF. Additional non-limiting examples of anti-VEGF agents useful in the present methods include a substance that specifically binds to one or more of a human vascular endothelial growth factor-A (VEGF-A), human vascular endothelial growth factor-B (VEGF-B), human vascular endothelial growth factor-C (VEGF-C), human vascular endothelial growth factor-D (VEGF-D) and human vascular endothelial growth, factor-E (VEGF-E), and an antibody that binds, to an epitope of VEGF.

In one embodiment, the anti-VEGF agent is the antibody ranibizumab or a pharmaceutically acceptable salt thereof. Ranibizumab is commercially available under the trademark LUCENTIS. In another embodiment, the anti-VEGF agent is the antibody bevacizumab or a pharmaceutically accept-able salt thereof. Bevacizumab is commercially available under the trademark AVASTIN. In another embodiment, the anti-VEGF agent is aflibercept or a pharmaceutically accept-able salt thereof. Aflibercept is commercially available under the trademark EYLEA. In one embodiment, the anti-VEGF agent is pegaptanib or a pharmaceutically acceptable salt thereof. Pegaptinib is commercially available under the trademark MACUGEN. In another embodiment, the anti-VEGF agent is an antibody or an antibody fragment that binds to an epitope of VEGF, such as an epitope of VEGF-A, VEGF-B, VEGF-C, VEGF-D, or VEGF-E. In some embodiments, the VEGF antagonist binds to an epitope of VEGF such that binding of VEGF and VEGFR are inhibited. In one embodiment, the epitope encompasses a component of the three dimensional structure of VEGF that is displayed, such that the epitope is exposed on the surface of the folded VEGF molecule. In one embodiment, the epitope is a linear amino acid sequence from VEGF.

In various embodiments, an agent is a renin angiotensin system (RAS) inhibitor. In some embodiments, the renin angiotensin system (RAS) inhibitor is one or more of an angiotensin-converting enzyme (ACE) inhibitor, an angio-tensin-receptor blocker, and a renin inhibitor.

Non-limiting examples of angiotensin-converting enzyme (ACE) inhibitors which are useful in the present embodi-ments include, but are not limited to: alacepril, alatriopril, altiopril calcium, ancovenin, benazepril, benazepril hydro-chloride, benazeprilat, benzazepril, benzoylcaptopril, capto-pril, captoprilcysteine, captoprilglutathione, ceranapril, ceranopril, ceronapril, cilazapril, cilazaprilat, converstatin, delapril, delaprildiacid, enalapril, enalaprilat, enalkiren, ena-pril, epicaptopril, foroxymithine, fosfenopril, fosenopril, fosenopril sodium, fosinopril, fosinopril sodium, fosinopri-lat, fosinoprilic acid, glycopril, hemorphin-4, idapril, imi-dapril, indolapril, indolaprilat, libenzapril, lisinopril, lyci-umin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spi-rapril hydrochloride, temocapril, temocapril hydrochloride, teprotide, trandolapril, trandolaprilat, utibapril, zabicipril, zabiciprilat, zofenopril, zofenoprilat, pharmaceutically acceptable salts thereof, and mixtures thereof.

Non-limiting examples of angiotensin-receptor blockers which are useful in the present embodiments include, but are not limited to: irbesartan (U.S. Pat. No. 5,270,317, hereby incorporated by reference in its entirety), candesartan (U.S. Pat. Nos. 5,196,444 and 5,705,517 hereby incorporated by reference in their entirety), valsartan (U.S. Pat. No. 5,399, 578, hereby incorporated by reference in its entirety), and losartan (U.S. Pat. No. 5,138,069, hereby incorporated by reference in its entirety).

Non-limiting examples of renin inhibitors which are use-ful in the present embodiments include, but are not limited to: aliskiren, ditekiren, enalkiren, remikiren, terlakiren, cip-rokiren and zankiren, pharmaceutically acceptable salts thereof, and mixtures thereof.

In various embodiments an agent is a steroid. In some embodiments, a steroid is a compound belonging to or related to the following illustrative families of compounds: corticosteroids, mmeralicosteroids, and sex steroids (includ-ing, for example, potentially androgenic or estrogenic or anti-andogenic and anti-estrogenic molecules). Included amongst these are, by way of non-limiting example, pred-nisone, prednisolone, methyl-prednisolone, triamcinolone, fluocinolone, aldosterone, spironolactone, danazol (other-wise known as OPTINA), and others.

In various embodiments an agent modulates autophagy, microautophagy, mitophagy or other forms of autophagy. In some embodiments, the candidate drug and/or compound is one or more of sirolimus, tacrolimis, rapamycin, everolimus, bafilomycin, chloroquine, hydroxychloroquine, spautin-1, metformin, perifosine, resveratrol, trichostatin, valproic acide, Z-VAD-FMK, or others known to those in the art. Without wishing to be bound by theory, agent that modulates autophagy, microautophagy, mitophagy or other forms of autophagy may alter the recycling of intra-cellular compo-nents, for example, but not limited to, cellular organelles, mitochondria, endoplasmic reticulum, lipid or others. With-out further wishing to be bound by theory, this agent may or may not act through microtubule-associated protein 1A/1B-light chain 3 (LC3).

The systems and methods disclosed herein are further described by the following non-limiting examples.

EXAMPLES

Example 1: DNIRA to Identify, Quantify and Follow Regions of Profoundly Hypofluorescent/Black Signal As analysis of DNIRA has not been previously reported, the inventors believe all observations to be novel. DNIRA can be used to identify regions of profoundly hypofluores-cent/black signal. These may or may not correspond with regions or distinguishing features identified by other imag-ing modalities. Unlike the profoundly hypofluorescent/black signal of FAF that represents absent RPE/photoreceptors and therefore remains the same in size or expands over time, dark regions of DNIRA are dynamic and can enlarge, decrease or remain the same. As such, software algorithms have been developed to identify and quantify the extent of absent DNIRA signal, and are predicated, without limitation, on software for registration, alignment, contrast adjustment, sharpening and segmentation. FIG. 10 is a graphical illustration of DNIRA image analysis Subject consent is used for all clinical research protocols are Research Ethics Board (REB) approved and subjects willing and able to consent are serially enrolled.

Baseline in vivo imaging: baseline AMDI images are acquired using a commercially available confocal scanning laser ophthalmoscope (cSLO) (e.g. Heidelberg Retinal Angiography, HRA-2, Heidelberg Engineering, Germany). Images are obtained prior to systemic injection using cSLO, and those with significant optical opacity are eliminated from further imaging (other than as clinically indicated). Amongst subjects with suitable optical clarity, additional images are also obtained in the red-free, FAF (488/500 nm excitation/emission), IR reflectance channel (830 nm) and ICG fluorescence channels (795/810 nm excitation/emission), along with optical coherence tomography (OCT) and color fundus photography. Within a suitably short time-frame, for example between 1 and 28 days, subjects undergo ICG injection that may or may not include angiography.

ICG injection: ICG dye (Cardiogreen, Sigma) is freshly prepared prior to experimentation to a final stock concentration of 5.0 mg/ml in sterile water. A fine gauge catheter is inserted intravenously, and ICG dye is infused. If angiography is performed, images are acquired prior to injection (baseline), during dye circulation, and at various intervals thereafter typically out to 40 minutes or 2 hours. Alternatively, ICG can be provided by oral administration, for example, by way of a a capsule, tablet, solution, or suspension.

AMD imaging: Within a suitable time-frame, for example 1 to 5 days (but potentially 24 hours to 120 days after ICG), subjects return for DNIRA images obtained with ICG excitation/emission filters or laser systems in place (795/810 nm) but without further injection of dye. Multiple images are acquired of each eye including those centered on the fovea and the optic nerve head. Images are also taken in four quadrants of the macula, thereby permitting visualization of a larger field and post-hoc analysis of "pseudo-composite" images.

Logical processes can be used for detection of regions of profoundly hypofluorescent/dark DNIRA signal.

Software and hardware unit can be used for the unprocessed high-resolution DNIRA images undergo registration, alignment and segmentation. In cases where baseline (pre-ICG injection) images have demonstrable signal prior to ICG injection, this signal is subtracted from all other images. Evaluated at a single timepoint, regions of profoundly hypofluorescent/black DNIRA signal are identified and quantified. Evaluated over several timepoints, images are registered and aligned, and the rates of change identified. DNIRA has the capability to detect black/hypofluorescent signal that can be subsequently analyzed and followed over time.

Example 2: Total Hypofluorescent DNIRA Areas as a Marker of Disease and Disease Burden (Diagnostic or Prognostic Biomarker)

Figure 24:
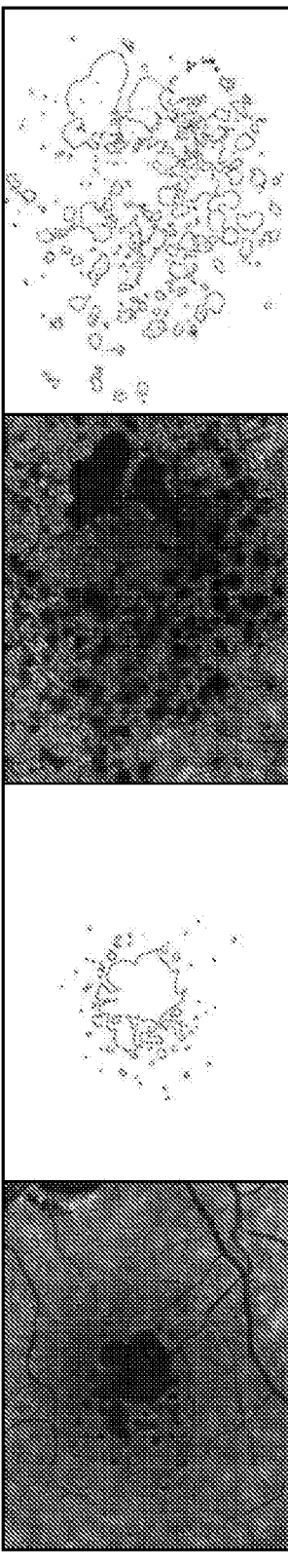
FIG. 24 depicts representative example of Total Hypofluorescent DNIRA Areas as a Marker of Disease and Disease Burden (Diagnostic or Prognostic Biomarker).

FIG. 24 is a graphical representation of this example.
The "Total Hypofluroescent DNIRA Area(s)" may reflect total burden of disease, at a given point in time. The hypofluorescent DNIRA signal is readily segmentable and quantifiable, providing the first readily tractable measure of disease in addition to GA (determined by FAF, not shown here).

Subject consent is used for all clinical research protocols are Research Ethics Board (REB) approved and subjects willing and able to consent are serially enrolled.

Baseline in vivo imaging: baseline DNIRA images are acquired using a commercially available confocal scanning laser ophthalmoscope (cSLO) (e.g. Heidelberg Retinal Angiography, HRA-2, Heidelberg Engineering, Germany). Images are obtained prior to systemic injection using cSLO, and those with significant optical opacity are eliminated from further imaging (other than as clinically indicated). Amongst subjects with suitable optical clarity, additional images are also obtained in the red-free, FAF (488/500 nm excitation/emission), IR reflectance channel (830 nm) and ICG fluorescence channels (795/810 nm excitation/emission), along with optical coherence tomography (OCT) and color fundus photography. Within a suitably short time-frame, for example between 1 and 28 days, subjects undergo ICG injection that may or may not include angiography.

ICG injection: ICG dye (Cardiogreen, Sigma) is freshly prepared prior to experimentation to a final stock concentration of 5.0 mg/ml in sterile water. A fine gauge catheter is inserted intravenously, and ICG dye is infused. If angiography is performed, images are acquired prior to injection (baseline), during dye circulation, and at various intervals thereafter typically out to 40 minutes or 2 hours.

DNIRA imaging: Within a suitable time-frame, for example 1 to 5 days (but potentially 24 hours to 120 days after ICG), subjects return for DNIRA images obtained with ICG excitation/emission filters or laser systems in place (795/810 nm) but without further injection of dye. Multiple images are acquired of each eye including those centered on the fovea and the optic nerve head. Images are also taken in four quadrants of the macula, thereby permitting visualization of a larger field and post-hoc analysis of "pseudo-composite" images.

Repeated DNIRA Imaging: to determine the temporal changes between DNIRA images over time, subjects return for repeated testing for example at 1, 2, 3, 4, 6, 8 or 12 month intervals, or longer.

Logical processes can be used for a temporal analysis of regions of expanding hypofluorescent DNIRA signal. Logical processes can also be used for an inter-modality analysis of regions of expanding hypofluorescent DNIRA signal.

The left pair of images show a patient who has a relatively small Total Hypofluroescent DNIRA Area. The right pair of images show a patient who has a relatively larger Total Hypofluorescent DNIRA Area. Comparing the two, a ratio or proportion can be established. In this case, the patient on the right has over 3 times greater identified as hypofluorescent using DNIRA. Such total areas can also be measured over time to provide a measure of progressive or dynamic change.

Example 3: Total Hypofluorescent DNIRA Areas as a Marker of Progressive and Dynamic Change (Monitoring, Predictive or Prognostic Biomarker)

FIGS. 17A and 17B are graphical representations of this example.
The "Total Hypofluroescent DNIRA Area(s)" may reflect total burden of disease, at a given point in time. The hypofluorescent DNIRA signal is readily segmentable and quantifiable, providing the first readily tractable measure of disease in addition to GA (determined by FAF, not shown here).

Subject consent is used for all clinical research protocols are Research Ethics Board (REB) approved and subjects willing and able to consent are serially enrolled.

Baseline in vivo imaging: baseline DNIRA images are acquired using a commercially available confocal scanning laser ophthalmoscope (cSLO) (e.g. Heidelberg Retinal Angiography, HRA-2, Heidelberg Engineering, Germany). Images are obtained prior to systemic injection using cSLO, and those with significant optical opacity are eliminated from further imaging (other than as clinically indicated). Amongst subjects with suitable optical clarity, additional images are also obtained in the red-free, FAF (488/500 nm excitation/emission), IR reflectance channel (830 nm) and ICG fluorescence channels (795/810 nm excitation/emission), along with optical coherence tomography (OCT) and color fundus photography. Within a suitably short time-frame, for example between 1 and 28 days, subjects undergo ICG injection that may or may not include angiography.

ICG injection: ICG dye (Cardiogreen, Sigma) is freshly prepared prior to experimentation to a final stock concentration of 5.0 mg/ml in sterile water. A fine gauge catheter is inserted intravenously, and ICG dye is infused. If angiography is performed, images are acquired prior to injection (baseline), during dye circulation, and at various intervals thereafter typically out to 40 minutes or 2 hours.

DNIRA imaging: Within a suitable time-frame, for example 1 to 5 days (but potentially 24 hours to 120 days after ICG), subjects return for DNIRA images obtained with ICG excitation/emission filters or laser systems in place (795/810 nm) but without further injection of dye. Multiple images are acquired of each eye including those centered on the fovea and the optic nerve head. Images are also taken in four quadrants of the macula, thereby permitting visualization of a larger field and post-hoc analysis of "pseudo-composite" images.

Repeated DNIRA Imaging: to determine the temporal changes between DNIRA images over time, subjects return for repeated testing for example at 1, 2, 3, 4, 6, 8 or 12 month intervals, or longer.

Logical processes can be used for a temporal analysis of regions of expanding hypofluorescent DNIRA signal. Logical processes can also be used for an inter-modality analysis of regions of expanding hypofluorescent DNIRA signal.

In FIG. 17A, The "Total Hypofluorescent DNIRA Area" may can be monitored over time, and compared repeatedly, against a specified starting time (baseline). Areas of profoundly hypofluorescent DNIRA can be segmented, and the features extracted and compared over time. Other embedded metadata of the images can also be used to extract other features. The example shows 3 timepoints over time where regions of hypofluorescence are segmented out (green trace) and compared against each other to detect changes at a given timepoint.

In FIG. 17B, the upper panel shows the green tracings illustrating borders of regions of profound hypofluorescent DNIRA (from images in middle panel), that unlike observations of GA, (detected using FAF or OCT), can become smaller in size over time. These data suggest a much more dynamic and changing aspect of disease not previously recognized, and illustrate that regions outside GA or macular atrophy (MA) can also be readily quantified. DNIRA images, also demonstrate complex, non-segmentable patterns that represent unstructured, image-based data suitable for cognitive or Artificial Intelligence (AI) based analytics. Other forms of metadata may also be used to describe the images. The lower right image shows that dynamic changes can be compared over time to provide a time-dependent measure. Such data can be used for disease prognosis, prediction, monitoring of patients over time, and help identify treatment strategies.

Figure 25:
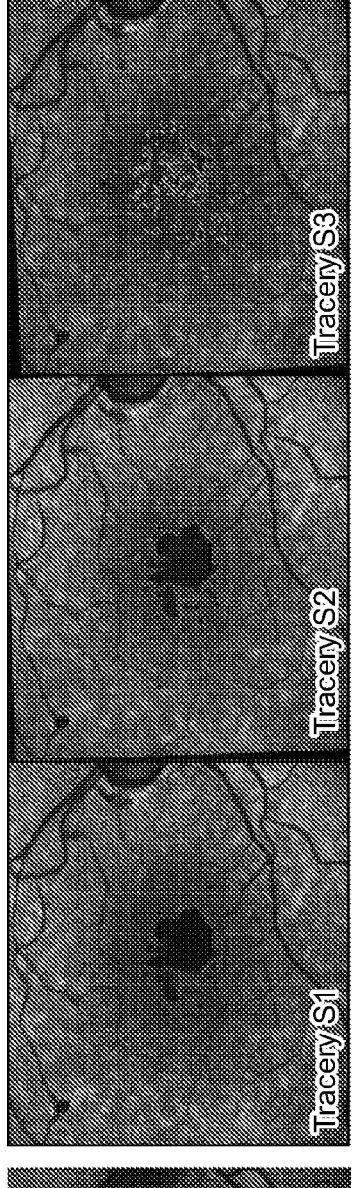
FIG. 25 depicts representative example of Rates of Change of Total Hypofluorescent DNIRA Areas as a Marker of Prognosis or Response to an Intervention.

Example 4: Rates of Change of Total Hypofluorescent DNIRA Areas as a Marker of Prognosis or Response to an Intervention FIG. 25 is a graphical illustration for this process.

With subject consent, all clinical procedures were performed as described in previous examples.

Logical processes were used for a temporal analysis of regions of expanding hypofluorescent AMDI signal. Logical processes were used for an inter-modality analysis of regions of expanding hypofluorescent AMDI signal The leftmost panel shows that this patient has early dry AMD, confirmed using FAF an absence of Geographic Atrophy (GA) throughout the course of study.

The middle and right panels show DNIRA, and green trace illustrates borders of regions of profound hypofluorescent DNIRA, that unlike observations of GA (detected using FAF or OCT), can become smaller in size over time. Compared with the patient shown in the previous example (Example 3, FIGS. 17A and 17B), the rate of change was more rapid, thus permitting comparisons between groups of individual and potentially predicting more rapid transition to late AMD.

These features may be particularly useful in identifying responses to an intervention that takes place in this time-frame, as well as prognosis of disease progression.

Example 5: DNIRA Identifies Regions of Profound Hypofluorescent/Black Signal that Extend Beyond the Regions of Hypofluorescent/Black FAF—the Calculation of "Delta" as a Measure of Disease Burden FIG. 14 is a graphical illustration of this concept.

DNIRA can identify regions of profound hypofluorescence/black signal in excess of that observed using FAF, the present gold standard for evaluation of subjects with late dry AMD. FAF identifies regions of RPE/photoreceptor loss known as GA (where the endogenous fluorophores such as lipofuscin are absent). When present, areas of GA always lie within areas of absent DNIRA signal. As such, logical and software algorithms have been developed to identify and quantify the extent of absent DNIRA signal in excess of absent FAF signal. This can represent a measure of the burden of disease, rather than areas where tissue is lost. FIGS. 15A and 15B are graphical illustrations for this example.

Subject consent: all clinical research protocols are Research Ethics Board (REB) approved and subjects willing and able to consent are serially enrolled.

Baseline in vivo imaging: baseline DNIRA images are acquired using a commercially available confocal scanning laser ophthalmoscope (cSLO) (e.g. Heidelberg Retinal Angiography, HRA-2, Heidelberg Engineering, Germany). Images are obtained prior to systemic injection using cSLO, and those with significant optical opacity are eliminated from further imaging (other than as clinically indicated). Amongst subjects with suitable optical clarity, additional images are also obtained in the red-free, FAF (488/500 nm excitation/emission), IR reflectance channel (830 nm) and ICG fluorescence channels (795/810 nm excitation/emission), along with optical coherence tomography (OCT) and color fundus photography. Within a suitably short time-frame, for example between 1 and 28 days, subjects undergo ICG injection that may or may not include angiography.

ICG injection: ICG dye (Cardiogreen, Sigma) is freshly prepared prior to experimentation to a final stock concentration of 5.0 mg/ml in sterile water. A fine gauge catheter is inserted intravenously, and ICG dye is infused. If angiography is performed, images are acquired prior to injection (baseline), during dye circulation, and at various intervals thereafter typically out to 40 minutes or 2 hours.

DNIRA imaging: Within a suitable time-frame, for example 1 to 5 days (but potentially 24 hours to 120 days after ICG), subjects return for DNIRA images obtained with ICG excitation/emission filters or laser systems in place (795/810 nm) but without further injection of dye. Multiple images are acquired of each eye including those centered on the fovea and the optic nerve head. Images are also taken in four quadrants of the macula, thereby permitting visualization of a larger field and post-hoc analysis of "pseudo-composite" images.

Logical processes were used for elimination of background signal. In some cases, where autofluorescent signal is obtained in the baseline DNIRA image (e.g., prior to dye injection), such baseline signal is mathematically eliminated prior to further image analysis.

Logical processes were used for calculation of "delta" the difference between hypofluorescent DNIRA and FAF images. In cases where GA is present, DNIRA identifies regions of profound hypofluorescence/black signal that are equivalent or larger than areas of profound hypofluorescent/black signal obtained using FAF.

Software and hardware unit for the unprocessed high-resolution DNIRA and FAF images to undergo registration, alignment and segmentation: In cases where baseline (pre-ICG injection) images demonstrate demonstrable signal prior to ICG injection, this signal is subtracted from all other images. Evaluated at a single timepoint, the registered DNIRA and FAF images are compared and the regions of hypofluorescent DNIRA that extend beyond the boundary of dark FAF or that exist in regions distinct from the dark FAF, are identified (both in a separate image and as part of a two-layer overlay) and quantified (following segmentation). In this example, DNIRA identifies multiple regions outside the FAF hypofluorescence that contain regions of black DNIRA signal, increasing the total number of black hypofluorescent signals, total area of black signal, and the perimeter or edge of the region of black.

Example 6: DNIRA Features to Identify Early Disease and Different Phenotypes of Early Disease (Diagnostic Biomarker)

Figure 26A:
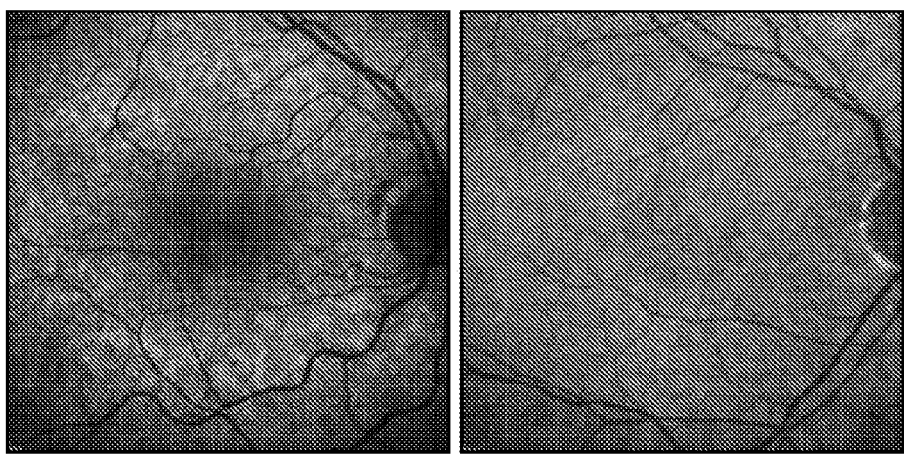
FIGS. 26A and 26B depict representative examples of DNIRA Features to Identify Early Disease and Different Phenotypes of Early Disease (Diagnostic Biomarker).
Figure 26B:
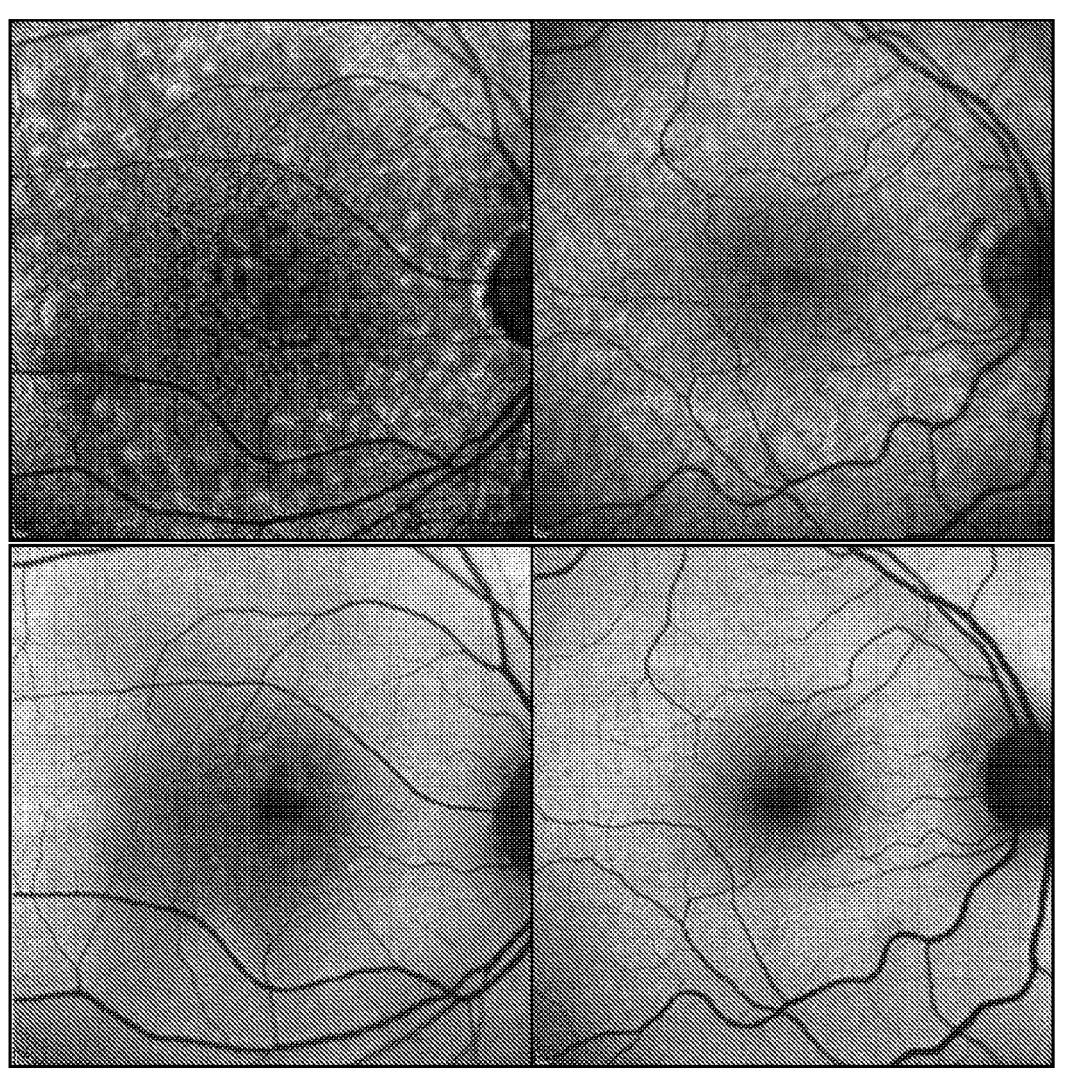

FIGS. 26A and 26B are graphical representations of this example.

DNIRA may distinguish different phenotypes of early AMD. These may represent differences in underlying biology (genetic or environmental), potentially amendable to different and targeted therapies. Although AMD has a strong genetic component, it accounts for only approximately up to ½ of disease susceptibility. Amongst patients with a genetic background, the statistical likelihood that they may or may not develop disease can be calculated for the population, but not for the individual. By contrast, early changes in DNIRA may confirm a positive inheritance, e.g. very early disease, even prior to the formation of drusen.

With subject consent, all clinical procedures were performed as described in previous examples. DNIRA imaging procedure was carried out on a patient having no personal history or known family history of disease at the time of presentation. However, in subsequent questioning a positive family history was obtained in the time between clinical visits In FIG. 26A, the left panel shows a case patient with family history of AMD but no personal diagnosis (absence of drusen was confirmed). DNIRA image shows complex, albeit faint hypofluorescent pattern. The right panel shows a decade-matched control patient with no family or personal history of AMD, and no drusen found. The absence of AMD using current clinical definitions (absence of drusen) was confirmed by clinical examination. This exemplifies the ability of DNIRA to detect subtle changes in patients that may otherwise not present with any identifiable features of disease.

In FIG. 26B, the upper panel shows two patients who have a diagnosis of early AMD based on clinical examination. On the left is a DNIRA image of patient with early AMD that shows marked dark grey, loose weave pattern. On the right is a DNIRA image that shows a subtle loose weave pattern. Corresponding FAF images confirm that these two patients have early dry AMD, however show relatively little difference with this modality. DNIRA and FAF images were obtained at the same timepoint.

Thus, DNIRA patterns observed in early AMD may assist in making personalized diagnose of AMD earlier than other methods, allowing for unique and targeted therapies.

Example 7: DNIRA Features to Identify Disease Subtypes Among Patients With a Known Diagnosis of AMD and to Correlate with Disease Pathogenesis (Predictive Biomarker)

FIGS. 21A-21E are graphical representations of this example.

It is known that blinding diseases such as AMD are complex, resulting from both multigenic inheritance (over 30 genes and 200 Single Nucleotide Polymorphisms) that is subject to significant environmental overlay, making successful treatment difficult. Novel groupings of disease and disease features correlate with complex inherited and epigenetic influences.

DNIRA and related methods can identify previously unseen features and complex new phenotypes of disease. For example, several complex 2D patterns, labeled "tight weave", "loose weave", "grey smudge", "oil stains", "bullet holes", etc. have been identified. As such, DNIRA can be used to define new phenotypes and thereby subsequent novel genotype-phenotype correlations.

With subject consent, all clinical procedures were performed as described in previous examples.

FIGS. 21A-21E depicts examples where DNIRA uniquely identifies novel image-based phenotypes, exemplified by the currently identified phenotypes termed: (FIG. 21A. "loose weave" pattern, FIG. 21B. "leopard spots", FIG. 21C. "grey smudge", FIG. 21D. "fingerling potatoes", and FIG. 21E. "very large bright spots."

These types of complex phenotypes are previously unknown and have not been identified using any other imaging modality, depicting the unique ability of DNIRA to capture them.

Example 8: DNIRA Features to Distinguish
Diseases of Similar Clinical Appearance to Assist
with Diagnostic Accuracy (Diagnostic Biomarker)

FIGS. 27A and 27B are graphical representations of this example.

Complex DNIRA patterns observed in association with other disorders, with no personal history of AMD, may provide an early diagnostic biomarker. For example early Vitelliform Disease, particular adult onset type (AVD), is characterized by central foveal lesions often mistaken for AMD. In some cases, the diagnosis is made following a non-response to anti-VEGF agents (prescribed for late neovascular "wet" AMD). However, as a potential diagnostic biomarker, DNIRA identifies complex 2D patterns of hypo/hyper-fluorescence not observed amongst patients with AVD. Another non-AMD disease that can be confused with AMD is Central Serous Retinopathy (CSR).

In the cases described here, with subject consent, all clinical procedures were performed as described in previous examples.

In FIG. 27A, the upper panels show images of the right eye of a patient with visual complaints and a tentative diagnosis of AMD owing to the presence of small, yellowish material in the central fovea (color image not shown). IR and FAF are unremarkable, while DNIRA shows a faint, variable appearance. The lower panels show images of the left eye of this patient, and confirm the diagnosis of AVD, with the appearance of an apparent "fluid line" across the central lesion. The middle lower panel shows DNIRA image with hypofluorescence in the area of the central lesion, with little background contrast (as noted in the other eye). This contrasts starkly with the DNIRA image obtained from a patient with early AMD (lower left) where a weave pattern is evident.

In FIG. 27B, a non-AMD patient with CSR in the left eye, showed a complex "loose weave" pattern in both eyes despite no family history nor personal history of AMD and no drusen in either eye. Over the course of study, drusen were detected in the non-CSR eye confirming a diagnosis of AMD and suggesting that DNIRA may be used as an early diagnostic tool for AMD (unable to evaluate in the afflicted eye due to CSR-induced damage).

The upper panel of B shows the right eye is normal using Infra-Red and FAF, but DNIRA shows "loose weave" pattern. The middle panels show the left eye that has both features of CSR and the weave. The lower panel shows color also confirm a normal eye exam, however OCT confirmed development of drusen in follow-up evaluation after this patent completed the study (approximately 2 years after 1st exam). The first OCT image taken in 2015 demonstrates that absence of drusen in a patient with no personal or family history of AMD, while the one below of the same patient in 2017 demonstrates the development of classic drusen, confirming the diagnosis of AMD. This diagnosis were surmised in 2015 by the presence of the "weave" pattern.

This exemplifies that DNIRA reveals some complex image-based patterns that are absent in patients with ocular conditions other than AMD, or frequently misdiagnosed as AMD, such as but not limited to Adult Vitelliform disease, Bietti's crystalline dystrophy, pattern dystrophy, and others.

Thus, DNIRA can be used to identify patients with disorders that clinically mimic AMD, may be used as a diagnostic biomarker to detect early eye disease and enable early therapeutic, lifestyle or environment intervention.

Example 9: DNIRA Features Identify Inherited
Monogenic Disorders and Disease that May Not
Yet Be Diagnosed (NYD)

FIGS. 28A and 28B are graphical representations of this example.

Complex DNIRA patterns may provide an early diagnostic biomarker for inherited monogenic disorders such as Stargardt disease, retinitis pigmentosa, Leber congenital amaurosis (LCA), or Bardet-Biedl syndrome (BBS).

In this example, a patient with inherited, monogenic disorder (Stargardt disease) illustrates the ability of DNIRA to detect disease, and detect regions at potential risk of disease progression from early to late in these types of disease.

With subject consent, all clinical procedures were performed as described in previous examples.

In FIG. 28A (left panel), the left and middle images show IR and FAF image of the left fundus of a patient with Stargardt disease, where bright, hyperfluorescent lesions with the characteristic "pisciform" shape can be observed. The right image shows DNIRA, where regions of profound hypofluorescence that are both segmentable and surmised to represent areas of poor dye uptake or accumulation, and/or potentially reduced choroidal flow can be observed. These are distinct from NIR-autofluorescence (NIR-AF) a method used in the evaluation of Stargardt disease that utilizes NIR light but without the earlier delivery of a NIR dye (so detecting autofluorescence from pigments such as melanin).

The enlarged yellow box (rightmost image) shows DNIRA and identifies small hyperfluorescent bright dots in association with areas of hypofluorescent DNIRA. These dots may represent actively phagocytic macrophages that ultimately lead to macular atrophy (MA) in this disease. Throughout the image they are found particularly in association with regions of hypofluorescent DNIRA signal, potentially ascribing macrophage activity to disease progression thus linking DNIRA with a potential treatment strategy (such as for example macrophage modulation or inhibition)

In FIG. 26B, a DNIRA image shows a presumed inherited eye disease that may share some aspects of genetic susceptibility with AMD, but has not yet been diagnosed (NYD) is shown.

Thus, DNIRA can be used to diagnose patients with disorders other than AMD, may be used as a diagnostic biomarker to detect early eye disease and enable early therapeutic, lifestyle or environment intervention.

Example 10: DNIRA Feature to Monitor
Progression of Disease or the Effect of a Treatment
Over Time (Monitoring Biomarker)

Figure 29:
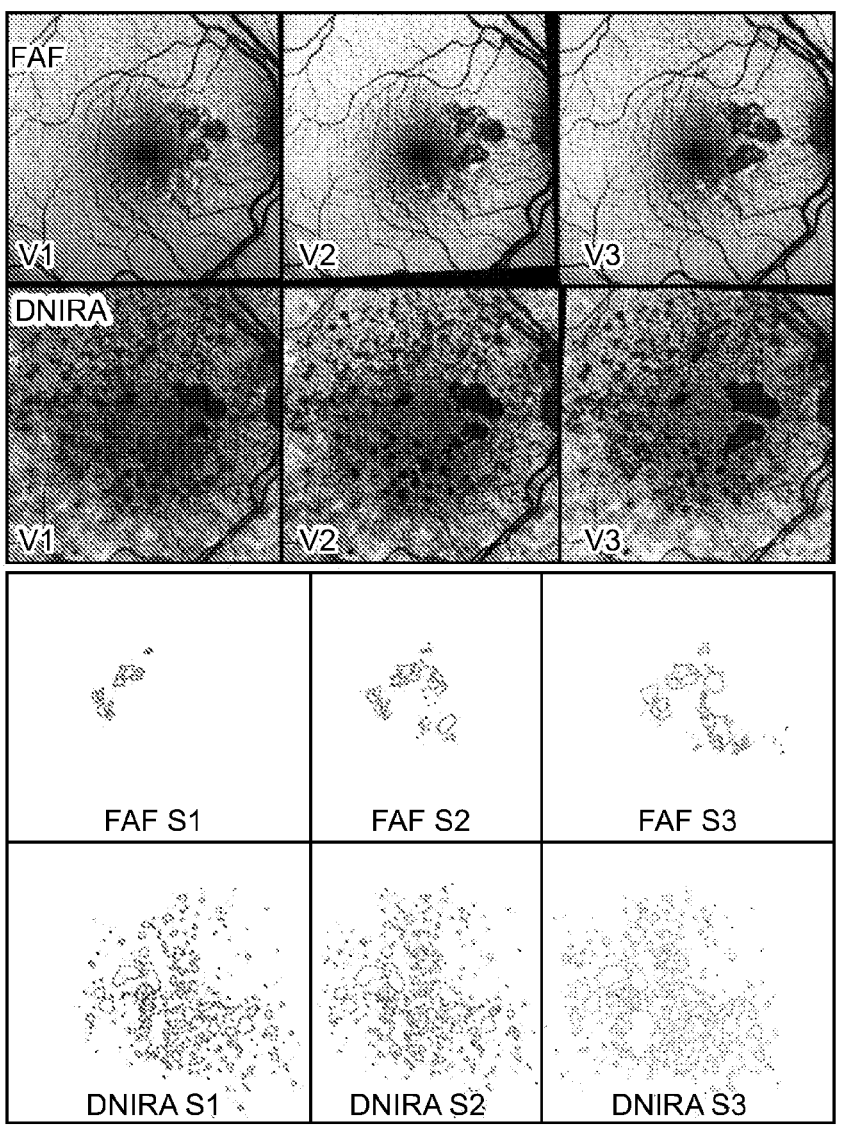
FIG. 29 depicts a representative example of DNIRA Feature to Monitor Progression of Disease or the Effect of a Treatment Over Time (Monitoring Biomarker).

FIG. 29 is a graphical representation of this example.

With subject consent, all clinical procedures were performed as described in previous examples.

Hypofluorescent features identified with DNIRA can be observed to expand over time. This is similar to observations made using Fundus Autofluorescence (FAF) to quantify the rate of expansion of geographic atrophy (GA), more recently performed using en face OCT.

At present, in the absence of other useful markers to drive clinical trial design for the potential treatment of dry AMD, the rate of GA expansion is an acceptable Phase III clinical trial endpoint. An example of this is shown in the top panel which depicts how FAF identifies regions of hypofluorescent signal, which followed over time demonstrate the expansion of GA. The lower panel shows that DNIRA identifies significantly more hypofluorescent signal, which changes over time and identifies more disease.

The faint purple lines have been used to trace the perimeter of the abnormal hypofluorescent FAF in the upper panel, and faint green lines to do the same in the lower DNIRA panel. These extracted image elements are shown in the lower 2 panels below the fundus images.

Thus, DNIRA can be used to monitor disease progression, in many cases providing more information than current methods such as FAF.

Example 11: DNIRA Feature to Monitor Disease Progression, Comparing Within and Across Modalities and Other Imaging Biomarkers Over Time (Monitoring and Prognostic Biomarker)

FIG. 30 is a graphical representation of this example.

With subject consent, all clinical procedures were performed as described in previous examples.

Shown in the figure are cases observed to date where DNIRA was compared across timepoints, and to other imaging modalities to identify features that can serve as monitoring and prognostic biomarkers.

FAF and DNIRA features were traced using purple and green lines respectively, and have been used to trace the perimeter of the abnormal hypofluorescent FAF or DNIRA signal. These extracted image elements are shown alongside the fundus images.

This patient has Central Serous Retinopathy in the left eye, and at first visit, no drusen in either eye. However, a marked complex 2D "weave" pattern was observed in both eyes. Over the course of study, drusen were detected in the non-CSR eye (unable to evaluate in the afflicted eye). The leftmost panel shows extensive regions of hypofluorescent DNIRA observed at baseline (DNIRA S1) in this patient.

The right two upper panel images show baseline and 8 month follow-up FAF images.

The lower panels show registered and segmented DNIRA (green outlines) and FAF (purple outlines) images taken over time and show progression of GA into regions of hypoDNIRA signal.

Comparing across timepoints DNIRA session 1 (S1) can be observed to detect features that are only apparent on FAF session 3 (S3), indicating that DNIRA can be used to monitor disease progression.

The expansion of GA into hypofluorescent regions using DNIRA is observed in all patients to date. By contrast, not all areas of hypofluorescent DNIRA become areas of GA (at least over the time course of this study)

Therefore, regions of GA extend only into areas of pre-existent hypofluorescent DNIRA. Thus, some regions of hypofluorescent DNIRA signal can be used to predict regions of GA expansion.

Example 12: DNIRA Feature as a Biomarker to Identify Patients Likely to Progress to Later Disease (Prognostic Biomarker)

Figure 31:
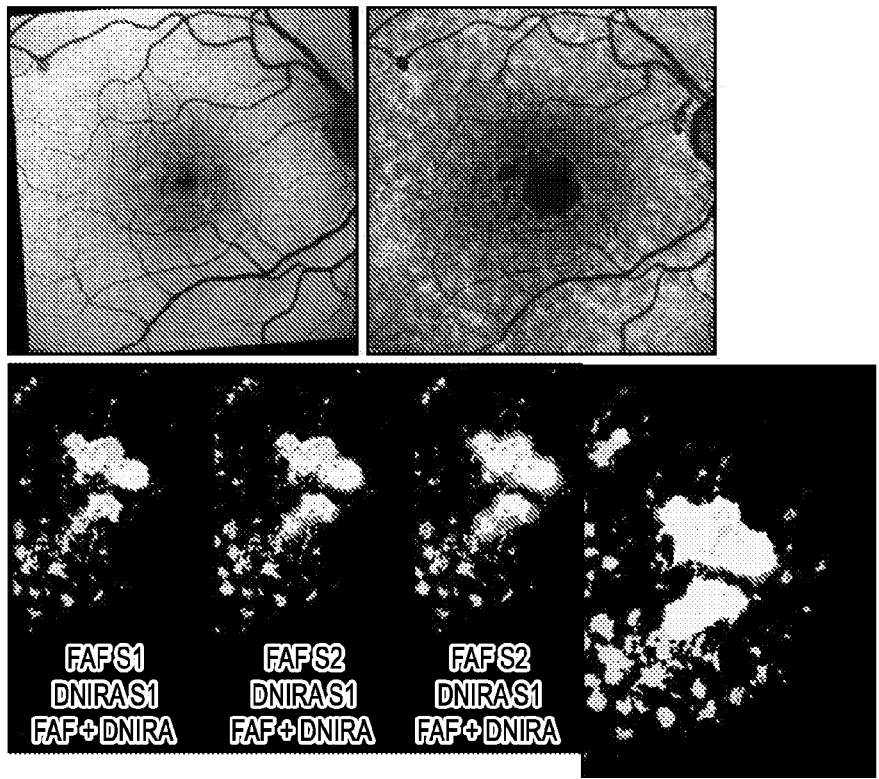
FIG. 31 depicts a representative example of DNIRA Feature as a Biomarker to Identify Patients Likely to Progress to Later Disease (Prognostic Biomarker).

FIG. 31 is a graphical representation of this example.

With subject consent, all clinical procedures were performed as described in previous examples.

Shown in the figure is a case where DNIRA was compared across timepoints, and to other imaging modalities to identify features that can serve as prognostic biomarkers where specific features and complex patterns observed using DNIRA may predict disease progression.

In some cases, these features may be not previously described, while in others, they may correlate with previously known risk-factors for disease progression such as the presence of large RPE detachments.

Exemplified is a patient with early dry AMD The left panel shows early AMD using FAF with no GA, indicated by absence of regions of abnormal profound hypofluorescence. The right panel shows the same region, imaged at the same timepoint with DNIRA. Here, DNIRA identifies multiple features of disease including both quantifiable regions of profound hypofluorescence and complex 3D patterns.

The middle panel depicts a second case, where heat map analysis performed at three timepoints (at a 4-month intervals) shows that compared against the DNIRA image (green) at Session 1 (S1, left), the corresponding FAF image (red) is smaller, but progressively "fills in" the region identified as vulnerable using DNIRA. By 8 months, the regions of GA identified using FAF expand beyond the regions originally predicted by DNIRA (noting that the DNIRA map also enlarged such that evaluated at the same timepoint, the GA signal remains within, ie smaller than, the DNIRA signal).

The lower panel shows (8 months later) simultaneous FAF and DNIRA imaging confirms that the DNIRA region also expanded over time and that the region of GA identified using FAF falls within its borders (the apparent extension of the FAF signal inferior to the merged signal reflects that ill-defined or "fuzzy" border of area of GA obtained using FAF)

Thus, DNIRA signal can be used to predict regions of GA expansion.

Example 13: DNIRA Feature as a Biomarker to Quantify Aspects of Disease Known to Predict Progression (Prognostic Biomarker)

Figure 32:
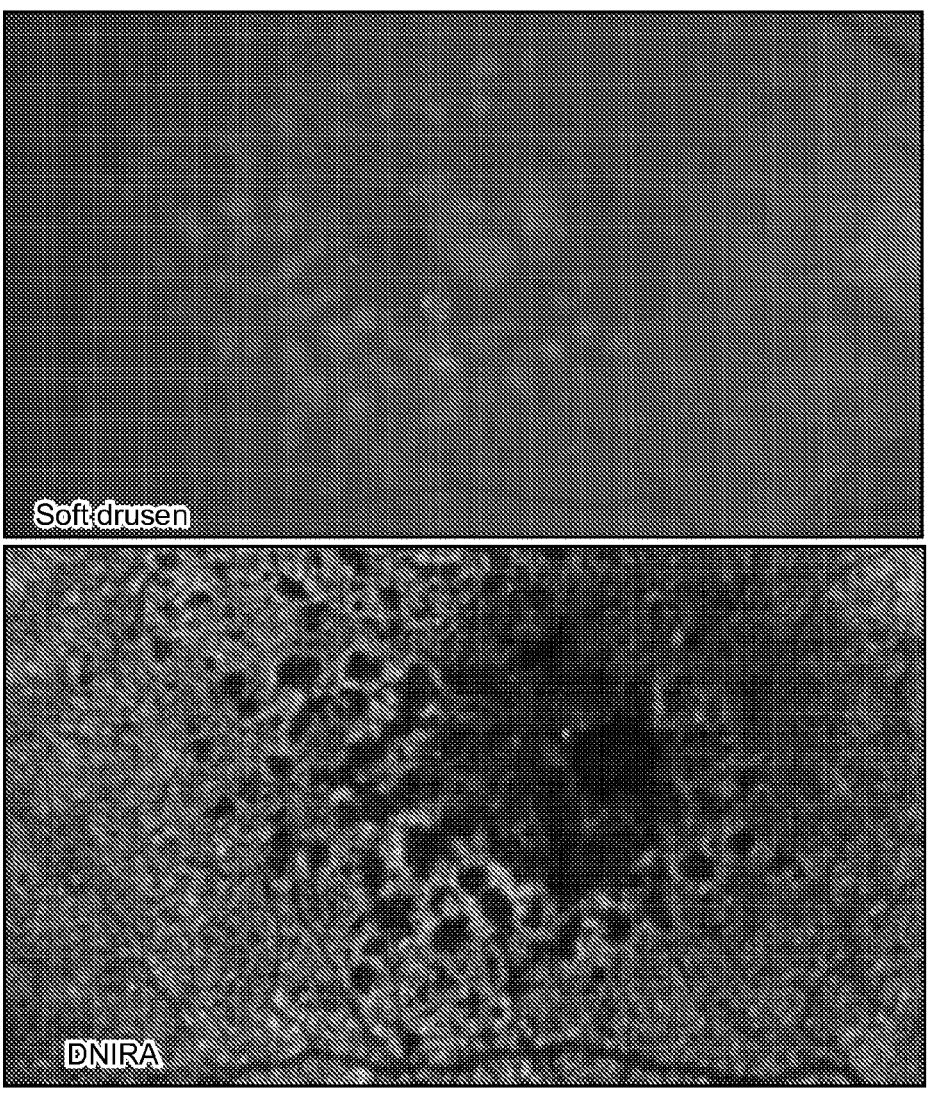
FIG. 32 depicts representative example of DNIRA Feature as a Biomarker to Quantify Aspects of Disease Known to Predict Progression (Prognostic Biomarker).

FIG. 32 is a graphical representation of this example.

DNIRA can readily identify, quantify and follow over time the spatiotemporal changes in disease features predicted to correlate with disease but currently not quantifiable and hence not demonstrated. For example, drusen were identified as a key prognostic factor predicting the 10 year risk of patients progressing to blinding late AMD (both wet and dry). The clinical utility of large soft and soft confluent drusen precludes their application in prevention studies owing to the large sample size necessary to adequately power a study. Large and medium drusen confer disease risk and risk of progression, but their dynamic changes over time are only recently described. Not readily quantifiable, it is currently not possible to provide a measure of their change.

With subject consent, all clinical procedures were performed as described in previous examples.

The figure depicts large soft and confluent soft drusen identified as yellowish circular/oval deposits observed on color fundus photography (CFP) in the upper panel. The lower panel correlates the same region of the image using DNIRA, depicting clearly demarcated areas of black where the drusen are localized.

Thus, DNIRA can readily identify and quantify known high-risk prognostic features of disease such as large, soft and confluent drusen.

With that, we describe a Dynamic Drusen Index (DDI) that can calculate total drusen burden at single or multiple timepoints, or can calculate the change in particular drusen subtypes. Relying on the current classification of drusen, and the utility of novel DNIRA images to identify drusen, we suggest Total DDI (for all drusen types), Large Confluent Dynamic Drusen Index (LC-DDI), Large Dynamic Drusen Index (L-DDI), Medium Dynamic Drusen Index (M-DDI), and Small Dynamic Drusen Index (S-DDI). DDI can instruct which patients to preferentially enlist in particular clinical trials, thereby serving a Predictive Biomarker Example 14: Using DNIRA to Correlate with Disease Pathogenesis (Predictive Biomarker)

Figure 33:
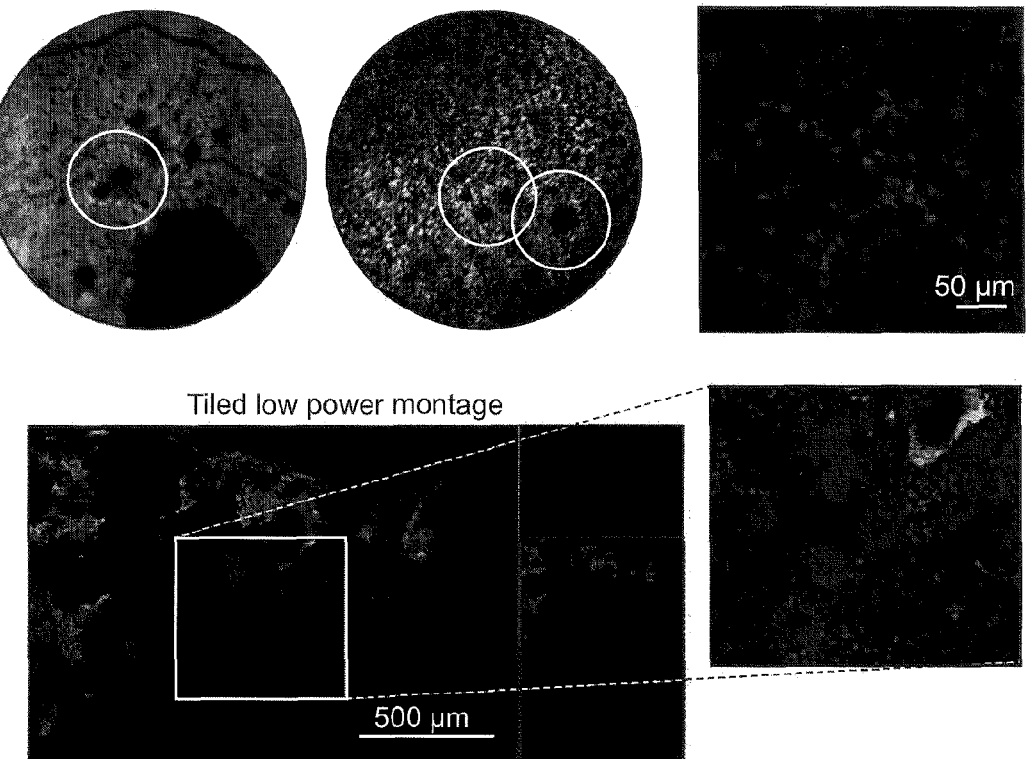
FIG. 33 depicts representative example of Using DNIRA to Correlate with Disease Pathogenesis (Predictive Biomarker).

FIG. 33 is a graphical representation of this example.

Drusen were identified as a key prognostic factor predicting the 10 year risk of patients progressing to blinding late AMD (both wet and dry). The clinical utility of large soft and soft confluent drusen precludes their application in prevention studies owing to the large sample size necessary to adequately power a study.

With subject consent, all clinical procedures were performed as described in previous examples.

To correlate DNIRA in patients to a valid model that depicts macrophages in the eye, retinal atrophy was induced in rabbits using systemic injection of oxidative agent, and imaged using the DNIRA method. DNIRA images were acquired using a commercially available confocal scanning laser ophthalmoscope (cSLO) (e.g. Heidelberg Retinal Angiography, HRA-2, Heidelberg Engineering, Germany). Images are obtained prior to systemic injection using cSLO, in the red-free, FAF (488/500 nm excitation/emission), IR reflectance channel (830 nm) and ICG fluorescence channels (795/810 nm excitation/emission). ICG dye (Cardiogreen, Sigma) is freshly prepared prior to experimentation to a final stock concentration of 5.0 mg/ml in sterile water. A fine gauge catheter is inserted intravenously into the marginal ear vein, and ICG dye is infused. Within 5-14 days after toxin injection, and 2-3 days after dye injection, DNIRA images obtained with ICG excitation/emission filters or laser systems in place (795/810 nm) but without further injection of dye. Multiple images are acquired of each eye, including at the center and in the periphery.

The image on the left shows a DNIRA image of a patient which demonstrates a ring of hyperfluorescent dots that correspond with presumptive macrophages positioned just beyond a region of hypofluroescence.

The middle image shows DNIRA images of a rabbit eye following acute oxidative stress demonstrate similar arrays of brightly hyperfluorescent dots around hypofluorescent regions.

After imaging, rabbit eyes are removed for immunofluorescent tissue analysis using markers for macrophages, such as Iba-1.

The right panel shows immunofluroscent labelled rabbit retinal tissue, with the presence of Iba-1 positive macrophages (red) surrounding the regions of outer retinal damage and RPE loss (blue nuclear stain).

Further, the lower panel confirms the distribution of Iba1+ macrophages surrounding small, newly formed areas of outer retinal damage (depicted by rings and convolutions of the outer nuclear layer (blue nuclei staining) and RPE loss (depicted by the sparse staining of RPE marker RPE65 in green) analogous to geographic atrophy.

Thus, DNIRA can identify presumptive macrophages in the eyes of patients with diseases such as AMD or ocular tumors, identifying individuals who are more likely than similar individuals without the biomarker to experience a favorable or unfavorable effect from exposure to a medical product such as macrophage modulating therapy or an environmental agent.

Example 15: Analysis of Tumor Associated Macrophages (TAMs) Using DNIRA (TAMI) as Predictor of Disease Severity in Ocular Melanoma FIGS. 18 and 19A-J are graphical representations of this example.

With subject consent, all clinical procedures were performed as described in previous examples.

Multimodal and cross-modal analysis for identification of regions of interest (ROIs) containing hyperfluorescent TAMI signal. Logical process for temporal analysis of discrete, dot or spot-like, hyperfluorescent TAMI signal. Logical process for temporal analysis of aggregates or accumulations of dot or spot-like TAMI signal. Logical process for inter-modality analysis of hyperfluorescent dots or spots.

FIG. 18 shows a comparison of DNIRA vs colour photos & clinical grading of uveal melanoma examples. The left two images show uveal nevi, middle right image shows an indeterminate lesion, and the right image shows a melanoma image. In the upper panel DNIRA images show the absence or presence of bright hyperfluorescent dots in the tumour area, or area of associated fluid. These images were used to perform analyses described in FIGS. 19A-G.

FIGS. 19A-G show TAMI composite images, for correlation of the TAMI imaging with currently available clinical imaging modalities. Assembly of TAMi composites allow for correlation of the novel imaging method with current clinical modalities. Fundus autofluorescence (FAF, FIG. 19B) and TAMi composites (FIG. 19C) were assembled as an overlay on colour photographs (FIG. 19A). Multi-modal analysis allowed identification of regions of interest including the tumour region (i), areas of current or previous fluid (ii), and peripheral (extra-lesional) regions (iii). FIG. 19D depicts multimodal analysis allowing identification of a tumor region. FIG. 19E depicts multimodal analysis allowing identification of a fluid region. FIG. 19F depicts identified regions of interest, including a tumor region (i), an area of current or previous fluid (ii), and an area of peripheral (extra-lesional) features. FIG. 19G depicts identification of regions of interest from composite images. Region area in $mm^2$ was determined using ImageJ measurements and used in hyperfluorescent dot density calculations (FIG. 19H). These were compared across patients with melanomas, indeterminate 74 lesions, or benign nevi, as determined by clinician ground truth.

Comparison to subject risk features including orange pigment presence, lesion area on color fundus photos, lesion thickness, lesion elevation, proximity to optic nerve head, presence of subretinal fluid, presence of hot spots, and degree of pigmentation. The risk features were analyzed in subjects with benign nevi, ocular melanoma, and control subjects, and compared to hyperfluorescent dot counts observed with TAMI/DNIRA imaging. Mean regional dot density is shown as number of dots/$mm^2$±SEM.

(FIG. 19I) One-way ANOVA and post hoc multiple caparisons show significantly higher dot densities in melanoma arms when considering lesion and fluid regions, but not in peripheral regions. (FIG. 19J) Multiple comparisons of dot density in each region within risk groups found melanomas had significantly higher regional dot density in lesion and fluid regions when compared to peripheral areas, and this was not observed in other risk groups.

Presence of hyperfluorescent dots was correlative to presence of ocular melanoma, but not to benign nevi, or control subjects, suggesting that hyperfluorescent dot presence can predict severity of ocular tumors.

Example 16: DNIRA to Detect Multiple Types of
Hyperfluorescent Dot Signals (Predictive
Biomarkers)

FIGS. 34A-34D are graphical representations of this example.

DNIRA has the potential to identify patients with increased presence of intraocular macrophages, serving as a predictive biomarker, and provide a unique link between imaging biomarkers and disease pathobiology. Since confirmatory ocular biopsy from human subjects is often not possible, analysis of these features were previously correlated to preclinical studies.

With subject consent, all clinical procedures were performed as described in previous examples.

Repeated analysis, exemplified here from just two patients, shows the size distribution of hyperfluorescent dots, demonstrated to be macrophages in correlative preclinical studies.

In FIG. 34A, the left panel shows small hyperfluorescent dots that can be seen in some patients using DNIRA. These have high degrees of circularity and are of approximately the same size. The middle panel shows another type of bright dots that have dark centers. The right panel shows very large bright dots that are observed in some forms of disease.

Figures 34B, 34C:
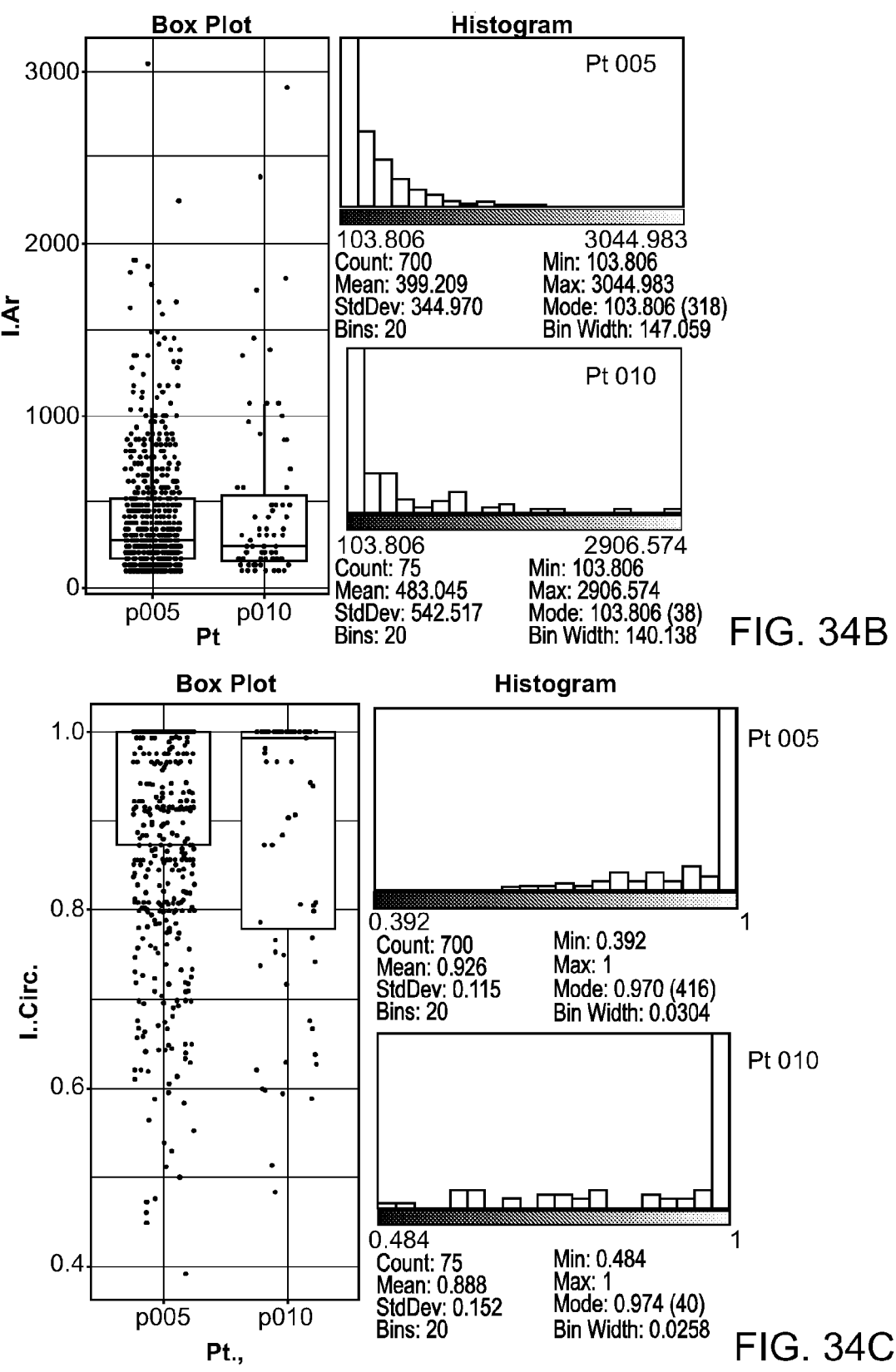

In FIG. 34B, Kruskal-Wallis analysis shows that size and uniformity of the dots is consistent with their cellular identity. The distributions of dot size are fairly similar—both qualitatively (histograms) and quantitatively (Kruskal-Wallis p-value 0.7577 indicates no significant difference). Mean size in pt 005 is 399 $\mu m^2$, with a mean diameter of 22.5 $\mu M$; mean size in pt 010 is 483 $\mu m^2$, with a mean diameter of 24.8 $\mu M$. Macrophages in the living organism are predicted to range from 15 to 40 $\mu m$ in diameter, depending on their activation status and other influences, indicating these dots are consistent with macrophage size.

In FIG. 34C, distributions of dot circularity are similar across patients—both qualitatively (histograms) and quantitatively (Kruskal-Wallis p-value 0.1055 indicates no significant difference). Mean circularity in pt 005 is 0.926; mean circularity in pt 010 is 0.888. These values are consistent with measurements from pre-clinical studies in the rabbit eye.

Figure 34D:
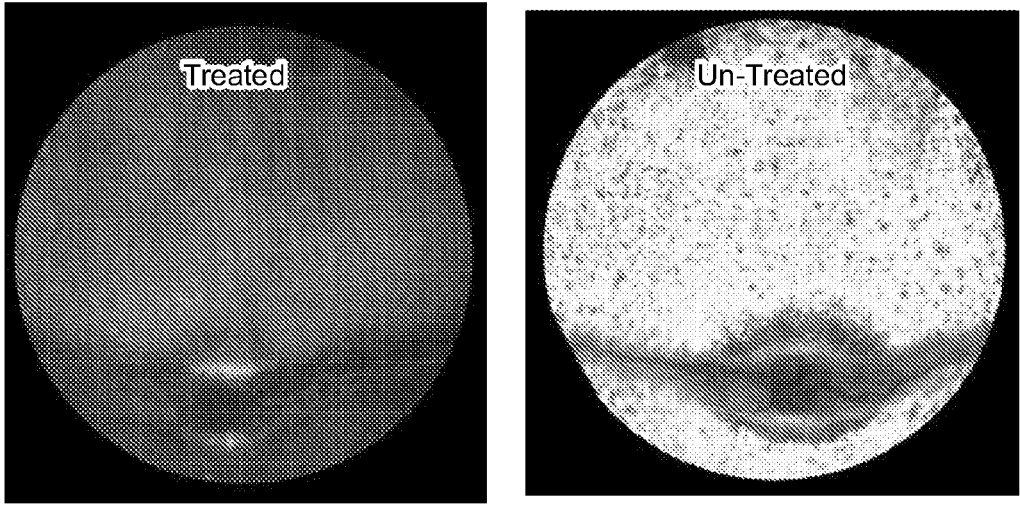

Finally, in FIG. 34D, in pre-clinical investigation using a macrophage modulator [such as, but not limited to bindarit and its derivatives, methotrexate, and others], we demonstrate that macrophage numbers, size and location are modified in treated animals compared to untreated controls, suggesting the utility of DNIRA to not only identify patients for clinical trial but to monitor drug response. Thus, DNIRA is a useful pharmacodynamic marker demonstrating significantly reduced signal following macrophage modulatory therapy in pre-clinical testing in the rabbit eye. It is anticipated that a similar reduction in hyperfluorescent signal may be observed in patients receiving macrophage- and immune-modulating drugs.

Example 17: DNIRA to Detect Static and Dynamic
Hyperfluorescent Dot Signals (Predictive
Biomarkers)

Figure 35:
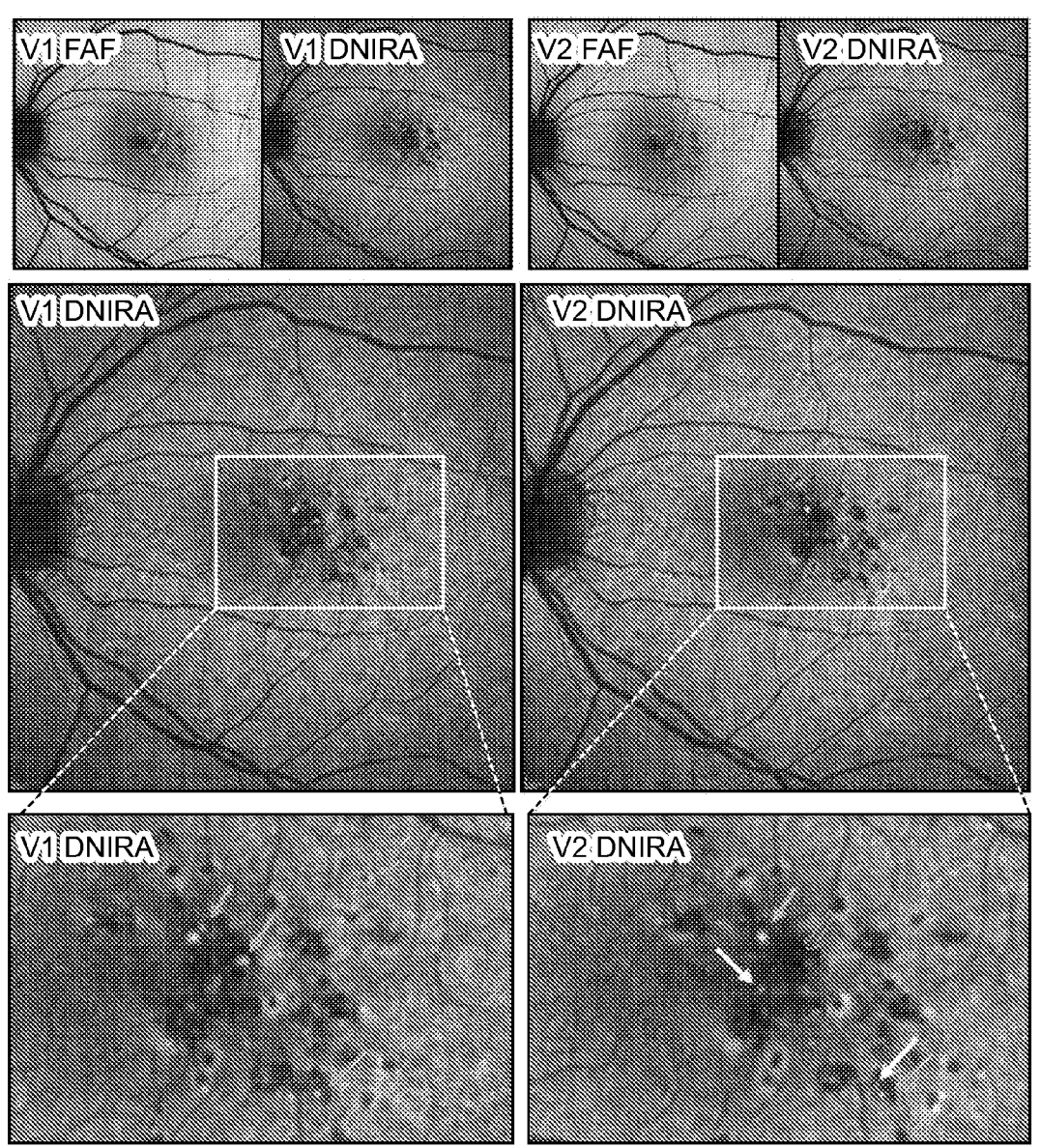
FIG. 35 depicts representative example of DNIRA to Detect Static and Dynamic Hyperfluorescent Dot Signals (Predictive Biomarkers).

FIG. 35 is a graphical representation of this example.

DNIRA images show hyperfluorescent (bright) dots that are ephemeral or transient in nature. Whether these dots have moved, disappears and reappeared, or whether new dots have arrived is not known.

With subject consent, all clinical procedures were performed as described in previous examples.

The upper panel on the left shows a pair of images comparing DNIRA against FAF.

DNIRA shows additional areas of hyperfluorescent signal, plus bright, hyperfluorescent dots found in association with these areas. In the right pair of images, the same set obtained at least three months later show subtle changes.

The middle panel shows two DNIRA fundus image of patient with Stargardt disease, taken at least 3 months apart. Magnification of these images indicates bright dots that are present at both time points (blue arrows). At other sites bright dots have appeared in the second visit that were not noted in the first (yellow arrows). The blue outline arrow in the right image indicates a site where a dot that was previously there moved, disappeared or become potentially less phagocytic and thus no longer takes up dye.

Example 18: DNIRA Detects Regions of Tissue
Damage and Macrophage Activity in Central
Serous Retinopathy (Predictive, Prognostic
Biomarkers)

Figure 36:
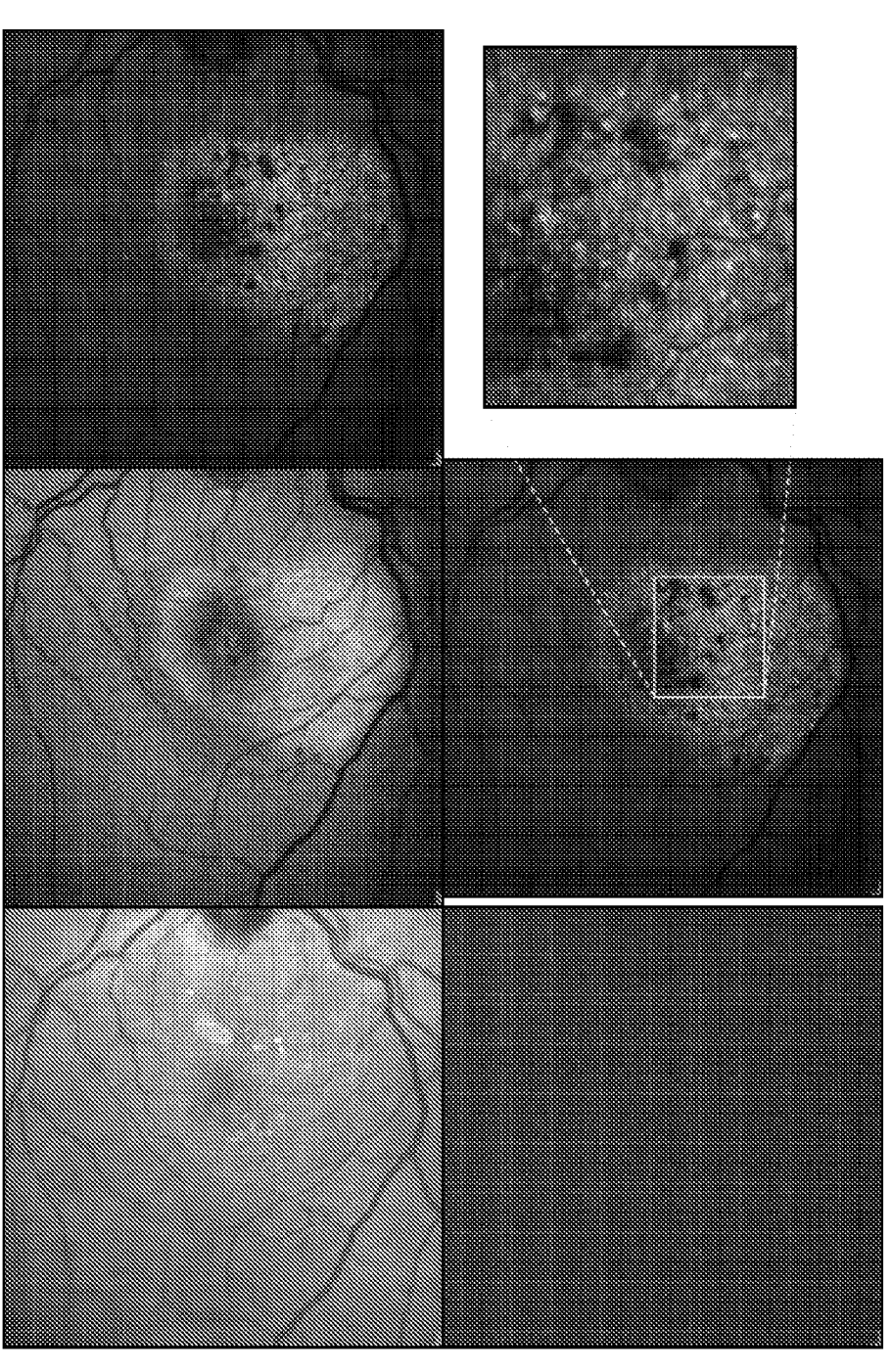
FIG. 36 depicts representative example of DNIRA to detect Regions of Tissue Damage and Macrophage Activity in Central Serous Retinopathy (Predictive, Prognostic Biomarkers).

FIG. 36 is a graphical representation of this example.

Central Serous Retinopathy (CSR) is a disease characterized by fluid movement from the choroid to the subretinal and intraretinal space. With time, persistent fluid is associated with irreversible chorioretinal atrophy (MA).

With subject consent, all clinical procedures were performed as described in previous examples.

Images of a patient with CSR in the upper panel shows IR, FAF and DNIRA images from left to right respectively. The FAF shows hyperfluorescence in area of previous (and potentially present) fluid. DNIRA similarly identifies region associated with fluid and also regions of decreased functional ability to uptake dye, appearing as black (hypofluorescent). These regions suggest vulnerability to future tissue loss (not yet evident as areas of GA using the standard method of FAF).

In the lower panel the left, image taken in the ICG channel prior to systemic dye injection has no signal. Middle and right images show that hyperfluorescent dots are found spatiotemporally within areas of CSR-associated fluid and tissue damage.

These data may suggest that macrophages contribute to tissue damage, and both macrophages and tissue damage can be detected using DNIRA, allowing for earlier detection and prognosis.

Example 19: DNIRA Detects Two Populations of
Bright Hyperfluorescent Dots in Diffuse-Tricking
AMD (Diagnostic, Prognostic Biomarkers)

FIG. 37 is a graphical representation of this example.

Diffuse Trickling form of late dry AMD is typically defined by a unique FAF pattern. Here we identify novel biomarkers of diffuse trickling subtype of AMD.

With subject consent, all clinical procedures were performed as described in previous examples.

In the upper panel, left and middle images show IR and FAF respectively, identifying extensive GA. The right image shows DNIRA, with regions of hypofluorescence that are of approximately the same area FAF, but also enlarged hyperfluorescent dots at the border.

The lower panel shows NIR imaging prior to the systemic delivery of ICG dye on the left, which shows no detectable signal. The middle image shows the same DNIRA image as above, and enlargements of specific areas. On the right, DNIRA demonstrates two populations of hyperfluorescent (bright) dots at the border and in the surrounding so-called "junctional zone". Some are of typical size as presumptive macrophages (e.g., as seen in association with tumours), while others are much larger, potentially pointing to accumulation of dye within RPE cells, or other cells.

Example 20: DNIRA to Detect Reticular Pseudodrusen

Figure 38:
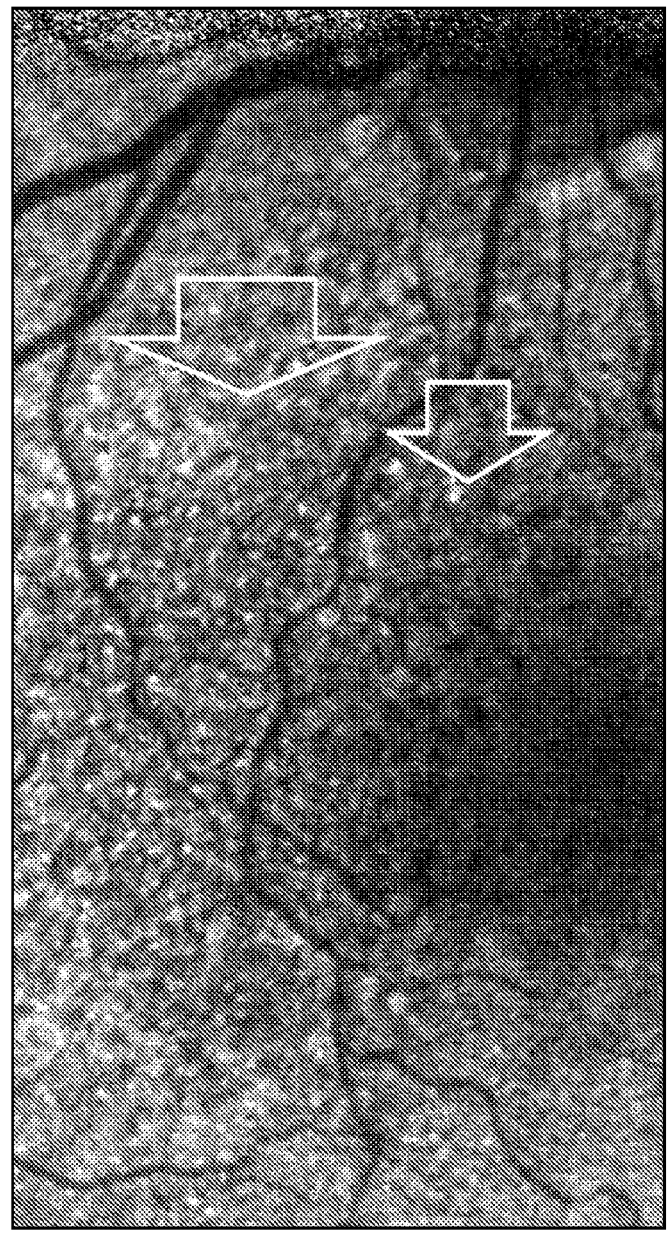
FIG. 38 depicts representative example of DNIRA to Detect Reticular Pseudodrusen.

FIG. 38 is a graphical illustration for this example.

Reticular pseudodrusen (RPD) is associated with particularly aggressive subtypes of dry AMD, and a higher rate of disease progression.

With subject consent, all clinical procedures were performed as described in previous examples.

DNIRA image and subsequent logical processes of a periphery of the fundus can be used to show the presence of discrete, dot or spot-like, hyperfluorescent signal. This signal can be used for temporal analysis of aggregates or accumulations of dot or spot-like DNIRA signal (indicated by arrows); and for inter-modality analysis of hyperfluorescent dots or spots.

This signal can subsequently be used to associate with reticular pseudodrusen (RPD) load, or disease burden, allowing for a potentially better predictive biomarker of disease progression.

Example 21: DNIRA to Detect Ocular Inflammatory Disease

Figure 39:
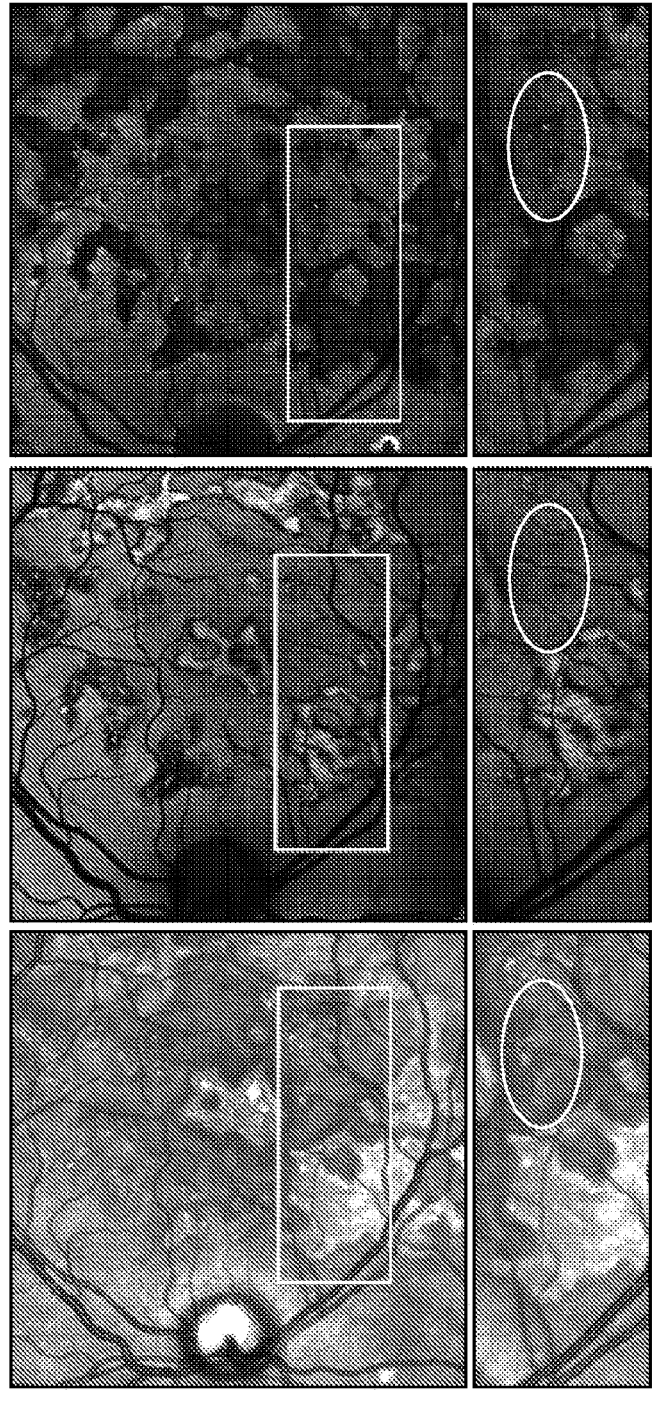
FIG. 39 depicts representative example of DNIRA applied to the analysis of ocular inflammatory disease. In this example of presumed Acute Multifocal Posterior Placoid Epitheliopathy (AMPPE), DNIRA demonstrates abnormal RPE/outer retina layer uptake of dye.

FIG. 39 is a graphical illustration for this example.

DNIRA can be applied to the analysis of ocular inflammatory disease. In this example of presumed Acute Multifocal Posterior Placoid Epitheliopathy (AMPPE), DNIRA demonstrates abnormal RPE/outer retina layer uptake of dye.

With subject consent, all clinical procedures were performed as described in previous examples.

In the left panel IR imaging shows variable reflectivity, including hyper- and hypo-reflective regions, and puntacte signals. In the middle panel, FAF similarly demonstrates hyper- and hypofluorescent regions, with regions of hyperfluorescence presumed to correlate with areas of potential disease activity. In the right panel DNIRA imaging shows multiple regions of profound hypofluorescence which likely correlate with areas of diseased tissue unable to accumulate dye, or potentially blocking its signal. Further, as shown within the box, a small area of hypofluorescence is forming (oval area), present only in the DNIRA image with little change in other channels. Within this region are two large hyperfluorescent dots. Based on pre-clinical studies, these dots correspond with phagocytic macrophages, and are of consistent size and shape as dots seen in other conditions such as ocular melanoma.

Therefore DNIRA outlines larger areas of damage than either FAF or IR imaging in ocular inflammatory disease, and can be used as a diagnostic or prognostic biomarker.

Example 22: DNIRA as a Marker of High Risk AMD Features (Predictive, Prognostic Biomarker)

FIG. 40 is a graphical illustration for this example.

DNIRA can be used, for the first time, to quantify and better characterize image-based features of diseases such as AMD, some of which are already known to confer high risk of progression from early to late disease (either atrophic or angiographic). Some of these features may correlate with histological features such as basal laminar deposits, basal linear deposits, or the deposition of extracellular, immune and ill-defined materials deposited sub-retinal space or in the sub-RPE space. Further, some deposits such as hyper-reflective material (in the sub-retinal space it is known as Subretinal Hyper-reflective Material, SRHM) are associated with high risk. However, much other material is observed using OCT is not hyper-reflective and therefore not seen en face, and is poorly defined. As such it is not possible to quantify or compare changes in these features over time.

With subject consent, all clinical procedures were performed as described in previous examples.

In the upper row, the left image shows an infrared image where variable signal can be observed, with hyper-reflective material believed to correspond with the accumulation of pigments such as melanin that are known to fluoresce in the IR spectrum. The upper right image shows that FAF confirms that this patient has early AMD, with no obvious GA, but also with hyper-reflective material present.

The middle row shows a sample DNIRA image prior to dye injection with no signal visible. The right image shows DNIRA obtained at the same session as the upper panel FAF and IR images, and shows regions of profound hypofluorescence. Further, small punctate hyper- and hypo-fluorescence are also observed, the former of which may correspond with dye-labeled macrophages or other phagocytic cells able to uptake the systemically delivered dye.

The lower row shows an OCT image where shallow drusen, sub-retinal material and a shallow sub-RPE cleft associated with profoundly hypofluorescent DNIRA signal is observed.

Thus DNIRA has the ability to highlight features of early AMD that may correspond to histological components associated with early disease, and those associated with a high risk of disease progression, serving as a predictive or prognostic biomarker.

Example 23: Using DNIRA to Detect and Quantify Known Risk Factors for Disease Progression FIG. 65 is a graphical representation of this example.

Drusen were identified as a key prognostic factor predicting the 10 year risk of patients progressing to blinding late AMD (both wet and dry). Despite their potential clinical utility, particularly for clinical trial design, soft drusen cannot be quantified or adequately described using current modalities as so their application is highly limited. As such, it is widely considered that large numbers of patients would be necessary to adequately power a study.

With subject consent, all clinical procedures were performed as described in previous examples.

Upper panel: left is a colour fundus photo showing soft drusen and drusenoid RPE detachments. They are obviously ill-defined. The middle image shows the area of soft drusen and RPEDs, with their outline in black. IN the right image, these signals can be segmented, or derived through the use of a general cross-modal training algorithm, with fusion of multiple modalities that includes confirmatory OCT analysis, prior to the generation of the OCT-driven segmentation map.

Lower panel: correspond OCT confirms that the yellow drusen observed clinical have a classic conformation. By contrast, the DNIRA image confirms that these drusend and RPEDs have a functional effect on the ability of systemically delivered dye to generate a signal, which is detected by the detector and processed by the classifier. The output is a colour map as shown.

Example 24: Detector—Soft Drusen

Figure 66:
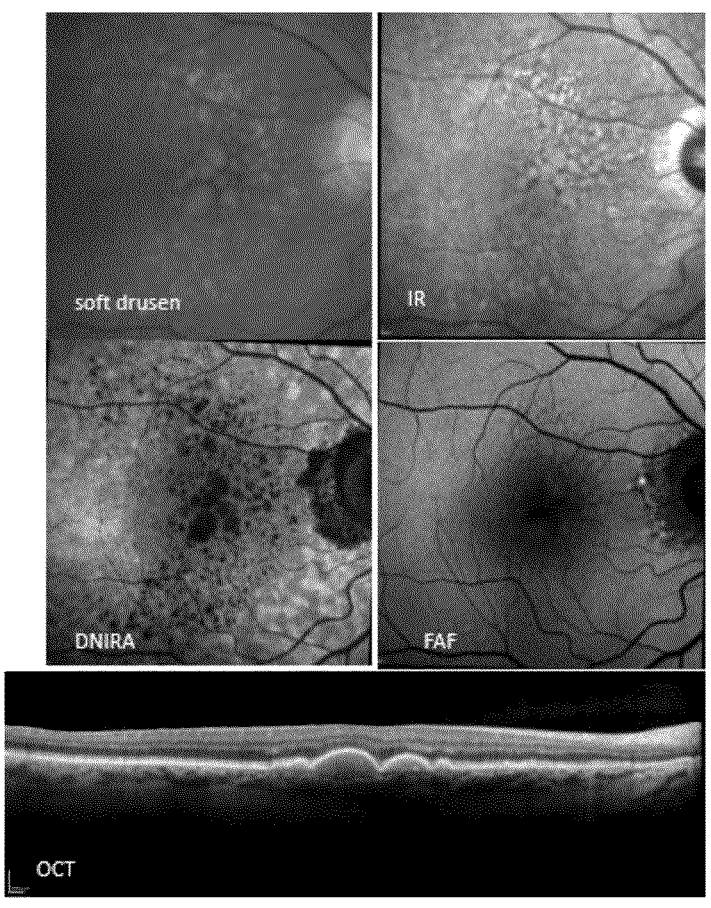
FIG. 66 depicts a representative example multi-modal imaging of soft drusen.

In one example, detector 1200 may be configured and trained to automatically detect regions of soft fuzzy drusen. FIG. 66 shows multi-modal imaging of soft drusen. Detection of large areas of soft drusen is of clinical interest as the soft drusen may merge to form RPE detachments.

Figure 67:
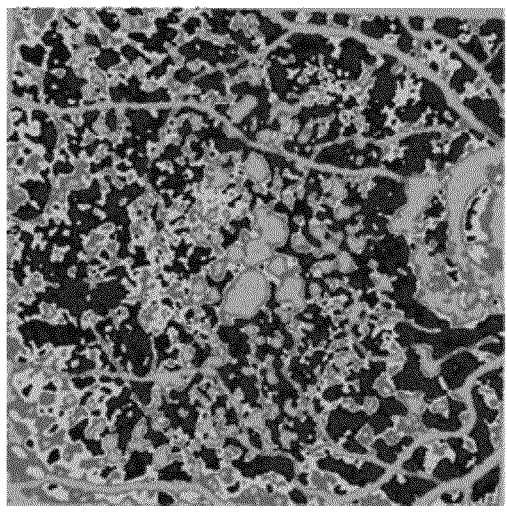
FIG. 67 depicts a region of soft drusen as detected by an embodiment of a detector.

Detector 1200 may be configured to process input data DNIRA image data, and optionally including multi-modal image, to detect regions of soft drusen. FIG. 67 shows a region of soft drusen as detected by an embodiment of detector 1200. The use of DNIRA image data allows the irregular borders of soft drusen to be identified. Significantly, this embodiment of detector 1200 may be used to provide automatic detection of functional behavior of retinal tissue, and automatic quantification of functional loss that accompanies soft drusen.

Figure 68:
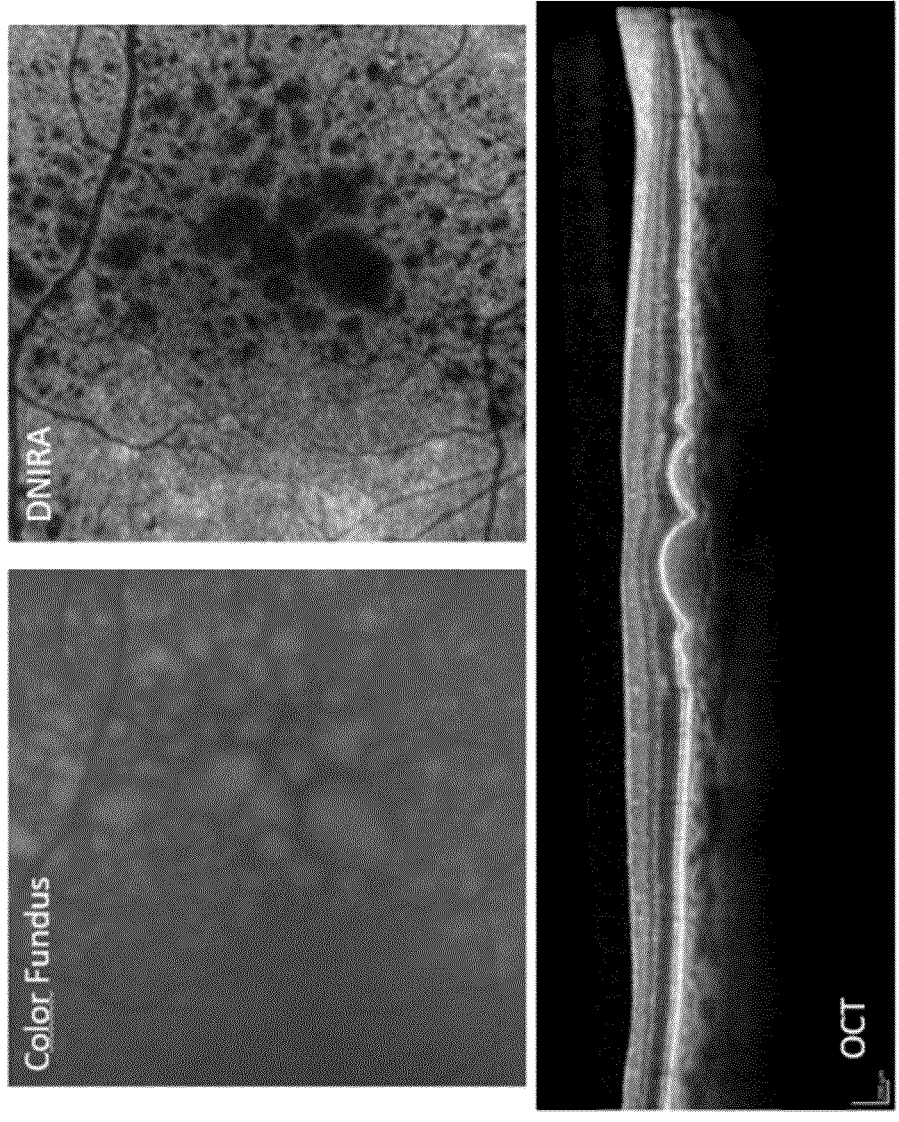
FIGS. 68-69 depict representative examples of analysis of soft drusen by the quantification of soft fuzzy drusen and RPEDs.
Figure 69:
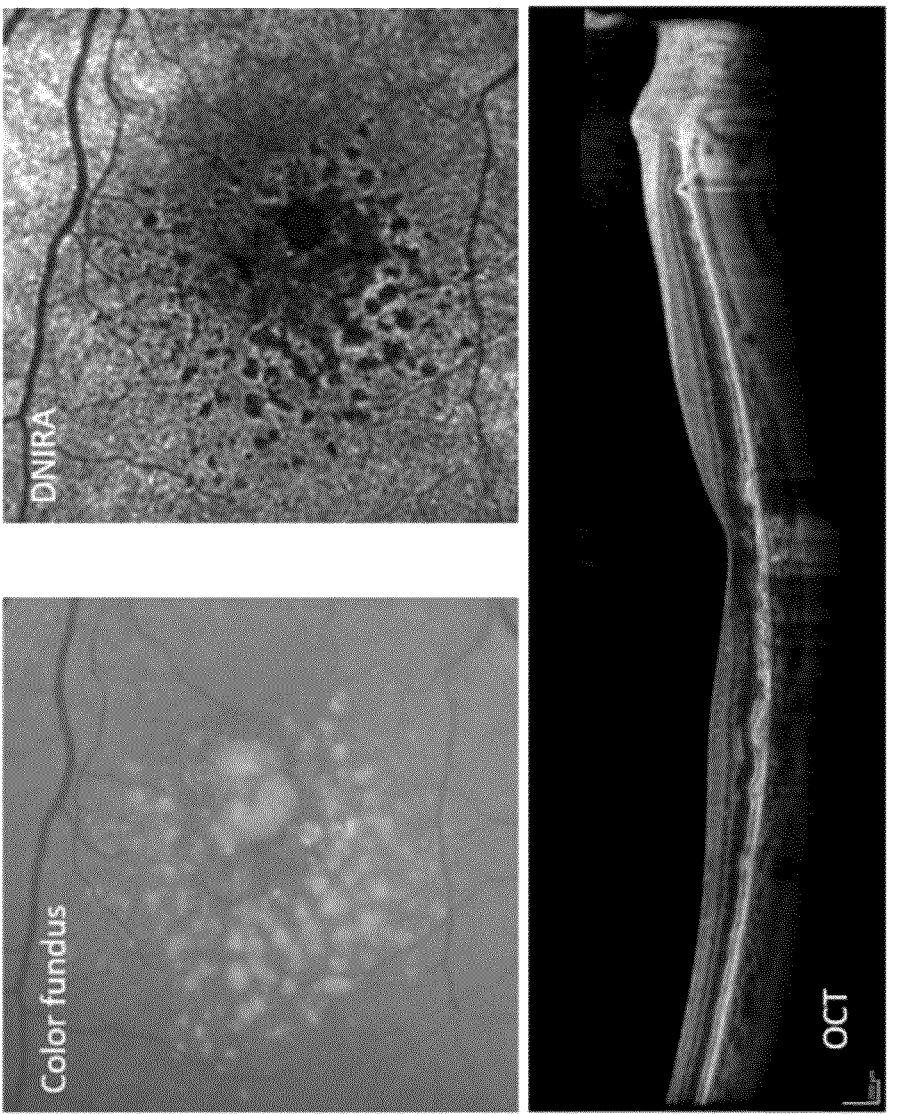

FIGS. 68-69 show an analysis of soft drusen by the quantification of soft fuzzy drusen and RPEDs, illustrating the utility of DNIRA for soft drusent imaging. These are examples of quantifying the biological effect of soft fuzzy drusen and large RPEDs on the transfer of dye from the choroid to the RPE/photoreceptor layer, that in turn, is the first functional imaging method. Large soft fuzzy drusen are the single best known predictor of progression from early to late AMD (both wet and dry, so CNVM and GA), thus is may be advantageous to quantify their biological significance.

Example 25: Detector—Macrophages

Figure 70:
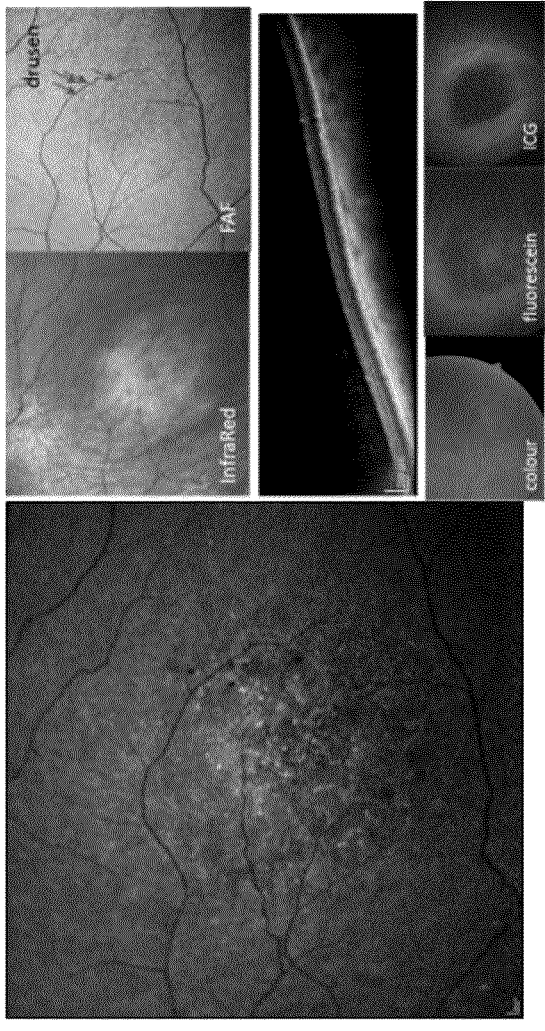
FIG. 70 depicts representative examples of multi-modal imaging of soft drusen.

In one example, detector 1200 may be configured and trained to automatically detect TAMs. FIG. 70 shows multi-modal imaging of soft drusen. Detection of TAMs is of clinical interest as the presence of TAM correlates with the severity of ocular tumors.

Figure 71:
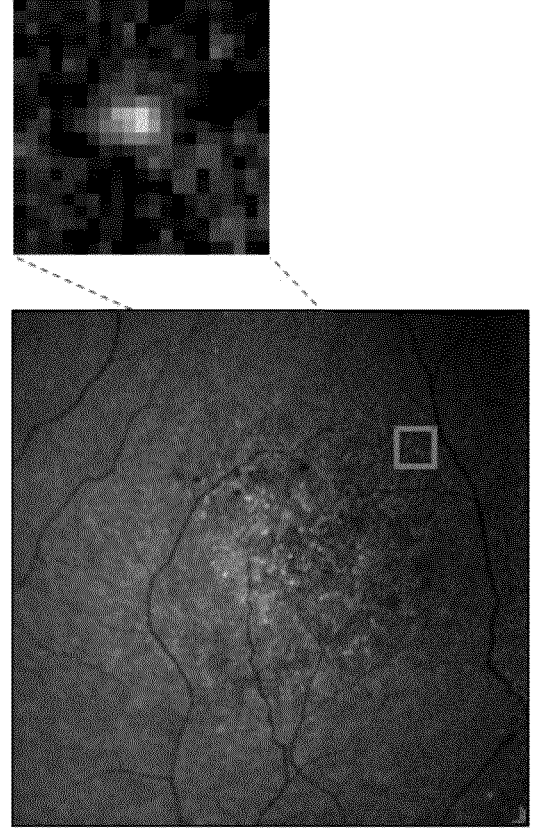
FIG. 71 depicts a TAM as detected by an embodiment of a detector.

Detector 1200 may be configured to process input data DNIRA image data, and optionally including multi-modal image, to detect regions containing hyperfluorescent TAMI signal. FIG. 71 shows a TAM as detected by an embodiment of detector 1200.

Figure 72:
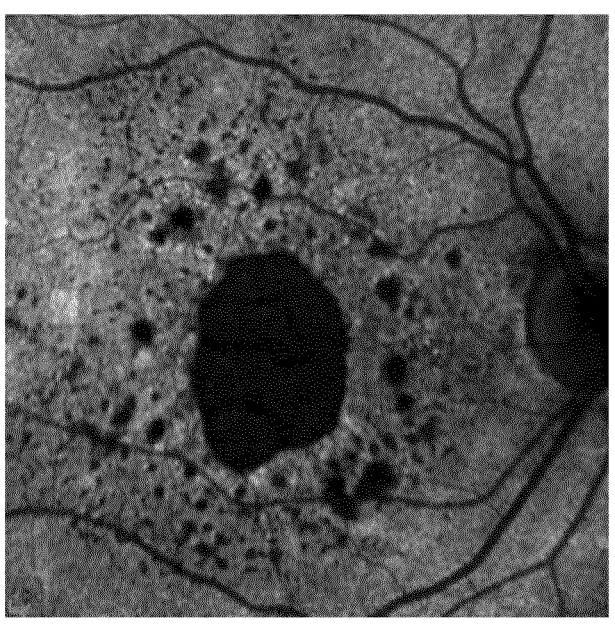
FIG. 72 depicts a representative example of a DNIRA image.

In another example, detector 1200 may be configured and trained to automatically detect macrophages associated with AMD. FIG. 72 shows a DNIRA image in which macrophages appear as bright dots. Detection of the macrophages is of clinical interest as macrophage activity may lead to GA and other forms of macular atrophy, and to CNV and other forms of neovascularization.

Detector 1200 may be configured to process input data including DNIRA image data, and optionally including multi-modal image data, to detect the macrophages in AMD. FIG. 73 shows macrophages as detected by an embodiment of detector 1200. Detector 1200 may, for example, implement Fast Fourier Transform (FFT) band pass filtering to detect high frequencies associated with the clustering of macrophages. Detector 1200 may be trained to find and utilize other features.

Embodiments of detector 1200 configured to detect macrophages may be used to assist in the development of a drug that targets macrophages, e.g., by measuring the efficacy of the drug.

Example 26: Detector—Grey Smudges

In one example, detector 1200 may be configured and trained to automatically detect regions of grey smudge.

Figure 74:
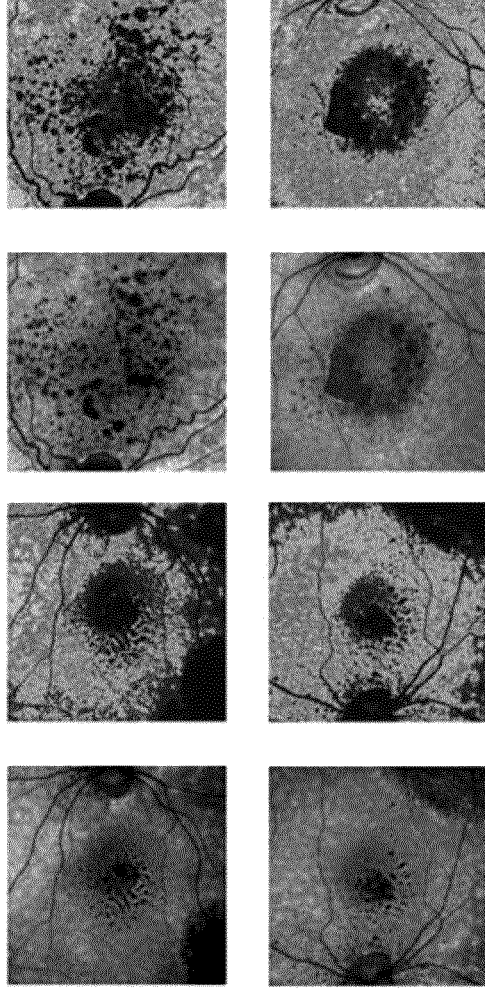
FIG. 74 depicts a representative example of the application of K-means segmentation to a set of four DNIRA images.

Detection of grey smudge is of clinical interest as they may indicate tissue dysfunction. Of note, tissue dysfunctional may be distinguished from tissue death, which results in a black signal. In one specific embodiment, detector 1200 is configured to perform a K-means clustering algorithm. In this case, detector 1200 converts a DNIRA image to a single long vector. This vector is divided into K intensity levels based on the nearest neighbor algorithm. A segmentation map is then reconstructed by reassigning the pixel to their cluster means. Regions of grey smudge may then identified by comparing the intensity levels of segments to predefined thresholds, or thresholds learned through training. FIG. 74 depicts the application of K-means (K=5) segmentation to a set of four DNIRA images, with regions of grey smudge shown in each image.

Complex 2D Patterns

Complex 2D patterns of grey-scale hypofluorescent signal may be observed in DNIRA images, including many patterns that are not observable using conventional imaging modalities such as FAF. Without wishing to be limited by theory, and by way of non-limiting example, these complex 2D patterns may represent different subtypes of disease, different stages of disease, different diseases, different likelihoods of progressing different rates of progression, different prognoses, different responses to treatment, different underlying biology, different concurrent diseases, different concurrent medical therapies, and/or different lifestyle choices (e.g., smoking).

Accordingly, in various embodiments, a detector 1200 may be configure to detect a given one of the various categories of 2D patterns. Further, in various embodiments, a classifier 1000 may be configured to classify an observed pattern into the various categories of 2D patterns.

Figure 75:
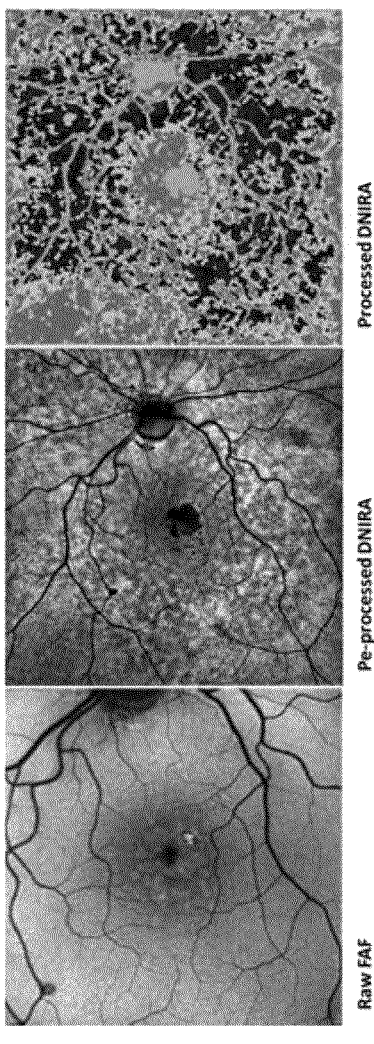
FIG. 75 depicts an example 2D pattern, as observed in an FAF image, a DNIRA image, and a DNIRA image with regions classified by an embodiment of a classifier.

FIG. 75 shows an example 2D pattern, as observed in an FAF image, a DNIRA image, and a DNIRA image with regions classified by an embodiment of a classifier 1000. As shown, the FAF image lacks clearly demarcated regions of profound hypofluorescence/black signal. However, in the processed DNIRA image, distinct regions are observable.

In some embodiments, a classifier 1000 provides for identification and quantification of regions of intermediate or grey-scale DNIRA signal. In some embodiments, a classifier 1000 reduces the complexity of an image through hierarchical feature extraction and dimensionality reduction.

Equivalents

While the disclosure has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present is not entitled to antedate such publication by virtue of prior invention.

As used herein, all headings are simply for organization and are not intended to limit the disclosure in any manner. The content of any individual section may be equally applicable to all sections.

What is claimed is:

1. A computer system comprising:
a processor;
a memory in communication with the processor, the memory storing instructions that, when executed by the processor cause the processor to:
at a training phase,
receive training data corresponding to a plurality of ocular images, wherein the plurality of ocular images of the training data correspond to a plurality of imaging modalities, said plurality of imaging modalities including delayed near-infrared analysis (DNIRA) and at least one imaging modality other than DNIRA;
generate delta image data based on a difference between said DNIRA images and images of said at least one imaging modality other than DNIRA;
perform feature extraction and feature selection to generate features based on the training data and the delta image data to build a pattern recognition model;
at a classification phase,
receive a plurality of ocular images corresponding to a plurality of imaging modalities;
classify features of the plurality of ocular images using the pattern recognition model.

2. The computer system of claim 1, wherein the pattern recognition model is at least one of a convolutional neural network, machine learning, decision trees, logistic regression, principal components analysis, naive Bayes model, support vector machine model, and nearest neighbor model.

3. The computer system of claim 1, wherein the feature extraction generates a masked image of defined shapes.

4. The computer system of claim 3, wherein the feature selection is based on at least one of focality of the defined shapes, a number of focal points per unit area of the defined shapes, and a square root of an area of the defined shapes.

5. The computer system of claim 1, wherein the features are defined by areas of hypofluorescence.

6. The computer system of claim 1, wherein the features are defined by areas of hyperfluorescence.

7. The computer system of claim 1, wherein the training phase further comprises building a pattern recognition model for each of the plurality of imaging modalities.

8. The computer system of claim 1, wherein the plurality of ocular images comprises a cross-section image.

9. The computer system of claim 1, wherein the plurality of ocular images comprises an en face image.

10. The computer system of claim 1, wherein the training phase further comprises registering the plurality of ocular images to a common coordinate system.

11. The computer system of claim 1, wherein the training phase further comprises cross-modal fusion of the plurality of ocular images to a common coordinate system.

12. The computer system of claim 1, wherein the plurality of imaging modalities other than DNIRA comprise at least one of infra-red reflectance (IR), confocal scanning laser ophthalmoscopy (cSLO), fundus autofluorescence (FAF), color fundus photography (CFP), optical coherence tomography (OCT), OCT-angiography, fluorescence lifetime imaging (FLI).

13. The computer system of claim 1, wherein the memory stores further instructions that, when executed by the processor cause the processor to:
generate a cross-section segmentation map corresponding to an en face region of an eye, each segment of the cross-section segmentation map corresponding to a cross-section image at that region of the eye;
classify each segment of the cross-section segmentation map as a phenotype of one of normal, drusen, retinal pigment epithelium detachments (RPEDs), pseudodrusen geographic atrophy, macular atrophy, or neovascularization based at least in part on classification of the cross-section image corresponding to that segment using the pattern recognition model.

14. The computer system of claim 1, wherein the plurality of ocular images comprises multiple cross-section images corresponding to multiple time points and the memory stores further instructions that, when executed by the processor cause the processor to:
generate, for each of the multiple time points, a cross-section segmentation map corresponding to an en face region of an eye, each segment of the cross-section segmentation map corresponding to a cross-section image at that region of the eye;
classify each segment of each cross-section segmentation map as a phenotype of tissue state of one of normal, drusen, retinal pigment epithelium detachments (RPEDs), pseudodrusen geographic atrophy, macular atrophy, or neovascularization, based at least in part on classification of the cross-section image corresponding to that segment using the pattern recognition model; and
generate a time series data model based on the cross-section segmentation map at each of the multiple time points.

15. The computer system of claim 14, wherein the time series data model is based at least in part on identified changes in the cross-section segmentation maps over time.

16. The computer system of claim 14, wherein the time series data model is used to generate a visual representation of disease progression.

17. The computer system of claim 14, wherein the time series data model is based at least in part on elapsed time between the multiple time points.

18. The computer system of claim 1, wherein the features selected comprise phenotypes of a user associated with the plurality of ocular images.

19. The computer system of claim 1, wherein the memory stores further instructions that, when executed by the processor cause the processor to: correlate the features with stage or grade variants of blinding eye disease including Age Related Macular Degeneration (AMD), monogenic eye disease, inherited eye disease and inflammatory eye disease.

20. The computer system of claim 1, wherein said at least one imaging modality other than DNIRA comprises fundus autofluorescence (FAF), and wherein generating said delta image data comprises a delta analysis comprising DNIRA subtracting FAF.

* * * * *